(12) United States Patent
Xia

(10) Patent No.: US 11,349,081 B2
(45) Date of Patent: May 31, 2022

(54) AZAINDOLOCARBAZOLE COMPOUNDS

(71) Applicant: BEIJING SUMMER SPROUT TECHNOLOGY CO., LTD., Beijing (CN)

(72) Inventor: Chuanjun Xia, Lawrenceville, NJ (US)

(73) Assignee: BEIJING SUMMER SPROUT TECHNOLOGY CO., LTD., Beijing (CN)

( * ) Notice: Subject to any disclaimer, the term of this patent is extended or adjusted under 35 U.S.C. 154(b) by 203 days.

(21) Appl. No.: 16/174,317

(22) Filed: Oct. 30, 2018

(65) Prior Publication Data

US 2019/0148646 A1    May 16, 2019

Related U.S. Application Data

(60) Provisional application No. 62/586,150, filed on Nov. 14, 2017.

(51) Int. Cl.
| | | |
|---|---|---|
| H01L 51/50 | (2006.01) | |
| H01L 51/00 | (2006.01) | |
| C09K 11/06 | (2006.01) | |
| C07D 495/22 | (2006.01) | |
| C07D 471/14 | (2006.01) | |
| C07D 495/14 | (2006.01) | |

(52) U.S. Cl.
CPC ........ H01L 51/0071 (2013.01); C07D 471/14 (2013.01); C07D 495/14 (2013.01); C07D 495/22 (2013.01); C09K 11/06 (2013.01); H01L 51/0056 (2013.01); H01L 51/0072 (2013.01); C09K 2211/1018 (2013.01); H01L 51/0054 (2013.01); H01L 51/0067 (2013.01); H01L 51/0074 (2013.01); H01L 51/5012 (2013.01); H01L 51/5016 (2013.01); H01L 51/5056 (2013.01); H01L 51/5072 (2013.01); H01L 51/5096 (2013.01)

(58) Field of Classification Search
None
See application file for complete search history.

(56) References Cited

U.S. PATENT DOCUMENTS

| | | |
|---|---|---|
| 5,703,436 A | 12/1997 | Forrest et al. |
| 5,707,745 A | 1/1998 | Forrest et al. |
| 5,844,363 A | 12/1998 | Gu et al. |
| 6,097,147 A | 8/2000 | Baldo et al. |
| 6,303,238 B1 | 10/2001 | Thompson et al. |

(Continued)

FOREIGN PATENT DOCUMENTS

| | | | | |
|---|---|---|---|---|
| KR | 2014039622 | * | 4/2014 | ............. H01L 51/50 |
| WO | WO 2010/126234 A1 | * | 11/2010 | ............. C09K 11/06 |

OTHER PUBLICATIONS

Tang, C. W. et al., "Organic electroluminescent diodes", Applied Physics Letters, 51(12): 913-915 (1987).

(Continued)

*Primary Examiner* — Gregory D Clark
(74) *Attorney, Agent, or Firm* — Brown Rudnick LLP

(57) ABSTRACT

New azaindolocarbazole compounds are disclosed, which can be used as hosts in an organic electroluminescent device. Compared to existing host materials, the compounds can effectively modulate the charge transporting properties in host materials and give OLEDs better performance. An electroluminescent device and a formulation are also disclosed.

13 Claims, 2 Drawing Sheets

(56) References Cited

U.S. PATENT DOCUMENTS

Figure 1:
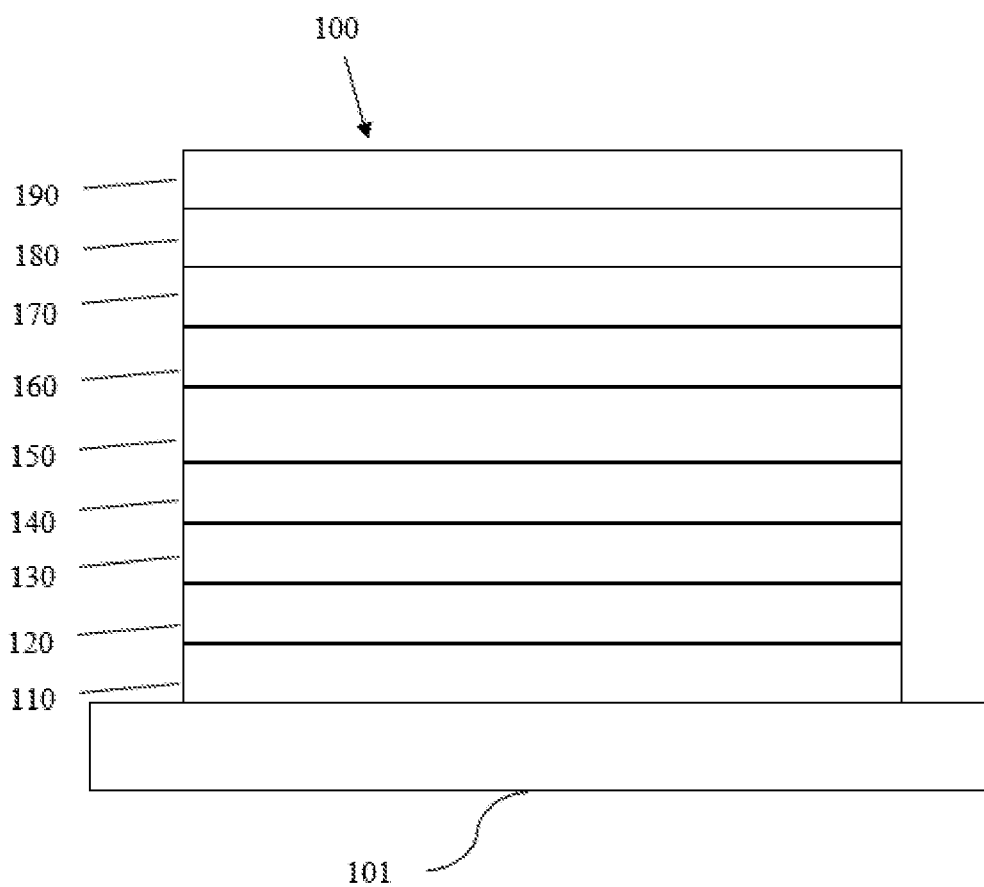

| | | |
|---|---|---|
| 7,279,704 B2 | 10/2007 | Walters et al. |
| 7,968,146 B2 | 6/2011 | Wagner et al. |
| 2003/0137239 A1* | 7/2003 | Matsuura ............ H01L 51/5016 313/503 |
| 2003/0230980 A1 | 12/2003 | Forrest et al. |
| 2004/0170863 A1* | 9/2004 | Kim .................... C07D 209/82 428/690 |
| 2004/0174116 A1 | 9/2004 | Lu et al. |
| 2015/0236262 A1* | 8/2015 | Cho .................... H01L 51/0058 257/40 |
| 2015/0349273 A1 | 12/2015 | Hung et al. |
| 2016/0233435 A1 | 8/2016 | Zeng et al. |
| 2016/0293853 A1 | 10/2016 | Zeng et al. |
| 2016/0293854 A1 | 10/2016 | Zeng et al. |
| 2016/0293855 A1 | 10/2016 | Zeng et al. |
| 2016/0293856 A1 | 10/2016 | Ji et al. |
| 2016/0359122 A1 | 12/2016 | Boudreault et al. |
| 2017/0069848 A1 | 3/2017 | Zeng et al. |
| 2020/0194688 A1 | 6/2020 | Zeng et al. |

OTHER PUBLICATIONS

Hiroki Uoyama et al., "Highly efficient organic light-emitting diodes from delayed fluorescence", Nature, vol. 492, pp. 234-238 (2012).

\* cited by examiner

AZAINDOLOCARBAZOLE COMPOUNDS

This application claims the benefit of U.S. Provisional Application No. 62/586,150, filed Nov. 14, 2017, the entire content of which is incorporated herein by reference.

1 FIELD OF THE INVENTION

The present invention relates to compounds for organic electronic devices, such as organic light emitting devices. More specifically, the present invention relates to azaindolocarbazole compounds, an organic electroluminescent device comprising the compounds and a formulation comprising the compounds.

2 BACKGROUND ART

An organic electronic device is preferably selected from the group consisting of organic light-emitting diodes (OLEDs), organic field-effect transistors (O-FETs), organic light-emitting transistors (OLETs), organic photovoltaic devices (OPVs), dye-sensitized solar cells (DSSCs), organic optical detectors, organic photoreceptors, organic field-quench devices (OFQDs), light-emitting electrochemical cells (LECs), organic laser diodes and organic plasmon emitting devices.

In 1987, Tang and Van Slyke of Eastman Kodak reported a bilayer organic electroluminescent device, which comprises an arylamine hole transporting layer and a tris-8-hydroxyquinolato-aluminum layer as the electron and emitting layer (Applied Physics Letters, 1987, 51 (12): 913-915). Once a bias is applied to the device, green light was emitted from the device. This invention laid the foundation for the development of modern organic light-emitting diodes (OLEDs). State-of-the-art OLEDs may comprise multiple layers such as charge injection and transporting layers, charge and exciton blocking layers, and one or multiple emissive layers between the cathode and anode. Since OLED is a self-emitting solid state device, it offers tremendous potential for display and lighting applications. In addition, the inherent properties of organic materials, such as their flexibility, may make them well suited for particular applications such as fabrication on flexible substrates.

OLED can be categorized as three different types according to its emitting mechanism. The OLED invented by Tang and van Slyke is a fluorescent OLED. It only utilizes singlet emission. The triplets generated in the device are wasted through nonradiative decay channels. Therefore, the internal quantum efficiency (IQE) of a fluorescent OLED is only 25%. This limitation hindered the commercialization of OLED. In 1997, Forrest and Thompson reported phosphorescent OLED, which uses triplet emission from heave metal containing complexes as the emitter. As a result, both singlet and triplets can be harvested, achieving 100% IQE. The discovery and development of phosphorescent OLED contributed directly to the commercialization of active-matrix OLED (AMOLED) due to its high efficiency. Recently, Adachi achieved high efficiency through thermally activated delayed fluorescence (TADF) of organic compounds. These emitters have small singlet-triplet gap that makes the transition from triplet back to singlet possible. In the TADF device, the triplet excitons can go through reverse intersystem crossing to generate singlet excitons, resulting in high IQE.

OLEDs can also be classified as small molecule and polymer OLEDs according to the forms of the materials used. Small molecule refers to any organic or organometallic material that is not a polymer. The molecular weight of a small molecule can be large as long as it has well defined structure. Dendrimers with well-defined structures are considered as small molecules. Polymer OLEDs include conjugated polymers and non-conjugated polymers with pendant emitting groups. Small molecule OLED can become a polymer OLED if post polymerization occurred during the fabrication process.

There are various methods for OLED fabrication. Small molecule OLEDs are generally fabricated by vacuum thermal evaporation. Polymer OLEDs are fabricated by solution process, such as spin-coating, ink-jet printing, and nozzle printing. Small molecule OLEDs can also be fabricated by solution process if the materials can be dissolved or dispersed in solvents.

The emitting color of an OLED can be achieved by emitter structural design. An OLED may comprise one emitting layer or a plurality of emitting layers to achieve desired spectrum. In the case of green, yellow, and red OLEDs, phosphorescent emitters have successfully reached commercialization. Blue phosphorescent emitters still suffer from non-saturated blue color, short device lifetime, and high operating voltage. Commercial full-color OLED displays normally adopt a hybrid strategy, using fluorescent blue and phosphorescent yellow, or red and green. At present, efficiency roll-off of phosphorescent OLEDs at high brightness remains a problem. In addition, it is desirable to have more saturated emitting color, higher efficiency, and longer device lifetime.

Host materials play a key role in the OLED device, such as the hole and electron transporting balance and the effective dispersion of light-emitting materials. The charge-transfer performance of the host materials often directly affects the driving voltage and efficiency of the OLED device. The introduction of aza-aromatics in the host materials effectively modulates their charge transporting properties, especially for electrons. The present invention provides a series of novel azaindolocarbazole compounds. These compounds can effectively modulate the charge transporting properties in the host materials and give OLEDs better performance.

3 SUMMARY OF THE INVENTION

The present invention aims to provide a series of azaindolocarbazole compounds to solve at least part of above problems. The compounds can be used as hosts in an organic electroluminescent device. Compared to existing host materials, the compounds can effectively modulate the charge transporting properties in host materials and give OLEDs better performance.

According to an embodiment of the present invention, a compound having formula 1 is disclosed:

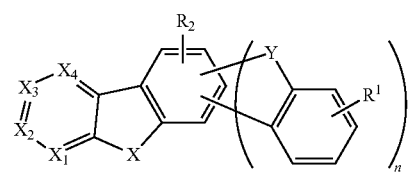

Formula 1

Wherein $X_1$ to $X_4$ are each independently selected from the group consisting of CR, and N;

At least one of $X_1$ to $X_4$ is N;

X and Y are each independently selected from the group consisting of O, S, Se, NR', and CR"R'";

$R_1$ represents mono, di, tri, or tetra substitution or no substitution;

$R_2$ represents mono or di substitution or no substitution;

R, R', R", R'", $R_1$, and $R_2$ are each independently selected from the group consisting of hydrogen, deuterium, halogen, a substituted or unsubstituted alkyl group having 1 to 20 carbon atoms, a substituted or unsubstituted cycloalkyl group having 3 to 20 ring carbon atoms, a substituted or unsubstituted heteroalkyl group having 1 to 20 carbon atoms, a substituted or unsubstituted arylalkyl group having 7 to 30 carbon atoms, a substituted or unsubstituted alkoxy group having 1 to 20 carbon atoms, a substituted or unsubstituted aryloxy group having 6 to 30 carbon atoms, a substituted or unsubstituted alkenyl group having 2 to 20 carbon atoms, a substituted or unsubstituted aryl group having 6 to 30 carbon atoms, a substituted or unsubstituted heteroaryl group having 3 to 30 carbon atoms, a substituted or unsubstituted alkylsilyl group having 3 to 20 carbon atoms, a substituted or unsubstituted arylsilyl group having 6 to 20 carbon atoms, a substituted or unsubstituted amino group having 0 to 20 carbon atoms, an acyl group, a carbonyl group, a carboxylic acid group, an ester group, a nitrile group, an isonitrile group, a sulfanyl group, a sulfinyl group, a sulfonyl group, a phosphino group, and combinations thereof;

Any adjacent substitution can be optionally joined to form a ring or fused structure;

n is 1 or 2;

when n is 2, each Y, $R_1$ can be the same or different.

According to another embodiment, an electroluminescent device is disclosed, which comprising:
an anode,
a cathode,
and an organic layer, disposed between the anode and the cathode, comprising a compound of formula 1:

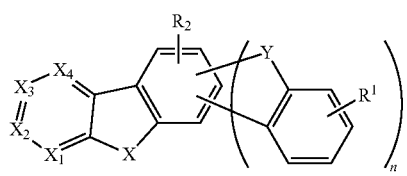

Formula 1

Wherein $X_1$ to $X_4$ are each independently selected from the group consisting of CR, and N;

At least one of $X_1$ to $X_4$ is N;

X and Y are each independently selected from the group consisting of O, S, Se, NR', and CR"R'";

$R_1$ represents mono, di, tri, or tetra substitution or no substitution;

$R_2$ represents mono or di substitution or no substitution;

R, R', R", R'", $R_1$, and $R_2$ are each independently selected from the group consisting of hydrogen, deuterium, halogen, a substituted or unsubstituted alkyl group having 1 to 20 carbon atoms, a substituted or unsubstituted cycloalkyl group having 3 to 20 ring carbon atoms, a substituted or unsubstituted heteroalkyl group having 1 to 20 carbon atoms, a substituted or unsubstituted arylalkyl group having 7 to 30 carbon atoms, a substituted or unsubstituted alkoxy group having 1 to 20 carbon atoms, a substituted or unsubstituted aryloxy group having 6 to 30 carbon atoms, a substituted or unsubstituted alkenyl group having 2 to 20 carbon atoms, a substituted or unsubstituted aryl group having 6 to 30 carbon atoms, a substituted or unsubstituted heteroaryl group having 3 to 30 carbon atoms, a substituted or unsubstituted alkylsilyl group having 3 to 20 carbon atoms, a substituted or unsubstituted arylsilyl group having 6 to 20 carbon atoms, a substituted or unsubstituted amino group having 0 to 20 carbon atoms, an acyl group, a carbonyl group, a carboxylic acid group, an ester group, a nitrile group, an isonitrile group, a sulfanyl group, a sulfinyl group, a sulfonyl group, a phosphino group, and combinations thereof;

Any adjacent substitution can be optionally joined to form a ring or fused structure;

n is 1 or 2;

when n is 2, each Y, $R_1$ can be the same or different.

According to yet another embodiment, a formulation comprising a compound of formula 1 is also disclosed.

The new azaindolocarbazole compounds disclosed in the present invention can be used as hosts in an organic electroluminescent device. Compared to existing host materials, the compounds can effectively modulate the charge transporting properties in host materials and give OLEDs better performance.

4 BRIEF DESCRIPTION OF THE DRAWINGS

FIG. 1 schematically shows an organic light emitting device that can incorporate the compound or formulation disclosed herein.

Figure 2:
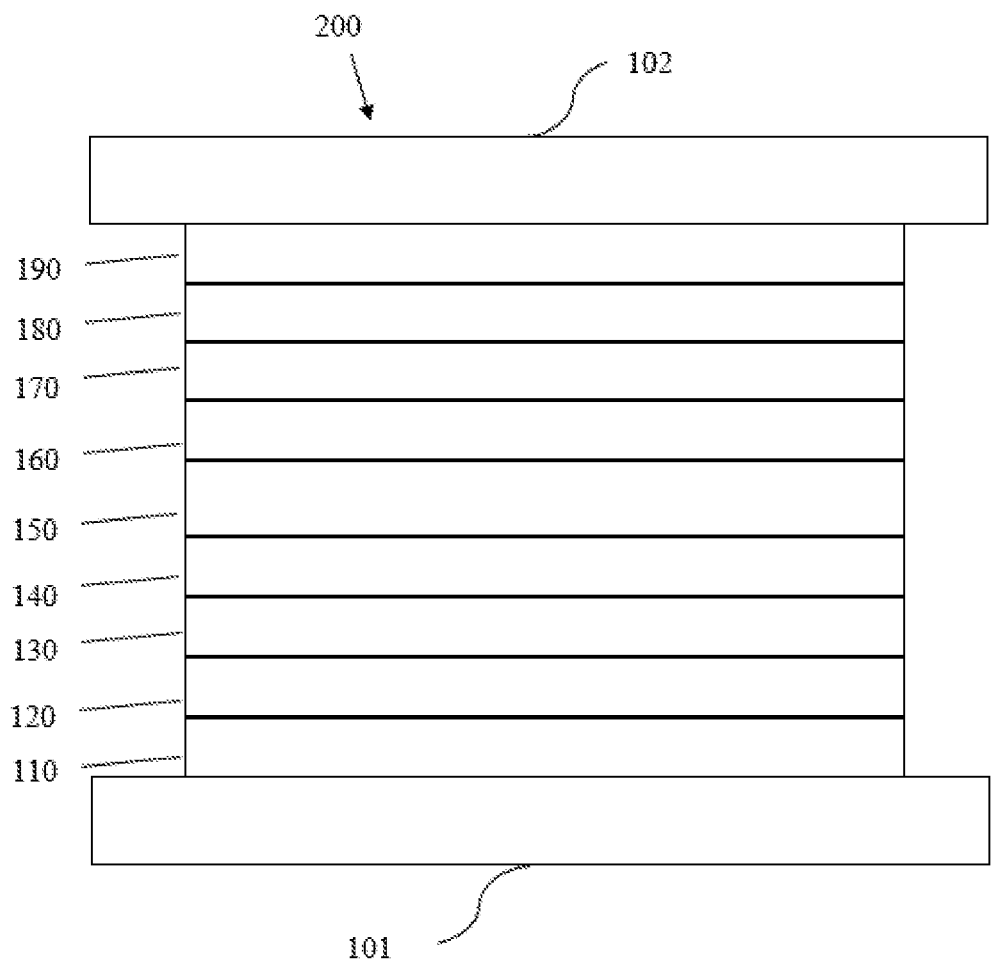

FIG. 2 schematically shows another organic light emitting device that can incorporate the compound or formulation disclosed herein.

Figure 3:
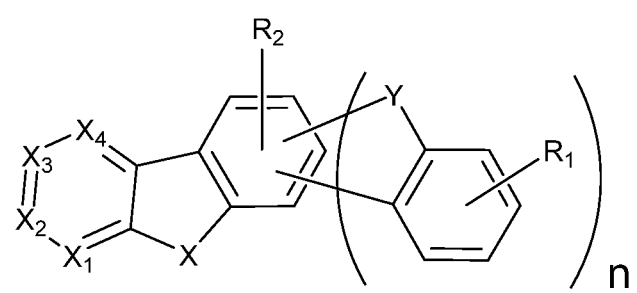

FIG. 3 shows the Formula 1 of the compound disclosed herein.

DETAILED DESCRIPTION

OLEDs can be fabricated on various types of substrates such as glass, plastic, and metal foil. FIG. 1 schematically shows the organic light emitting device 100 without limitation. The figures are not necessarily drawn to scale. Some of the layer in the figure can also be omitted as needed. Device 100 may include a substrate 101, an anode 110, a hole injection layer 120, a hole transport layer 130, an electron blocking layer 140, an emissive layer 150, a hole blocking layer 160, an electron transport layer 170, an electron injection layer 180 and a cathode 190. Device 100 may be fabricated by depositing the layers described in order. The properties and functions of these various layers, as well as example materials, are described in more detail in U.S. Pat. No. 7,279,704 at cols. 6-10, which are incorporated by reference in its entirety.

More examples for each of these layers are available. For example, a flexible and transparent substrate-anode combination is disclosed in U.S. Pat. No. 5,844,363, which is incorporated by reference in its entirety. An example of a p-doped hole transport layer is m-MTDATA doped with F4-TCNQ at a molar ratio of 50:1, as disclosed in U.S. Patent Application Publication No. 2003/0230980, which is incorporated by reference in its entirety. Examples of host materials are disclosed in U.S. Pat. No. 6,303,238 to Thompson et al., which is incorporated by reference in its entirety. An example of an n-doped electron transport layer is BPhen doped with Li at a molar ratio of 1:1, as disclosed in U.S. Patent Application Publication No. 2003/0230980, which is incorporated by reference in its entirety. U.S. Pat. Nos. 5,703,436 and 5,707,745, which are incorporated by reference in their entireties, disclose examples of cathodes including compound cathodes having a thin layer of metal such as Mg:Ag with an overlying transparent, electrically-conductive, sputter-deposited ITO layer. The theory and use of blocking layers is described in more detail in U.S. Pat. No. 6,097,147 and U.S. Patent Application Publication No. 2003/0230980, which are incorporated by reference in their entireties. Examples of injection layers are provided in U.S. Patent Application Publication No. 2004/0174116, which is incorporated by reference in its entirety. A description of protective layers may be found in U.S. Patent Application Publication No. 2004/0174116, which is incorporated by reference in its entirety.

The layered structure described above is provided by way of non-limiting example. Functional OLEDs may be achieved by combining the various layers described in different ways, or layers may be omitted entirely. It may also include other layers not specifically described. Within each layer, a single material or a mixture of multiple materials can be used to achieve optimum performance. Any functional layer may include several sublayers. For example, the emissive layer may have a two layers of different emitting materials to achieve desired emission spectrum.

In one embodiment, an OLED may be described as having an "organic layer" disposed between a cathode and an anode. This organic layer may comprise a single layer or multiple layers.

An OLED can be encapsulated by a barrier layer to protect it from harmful species from the environment such as moisture and oxygen. FIG. 2 schematically shows the organic light emitting device 200 without limitation. FIG. 2 differs from FIG. 1 in that the organic light emitting device 200 include a barrier layer 102, which is above the cathode 190. Any material that can provide the barrier function can be used as the barrier layer such as glass and organic-inorganic hybrid layers. The barrier layer should be placed directly or indirectly outside of the OLED device. Multilayer thin film encapsulation was described in U.S. Pat. No. 7,968,146, which is herein incorporated by reference in its entirety.

Devices fabricated in accordance with embodiments of the invention can be incorporated into a wide variety of consumer products that have one or more of the electronic component modules (or units) incorporated therein. Some examples of such consumer products include flat panel displays, monitors, medical monitors, televisions, billboards, lights for interior or exterior illumination and/or signaling, heads-up displays, fully or partially transparent displays, flexible displays, smart phones, tablets, phablets, wearable devices, smart watches, laptop computers, digital cameras, camcorders, viewfinders, micro-displays, 3-D displays, vehicles displays, and vehicle tail lights.

The materials and structures described herein may be used in other organic electronic devices listed above.

As used herein, "top" means furthest away from the substrate, while "bottom" means closest to the substrate. Where a first layer is described as "disposed over" a second layer, the first layer is disposed further away from substrate. There may be other layers between the first and second layer, unless it is specified that the first layer is "in contact with" the second layer. For example, a cathode may be described as "disposed over" an anode, even though there are various organic layers in between.

As used herein, "solution processible" means capable of being dissolved, dispersed, or transported in and/or deposited from a liquid medium, either in solution or suspension form.

A ligand may be referred to as "photoactive" when it is believed that the ligand directly contributes to the photoactive properties of an emissive material. A ligand may be referred to as "ancillary" when it is believed that the ligand does not contribute to the photoactive properties of an emissive material, although an ancillary ligand may alter the properties of a photoactive ligand.

It is believed that the internal quantum efficiency (IQE) of fluorescent OLEDs can exceed the 25% spin statistics limit through delayed fluorescence. As used herein, there are two types of delayed fluorescence, i.e. P-type delayed fluorescence and E-type delayed fluorescence. P-type delayed fluorescence is generated from triplet-triplet annihilation (TTA).

On the other hand, E-type delayed fluorescence does not rely on the collision of two triplets, but rather on the transition between the triplet states and the singlet excited states. Compounds that are capable of generating E-type delayed fluorescence are required to have very small singlet-triplet gaps to convert between energy states. Thermal energy can activate the transition from the triplet state back to the singlet state. This type of delayed fluorescence is also known as thermally activated delayed fluorescence (TADF). A distinctive feature of TADF is that the delayed component increases as temperature rises. If the reverse intersystem crossing rate is fast enough to minimize the non-radiative decay from the triplet state, the fraction of back populated singlet excited states can potentially reach 75%. The total singlet fraction can be 100%, far exceeding 25% of the spin statistics limit for electrically generated excitons.

E-type delayed fluorescence characteristics can be found in an exciplex system or in a single compound. Without being bound by theory, it is believed that E-type delayed fluorescence requires the luminescent material to have a small singlet-triplet energy gap ($\Delta E_{S-T}$). Organic, non-metal containing, donor-acceptor luminescent materials may be able to achieve this. The emission in these materials is often characterized as a donor-acceptor charge-transfer (CT) type emission. The spatial separation of the HOMO and LUMO in these donor-acceptor type compounds often results in small $\Delta F_{S-T}$. These states may involve CT states. Often, donor-acceptor luminescent materials are constructed by connecting an electron donor moiety such as amino- or carbazole-derivatives and an electron acceptor moiety such as N-containing six-membered aromatic rings.

Definition of Terms of Substituents halogen or halide—as used herein includes fluorine, chlorine, bromine, and iodine.

Alkyl—contemplates both straight and branched chain alkyl groups. Examples of the alkyl group include methyl group, ethyl group, propyl group, isopropyl group, n-butyl group, s-butyl group, isobutyl group, t-butyl group, n-pentyl group, n-hexyl group, n-heptyl group, n-octyl group, n-nonyl group, n-decyl group, n-undecyl group, n-dodecyl group, n-tridecyl group, n-tetradecyl group, n-pentadecyl group, n-hexadecyl group, n-heptadecyl group, n-octadecyl group, neopentyl group, 1-methylpentyl group, 2-methylpentyl group, 1-pentylhexyl group, 1-butylpentyl group, 1-heptyloctyl group, 3-methylpentyl group. Additionally, the alkyl group may be optionally substituted. The carbons in the alkyl chain can be replaced by other hetero atoms. Of the above, preferred are methyl group, ethyl group, propyl group, isopropyl group, n-butyl group, s-butyl group, isobutyl group, t-butyl group, n-pentyl group, and neopentyl group.

Cycloalkyl—as used herein contemplates cyclic alkyl groups. Preferred cycloalkyl groups are those containing 4 to 10 ring carbon atoms and includes cyclobutyl, cyclopentyl, cyclohexyl, 4-methylcyclohexyl, 4,4-dimethylcylcohexyl, 1-adamantyl, 2-adamantyl, 1-norbornyl, 2-norbornyl and the like. Additionally, the cycloalkyl group may be optionally substituted. The carbons in the ring can be replaced by other hetero atoms.

Alkenyl—as used herein contemplates both straight and branched chain alkene groups. Preferred alkenyl groups are those containing two to fifteen carbon atoms. Examples of the alkenyl group include vinyl group, allyl group, 1-butenyl group, 2-butenyl group, 3-butenyl group, 1,3-butandienyl group, 1-methylvinyl group, styryl group, 2,2-diphenylvinyl group, 1,2-diphenylvinyl group, 1-methylallyl group, 1,1-dimethylallyl group, 2-methylallyl group, 1-phenylallyl group, 2-phenylallyl group, 3-phenylallyl group, 3,3-diphenylallyl group, 1,2-dimethylallyl group, 1-phenyl 1-butenyl group, and 3-phenyl-1-butenyl group. Additionally, the alkenyl group may be optionally substituted.

Alkynyl—as used herein contemplates both straight and branched chain alkyne groups. Preferred alkynyl groups are those containing two to fifteen carbon atoms. Additionally, the alkynyl group may be optionally substituted.

Aryl or aromatic group—as used herein contemplates noncondensed and condensed systems. Preferred aryl groups are those containing six to sixty carbon atoms, preferably six to twenty carbon atoms, more preferably six to twelve carbon atoms. Examples of the aryl group include phenyl, biphenyl, terphenyl, triphenylene, tetraphenylene, naphthalene, anthracene, phenalene, phenanthrene, fluorene, pyrene, chrysene, perylene, and azulene, preferably phenyl, biphenyl, terphenyl, triphenylene, fluorene, and naphthalene. Additionally, the aryl group may be optionally substituted. Examples of the non-condensed aryl group include phenyl group, biphenyl-2-yl group, biphenyl-3-yl group, biphenyl-4-yl group, p-terphenyl-4-yl group, p-terphenyl-3-yl group, p-terphenyl-2-yl group, m-terphenyl-4-yl group, m-terphenyl-3-yl group, m-terphenyl-2-yl group, o-tolyl group, m-tolyl group, p-tolyl group, p-t-butylphenyl group, p-(2-phenylpropyl)phenyl group, 4'-methylbiphenylyl group, 4"-t-butyl p-terphenyl-4-yl group, o-cumenyl group, m-cumenyl group, p-cumenyl group, 2,3-xylyl group, 3,4-xylyl group, 2,5-xylyl group, mesityl group, and m-quarterphenyl group.

Heterocyclic group or heterocycle—as used herein contemplates aromatic and non-aromatic cyclic groups. Heteroaromatic also means heteroaryl. Preferred non-aromatic heterocyclic groups are those containing 3 to 7 ring atoms which includes at least one hetero atom such as nitrogen, oxygen, and sulfur. The heterocyclic group can also be an aromatic heterocyclic group having at least one heteroatom selected from nitrogen atom, oxygen atom, sulfur atom, and selenium atom.

Heteroaryl—as used herein contemplates noncondensed and condensed hetero-aromatic groups that may include from one to five heteroatoms. Preferred heteroaryl groups are those containing three to thirty carbon atoms, preferably three to twenty carbon atoms, more preferably three to twelve carbon atoms. Suitable heteroaryl groups include dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine, preferably dibenzothiophene, dibenzofuran, dibenzoselenophene, carbazole, indolocarbazole, imidazole, pyridine, triazine, benzimidazole, 1,2-azaborine, 1,3-azaborine, 1,4-azaborine, borazine, and aza-analogs thereof. Additionally, the heteroaryl group may be optionally substituted.

Alkoxy—it is represented by —O-Alkyl. Examples and preferred examples thereof are the same as those described above. Examples of the alkoxy group having 1 to 20 carbon atoms, preferably 1 to 6 carbon atoms include methoxy group, ethoxy group, propoxy group, butoxy group, pentyloxy group, and hexyloxy group. The alkoxy group having 3 or more carbon atoms may be linear, cyclic or branched.

Aryloxy—it is represented by —O-Aryl or —O-heteroaryl. Examples and preferred examples thereof are the same as those described above. Examples of the aryloxy group having 6 to 40 carbon atoms include phenoxy group and biphenyloxy group.

Arylalkyl—as used herein contemplates an alkyl group that has an aryl substituent. Additionally, the arylalkyl group may be optionally substituted. Examples of the arylalkyl group include benzyl group, 1-phenylethyl group, 2-phenylethyl group, 1-phenylisopropyl group, 2-phenylisopropyl group, phenyl-t-butyl group, alpha.-naphthylmethyl group, 1-alpha.-naphthylethyl group, 2-alpha-naphthylethyl group, 1-alpha-naphthylisopropyl group, 2-alpha-naphthylisopropyl group, beta-naphthylmethyl group, 1-beta-naphthylethyl group, 2-beta-naphthylethyl group, 1-beta-naphthylisopropyl group, 2-beta-naphthylisopropyl group, p-methylbenzyl group, m-methylbenzyl group, o-methylbenzyl group, p-chlorobenzyl group, m-chlorobenzyl group, o-chlorobenzyl group, p-bromobenzyl group, m-bromobenzyl group, o-bromobenzyl group, p-iodobenzyl group, m-iodobenzyl group, o-iodobenzyl group, p-hydroxybenzyl group, m-hydroxybenzyl group, o-hydroxybenzyl group, p-aminobenzyl group, m-aminobenzyl group, o-aminobenzyl group, p-nitrobenzyl group, m-nitrobenzyl group, o-nitrobenzyl group, p-cyanobenzyl group, m-cyanobenzyl group, o-cyanobenzyl group, 1-hydroxy-2-phenylisopropyl group, and 1-chloro2-phenylisopropyl group. Of the above, preferred are benzyl group, p-cyanobenzyl group, m-cyanobenzyl group, o-cyanobenzyl group, 1-phenylethyl group, 2-phenylethyl group, 1-phenylisopropyl group, and 2-phenylisopropyl group.

The term "aza" in azadibenzofuran, aza-dibenzothiophene, etc. means that one or more of the C—H groups in the respective aromatic fragment are replaced by a nitrogen atom. For example, azatriphenylene encompasses dibenzo[f,h]quinoxaline,dibenzo[f,h]quinoline and other analogues with two or more nitrogens in the ring system. One of ordinary skill in the art can readily envision other nitrogen analogs of the aza-derivatives described above, and all such analogs are intended to be encompassed by the terms as set forth herein.

The alkyl, cycloalkyl, alkenyl, alkynyl, aralkyl, heterocyclic group, aryl, and heteroaryl may be unsubstituted or may be substituted with one or more substituents selected from the group consisting of deuterium, halogen, alkyl, cycloalkyl, arylalkyl, alkoxy, aryloxy, amino, cyclic amino, silyl, alkenyl, cycloalkenyl, heteroalkenyl, alkynyl, aryl, heteroaryl, an acyl group, a carbonyl group, a carboxylic acid group, an ether group, an ester group, a nitrile group, an isonitrile group, a sulfanyl group, a sulfinyl group, a sulfonyl group, a phosphino group, and combinations thereof.

It is to be understood that when a molecular fragment is described as being a substituent or otherwise attached to another moiety, its name may be written as if it were a fragment (e.g. phenyl, phenylene, naphthyl, dibenzofuryl) or as if it were the whole molecule (e.g. benzene, naphthalene, dibenzofuran). As used herein, these different ways of designating a substituent or attached fragment are considered to be equivalent.

In the compounds mentioned in this disclosure, the hydrogen atoms can be partially or fully replaced by deuterium. Other atoms such as carbon and nitrogen, can also be replaced by their other stable isotopes. The replacement by other stable isotopes in the compounds may be preferred due to its enhancements of device efficiency and stability.

In the compounds mentioned in this disclosure, multiple substitutions refer to a range that includes a double substitution, up to the maximum available substitutions.

In the compounds mentioned in this disclosure, the expression that adjacent substituents are optionally joined to form a ring is intended to be taken to mean that two radicals are linked to each other by a chemical bond. This is illustrated by the following scheme:

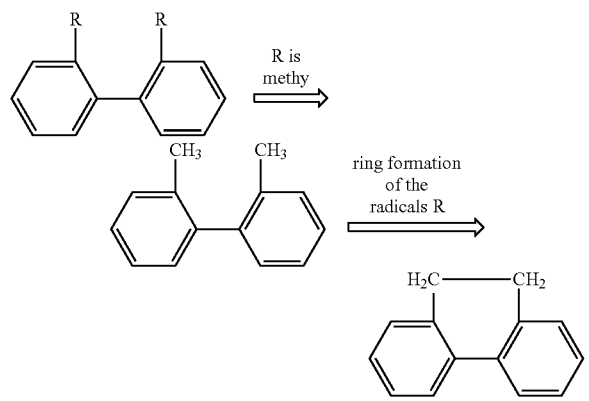

Furthermore, the expression that adjacent substituents are optionally joined to form a ring is also intended to be taken to mean that in the case where one of the two radicals represents hydrogen, the second radical is bonded at a position to which the hydrogen atom was bonded, with formation of a ring. This is illustrated by the following scheme:

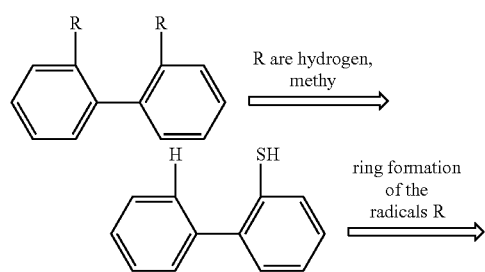

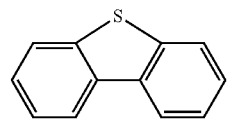

According to an embodiment of the present invention, a compound having a formula 1 is disclosed:

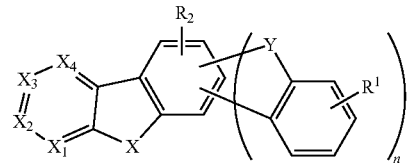

Formula 1

Wherein $X_1$ to $X_4$ are each independently selected from the group consisting of CR, and N;

At least one of $X_1$ to $X_4$ is N;

X and Y are each independently selected from the group consisting of O, S, Se, NR', and CR"R'";

$R_1$ represents mono, di, tri, or tetra substitution or no substitution;

$R_2$ represents mono or di substitution or no substitution;

R, R', R", R'", $R_1$, and $R_2$ are each independently selected from the group consisting of hydrogen, deuterium, halogen, a substituted or unsubstituted alkyl group having 1 to 20 carbon atoms, a substituted or unsubstituted cycloalkyl group having 3 to 20 ring carbon atoms, a substituted or unsubstituted heteroalkyl group having 1 to 20 carbon atoms, a substituted or unsubstituted arylalkyl group having 7 to 30 carbon atoms, a substituted or unsubstituted alkoxy group having 1 to 20 carbon atoms, a substituted or unsubstituted aryloxy group having 6 to 30 carbon atoms, a substituted or unsubstituted alkenyl group having 2 to 20 carbon atoms, a substituted or unsubstituted aryl group having 6 to 30 carbon atoms, a substituted or unsubstituted heteroaryl group having 3 to 30 carbon atoms, a substituted or unsubstituted alkylsilyl group having 3 to 20 carbon atoms, a substituted or unsubstituted arylsilyl group having 6 to 20 carbon atoms, a substituted or unsubstituted amino group having 0 to 20 carbon atoms, an acyl group, a carbonyl group, a carboxylic acid group, an ester group, a nitrile group, an isonitrile group, a sulfanyl group, a sulfinyl group, a sulfonyl group, a phosphino group, and combinations thereof;

Any adjacent substitution can be optionally joined to form a ring or fused structure;

n is 1 or 2;

when n is 2, each Y and/or each $R_1$ can be the same or different.

In one embodiment, wherein $X_1$ is N.

In one embodiment, wherein $X_1$ and $X_3$ is N.

In one embodiment, wherein $X_2$ and $X_4$ is N.

In one embodiment, wherein X and Y are each independently NR'.

In one embodiment, wherein X is S and Y is NR'.

In one preferred embodiment, wherein the compound has the formula:

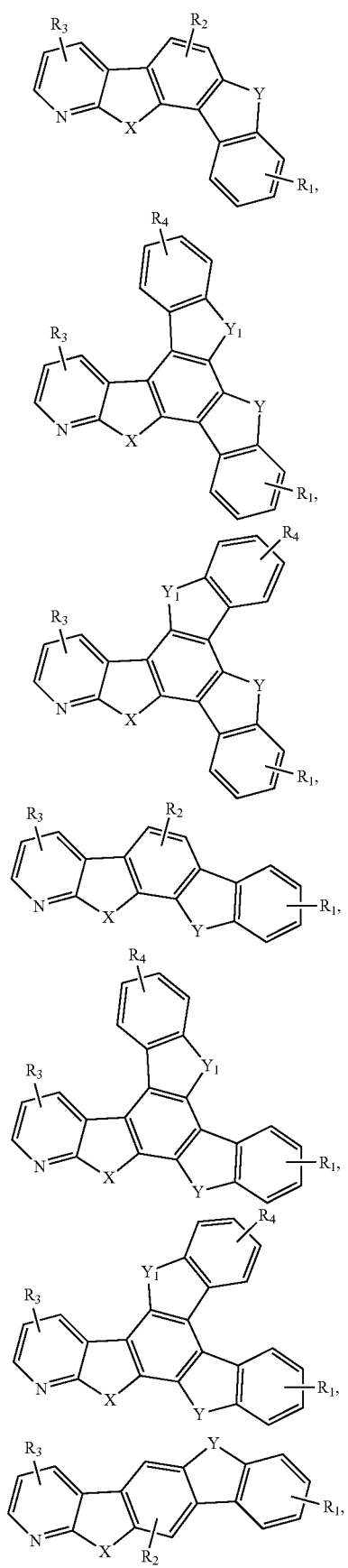
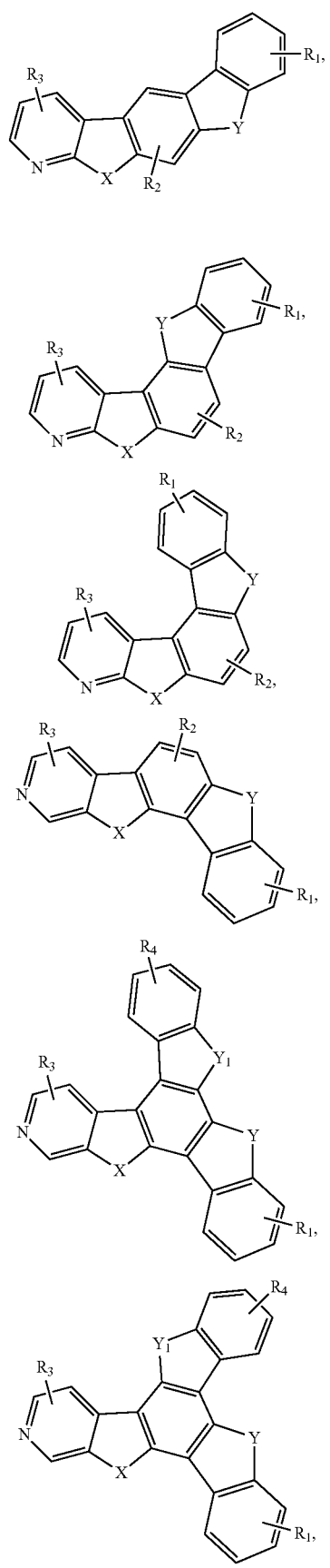

-continued
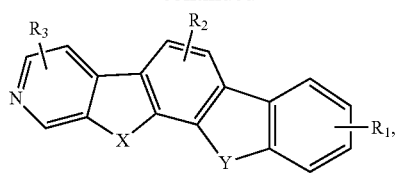
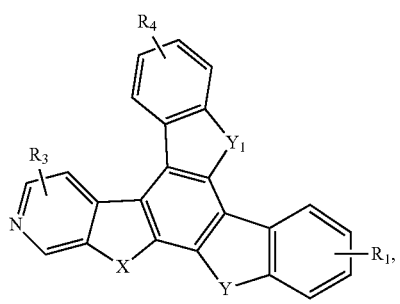
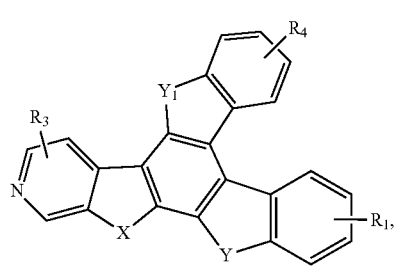
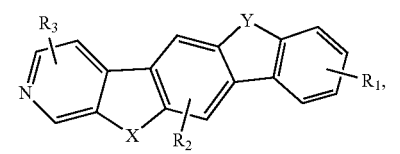
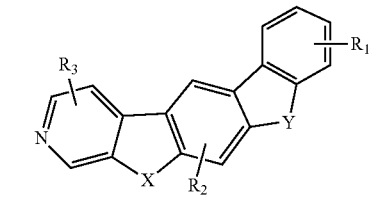
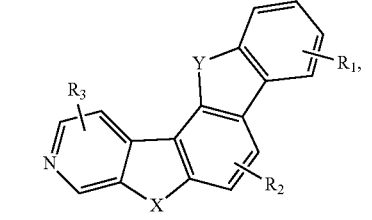
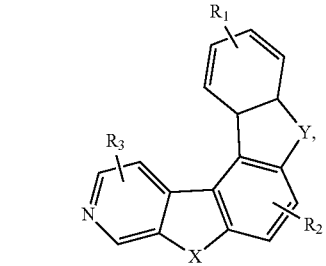
-continued
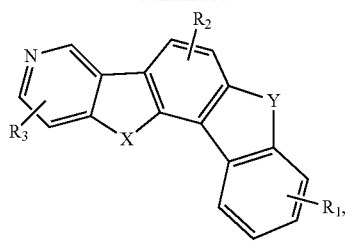
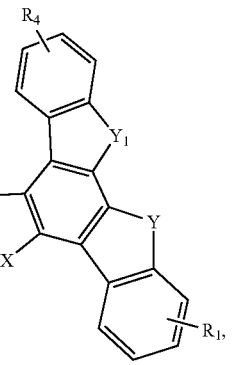
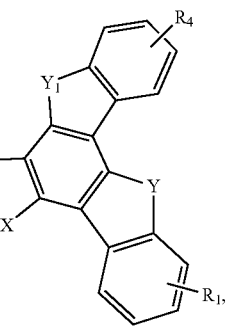
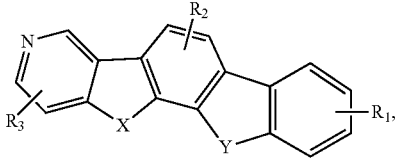
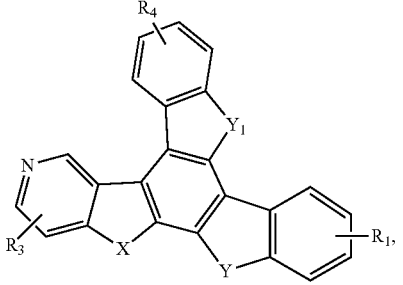
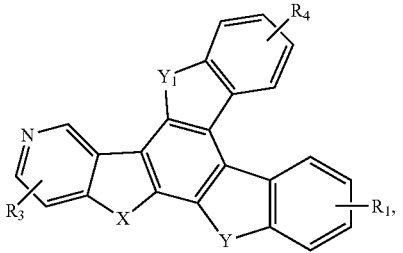

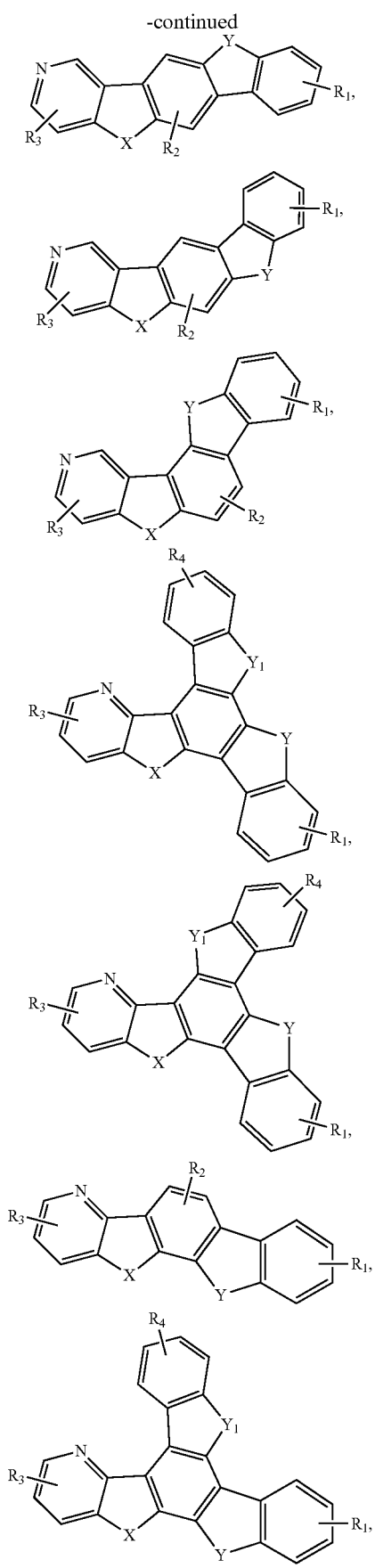
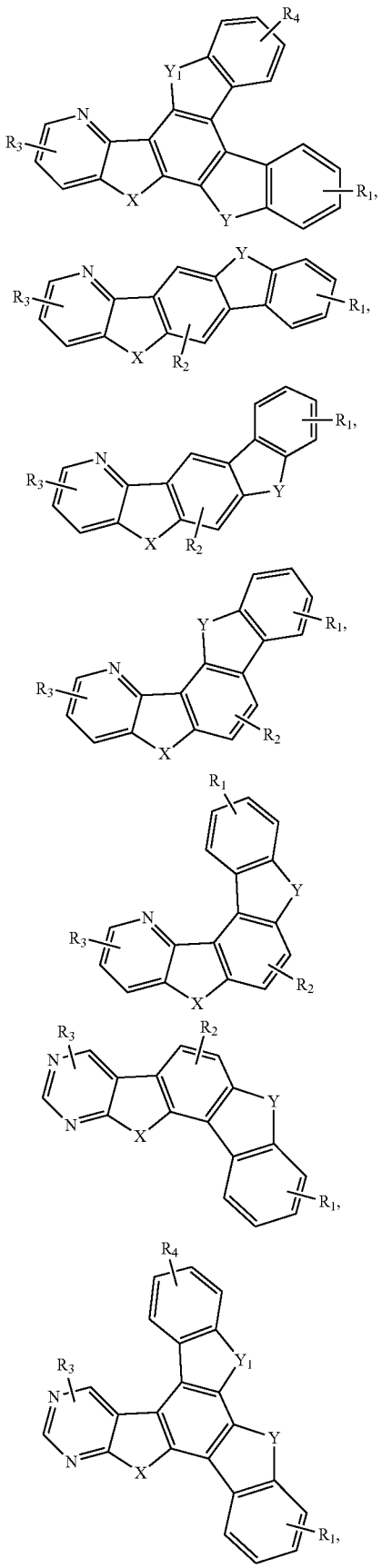

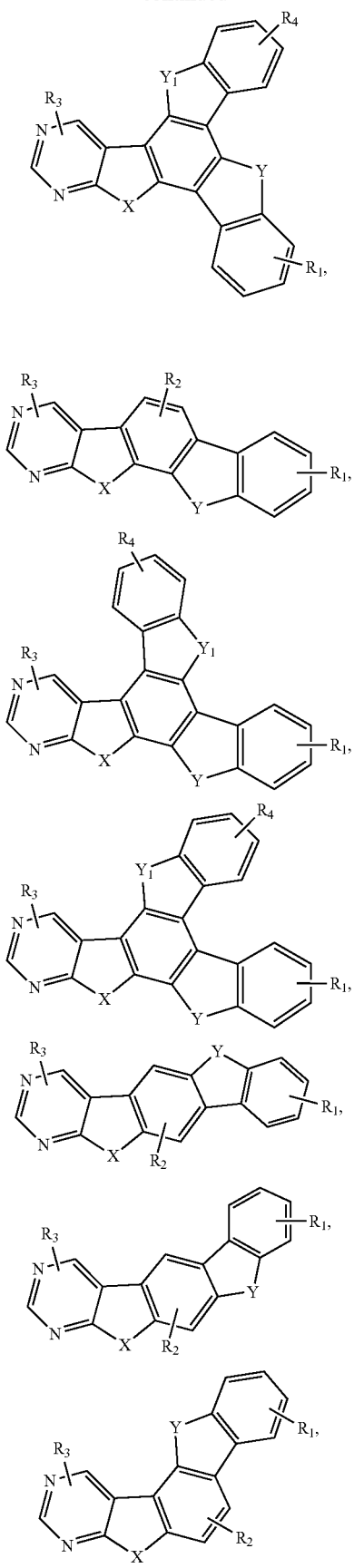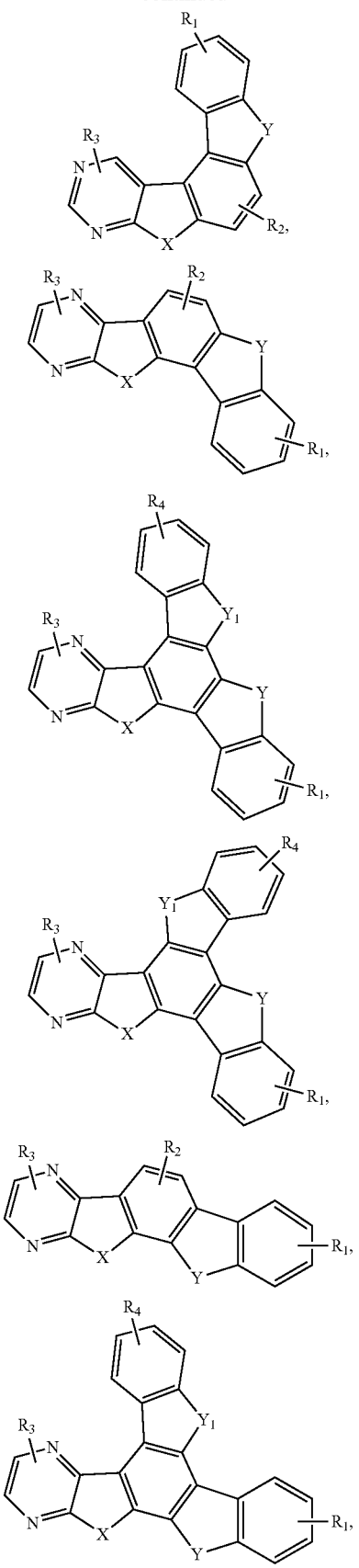

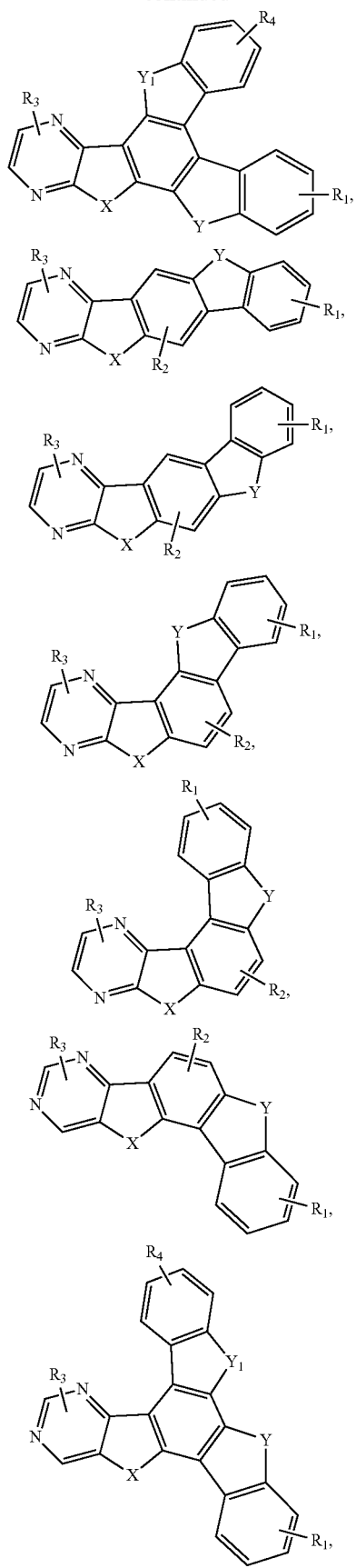
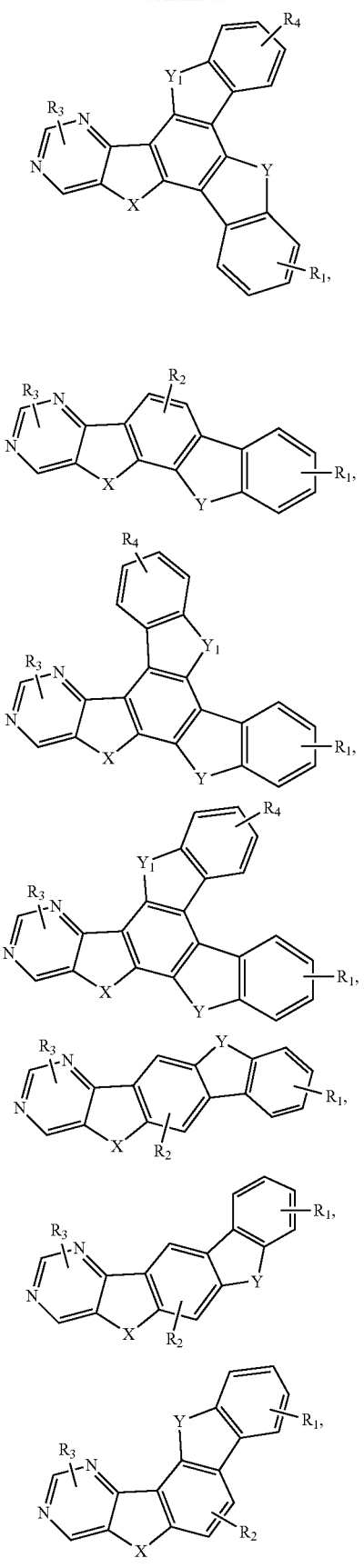

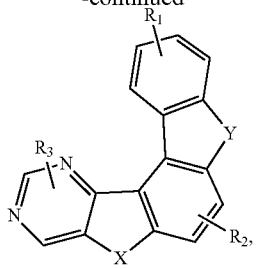

X, Y, and $Y_1$ are each independently selected from the group consisting of O, S, Se, NR', and CR"R'";

R', R", R''', $R_1$, $R_2$, $R_3$, and $R_4$ are each independently selected from the group consisting of hydrogen, deuterium, halogen, a substituted or unsubstituted alkyl group having 1 to 20 carbon atoms, a substituted or unsubstituted cycloalkyl group having 3 to 20 ring carbon atoms, a substituted or unsubstituted heteroalkyl group having 1 to 20 carbon atoms, a substituted or unsubstituted arylalkyl group having 7 to 30 carbon atoms, a substituted or unsubstituted alkoxy group having 1 to 20 carbon atoms, a substituted or unsubstituted aryloxy group having 6 to 30 carbon atoms, a substituted or unsubstituted alkenyl group having 2 to 20 carbon atoms, a substituted or unsubstituted aryl group having 6 to 30 carbon atoms, a substituted or unsubstituted heteroaryl group having 3 to 30 carbon atoms, a substituted or unsubstituted alkylsilyl group having 3 to 20 carbon atoms, a substituted or unsubstituted arylsilyl group having 6 to 20 carbon atoms, a substituted or unsubstituted amino group having 0 to 20 carbon atoms, an acyl group, a carbonyl group, a carboxylic acid group, an ester group, a nitrile group, an isonitrile group, a sulfanyl group, a sulfinyl group, a sulfonyl group, a phosphino group, and combinations thereof;

Any adjacent substitution can be optionally joined to form a ring or fused structure;

In this embodiment, when n is 2, two Y corresponding to the structure of Formula 1 are respectively represented by Y and $Y_1$, and two $R_1$ corresponding to the structure of Formula 1 are respectively represented by $R_1$ and $R_4$.

In one preferred embodiment, wherein R' is selected from the group consisting of:

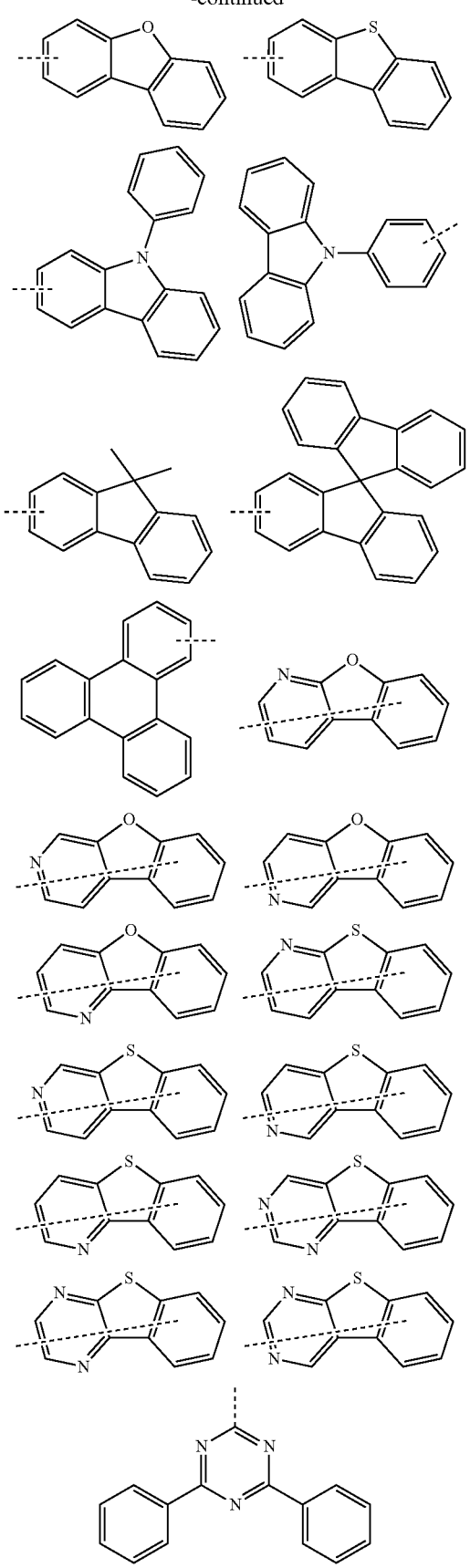

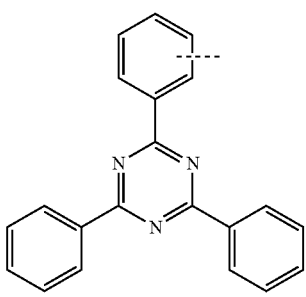
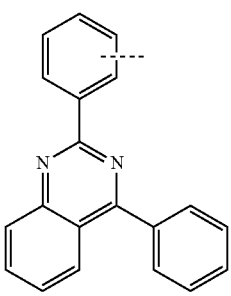
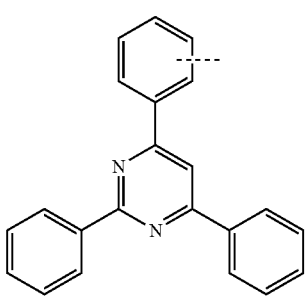
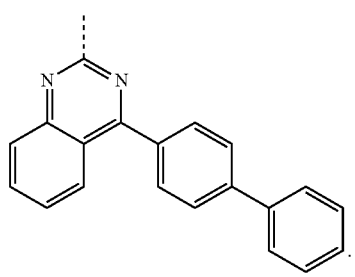
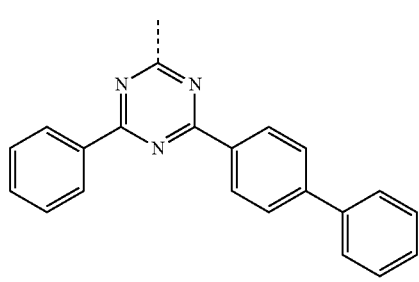
In one preferred embodiment, wherein the compound is selected from the group consisting of:
Compound 1
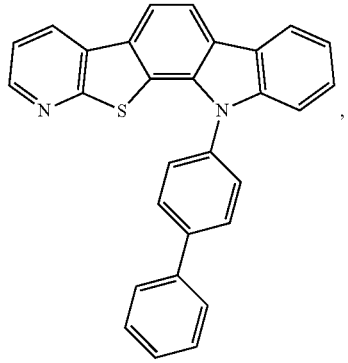
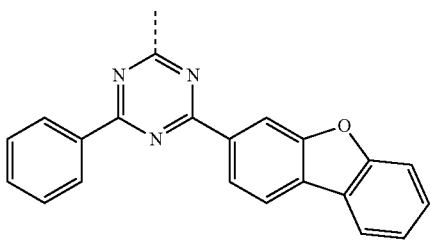
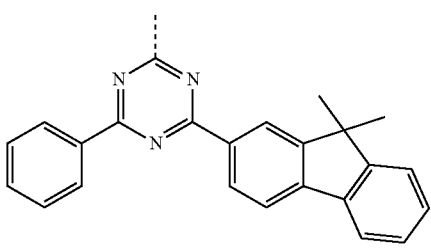
Compound 2
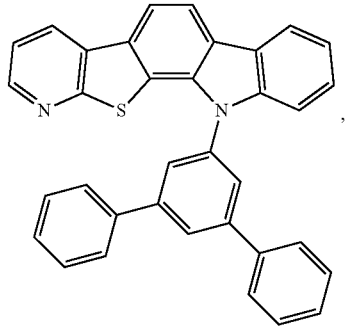

-continued
Compound 3
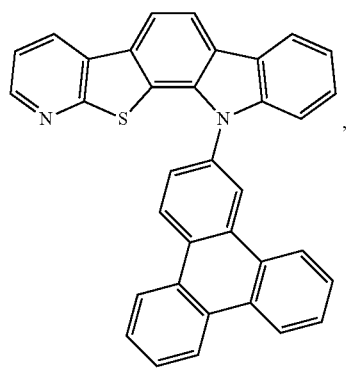
Compound 4
Compound 5
Compound 6
Compound 7
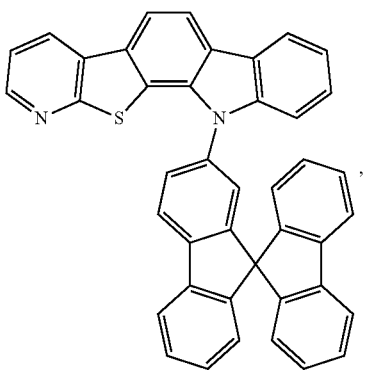
Compound 8
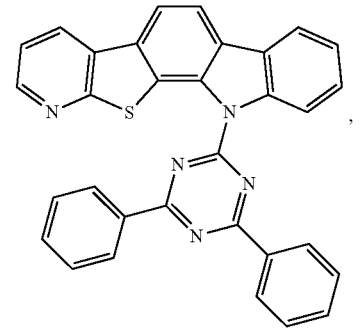
Compound 9
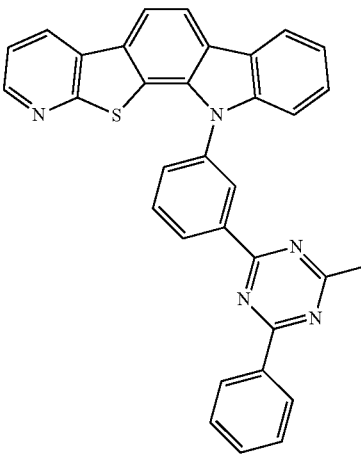
Compound 10
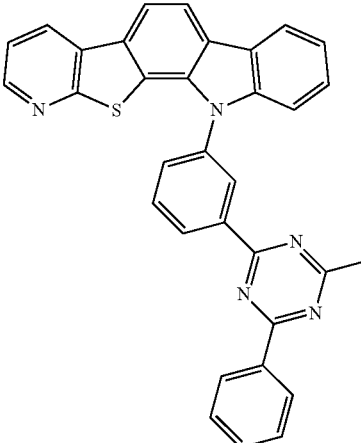

Compound 11
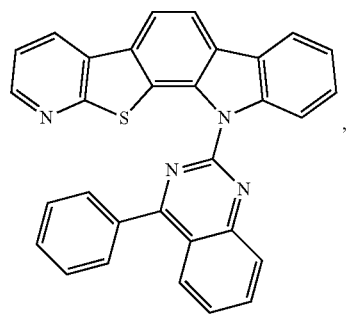
Compound 12
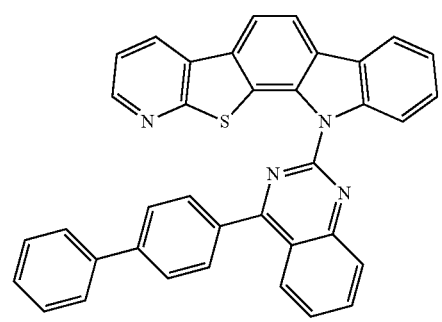
Compound 13
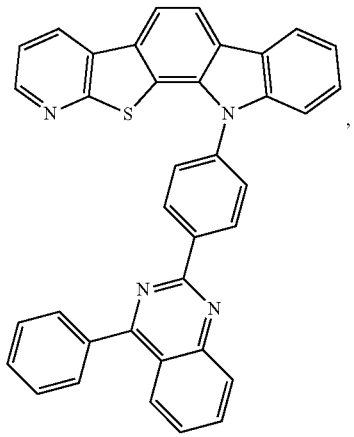
Compound 14
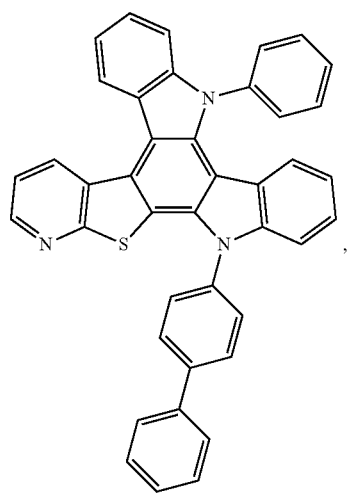
Compound 15
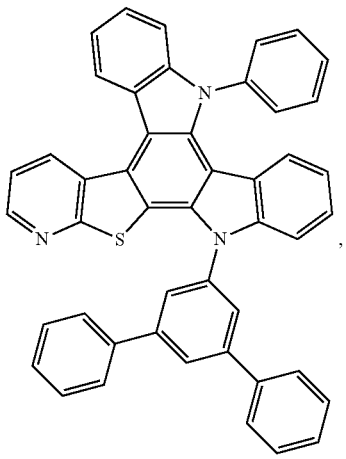
Compound 16
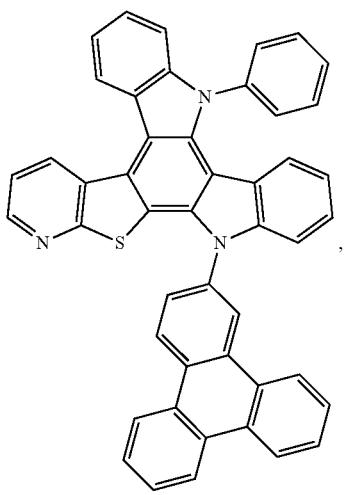
Compound 17
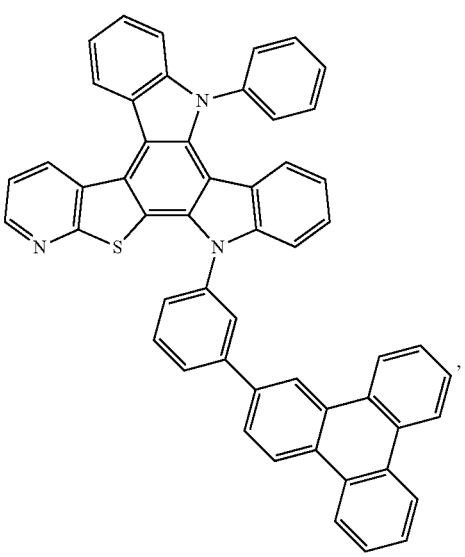

Compound 18
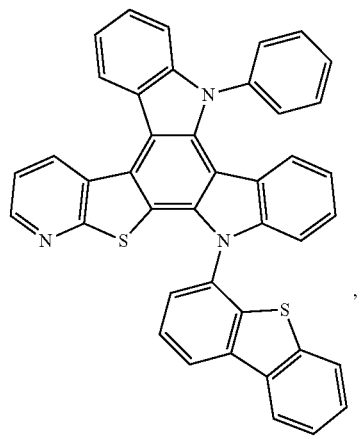
Compound 19
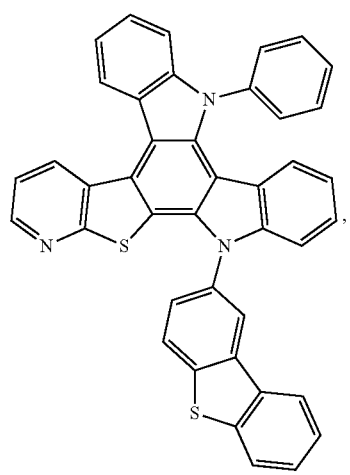
Compound 20
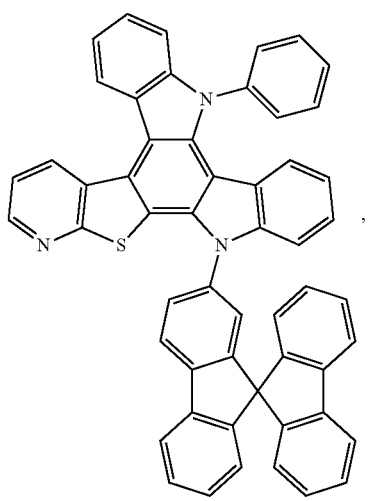
Compound 21
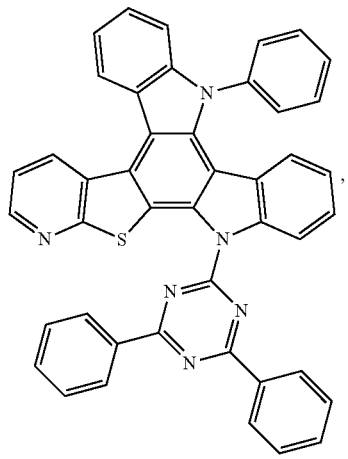
Compound 22
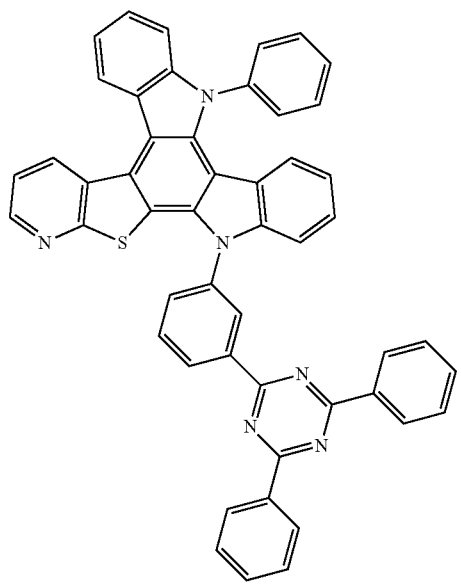
Compound 23
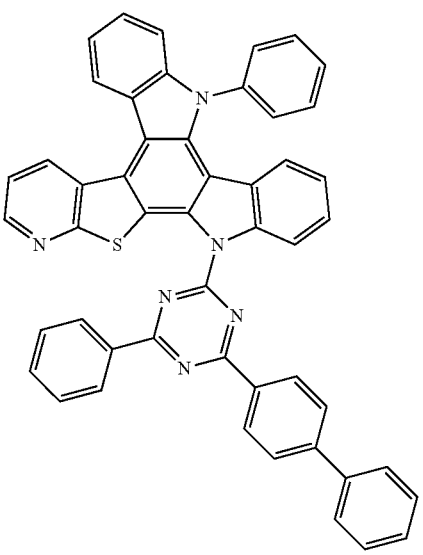

-continued
Compound 24
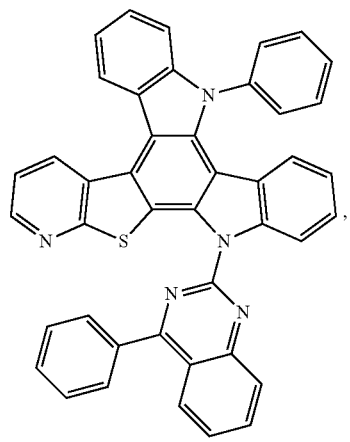
Compound 25
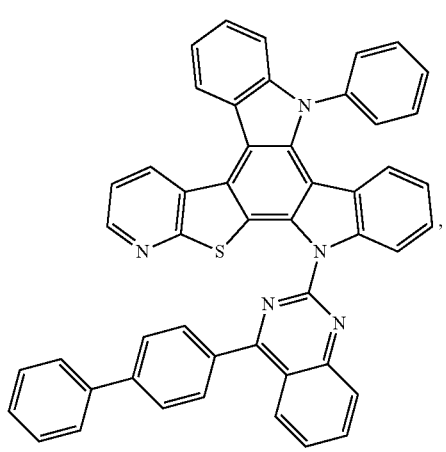
Compound 26
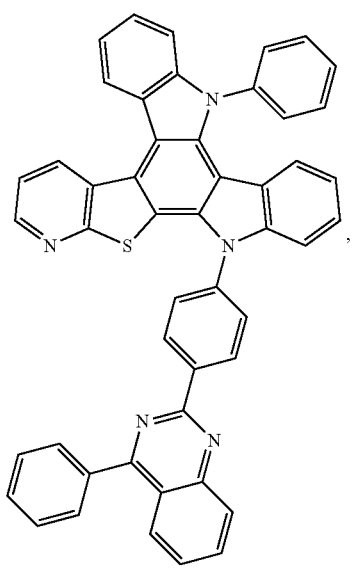
Compound 27
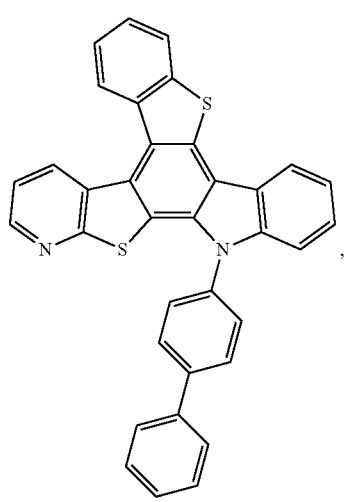
Compound 28
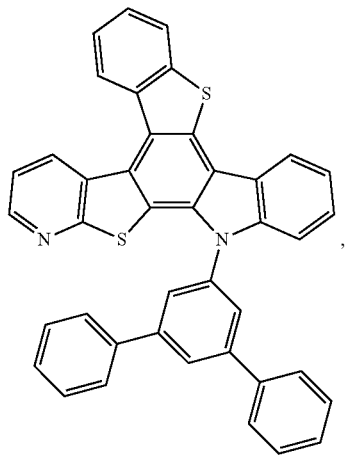
Compound 29
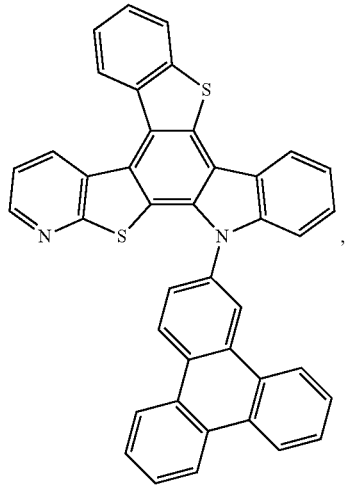

Compound 30
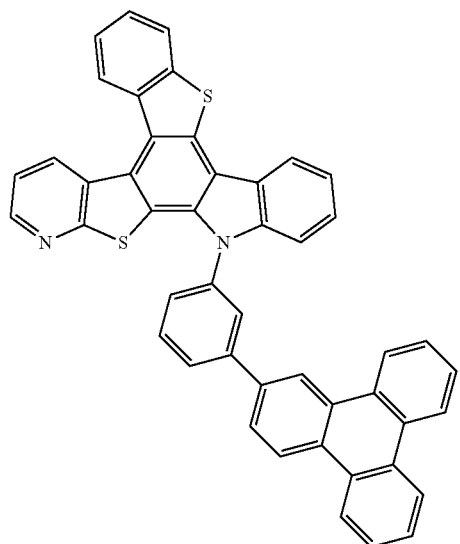
Compound 31
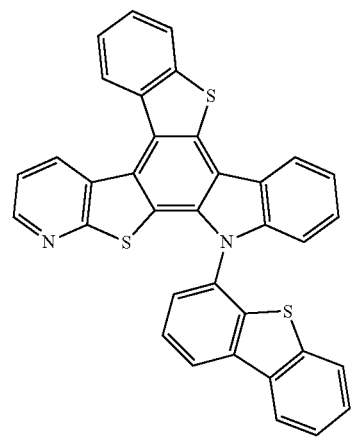
Compound 32
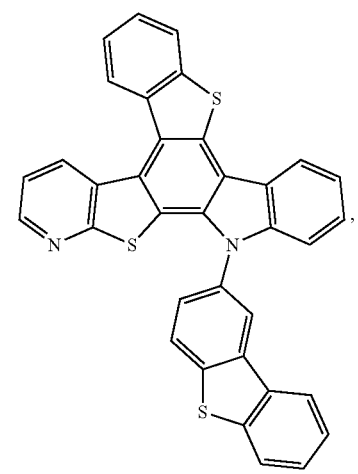
Compound 33
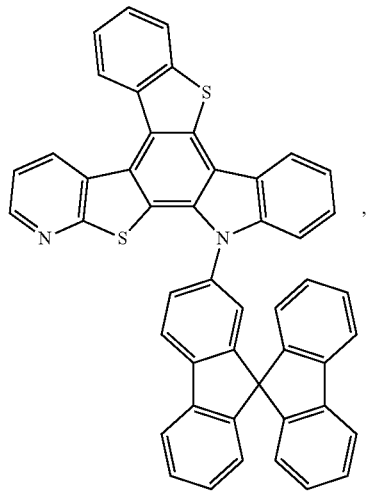
Compound 34
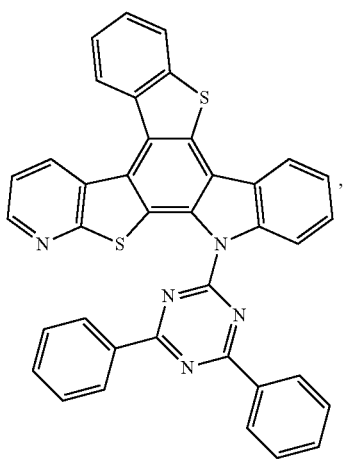
Compound 35
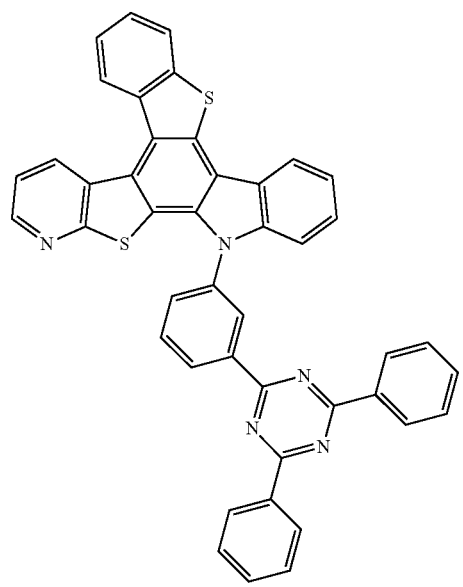

Compound 36
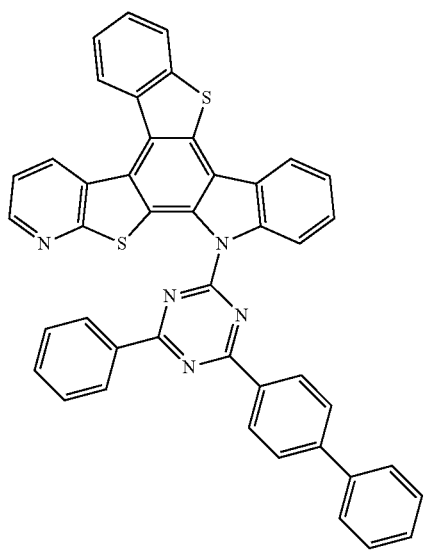
Compound 37
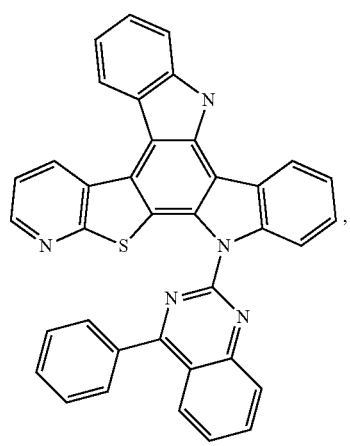
Compound 38
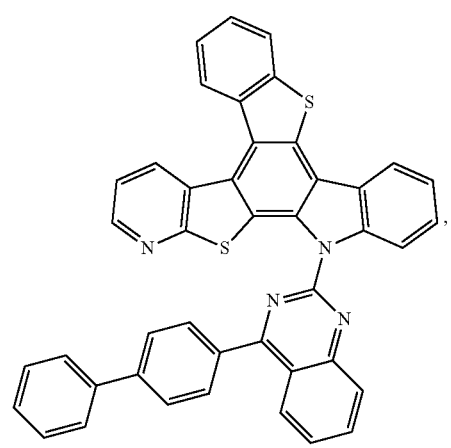
Compound 39
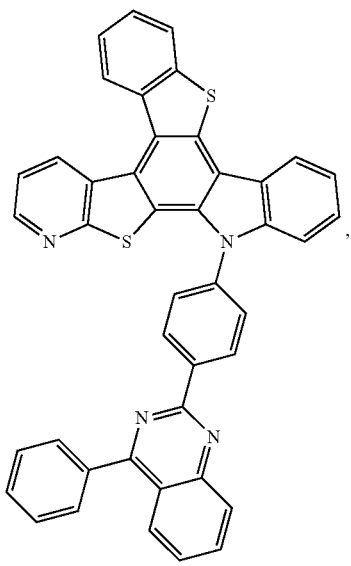
Compound 40
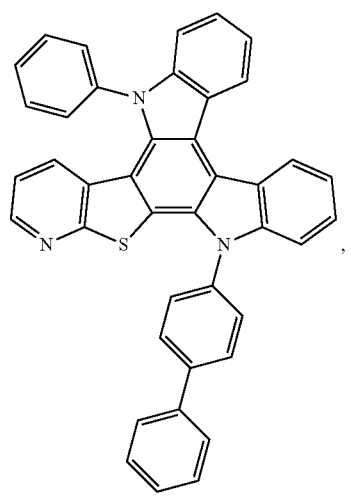
Compound 41
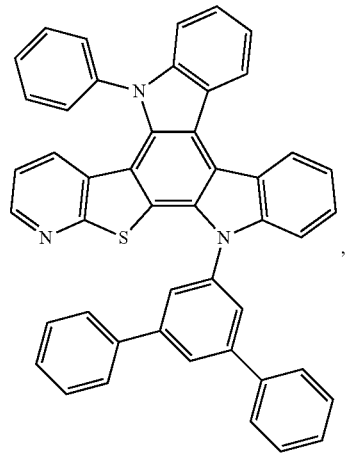

-continued
Compound 42
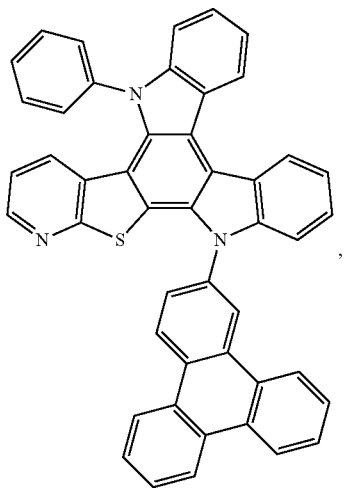
Compound 45
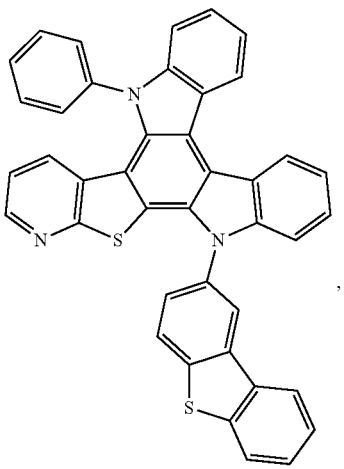
Compound 43
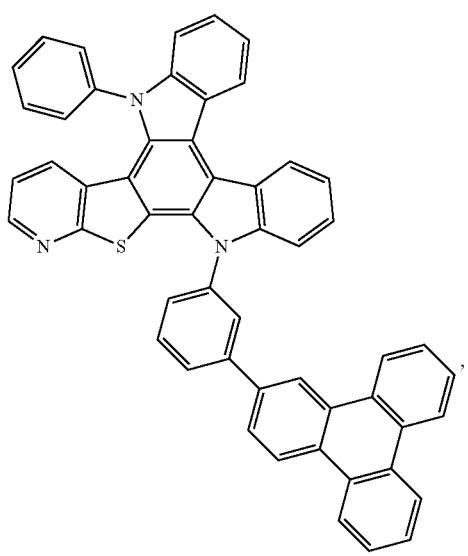
Compound 46
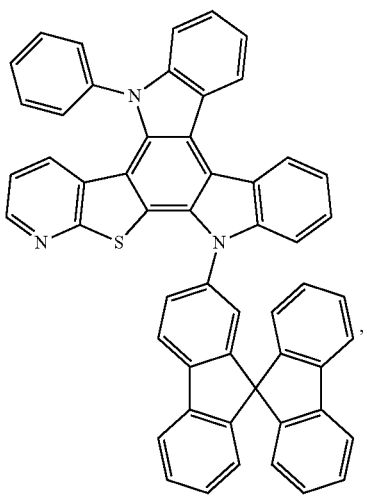
Compound 44
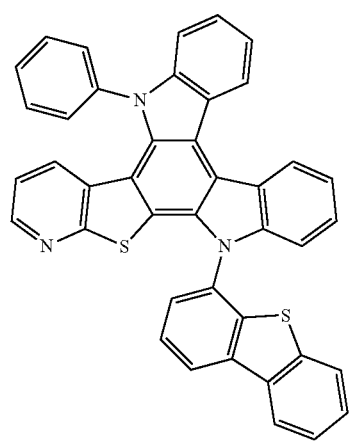
Compound 47
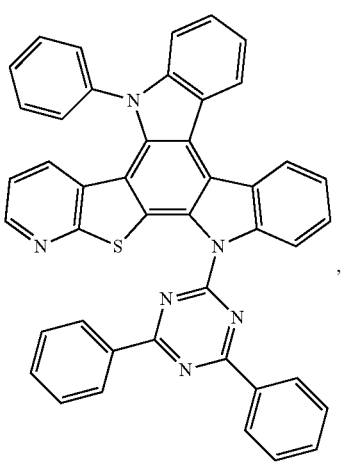

Compound 48
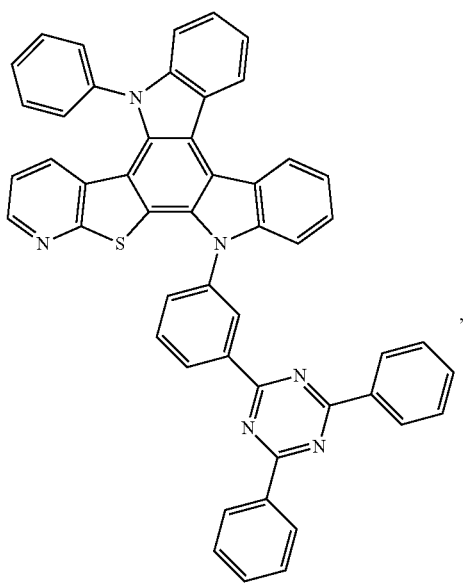
Compound 49
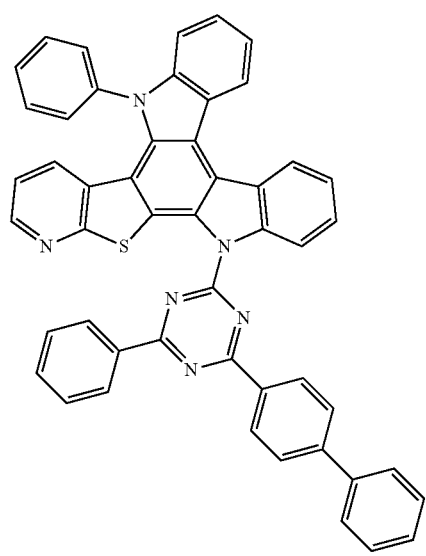
Compound 50
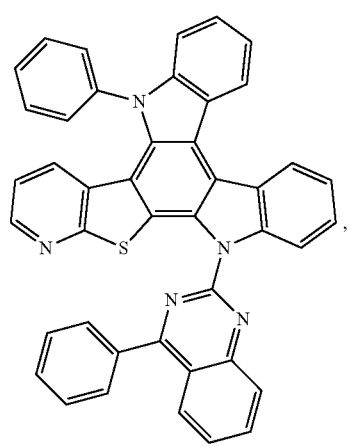
Compound 51
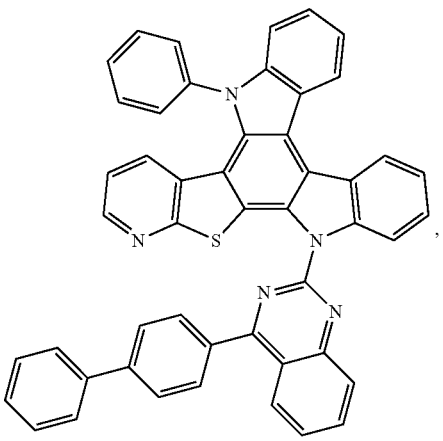
Compound 52
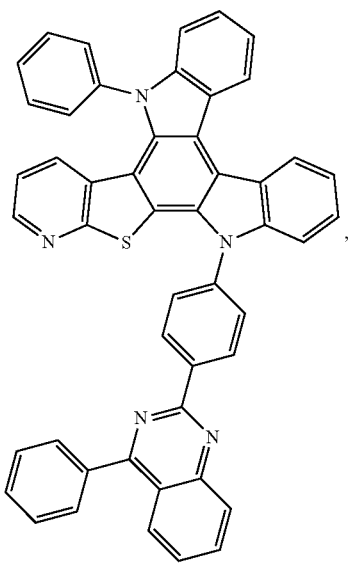
Compound 53
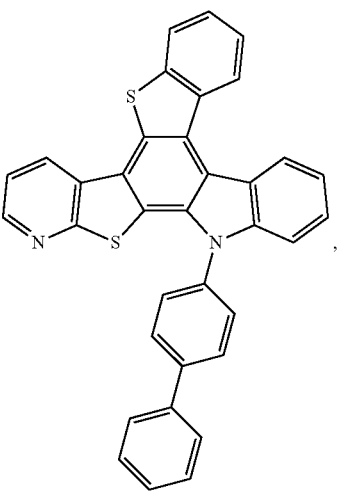

-continued
Compound 54
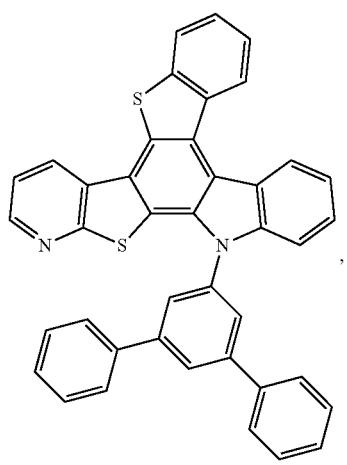
Compound 55
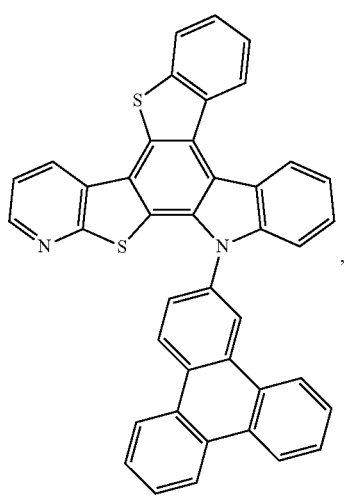
Compound 56
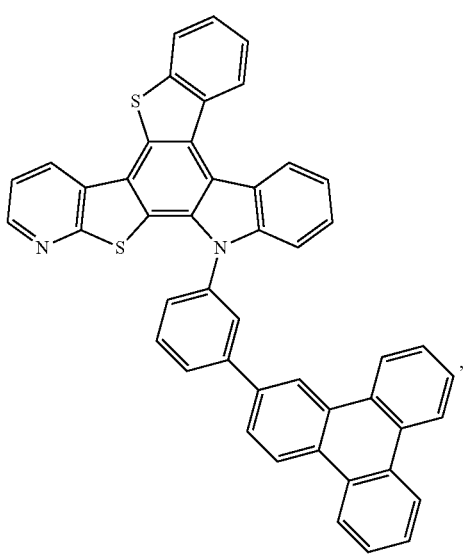
-continued
Compound 57
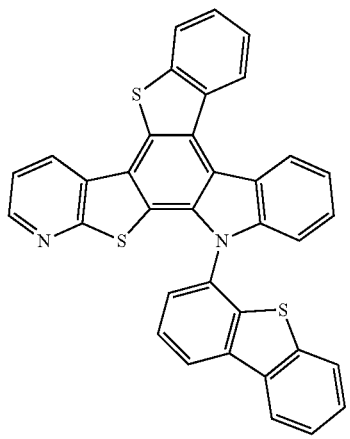
Compound 58
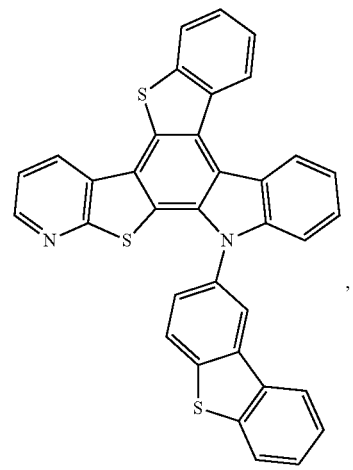
Compound 59
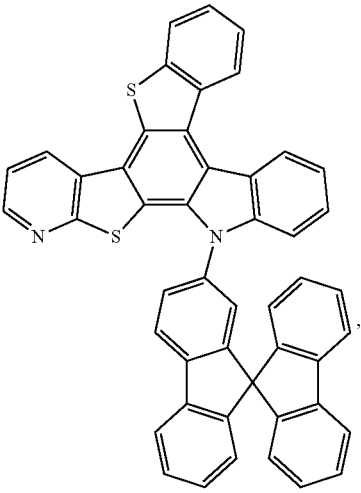

Compound 60
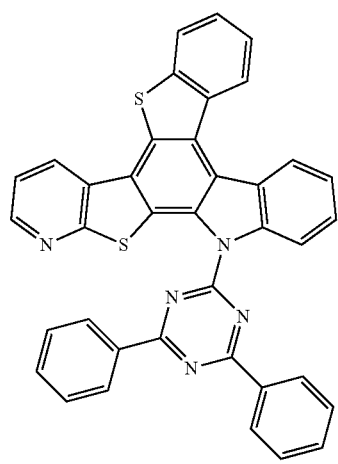
Compound 61
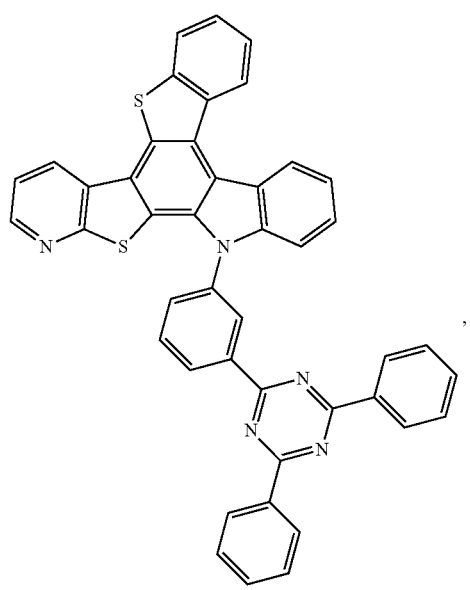
Compound 62
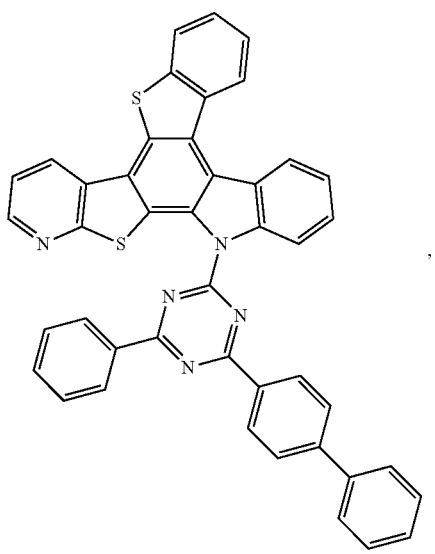
Compound 63
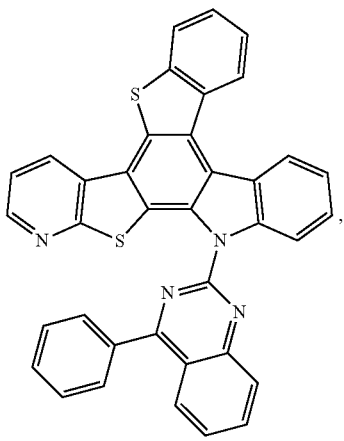
Compound 64
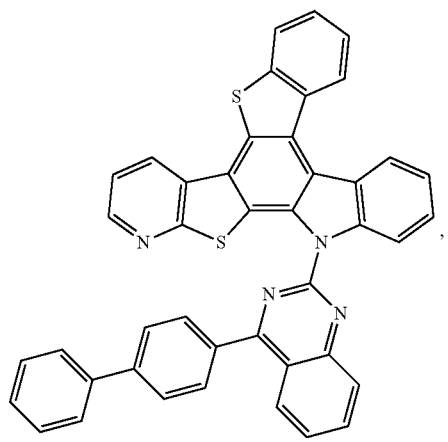
Compound 65
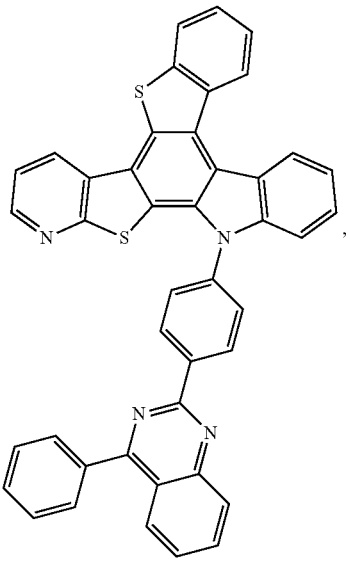

-continued
Compound 66
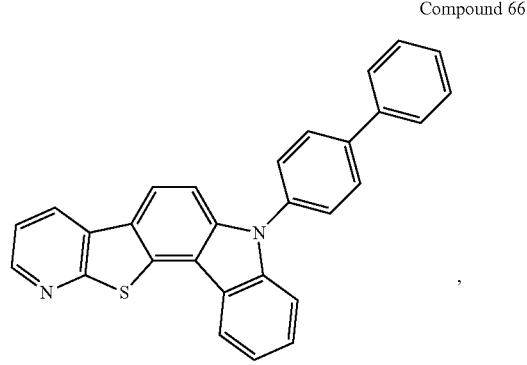
Compound 67
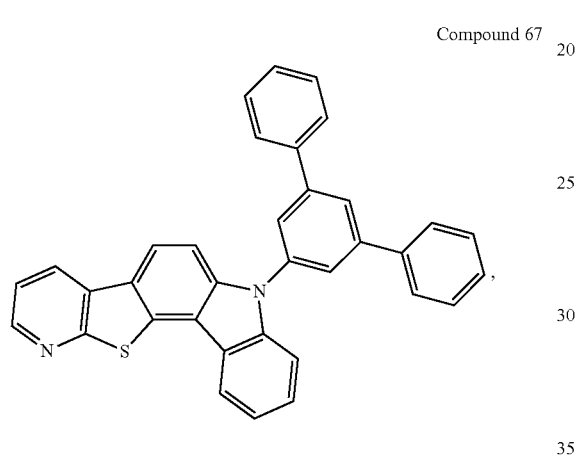
Compound 68
Compound 69
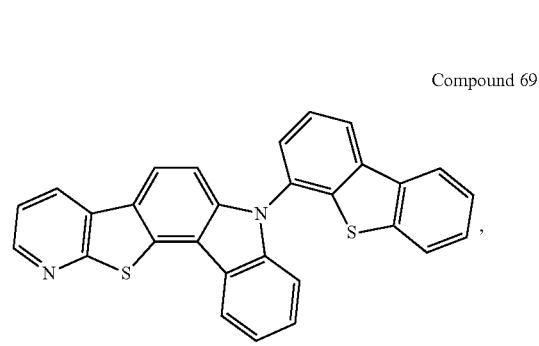
-continued
Compound 70
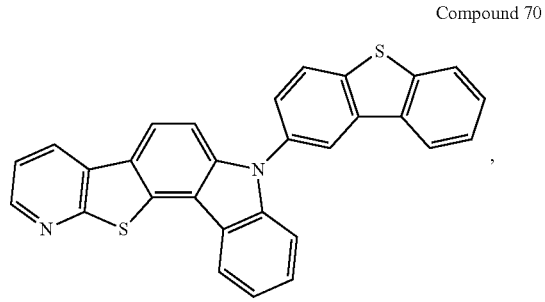
Compound 71
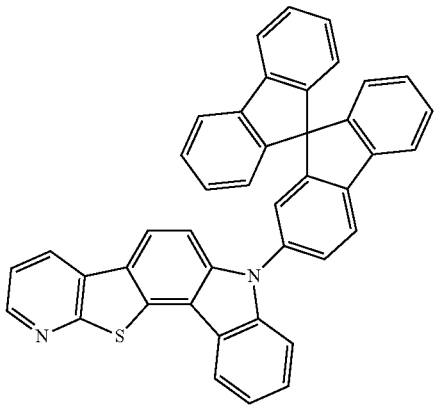
Compound 72
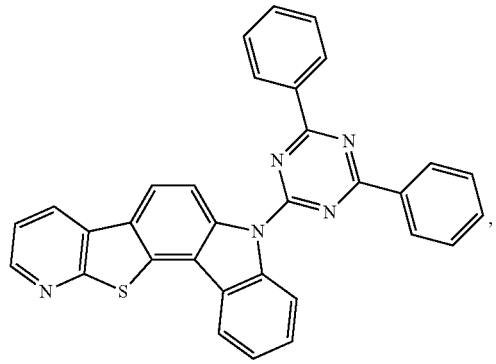
Compound 73
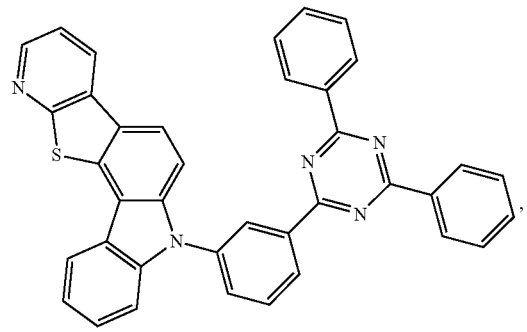

Compound 74
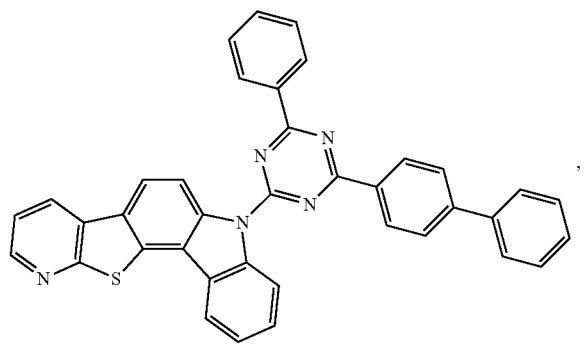
Compound 75
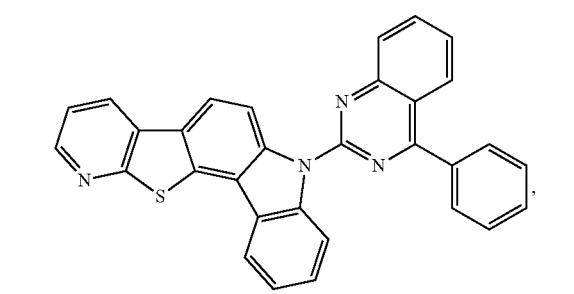
Compound 76
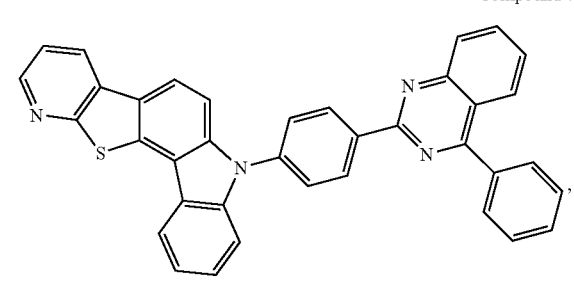
Compound 77
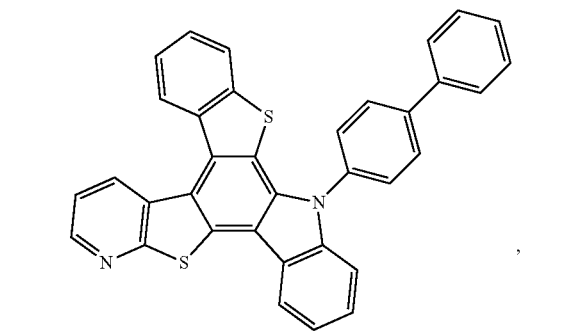
Compound 78
Compound 79
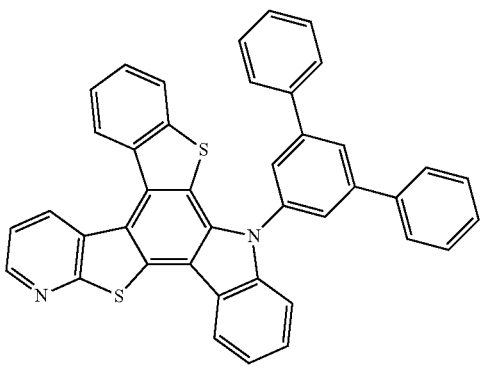
Compound 80
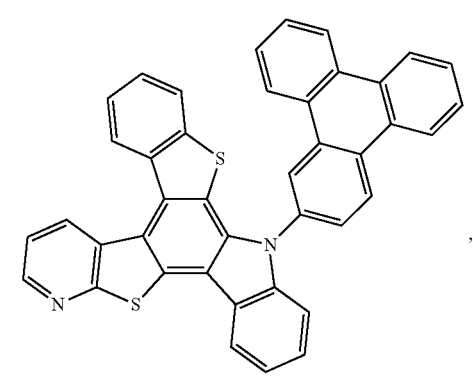
Compound 81
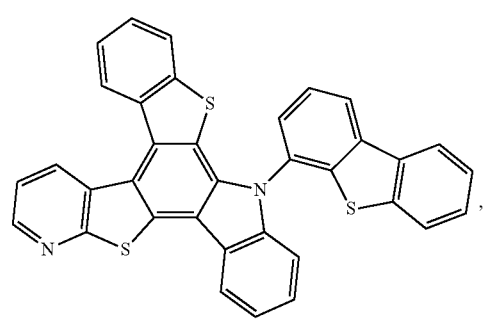
Compound 82
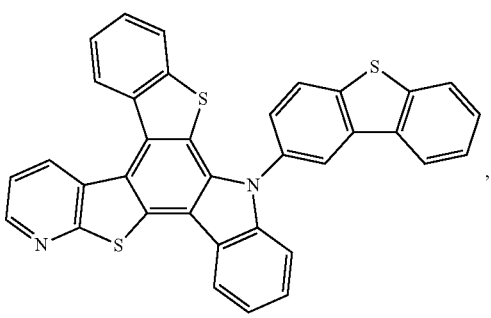

Compound 83
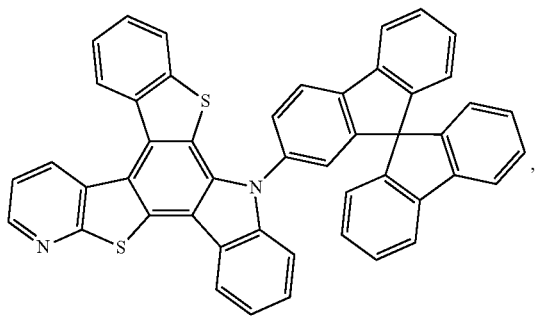
Compound 87
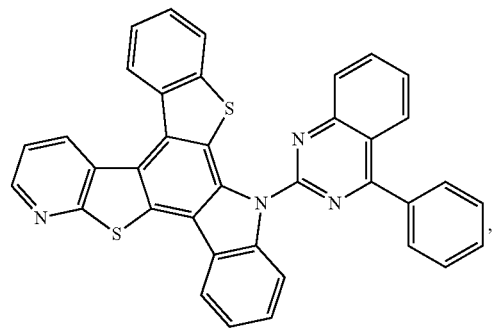
Compound 84
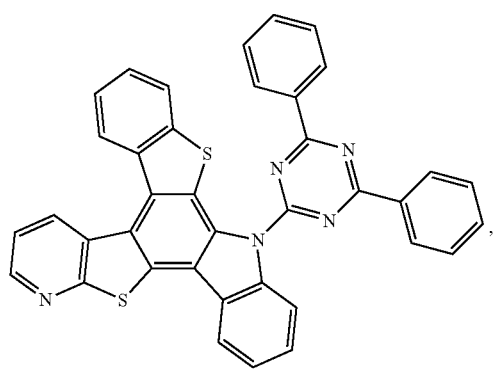
Compound 88
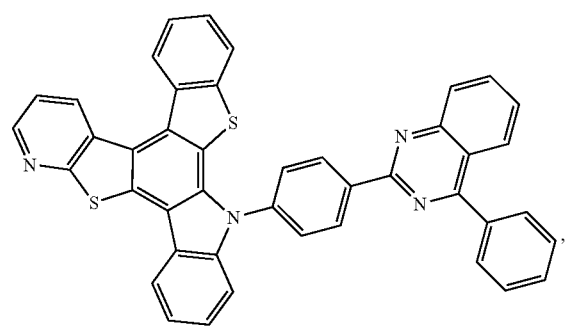
Compound 85
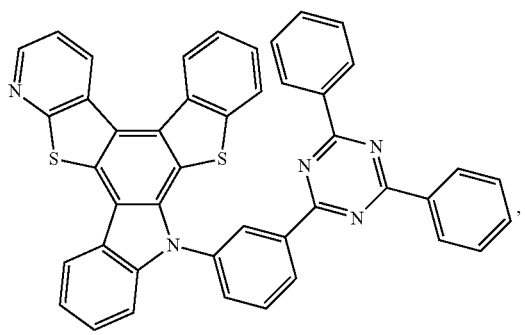
Compound 89
Compound 86
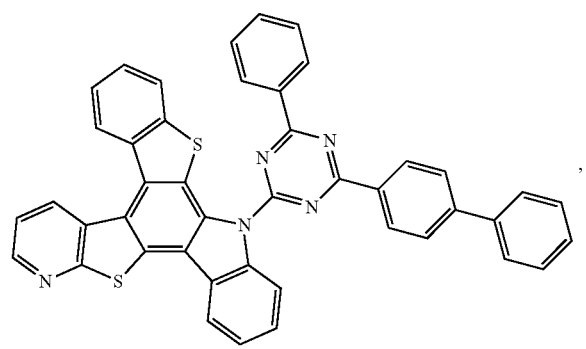
Compound 90
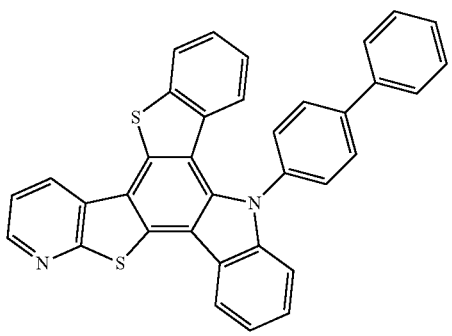

-continued
Compound 91
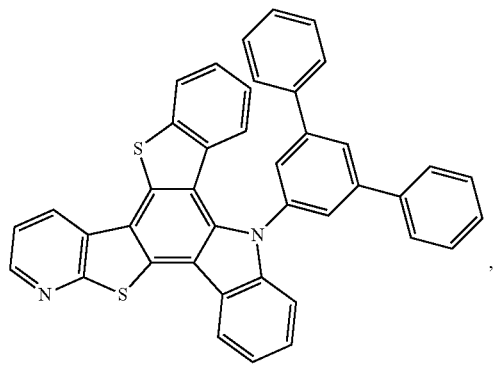
Compound 92
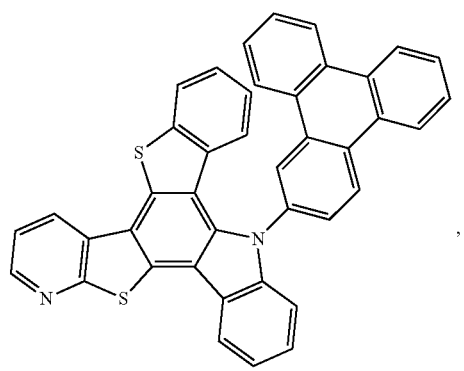
Compound 93
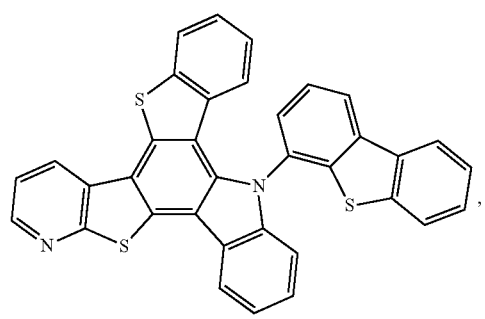
Compound 94
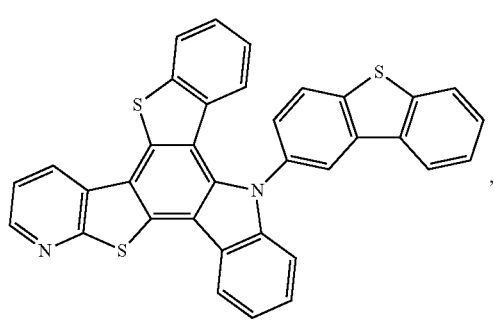
-continued
Compound 95
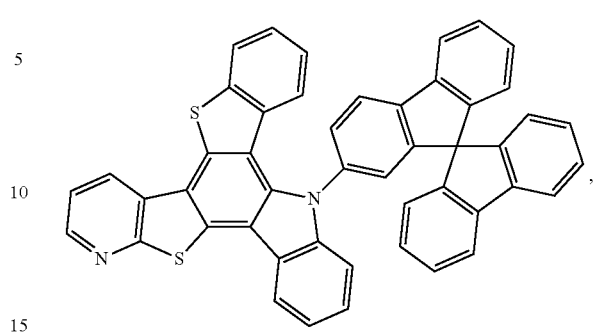
Compound 96
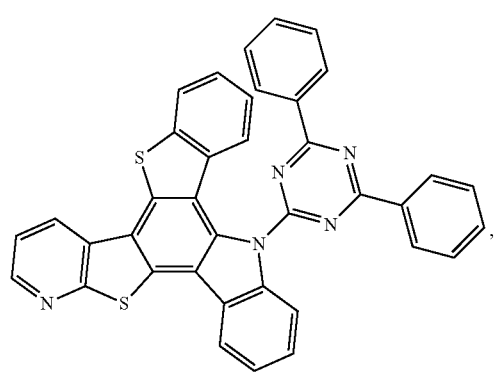
Compound 97
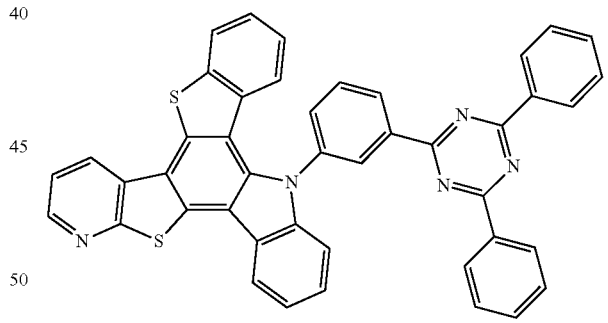
Compound 98
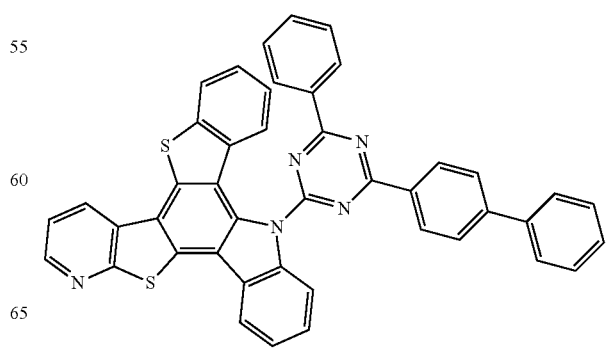

-continued
Compound 99
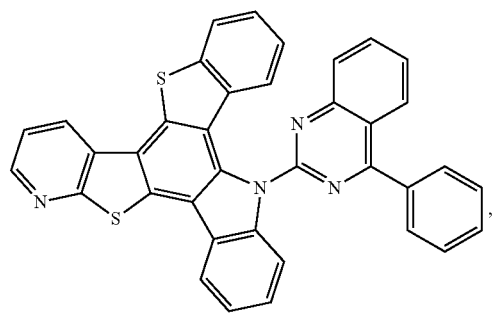
Compound 100
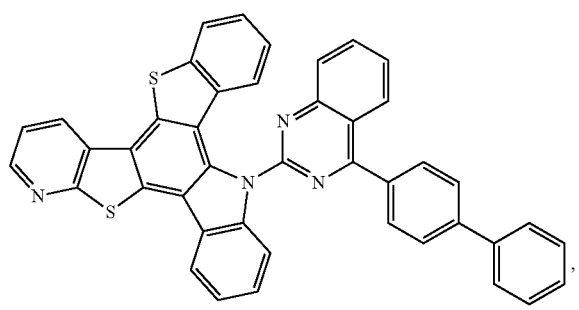
Compound 101
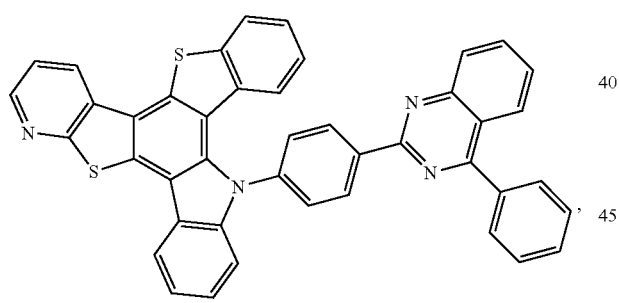
Compound 102
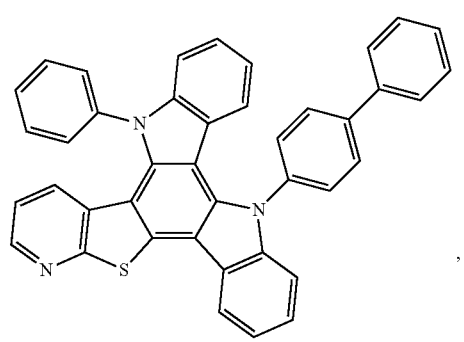
-continued
Compound 103
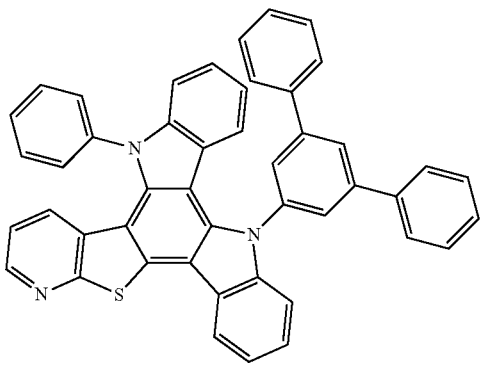
Compound 104
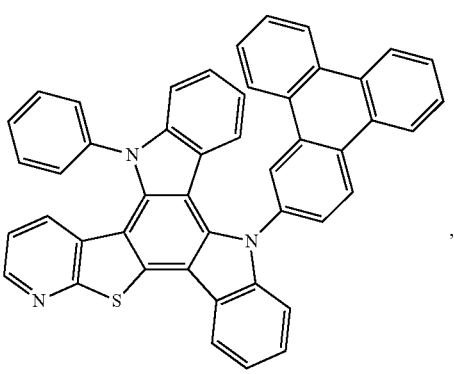
Compound 105
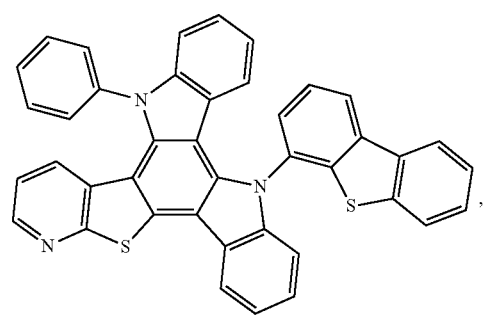
Compound 106
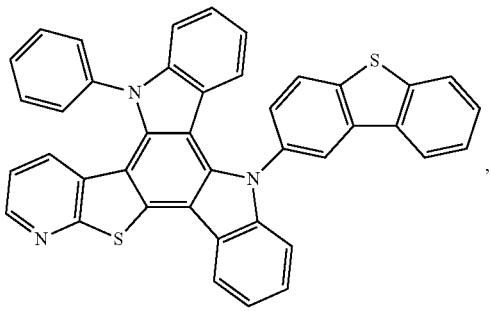

Compound 107
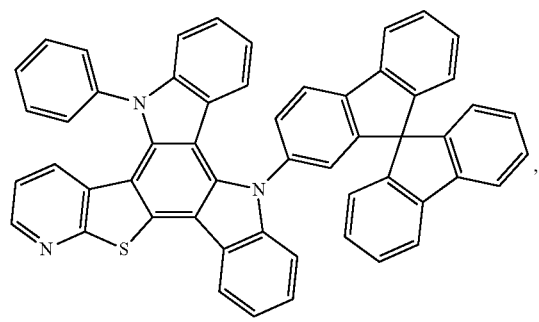
Compound 111
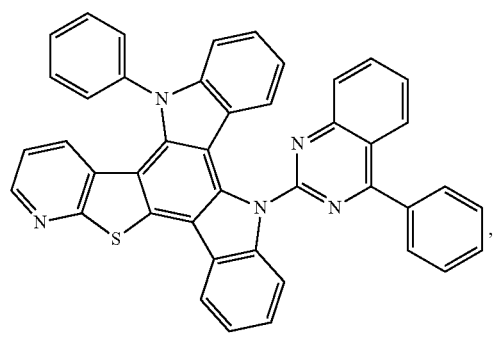
Compound 108
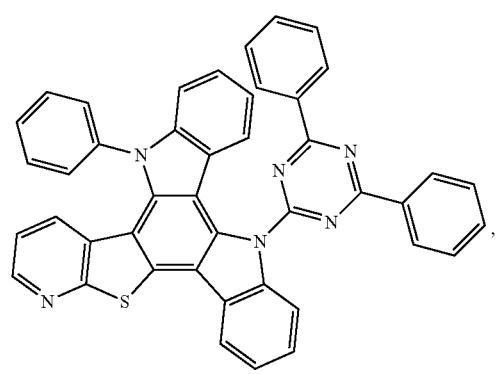
Compound 112
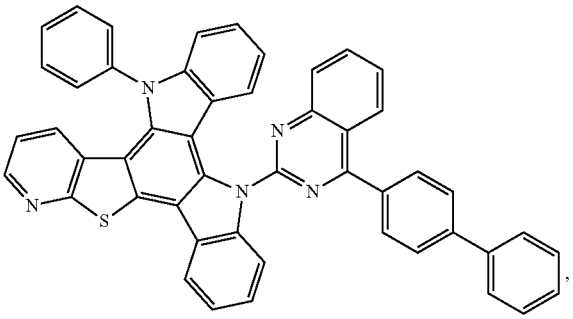
Compound 109
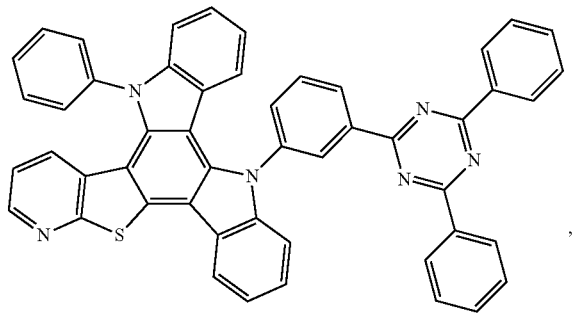
Compound 113
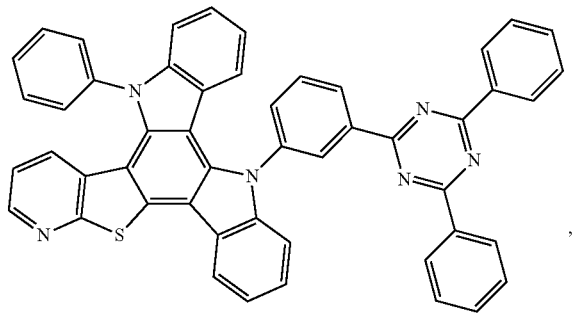
Compound 110
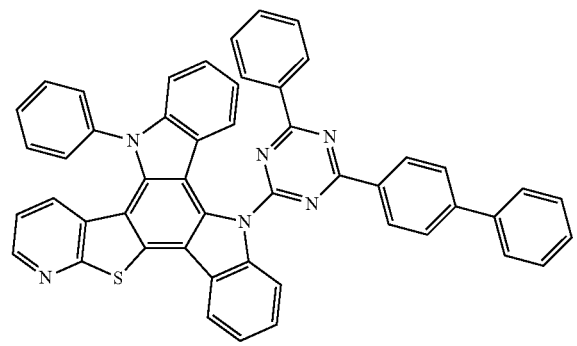
Compound 114
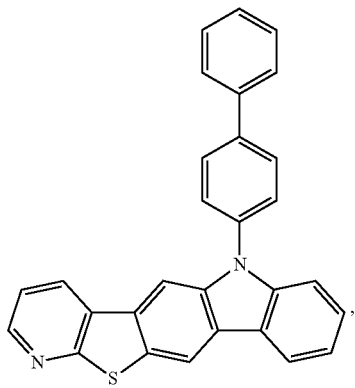

Compound 115
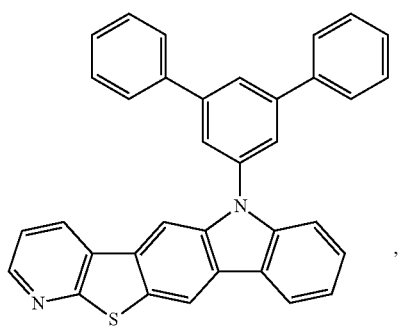
Compound 116
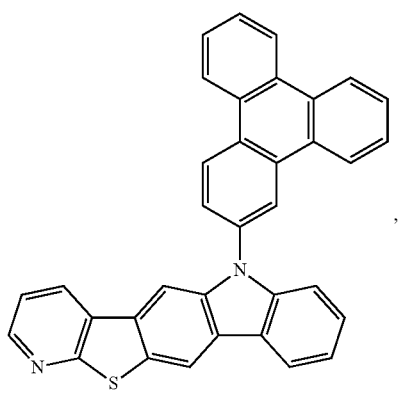
Compound 117
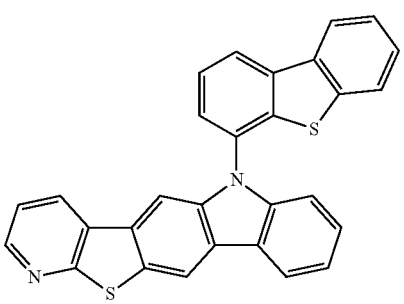
Compound 118
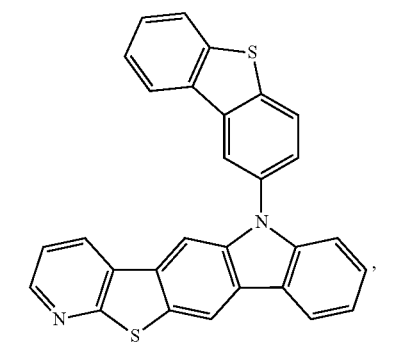
Compound 119
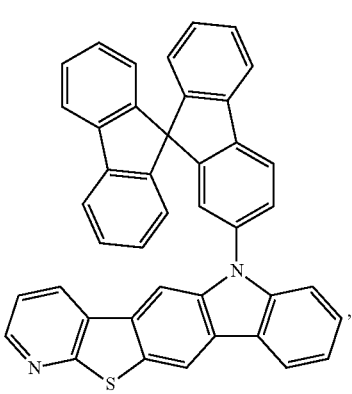
Compound 120
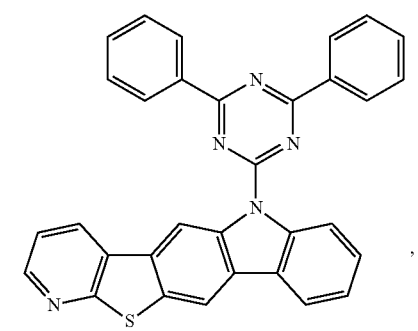
Compound 121
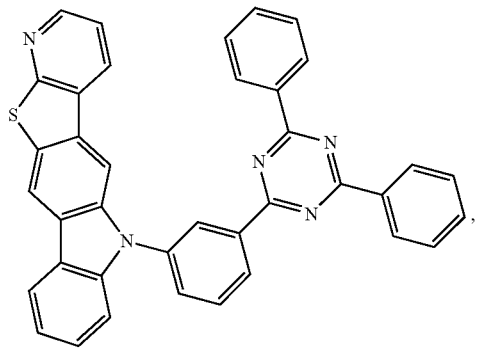
Compound 122
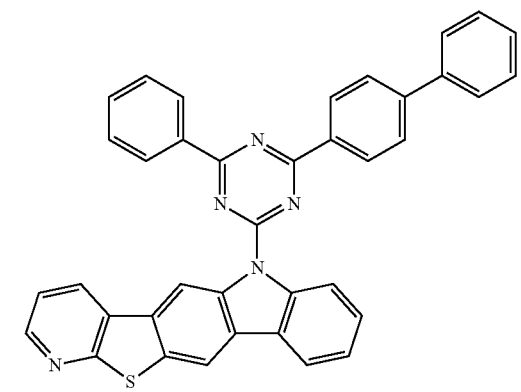

Compound 123
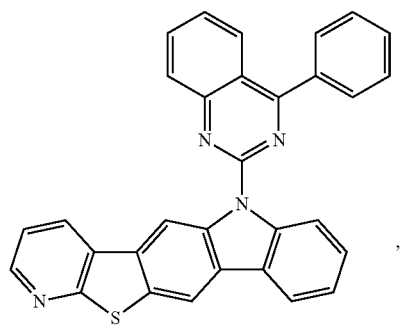
Compound 124
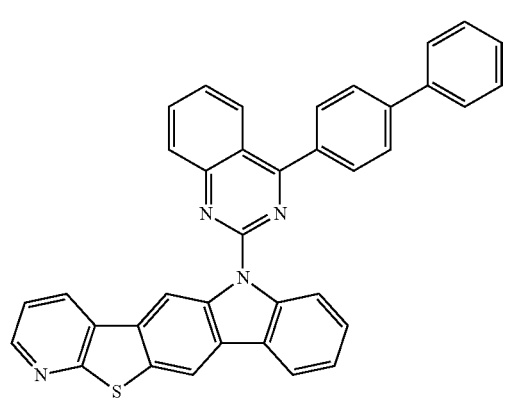
Compound 125
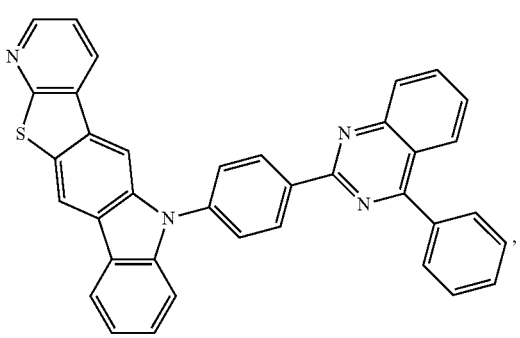
Compound 126
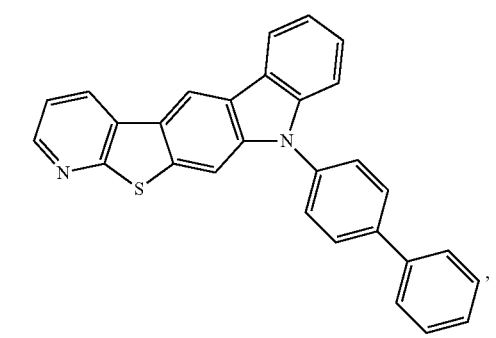
Compound 127
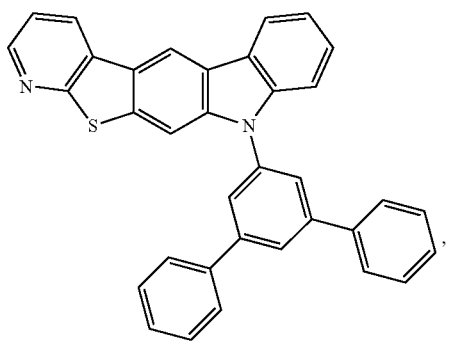
Compound 128
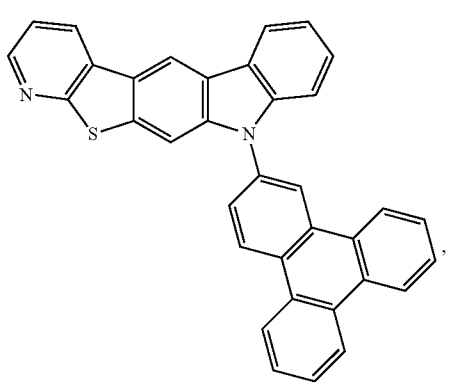
Compound 129
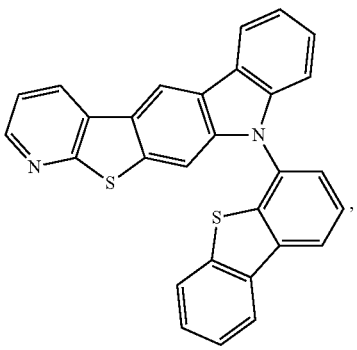
Compound 130
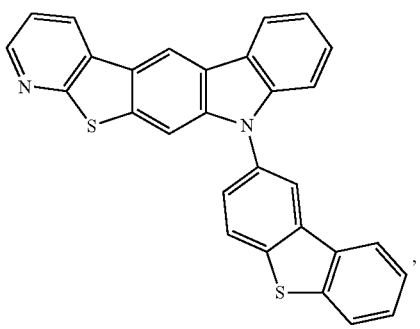

Compound 131
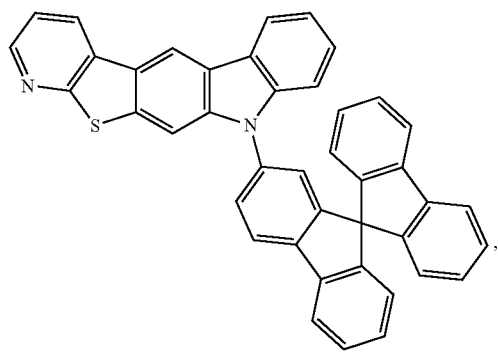
Compound 132
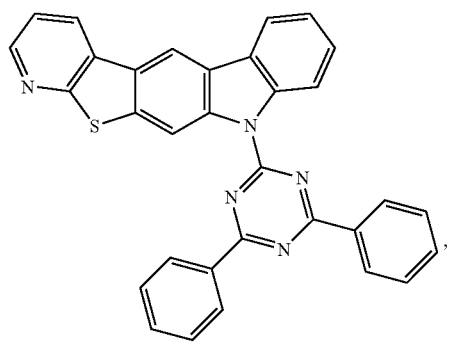
Compound 133
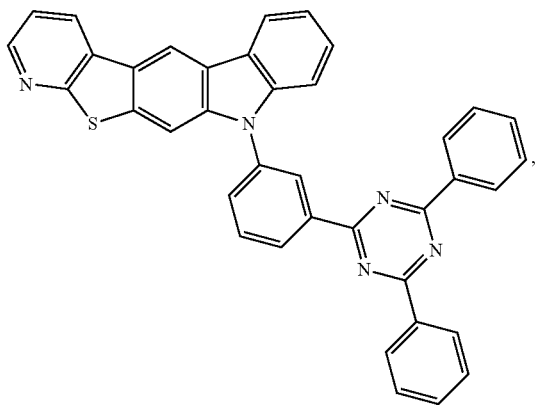
Compound 134
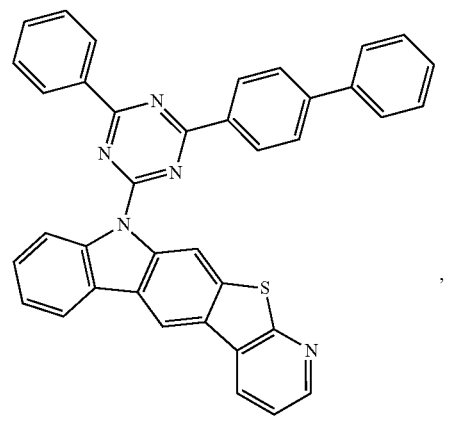
Compound 135
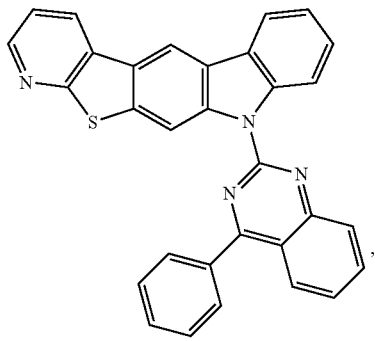
Compound 136
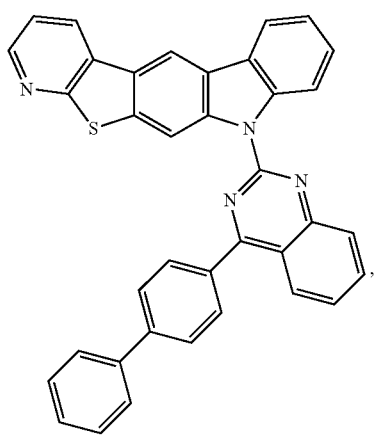
Compound 137
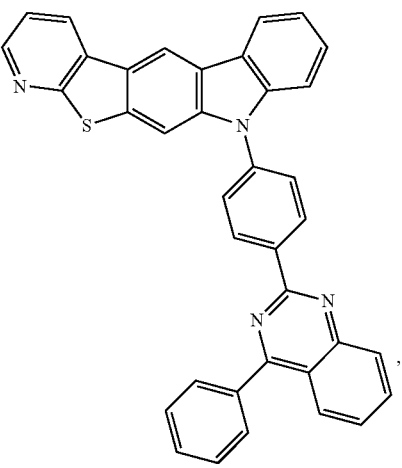
Compound 138
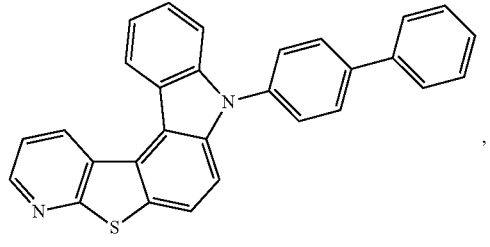

Compound 139
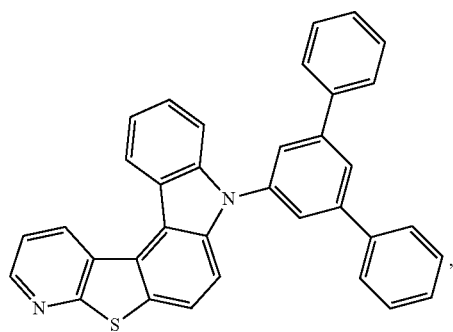
Compound 140
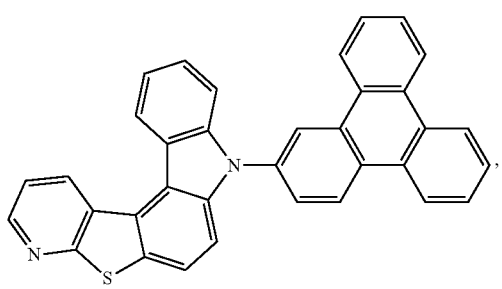
Compound 141
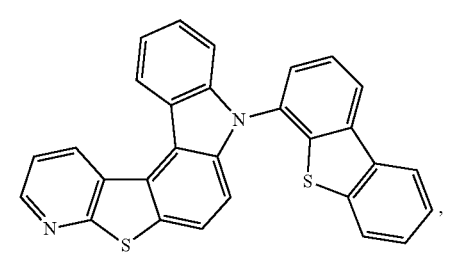
Compound 142
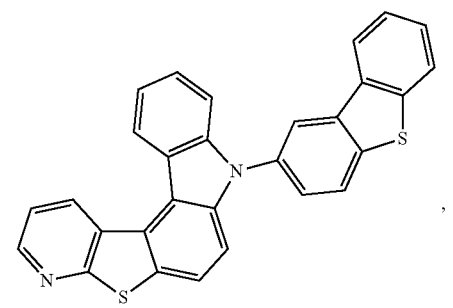
Compound 143
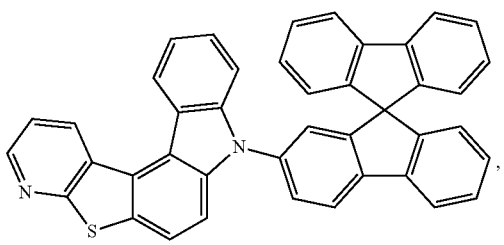
Compound 144
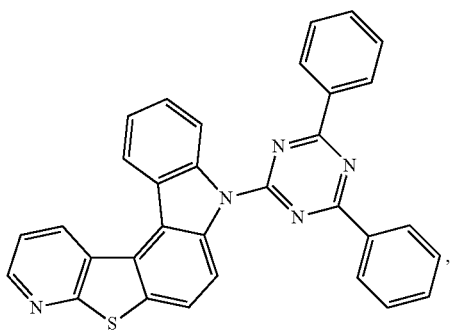
Compound 145
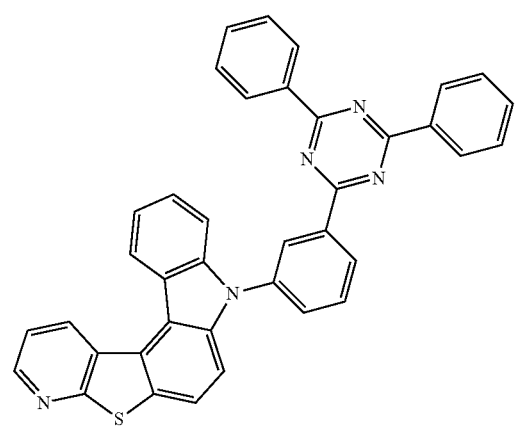
Compound 146
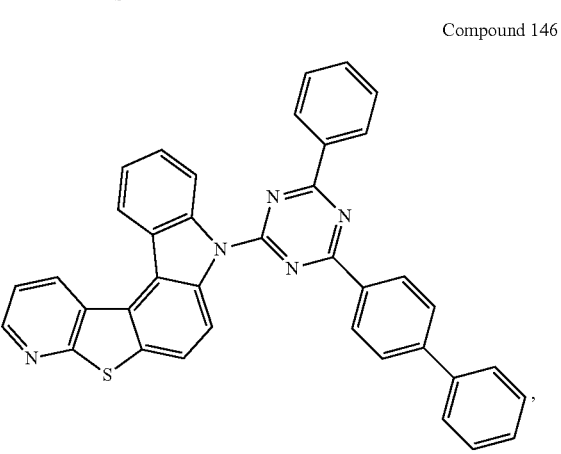
Compound 147
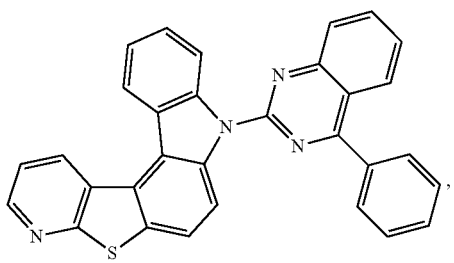

Compound 148
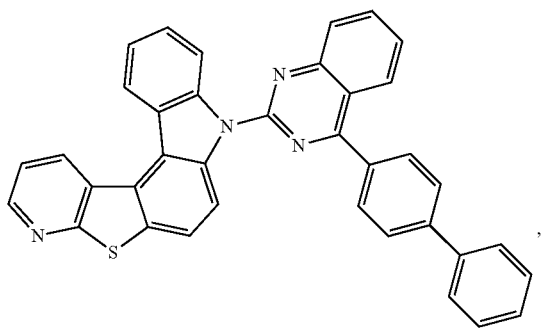
Compound 149
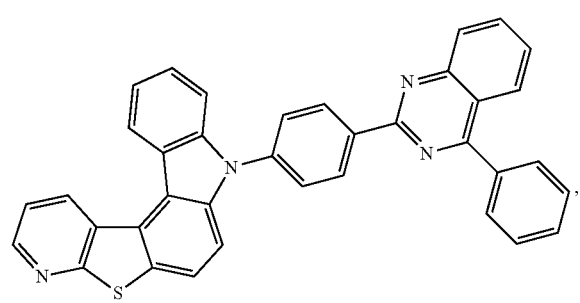
Compound 150
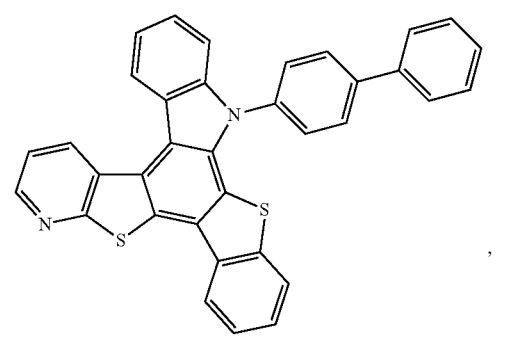
Compound 151
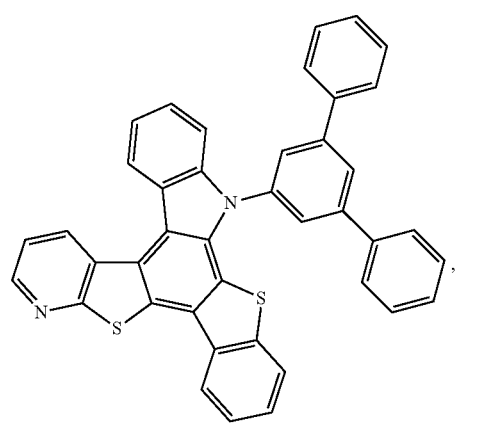
Compound 152
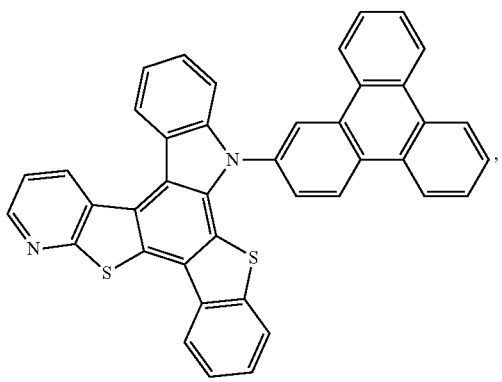
Compound 153
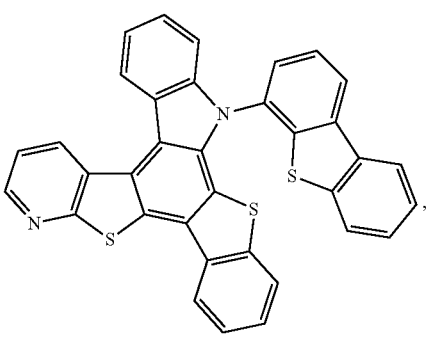
Compound 154
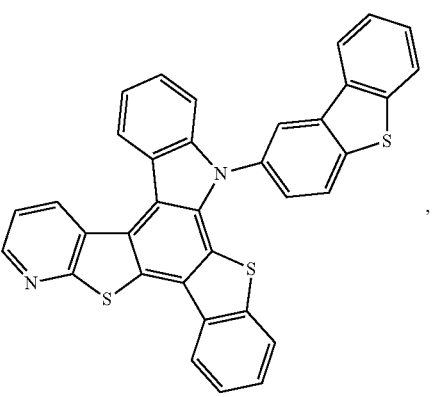
Compound 155
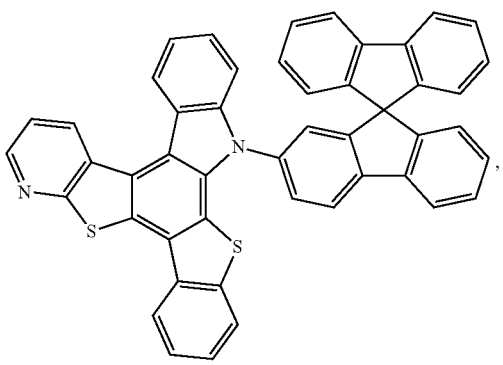

Compound 156
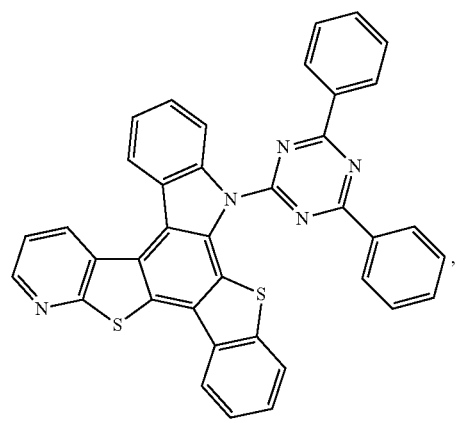
Compound 157
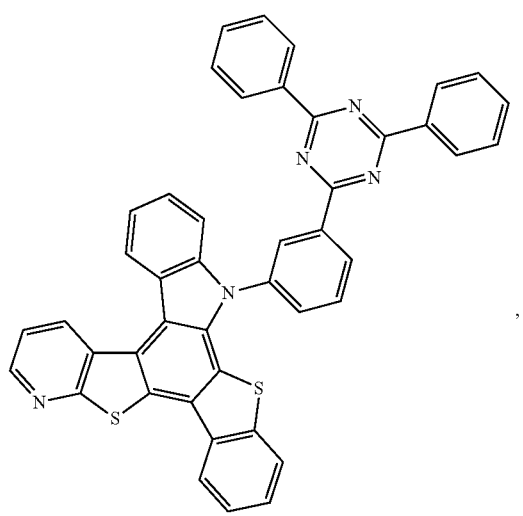
Compound 158
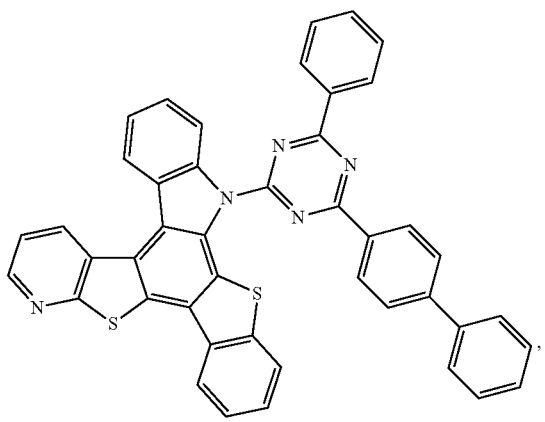
Compound 159
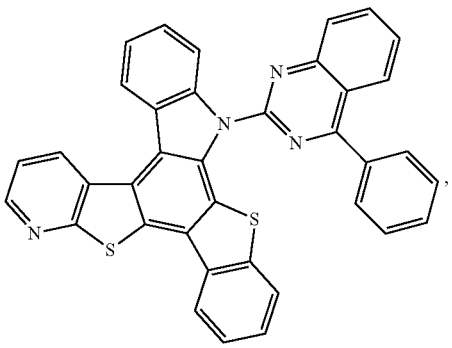
Compound 160
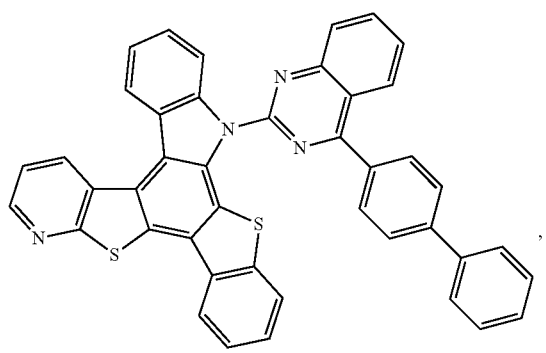
Compound 161
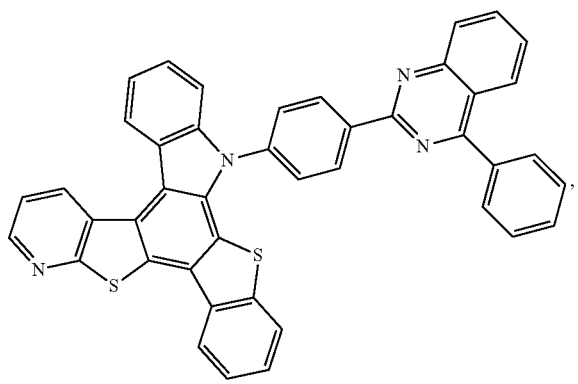
Compound 162
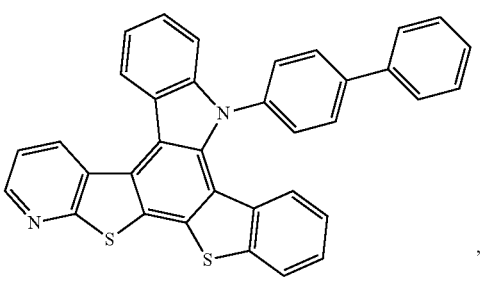

Compound 163
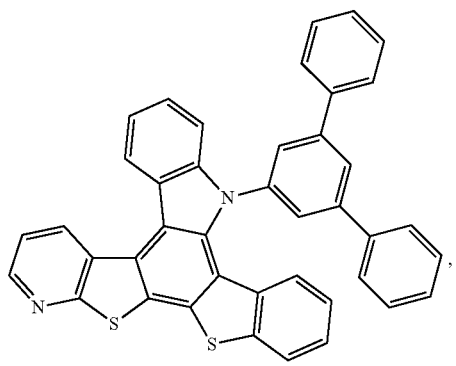
Compound 164
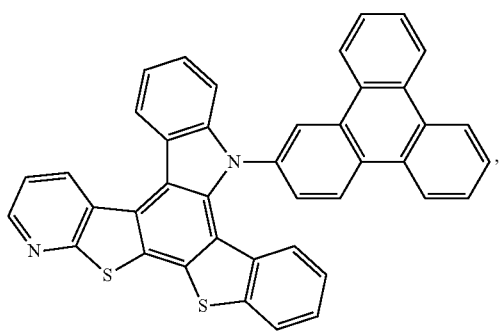
Compound 165
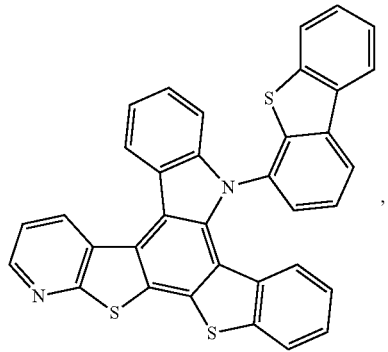
Compound 166
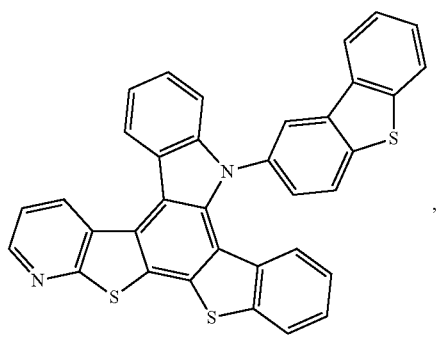
Compound 167
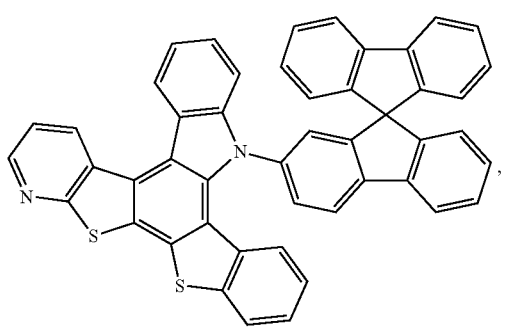
Compound 168
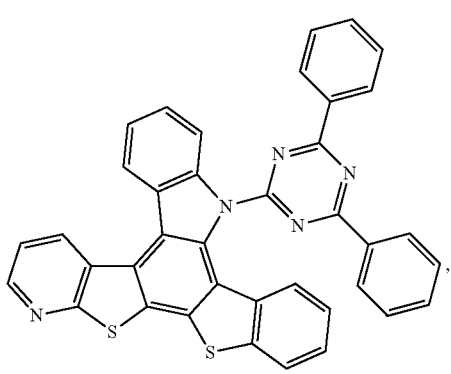
Compound 169
Compound 170

Compound 171
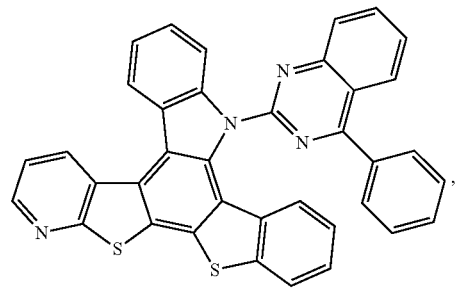
Compound 172
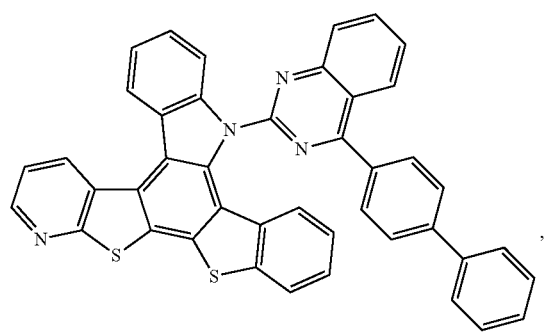
Compound 173
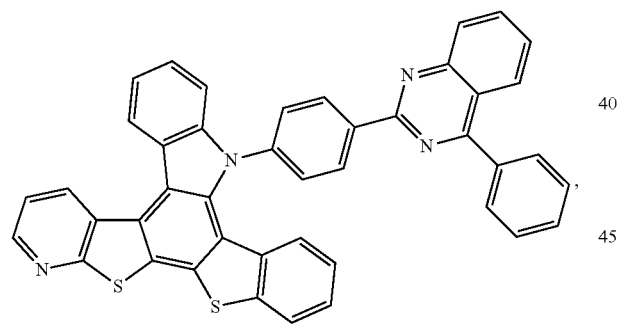
Compound 174
Compound 175
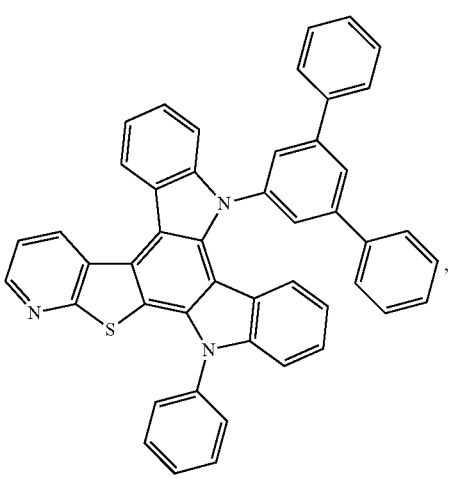
Compound 176
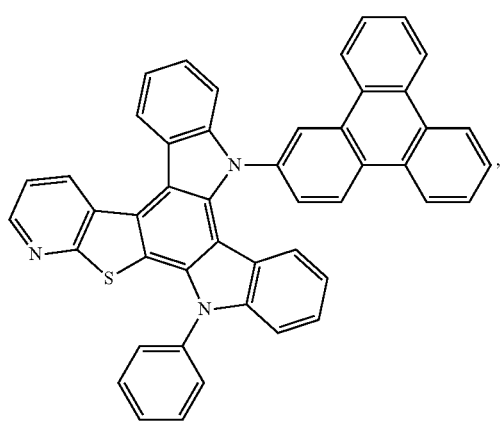
Compound 177
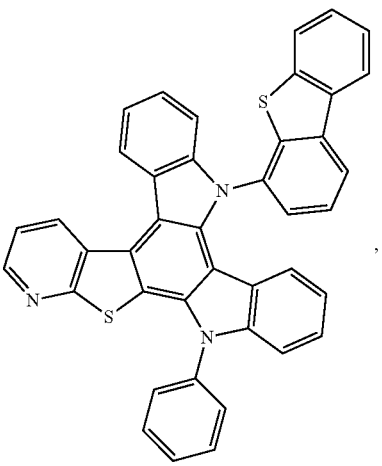

-continued
Compound 178
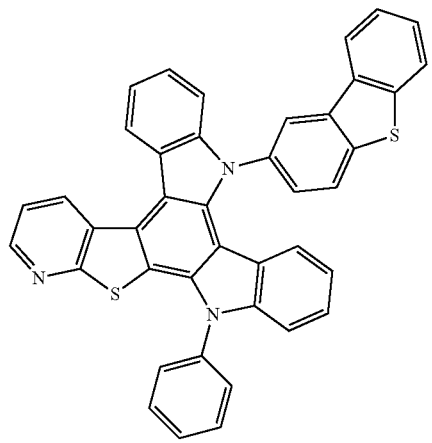
Compound 179
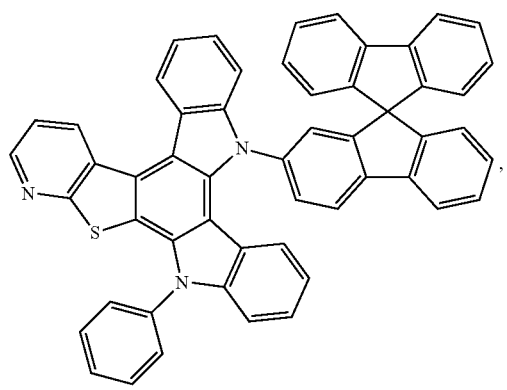
Compound 180
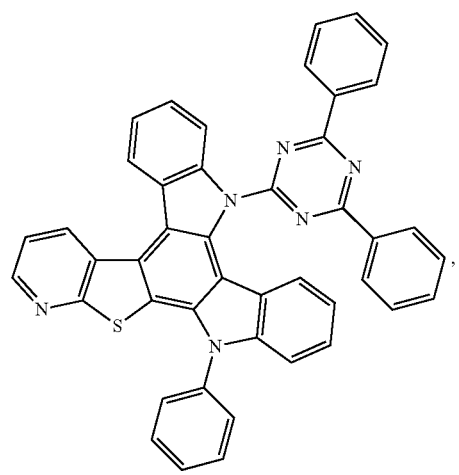
-continued
Compound 181
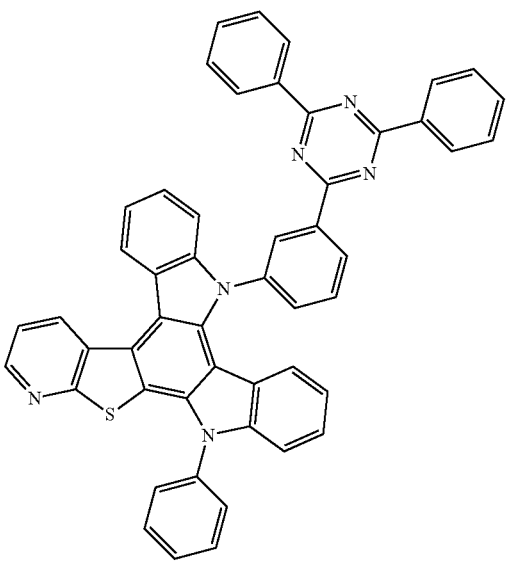
Compound 182
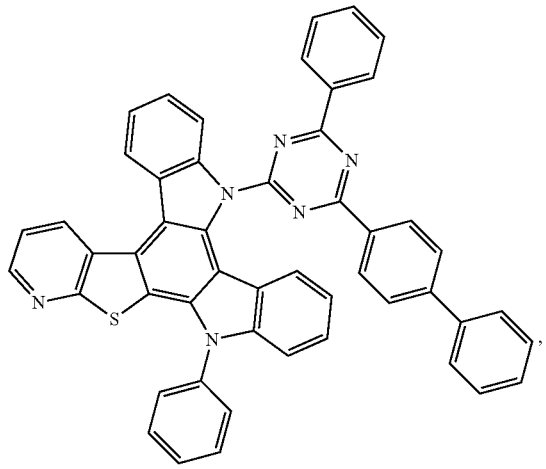
Compound 183
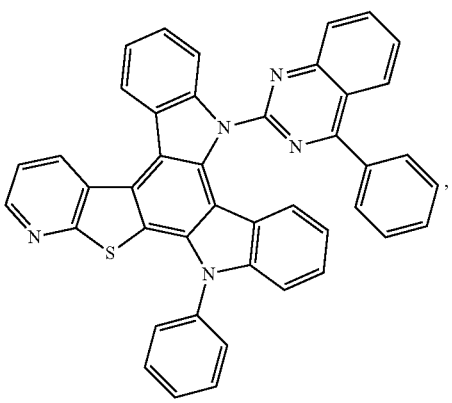

Compound 184
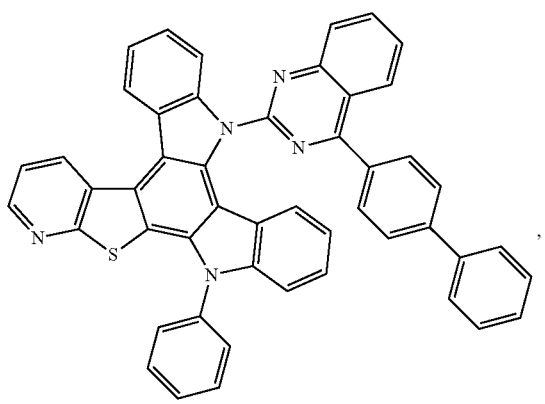
Compound 185
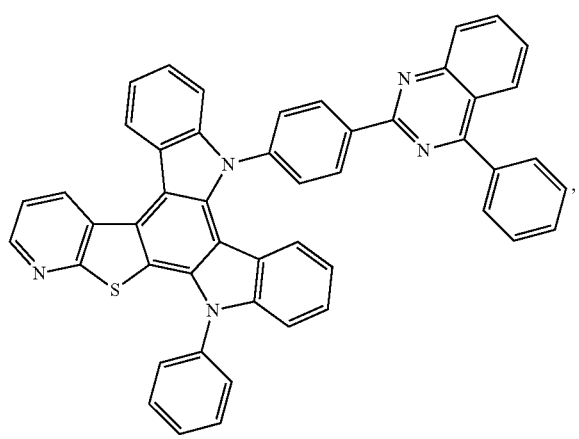
Compound 186
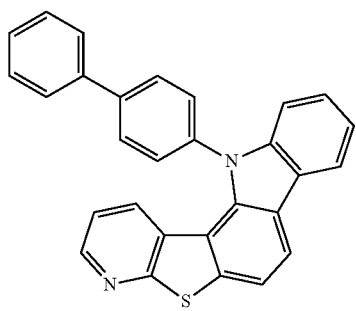
Compound 187
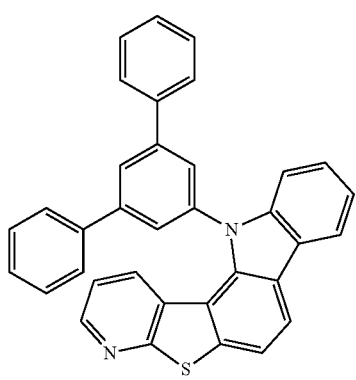
Compound 188
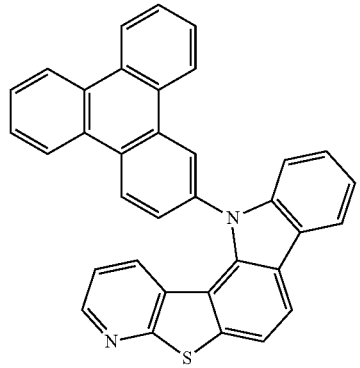
Compound 189
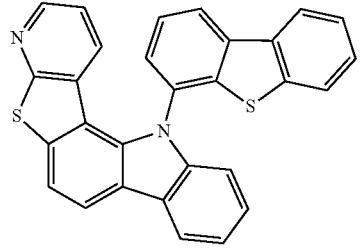
Compound 190
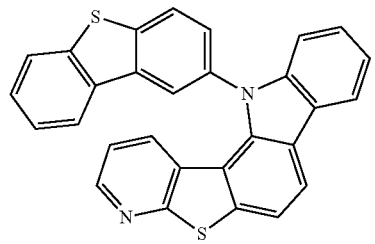
Compound 191
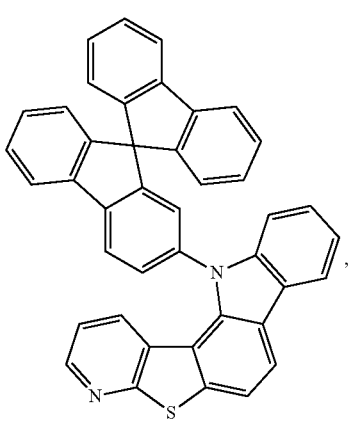

Compound 192
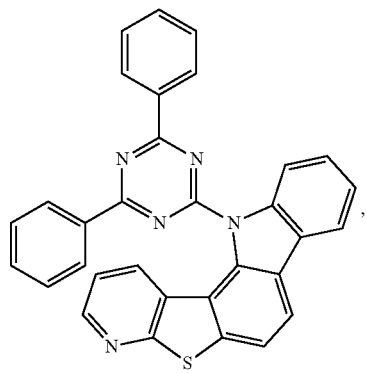
Compound 193
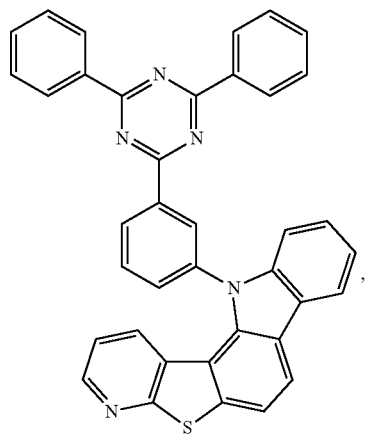
Compound 194
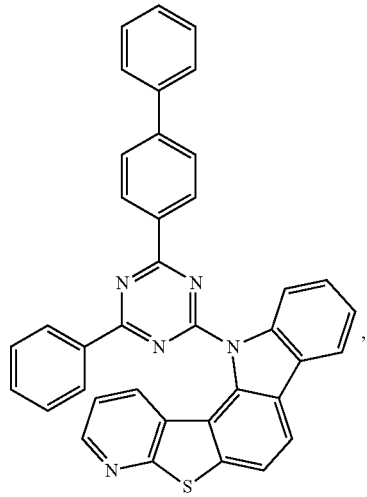
Compound 195
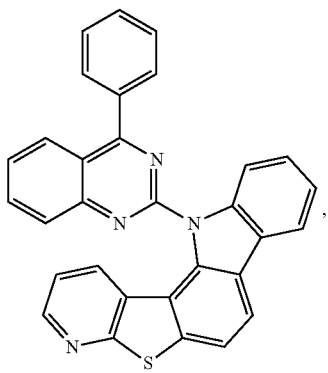
Compound 196
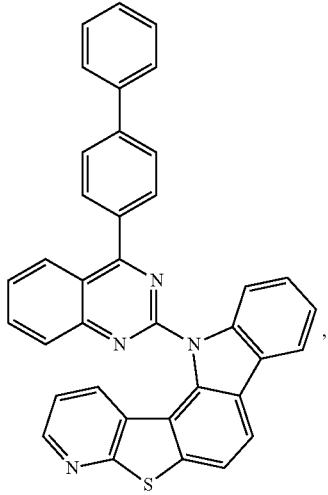
Compound 197
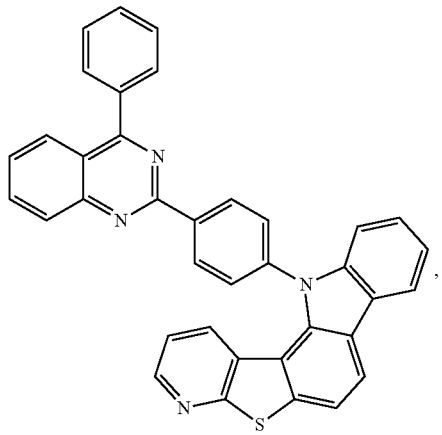

Compound 198
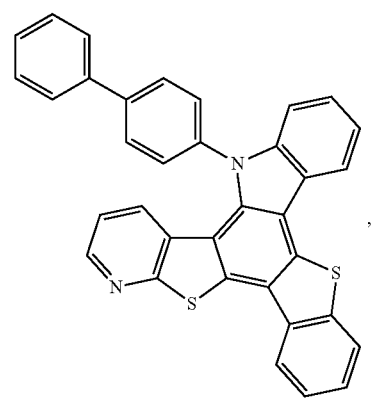
Compound 199
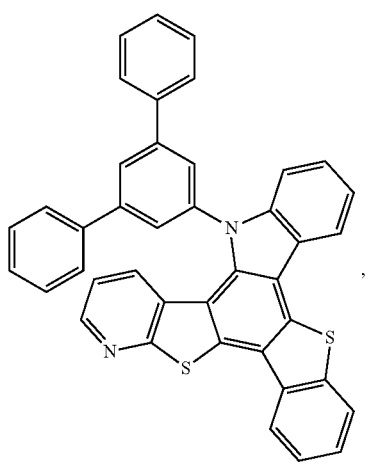
Compound 200
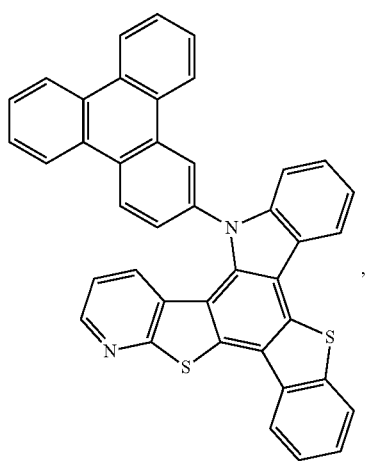
Compound 201
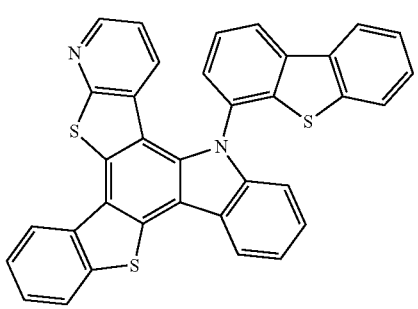
Compound 202
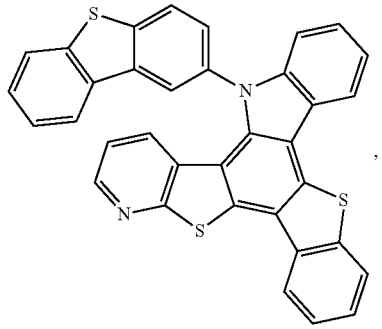
Compound 203
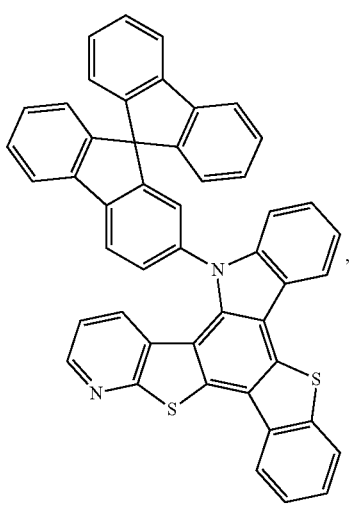
Compound 204
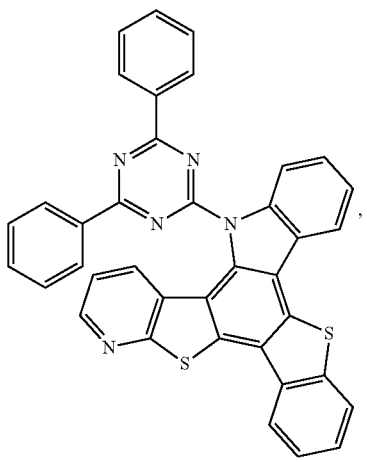

Compound 205
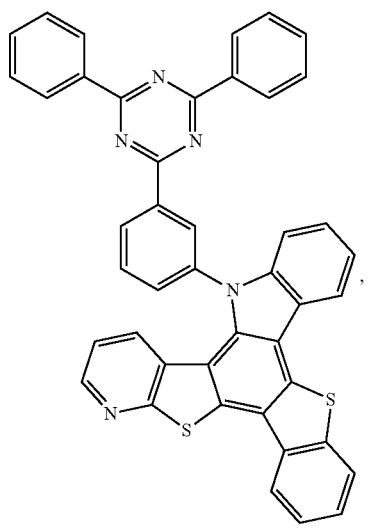
Compound 206
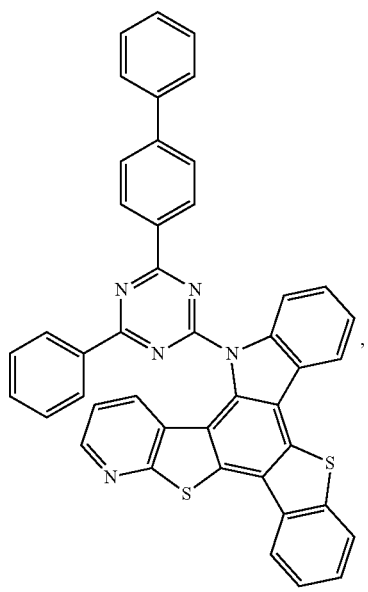
Compound 207
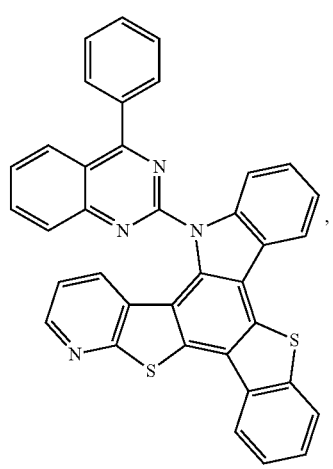
Compound 208
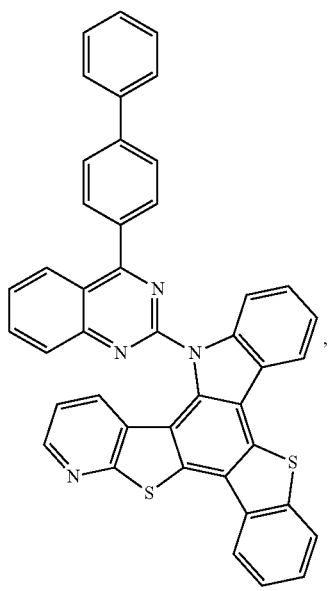
Compound 209
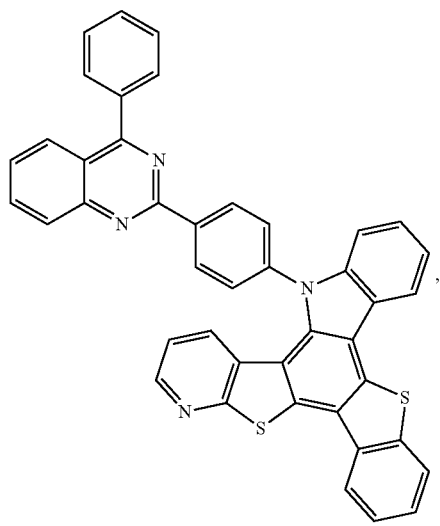
Compound 210
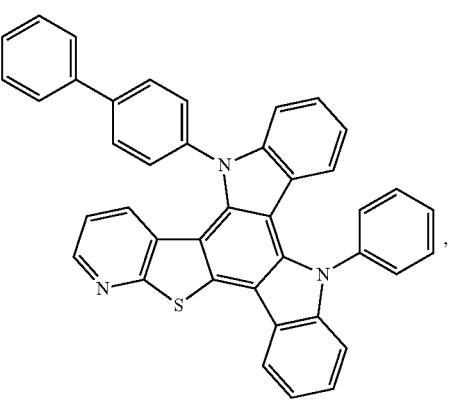

Compound 211
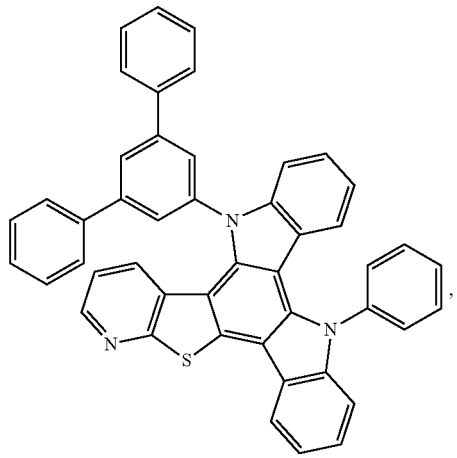
Compound 212
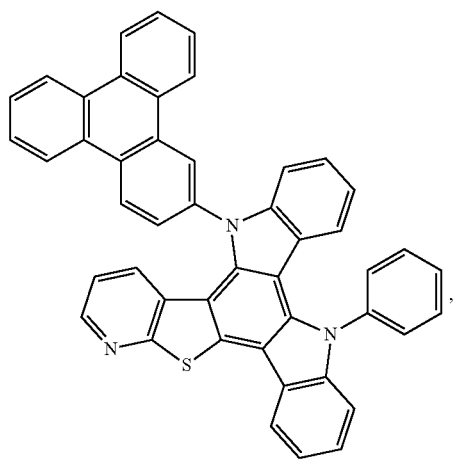
Compound 213
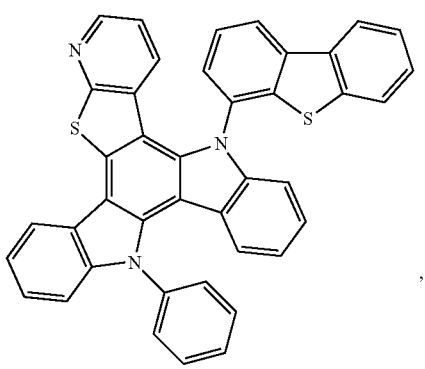
Compound 214
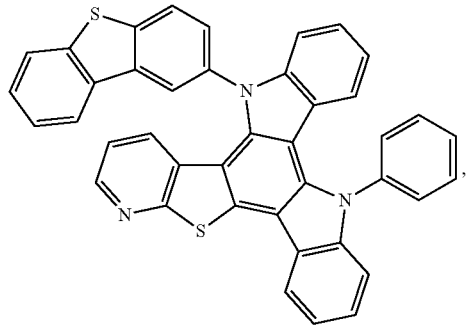
Compound 215
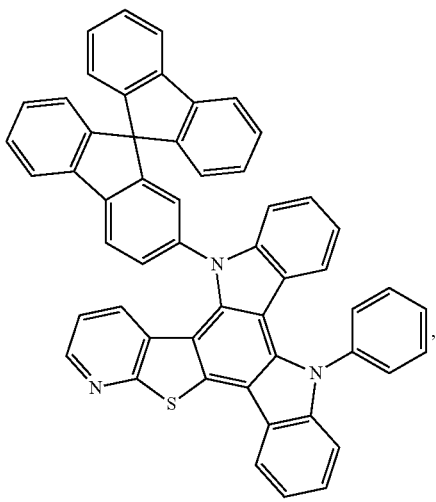
Compound 216
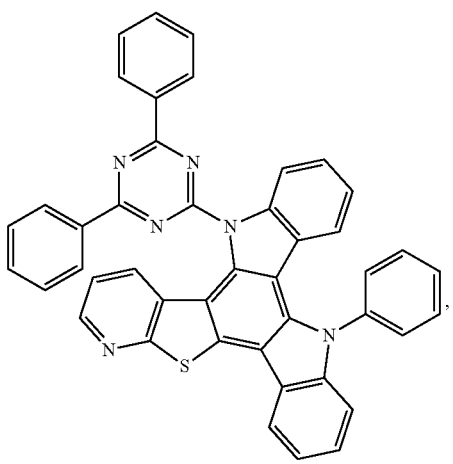

Compound 217
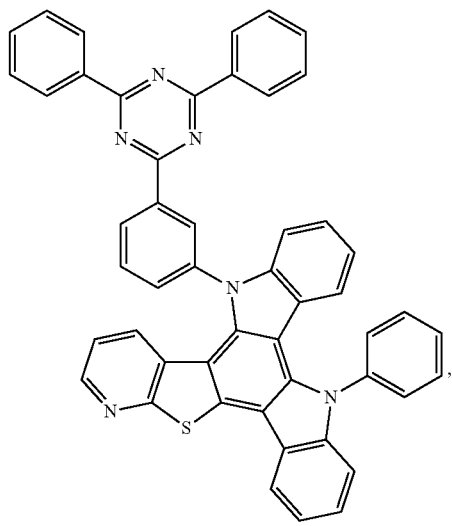
Compound 218
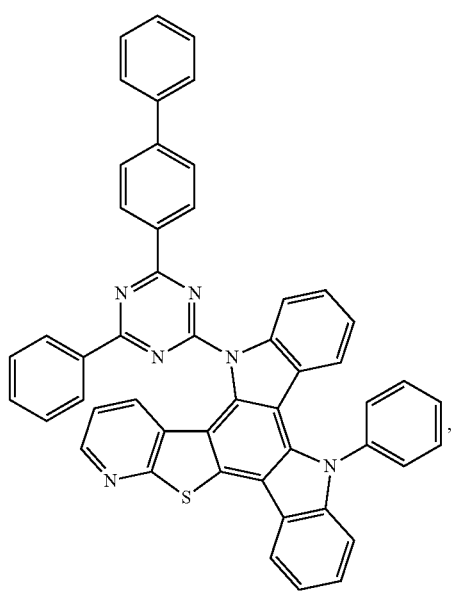
Compound 219
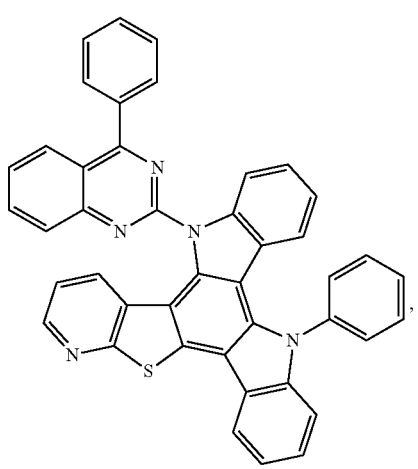
Compound 220
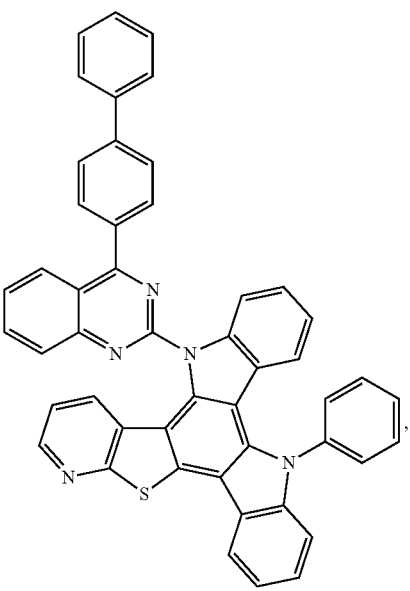
Compound 221
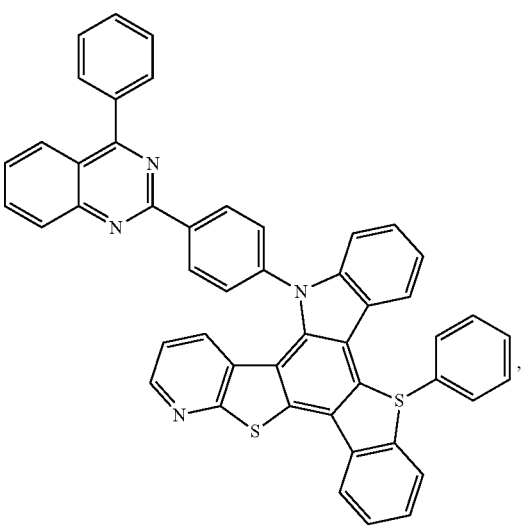
Compound 222
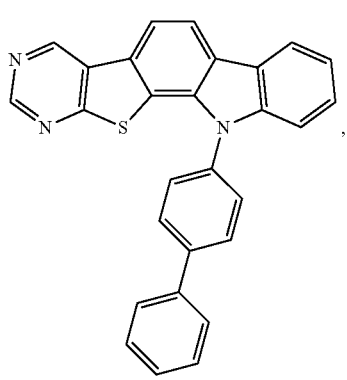

Compound 223
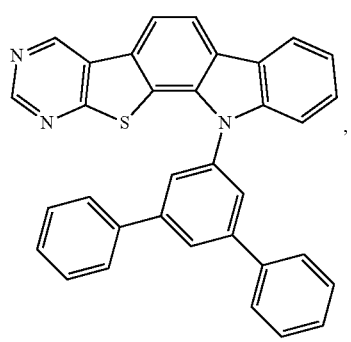
Compound 224
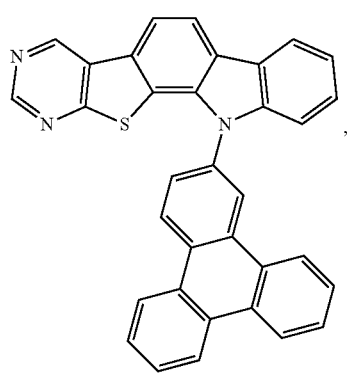
Compound 225
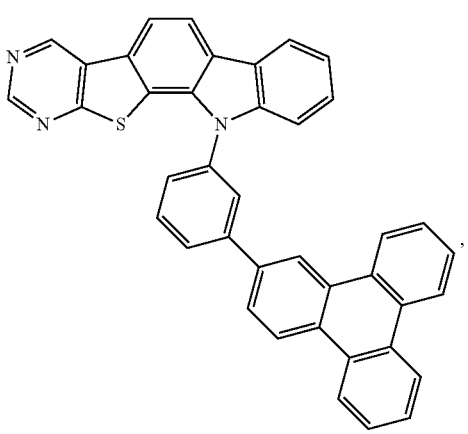
Compound 226
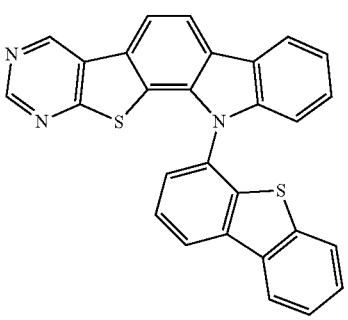
Compound 227
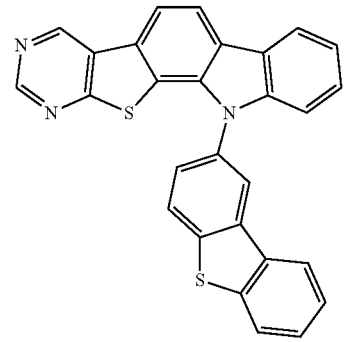
Compound 228
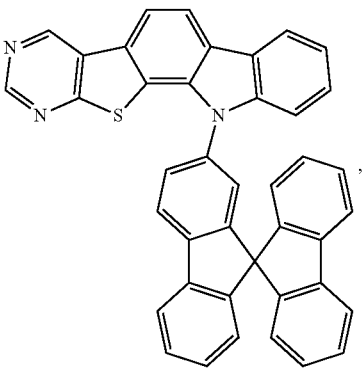
Compound 229
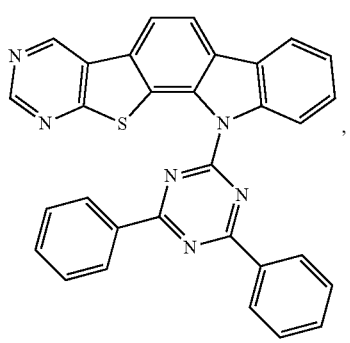
Compound 230
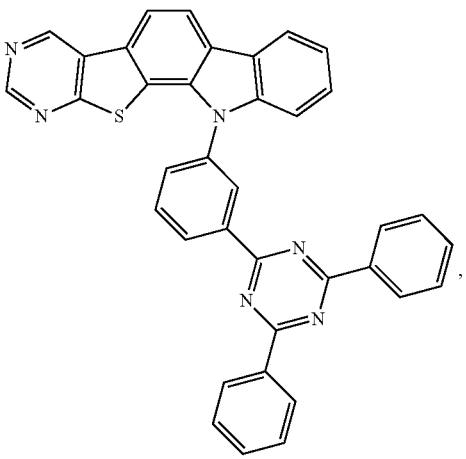

Compound 231
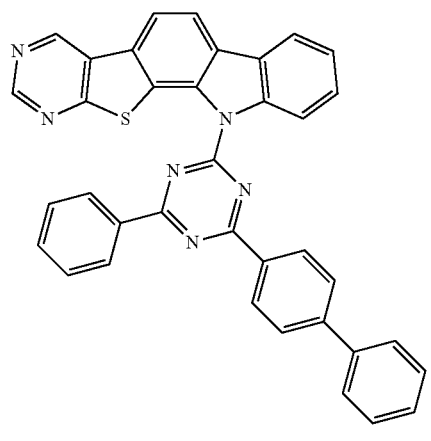
Compound 232
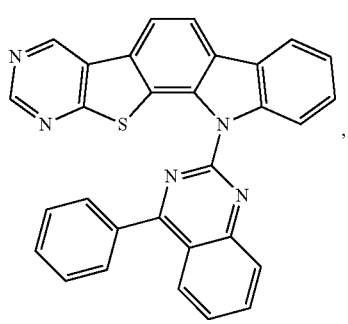
Compound 233
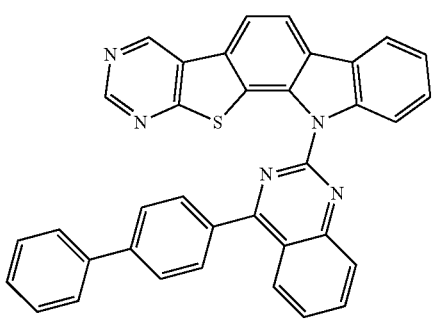
Compound 234
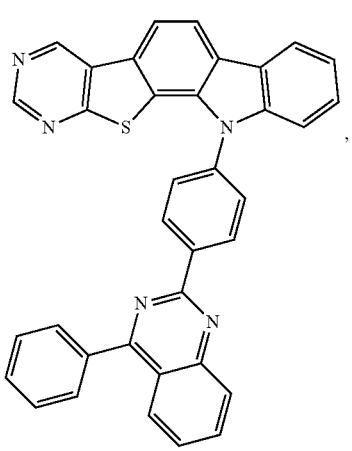
Compound 235
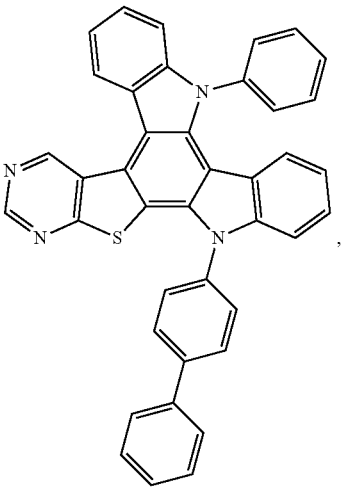
Compound 236
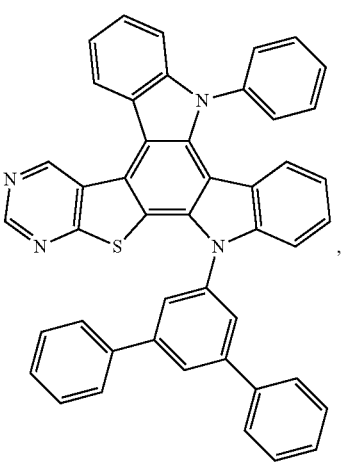
Compound 237
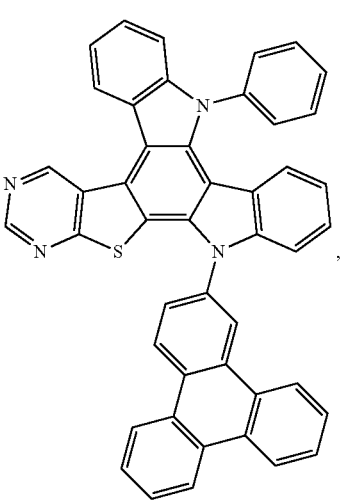

Compound 238
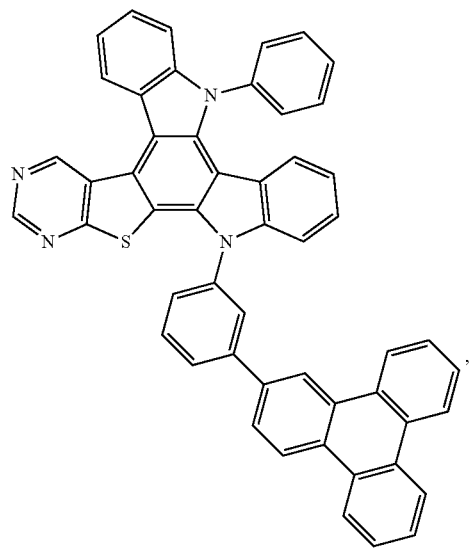
Compound 239
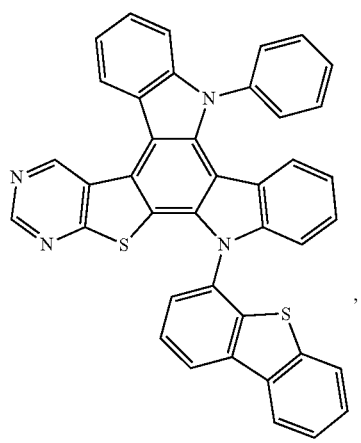
Compound 240
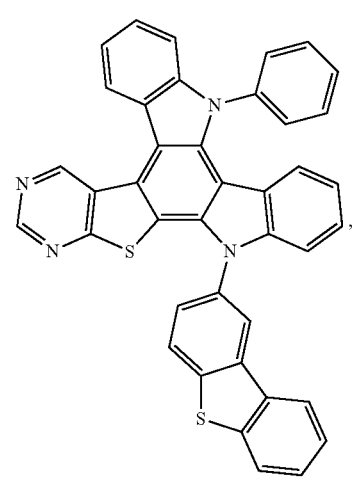
Compound 241
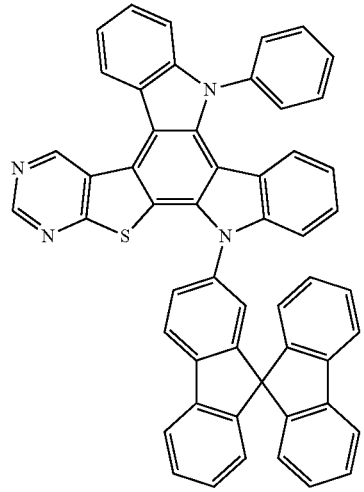
Compound 242
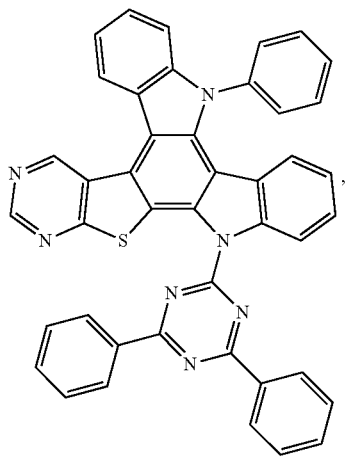
Compound 243
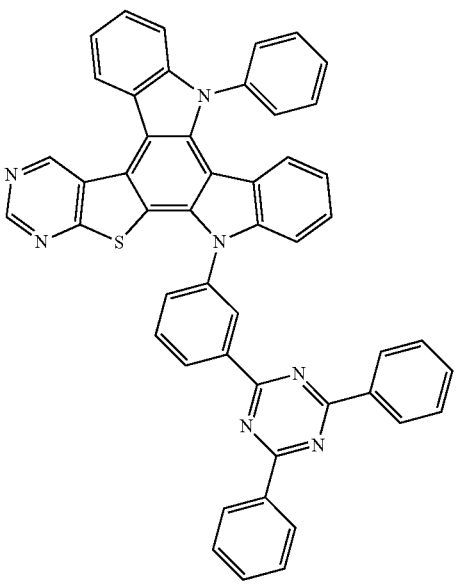

Compound 244
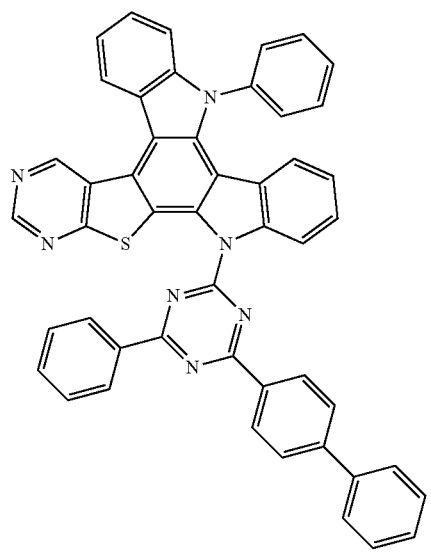
Compound 245
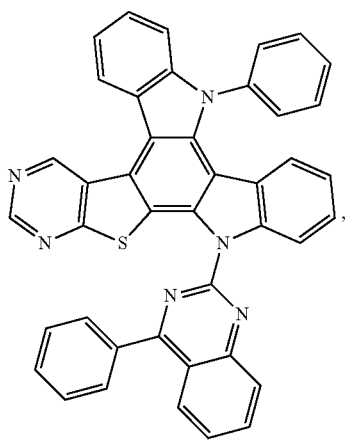
Compound 246
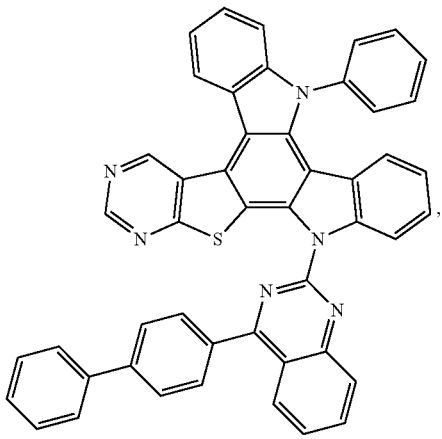
Compound 247
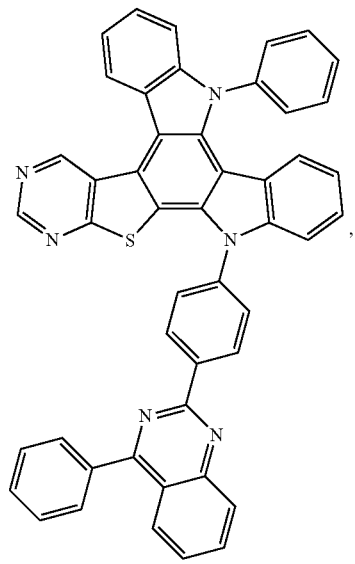
Compound 248
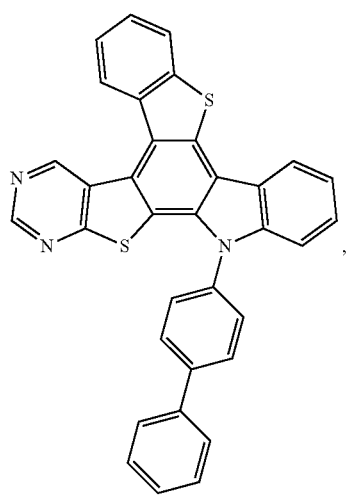
Compound 249
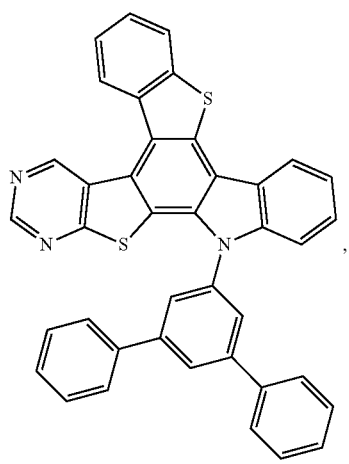

Compound 250
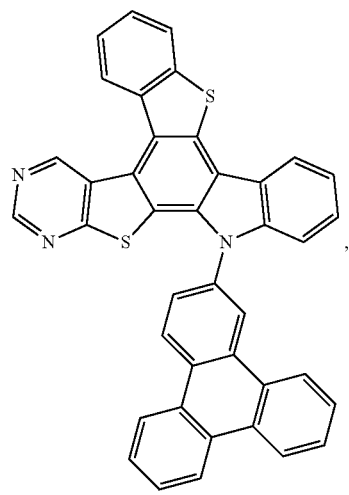
Compound 253
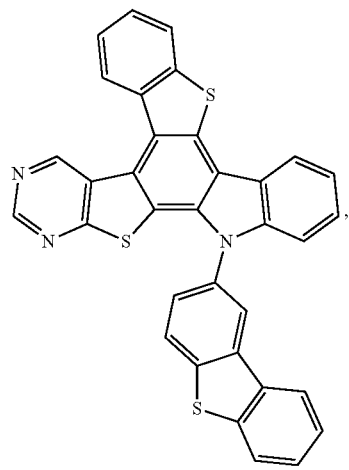
Compound 251
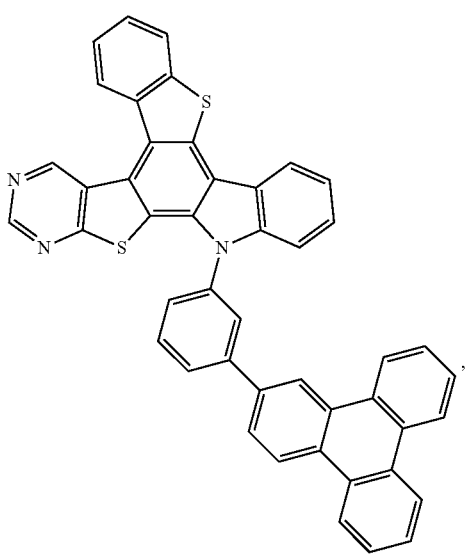
Compound 254
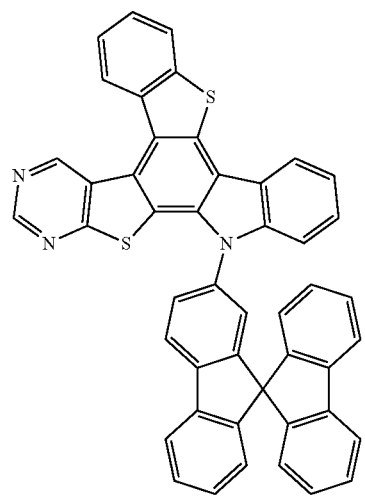
Compound 252
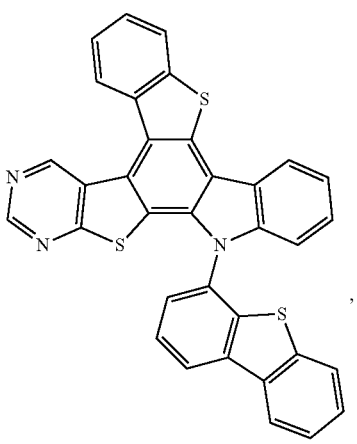
Compound 255
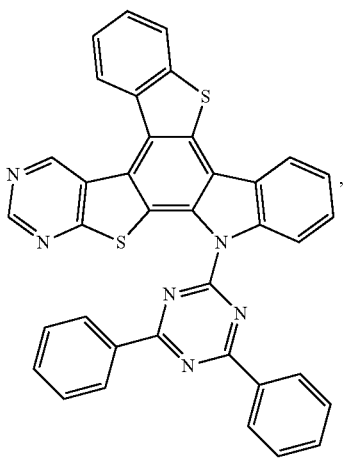

Compound 256
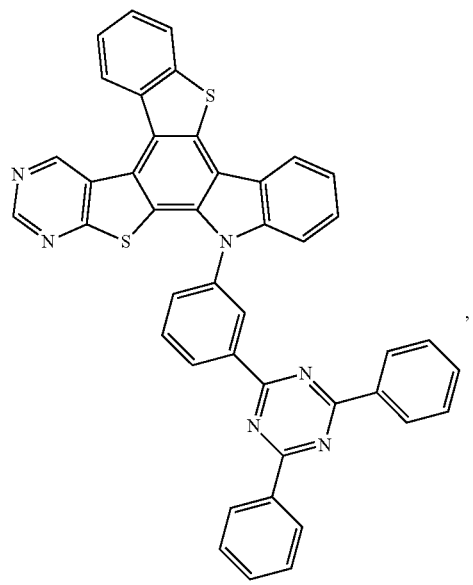
Compound 257
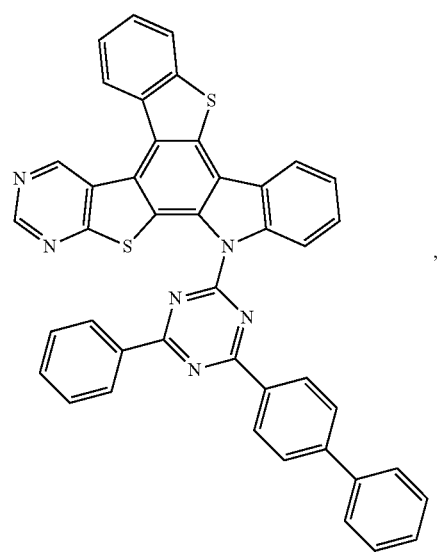
Compound 258
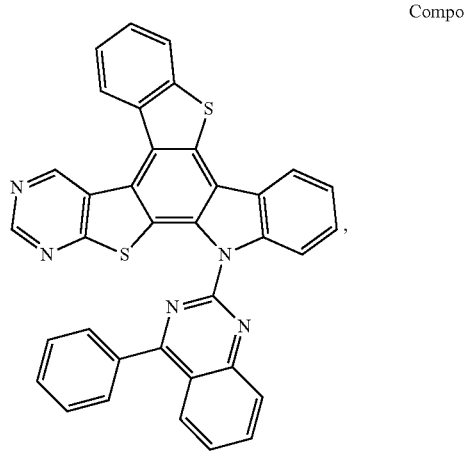
Compound 259
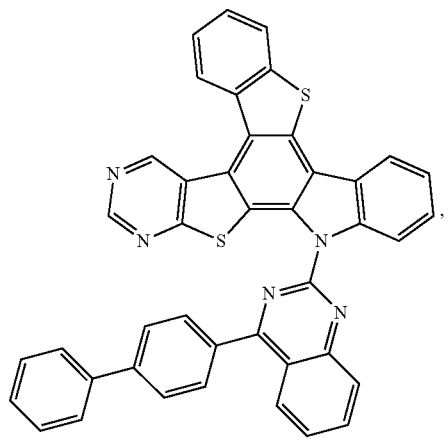
Compound 260
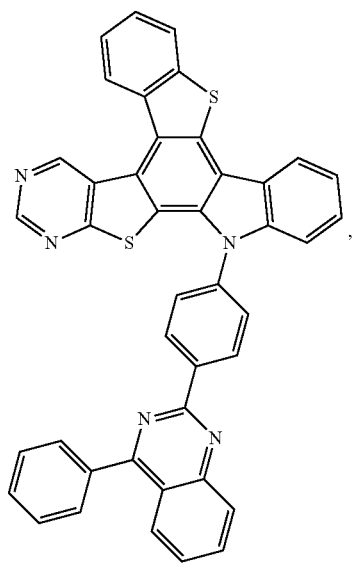
Compound 261
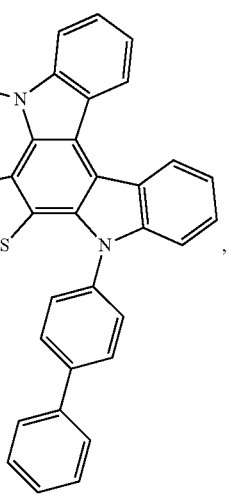

Compound 262
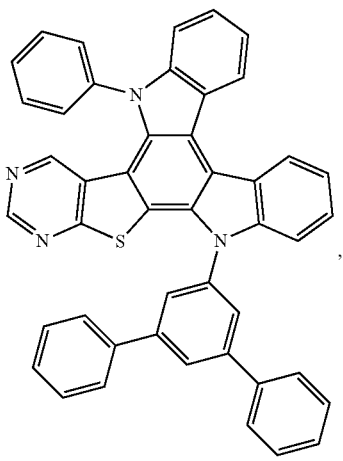
Compound 265
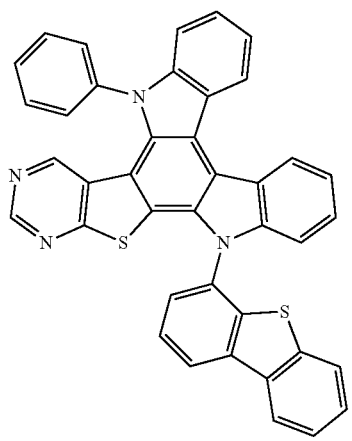
Compound 263
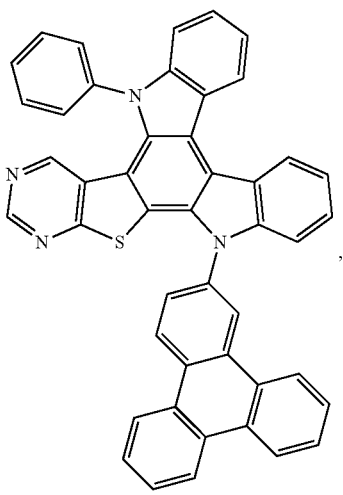
Compound 266
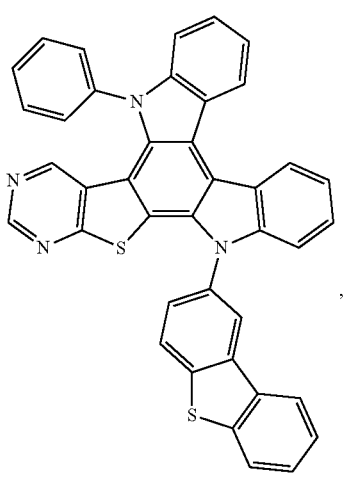
Compound 264
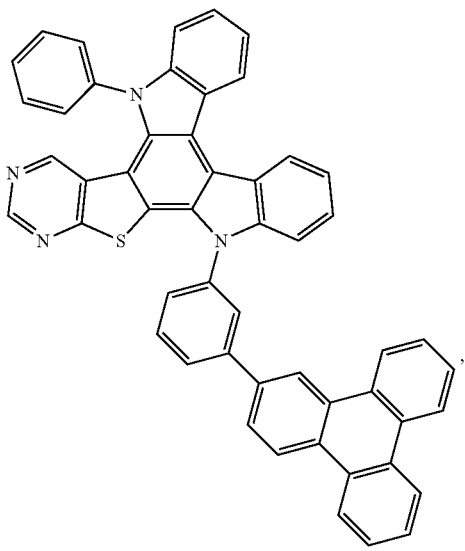
Compound 267
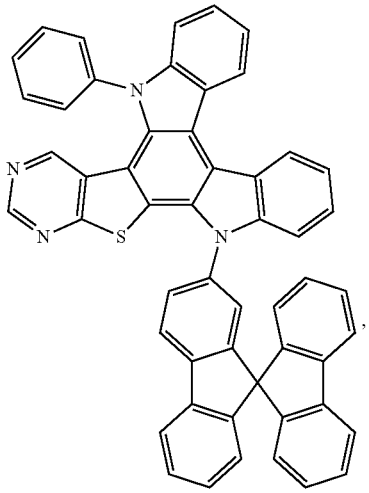

Compound 268
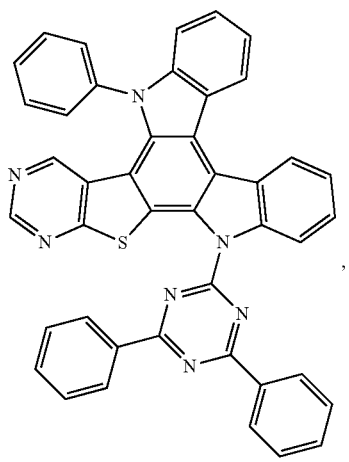
Compound 269
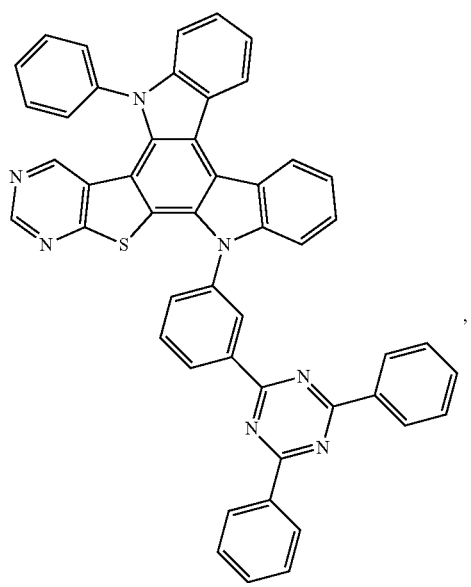
Compound 270
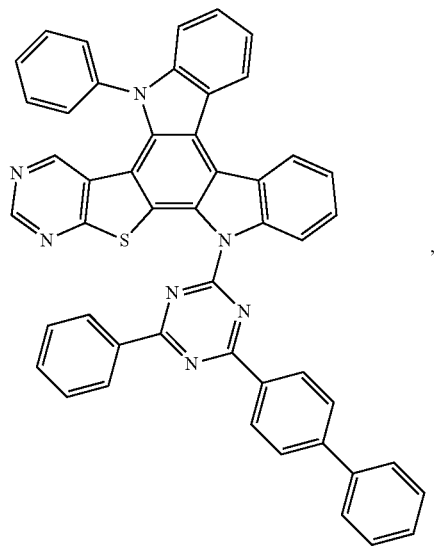
Compound 271
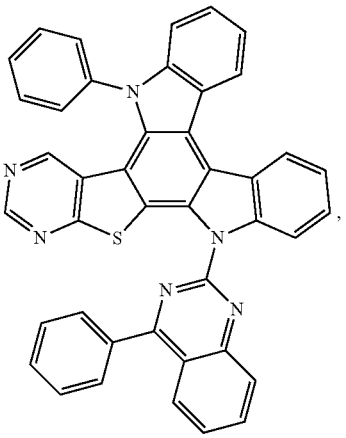
Compound 272
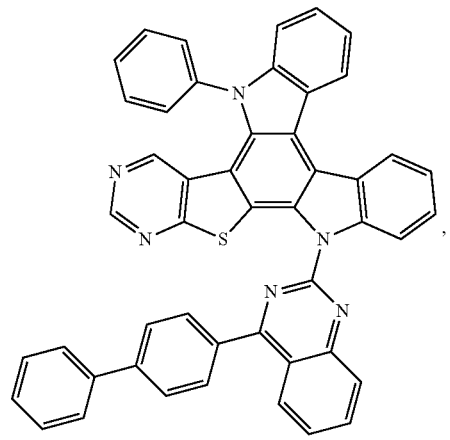
Compound 273
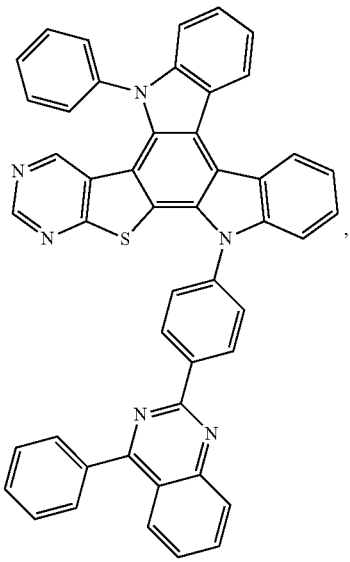

Compound 274
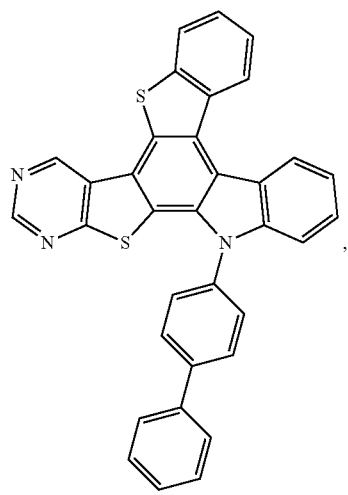
Compound 275
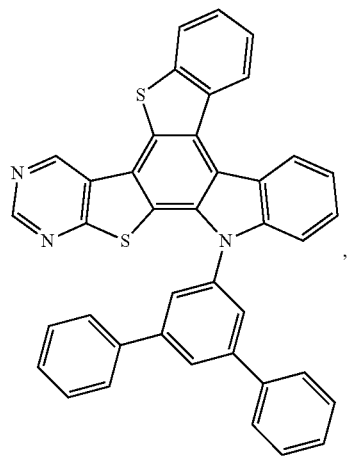
Compound 276
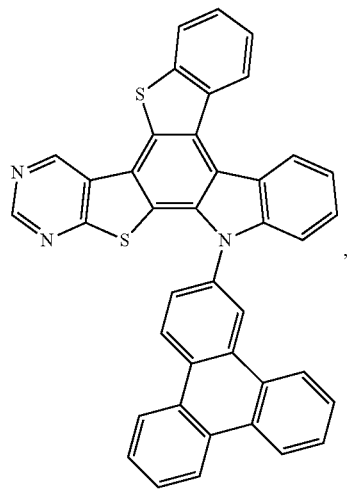
Compound 277
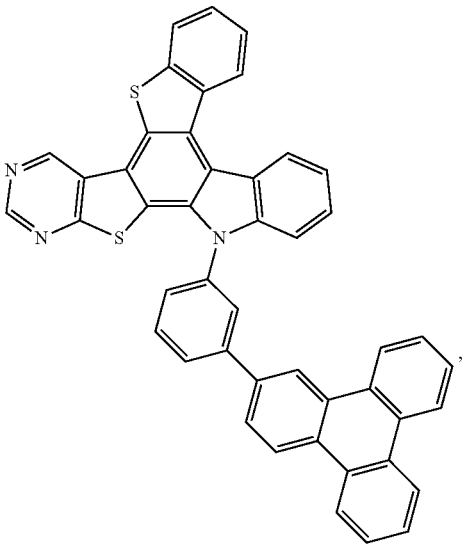
Compound 278
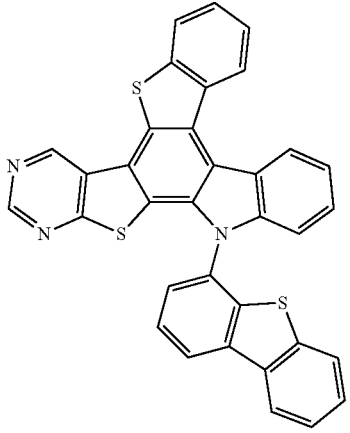
Compound 279
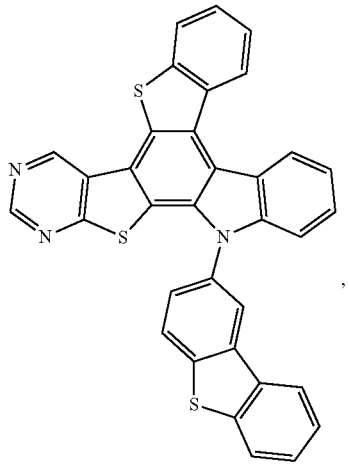

Compound 280
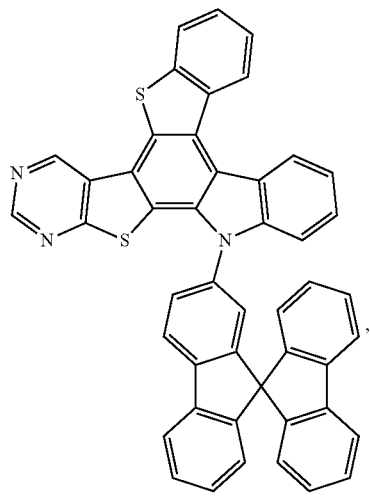
Compound 281
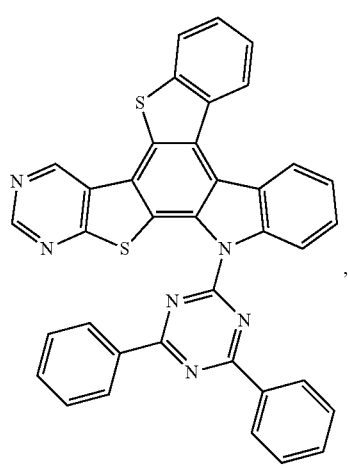
Compound 282
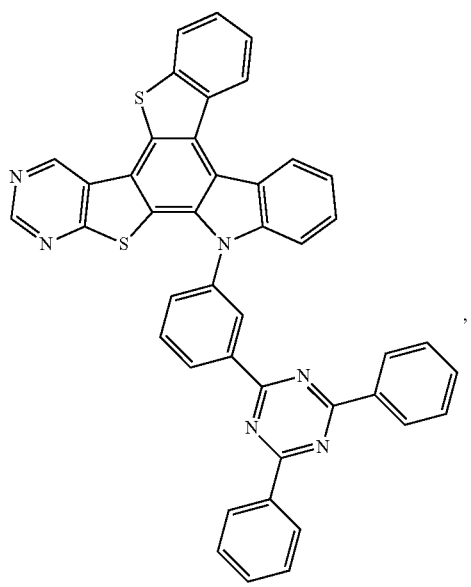
Compound 283
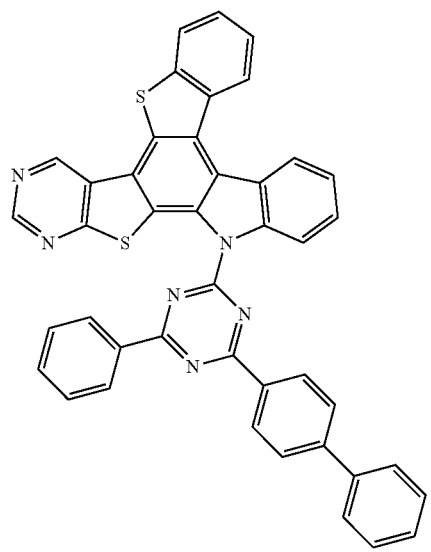
Compound 284
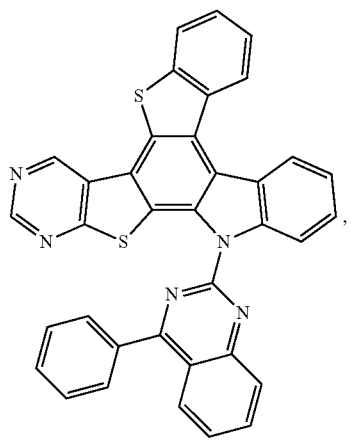
Compound 285
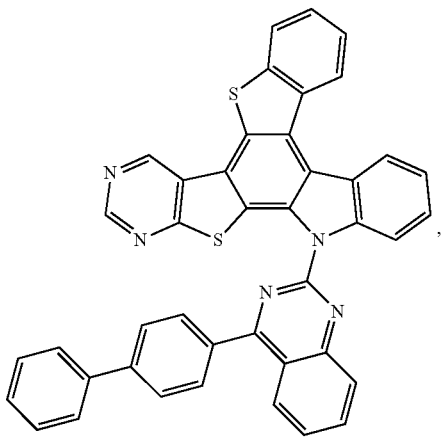

Compound 286
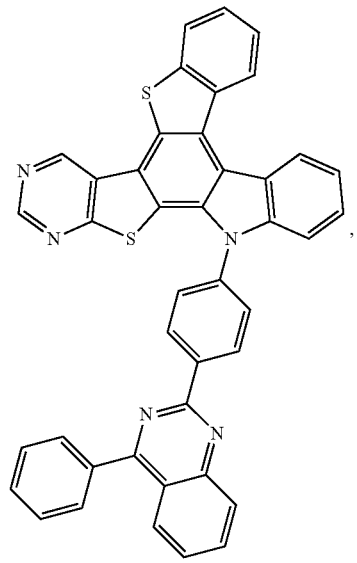
Compound 287
Compound 288
Compound 289
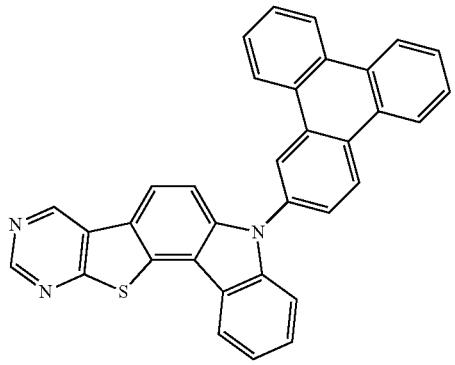
Compound 290
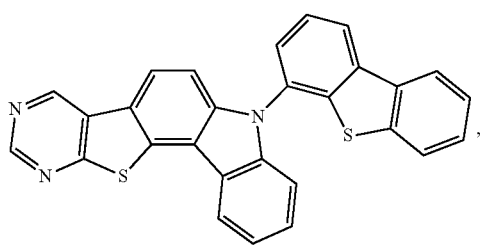
Compound 291
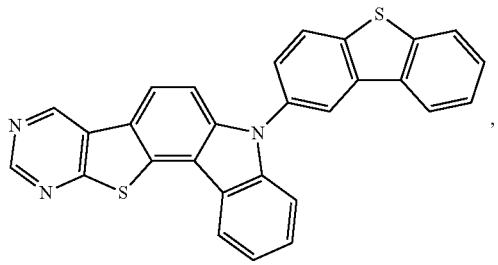
Compound 292
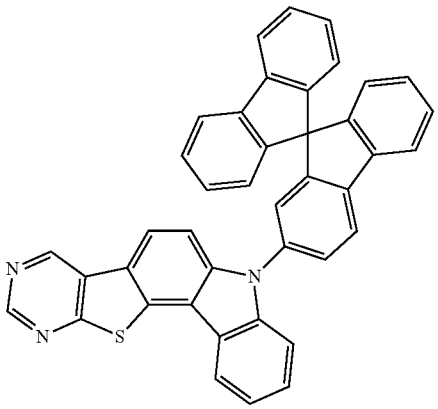

Compound 293
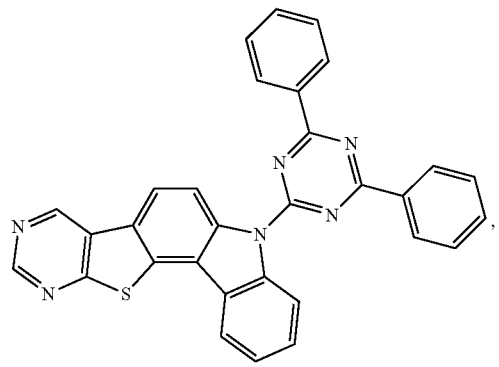
Compound 294
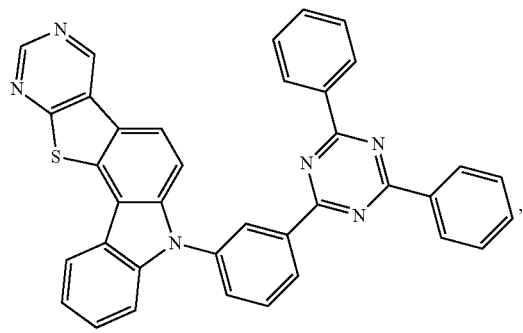
Compound 295
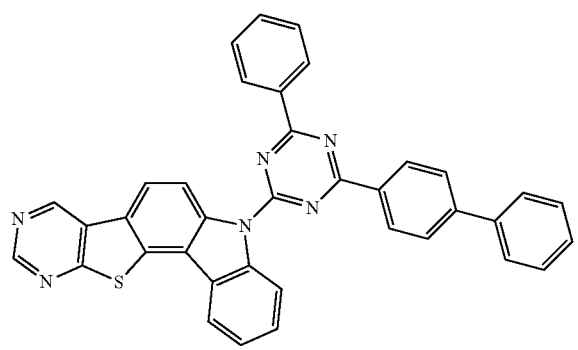
Compound 296
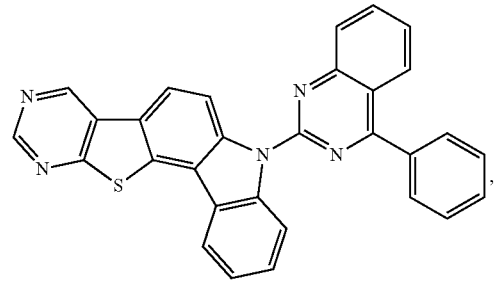
Compound 297
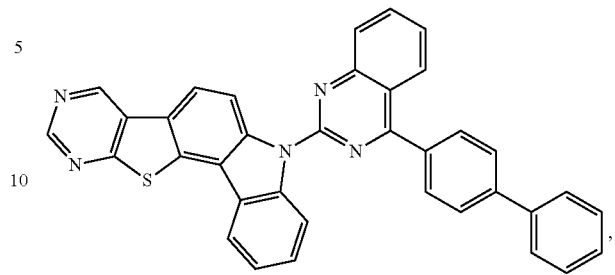
Compound 298
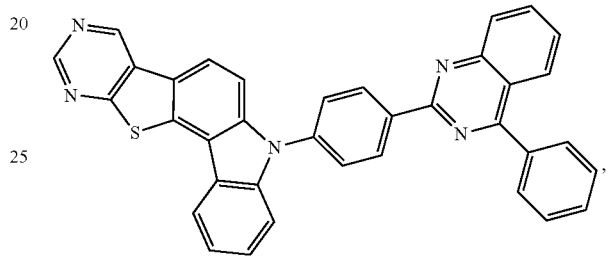
Compound 299
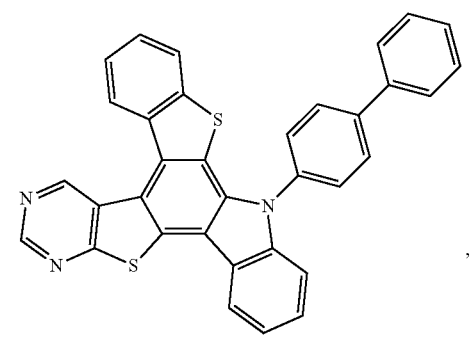
Compound 300

Compound 301
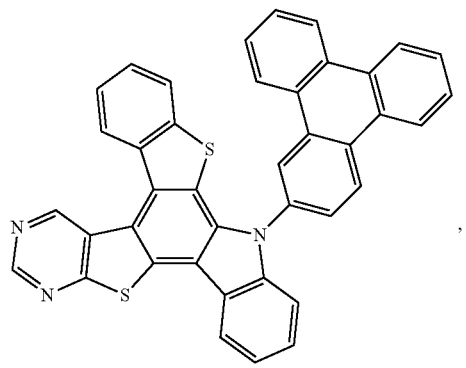
Compound 302
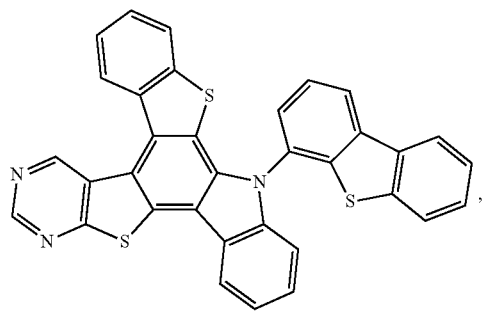
Compound 303
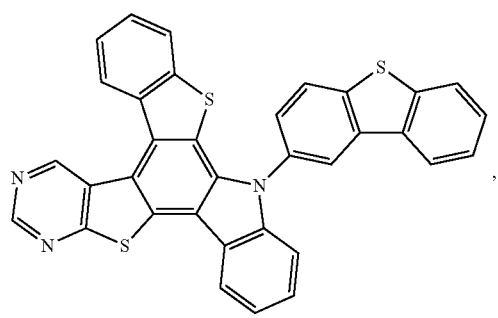
Compound 304
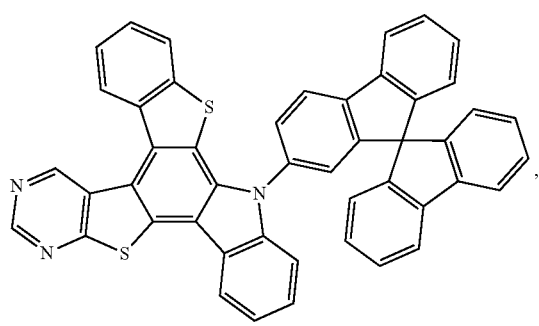
Compound 305
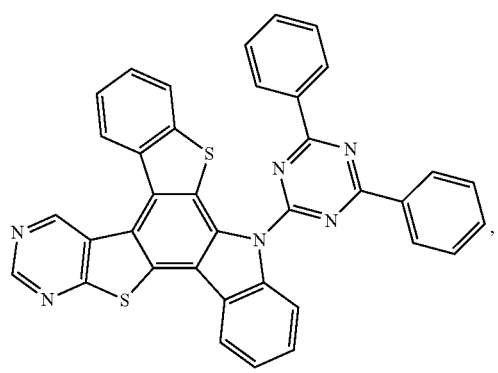
Compound 306
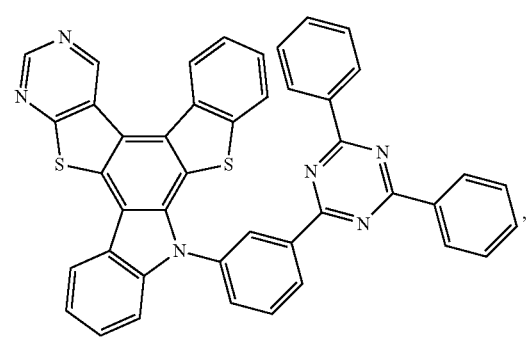
Compound 307
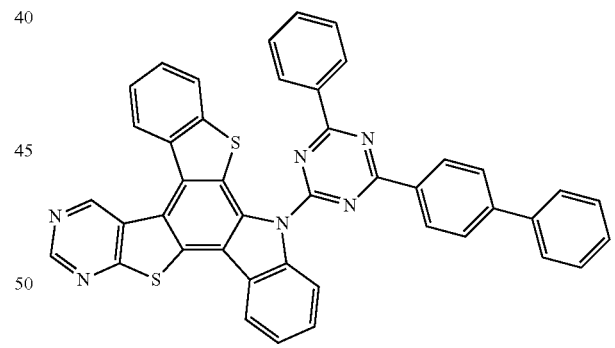
Compound 308
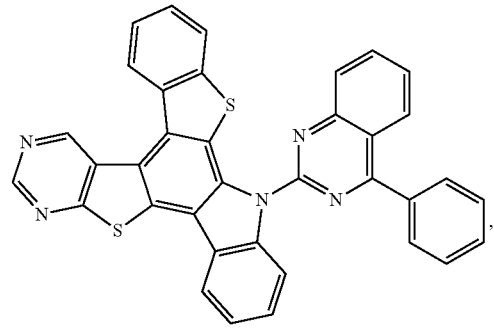

Compound 309
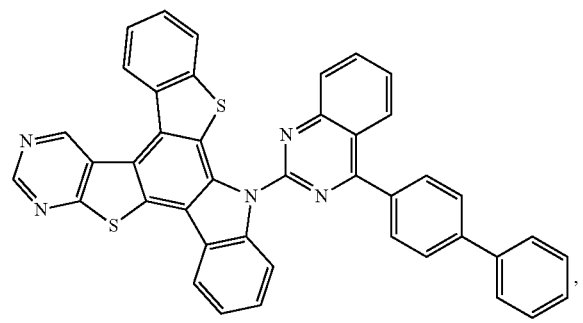
Compound 313
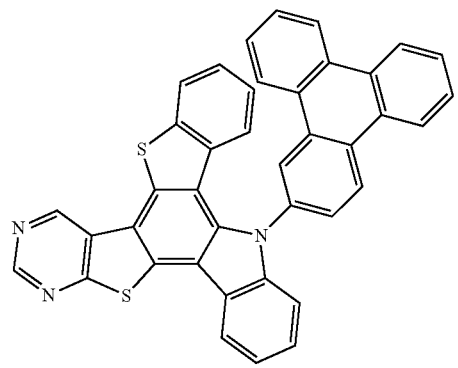
Compound 310
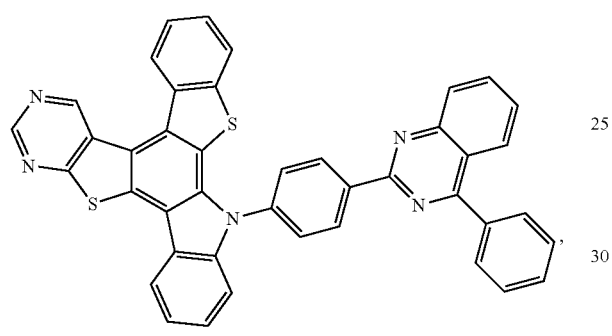
Compound 314
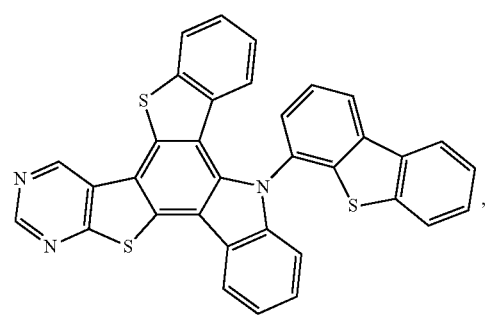
Compound 311
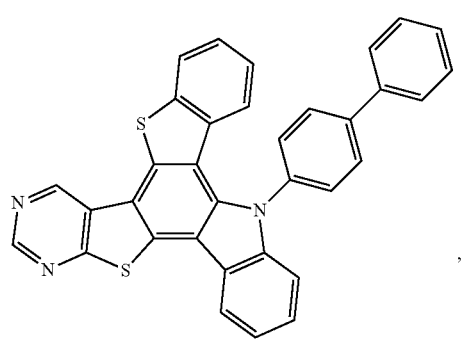
Compound 315
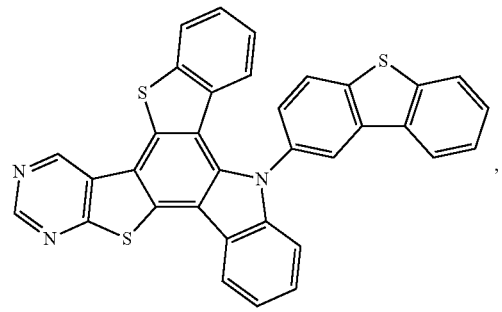
Compound 312
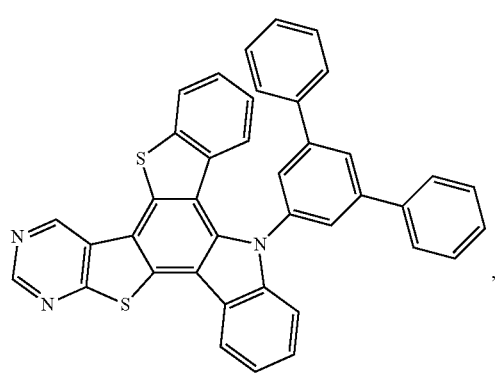
Compound 316
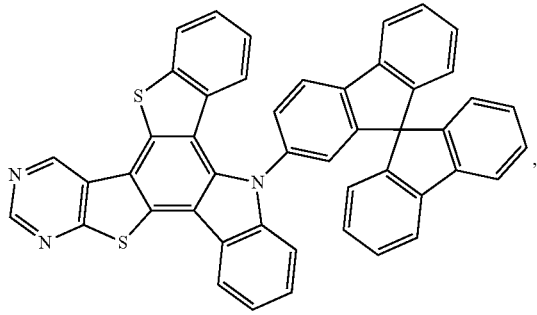

Compound 317
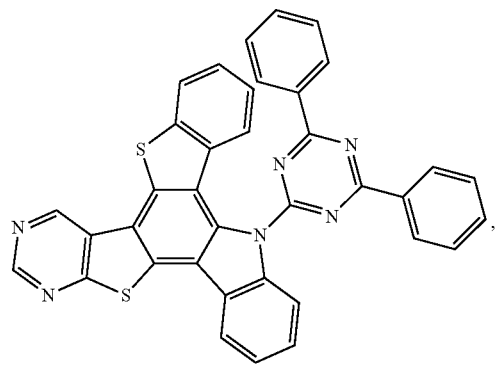
Compound 321
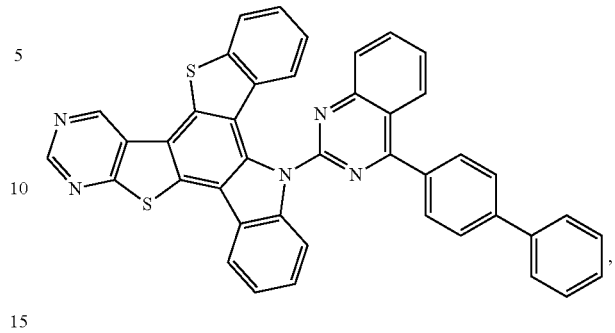
Compound 318
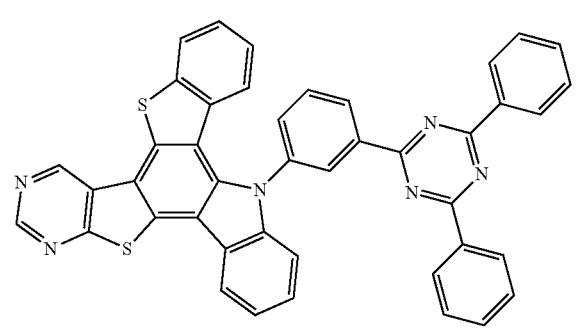
Compound 322
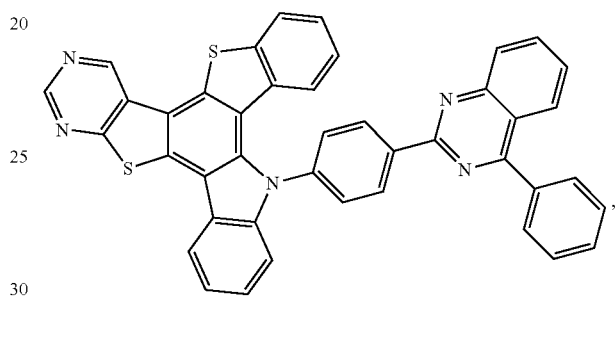
Compound 319
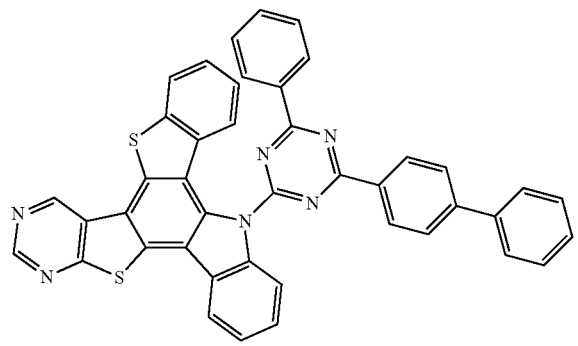
Compound 323
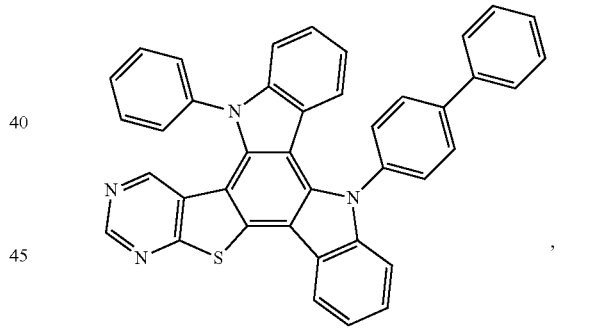
Compound 320
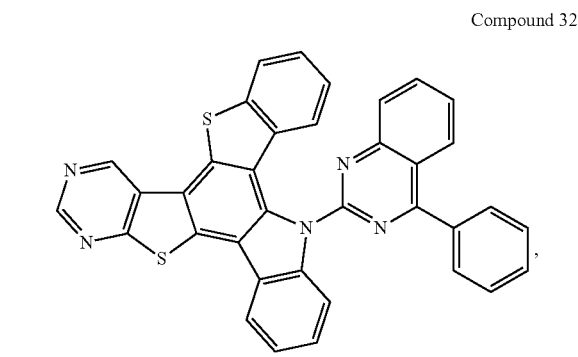
Compound 324
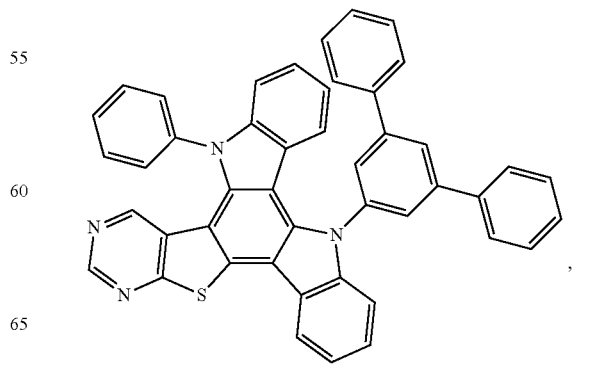

Compound 325
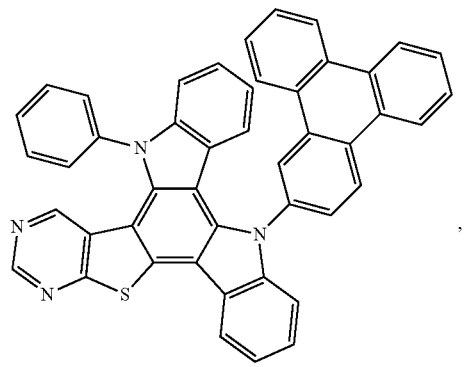
Compound 326
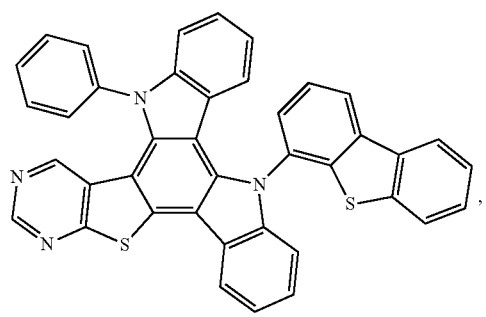
Compound 327
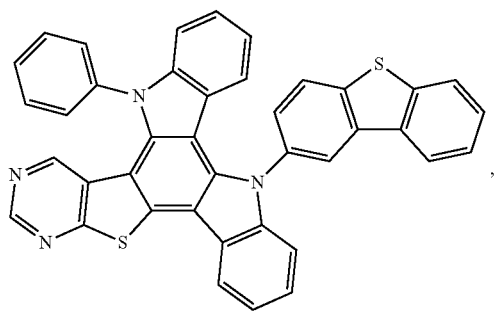
Compound 328
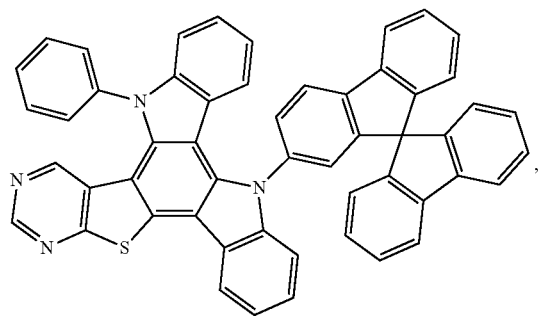
Compound 329
Compound 330
Compound 331
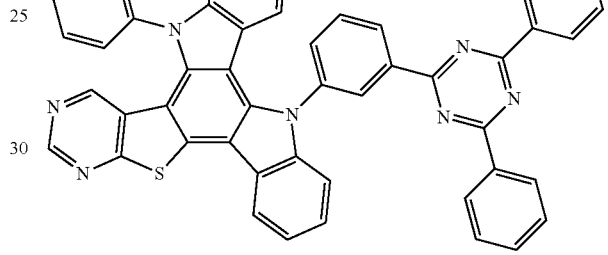
Compound 332
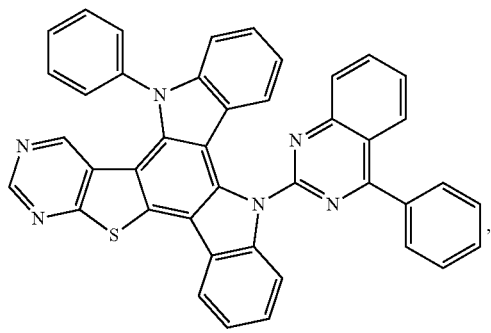

Compound 333
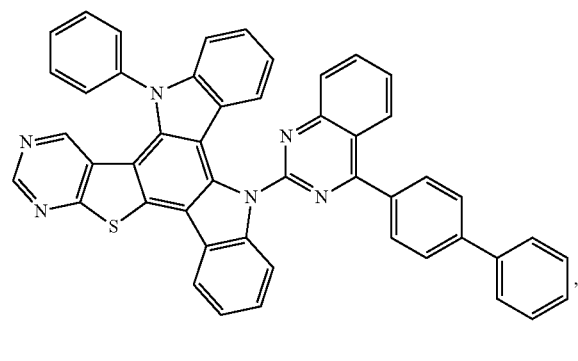
Compound 334
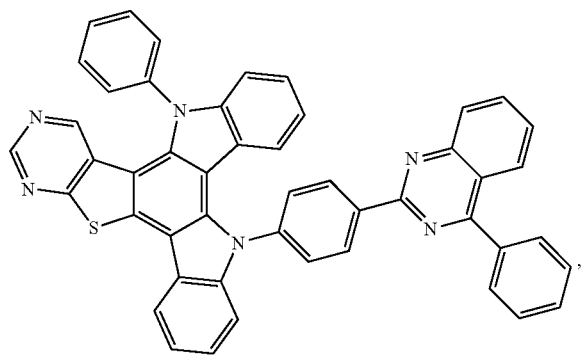
Compound 335
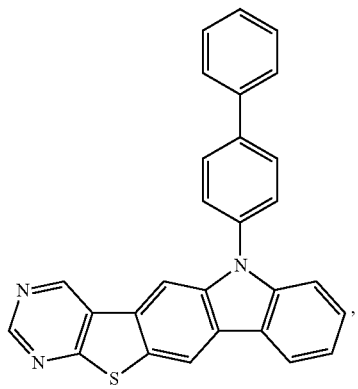
Compound 336
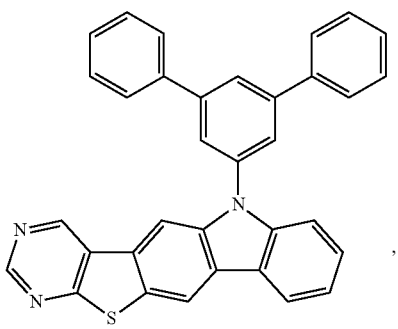
Compound 337
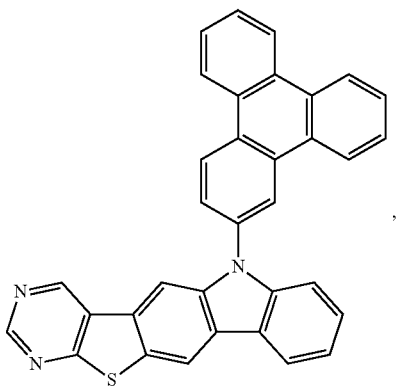
Compound 338
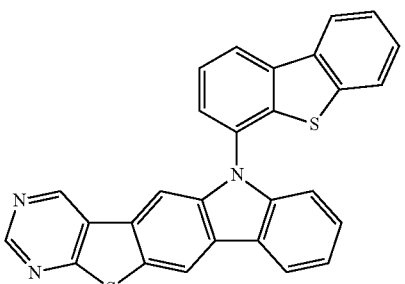
Compound 339
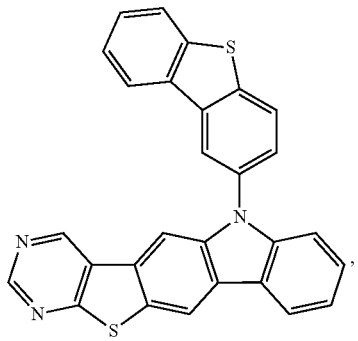
Compound 340
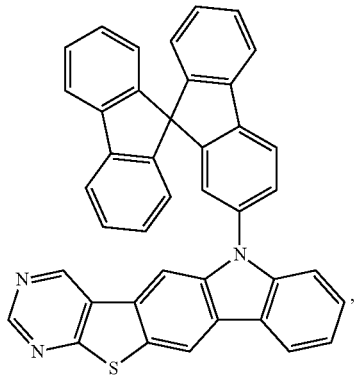

-continued
Compound 341
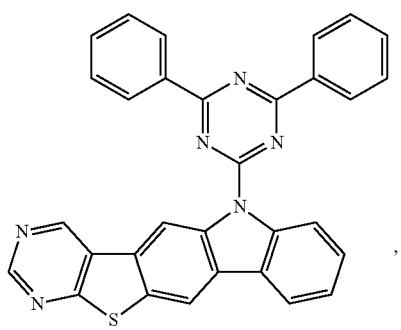,
Compound 342
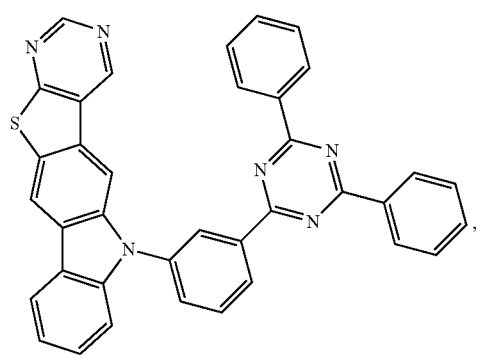,
Compound 343
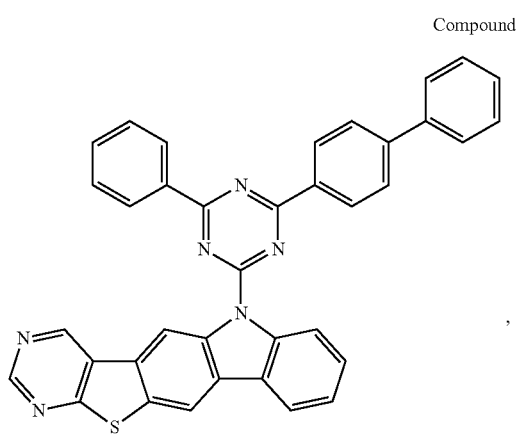,
Compound 344
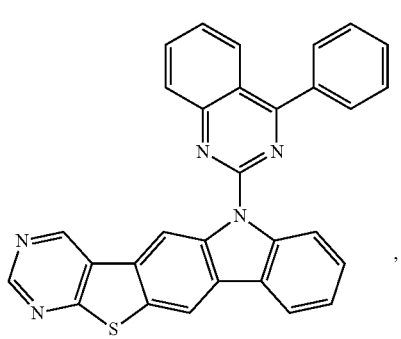,
-continued
Compound 345
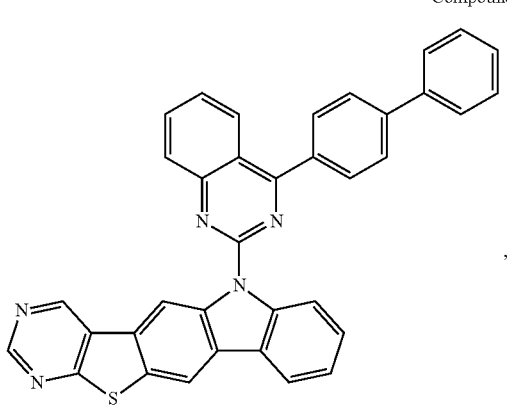,
Compound 346
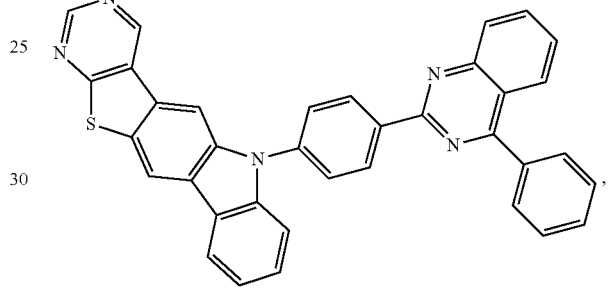,
Compound 347
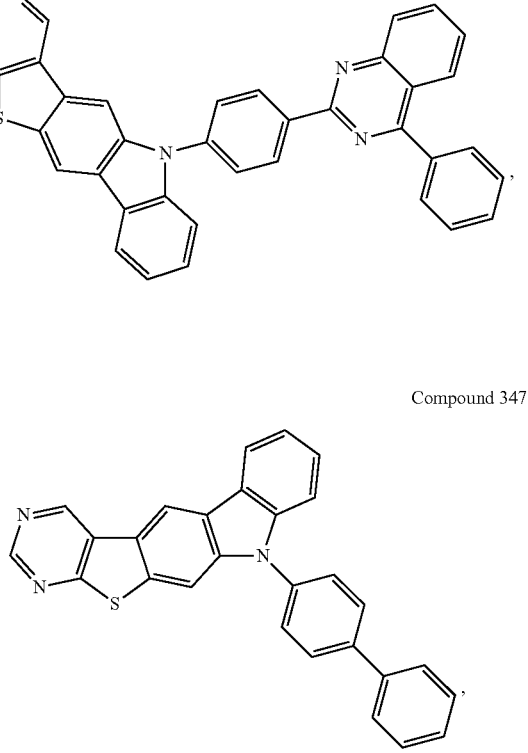,
Compound 348
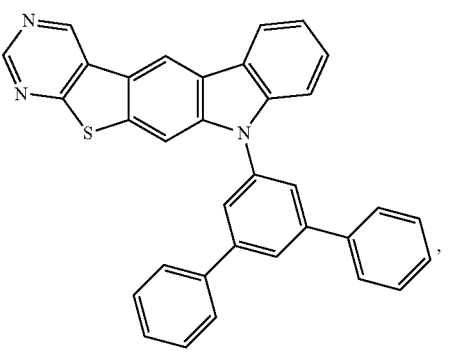, Compound 349
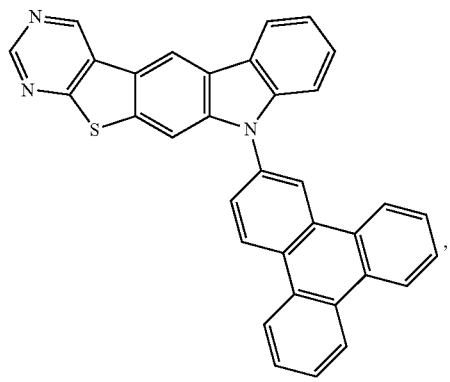
Compound 350
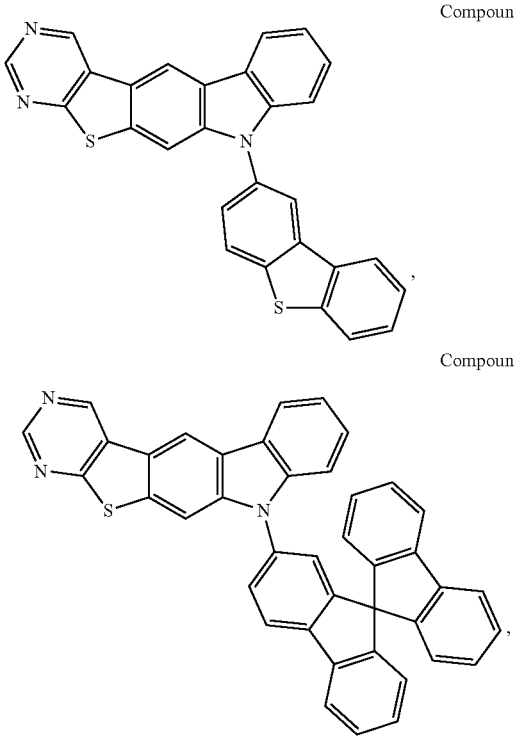
Compound 351
Compound 352
Compound 353
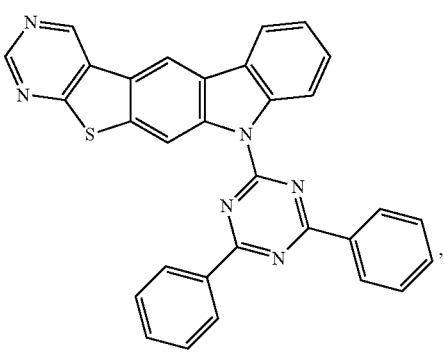
Compound 354
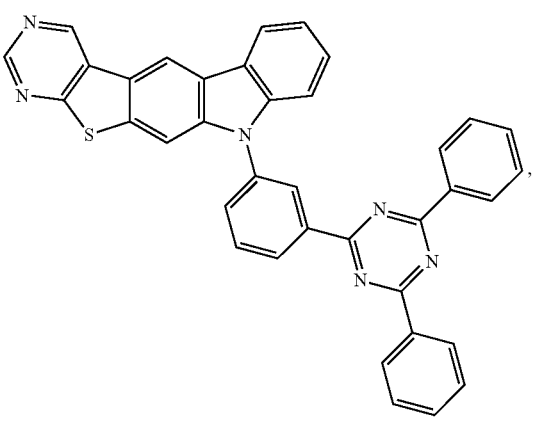
Compound 355
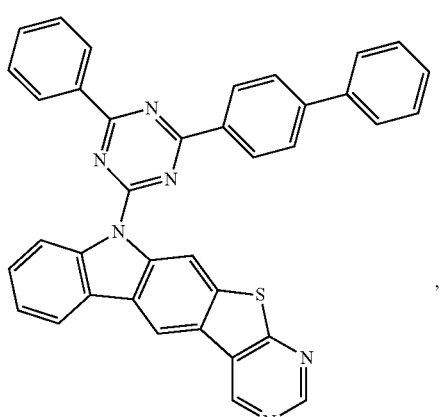
Compound 356
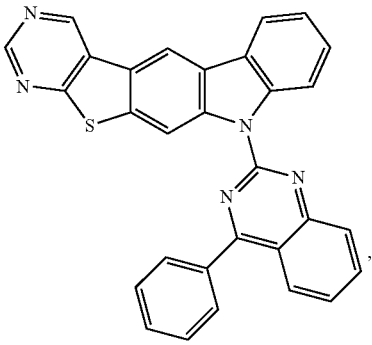

Compound 357
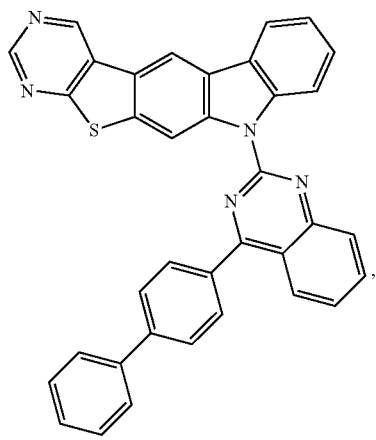
Compound 358
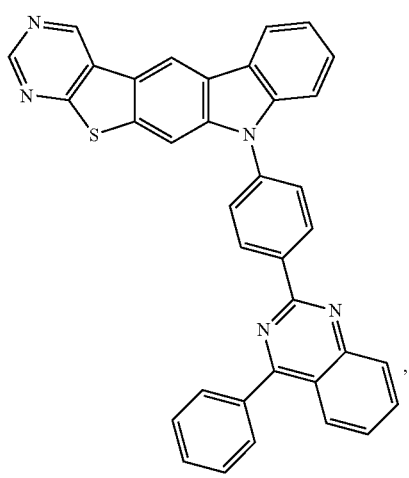
Compound 359
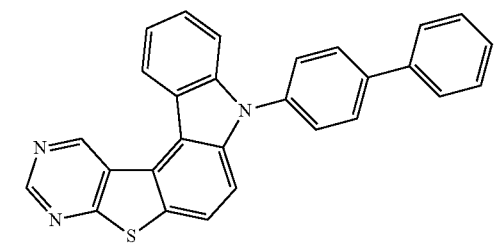
Compound 360
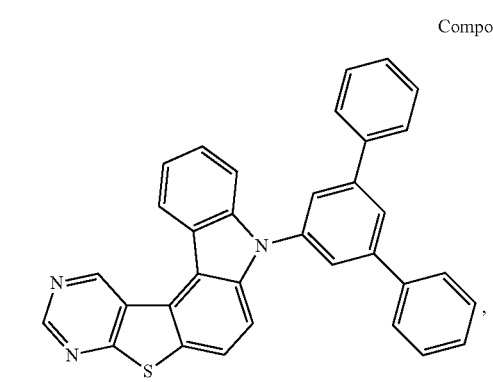
Compound 361
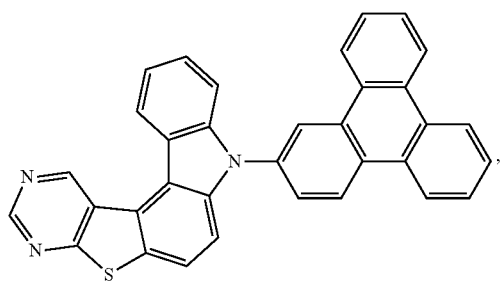
Compound 362
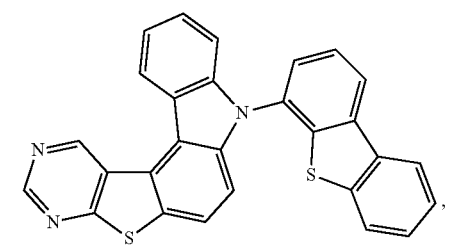
Compound 363
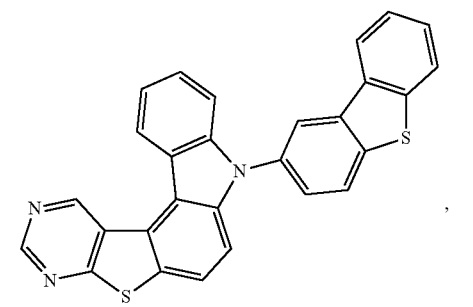
Compound 364
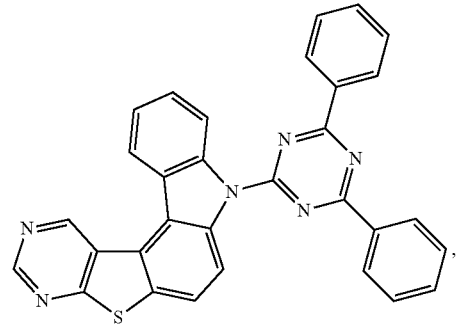
Compound 365

Compound 366
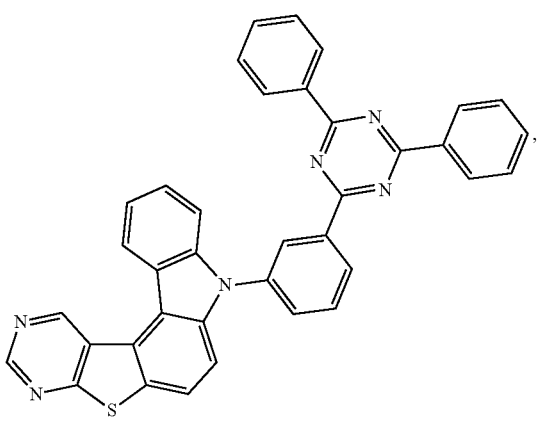
Compound 367
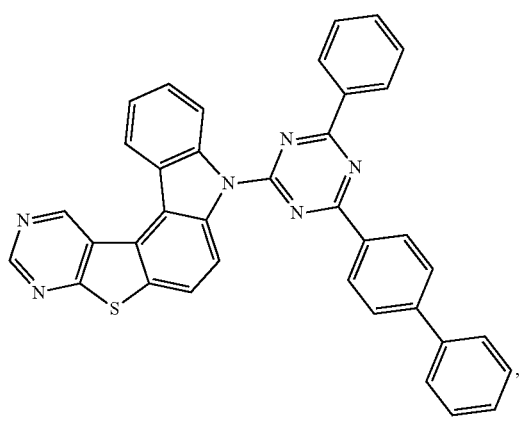
Compound 368
Compound 369
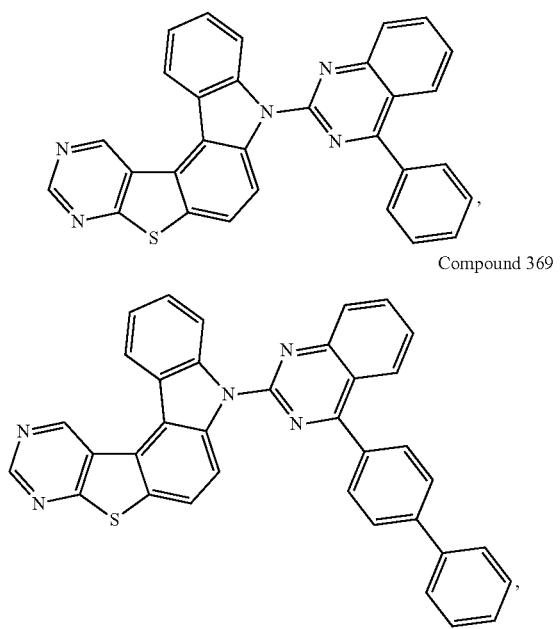
-continued
Compound 370
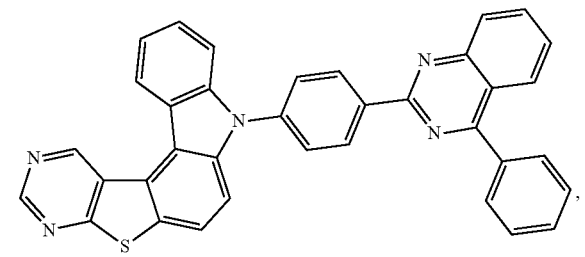
Compound 371
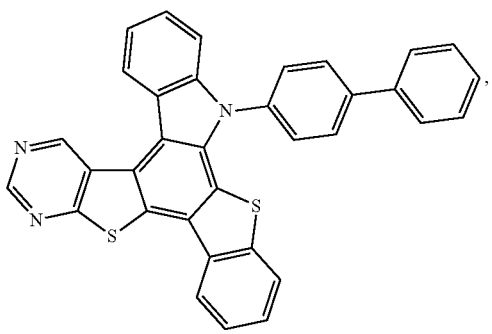
Compound 372
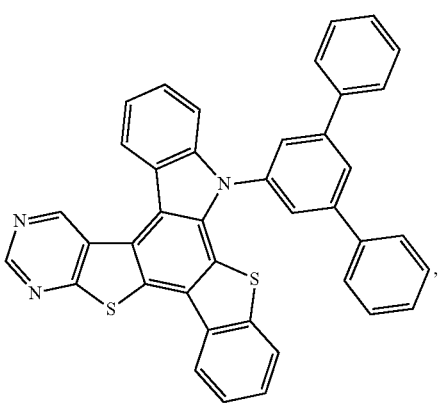
Compound 373
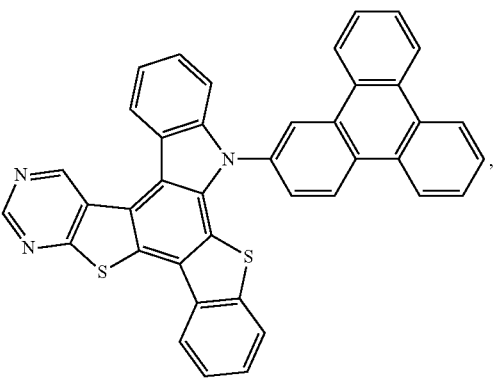

-continued
Compound 374
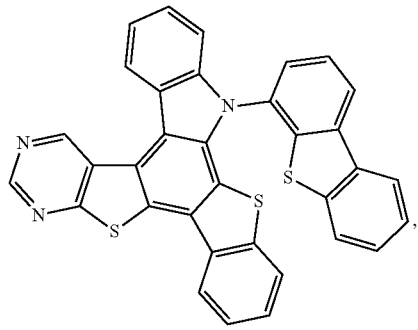
Compound 375
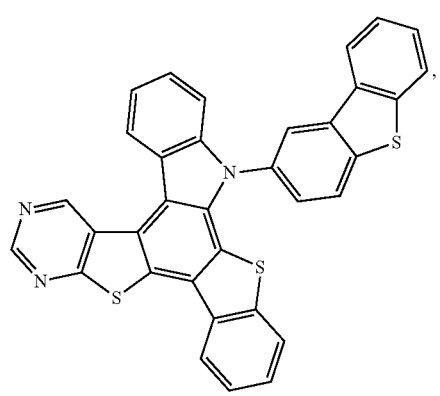
Compound 376
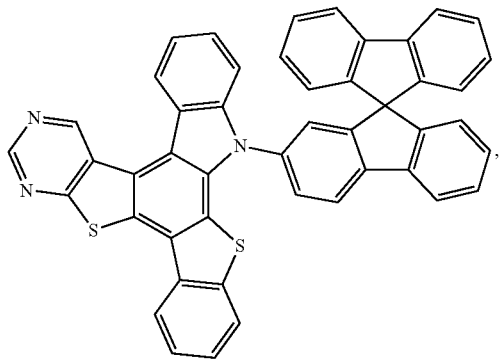
Compound 377
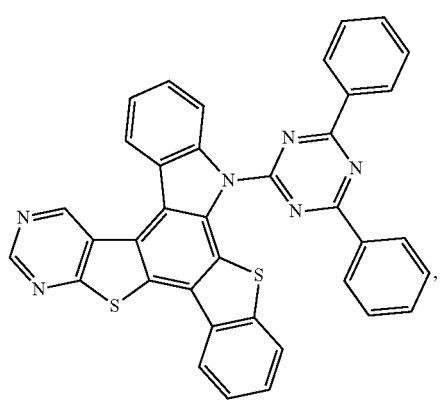
-continued
Compound 378
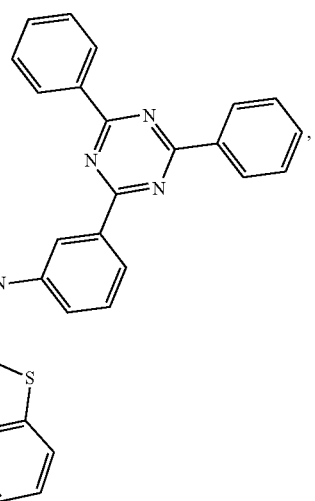
Compound 379
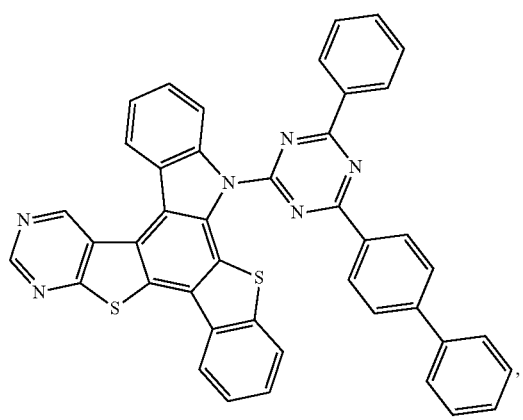
Compound 380
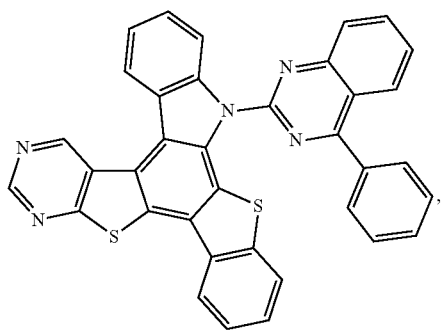

Compound 381
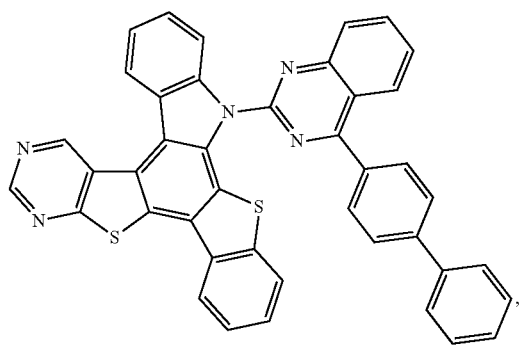
Compound 385
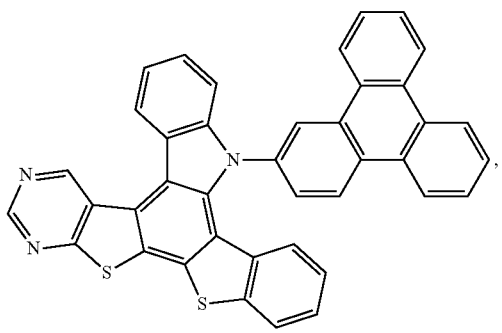
Compound 382
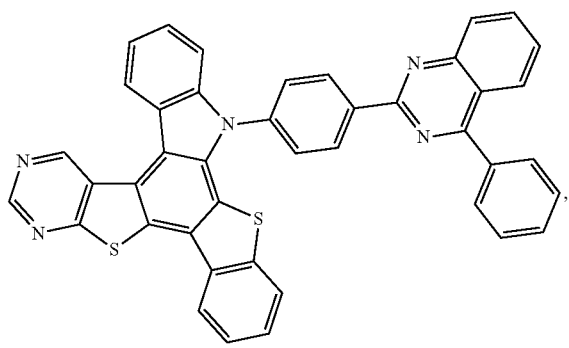
Compound 386
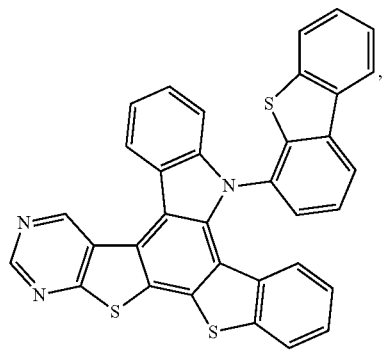
Compound 383
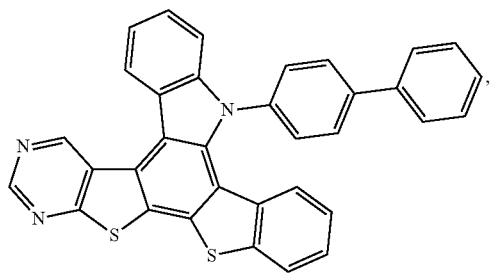
Compound 387
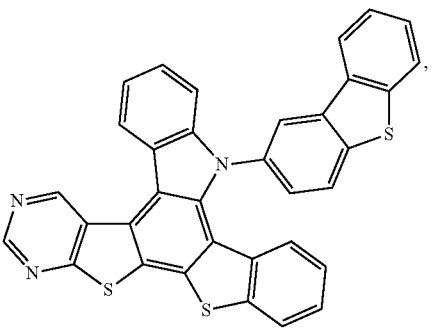
Compound 384
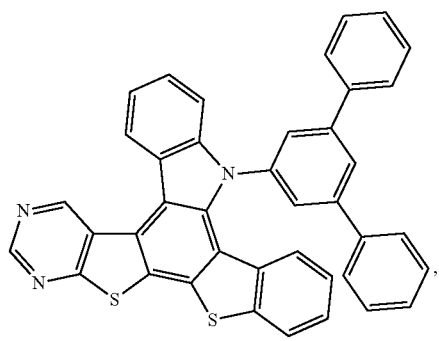
Compound 388
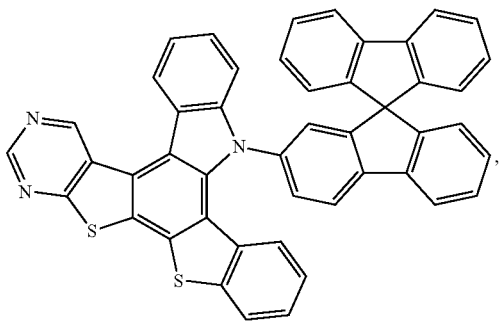

-continued
Compound 389
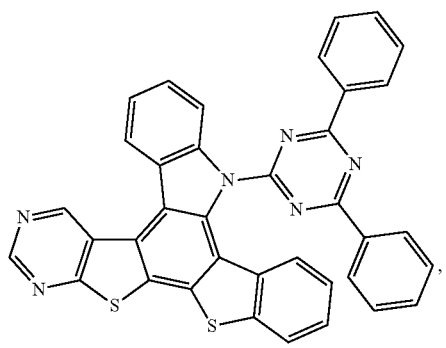
Compound 390
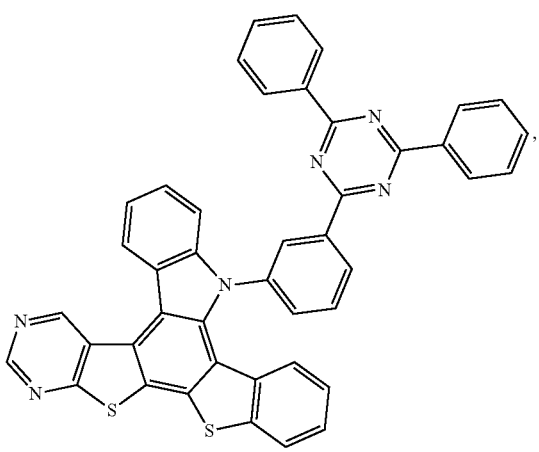
Compound 391
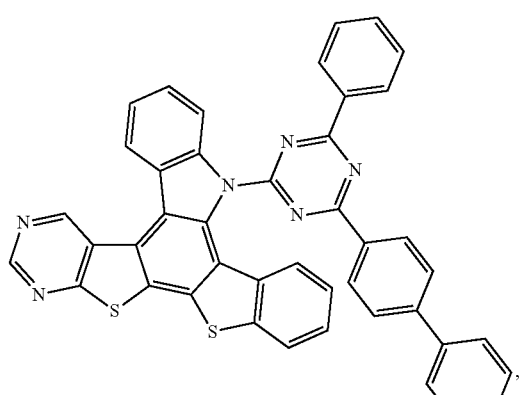
Compound 392
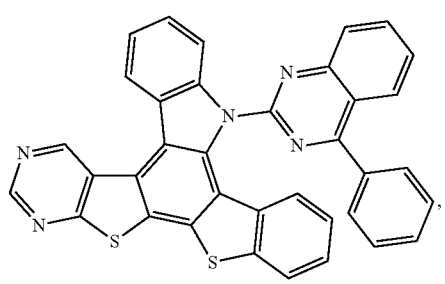
-continued
Compound 393
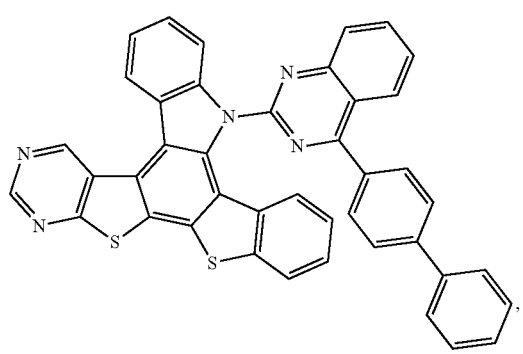
Compound 394
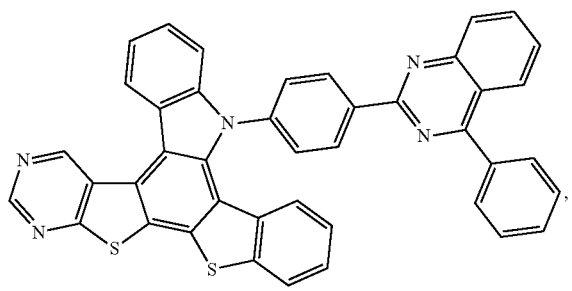
Compound 395
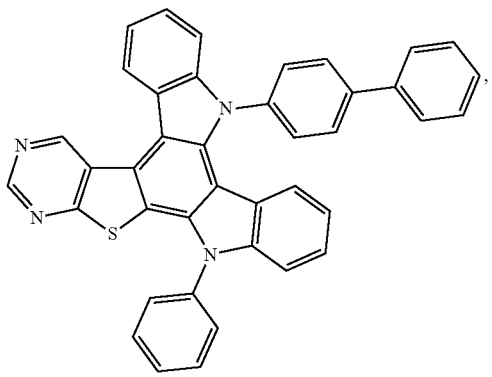
Compound 396
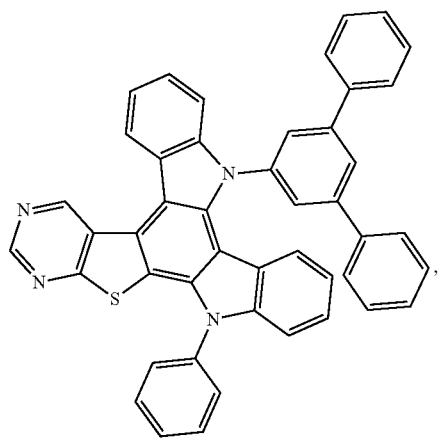

Compound 397
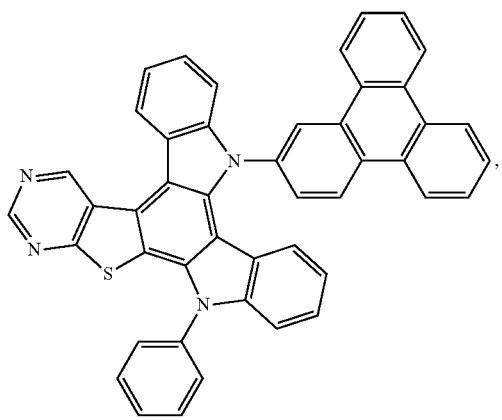
Compound 398
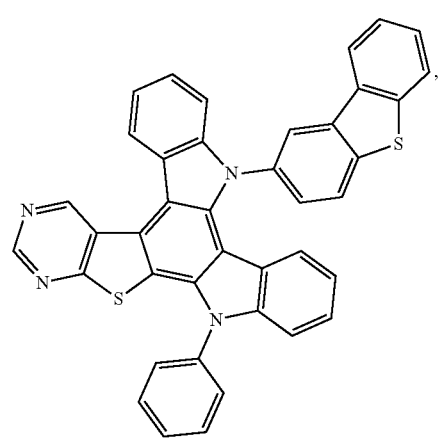
Compound 399
Compound 400
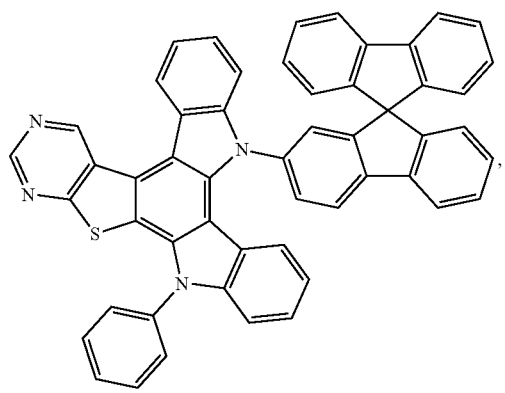
Compound 401
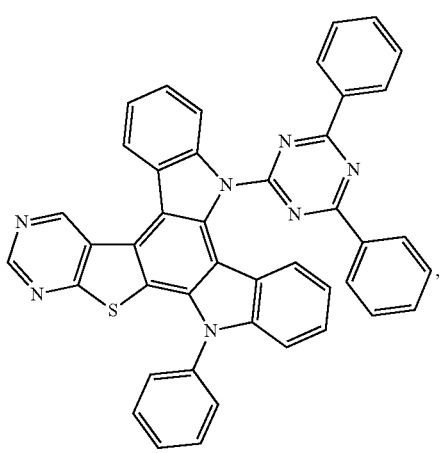
Compound 402
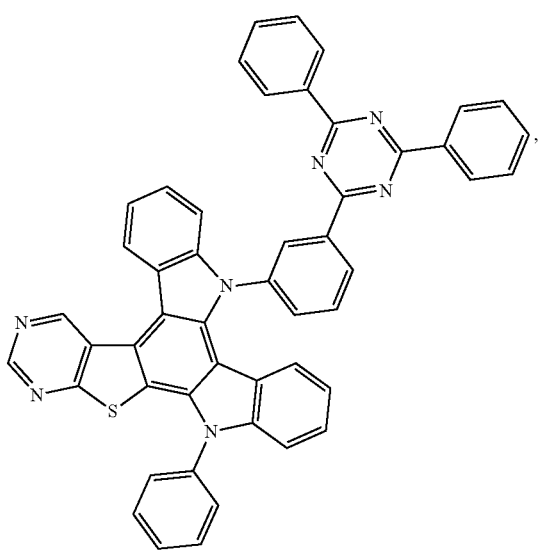

Compound 403
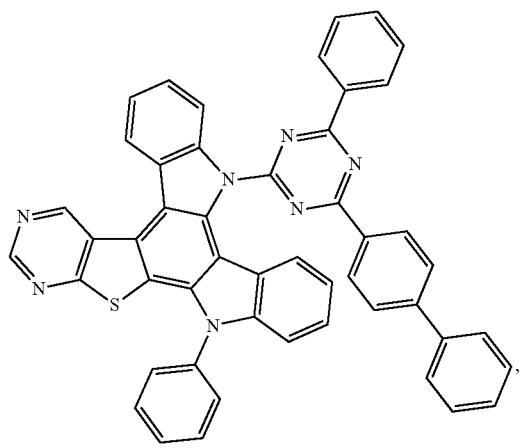
Compound 404
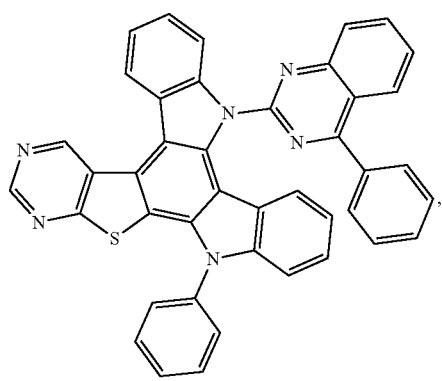
Compound 405
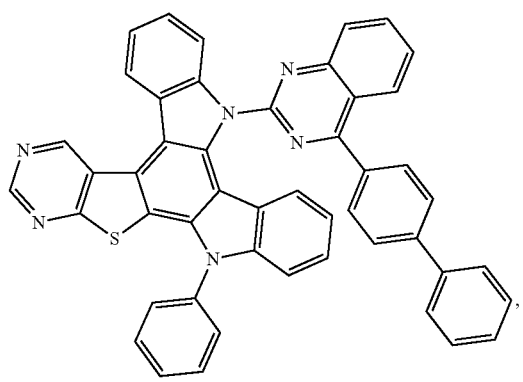
Compound 406
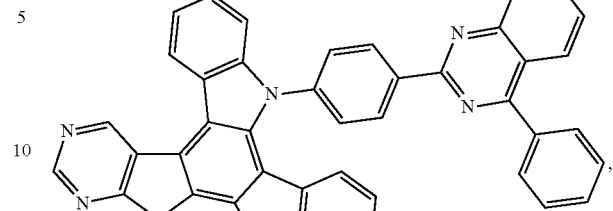
Compound 407
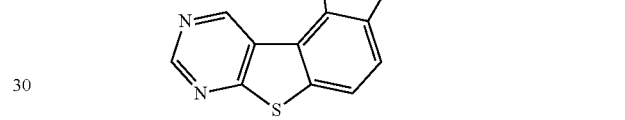
Compound 408
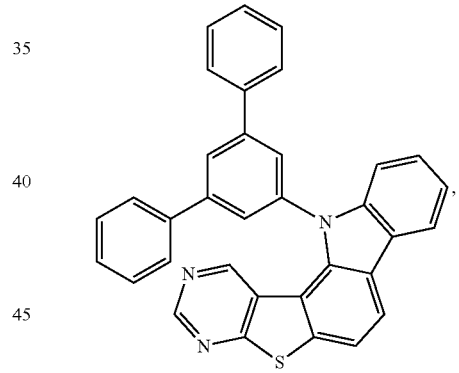
Compound 409
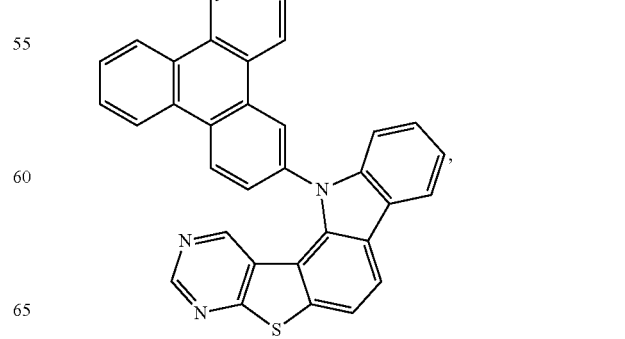

Compound 410
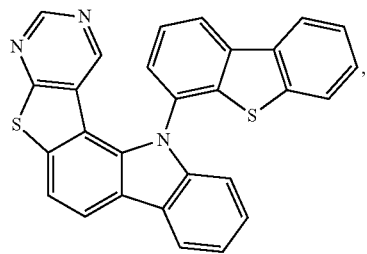
Compound 411
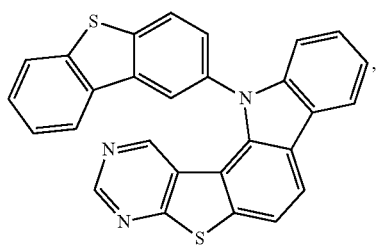
Compound 412
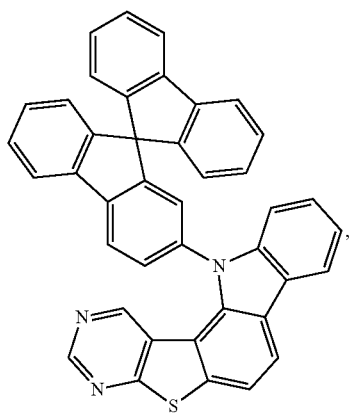
Compound 413
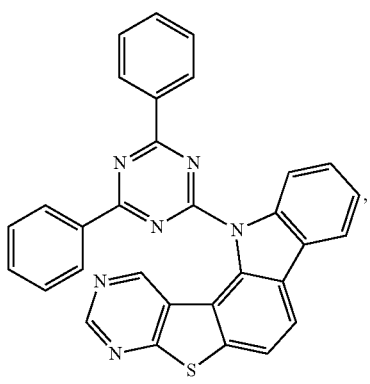
Compound 414
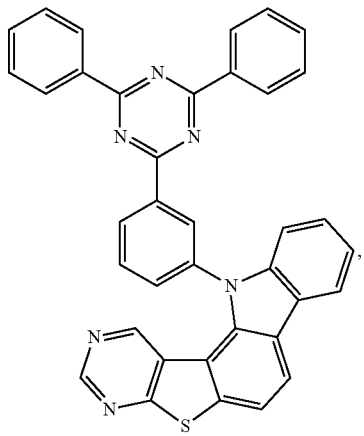
Compound 415
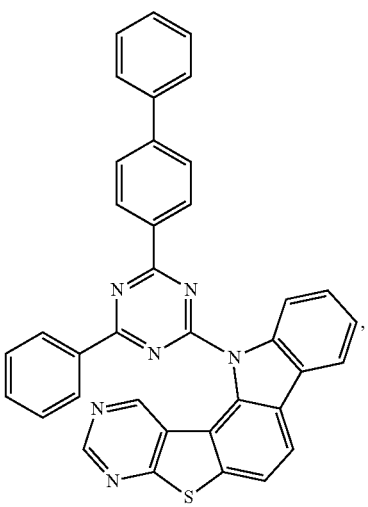
Compound 416
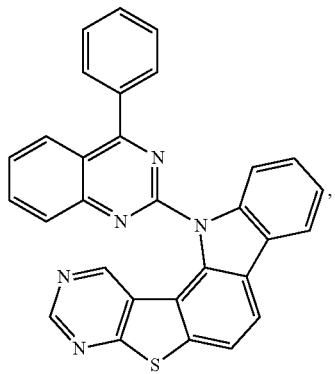

-continued
Compound 417
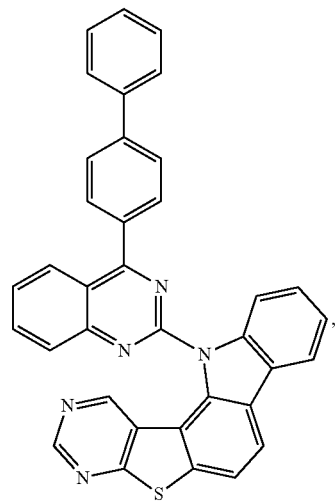
Compound 418
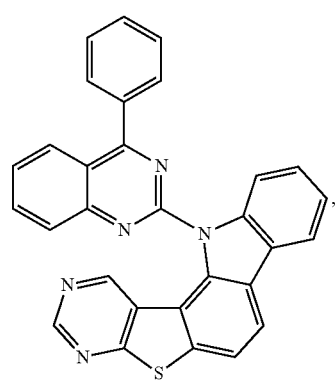
Compound 419
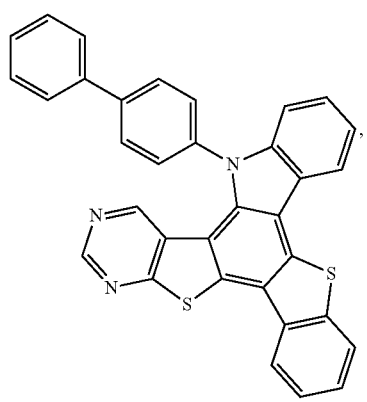
-continued
Compound 420
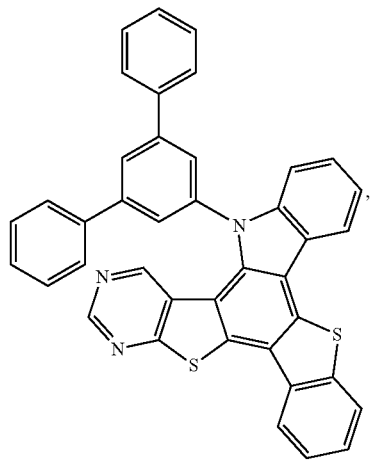
Compound 421
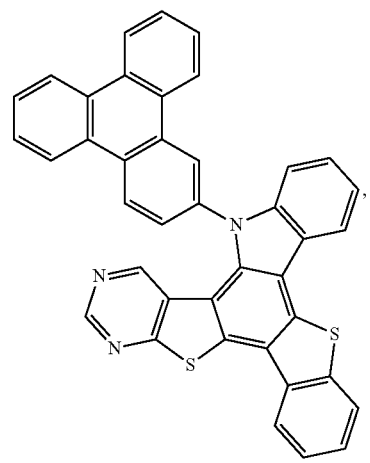
Compound 422
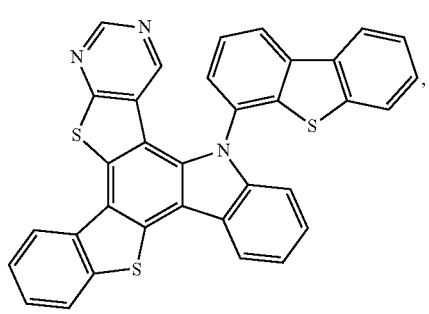
Compound 423
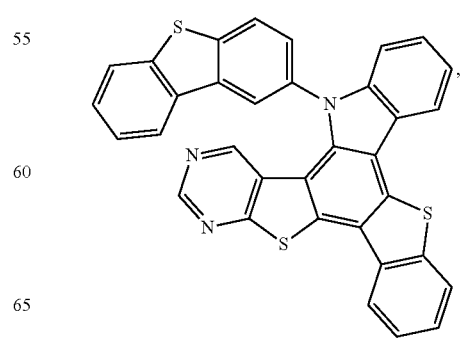

Compound 424
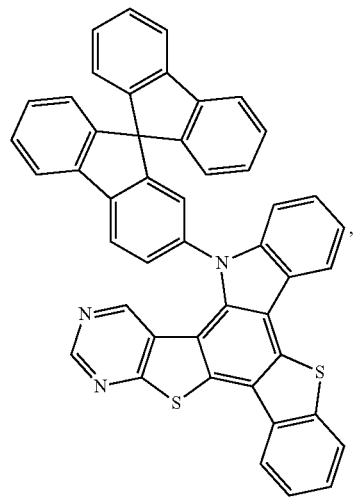
Compound 425
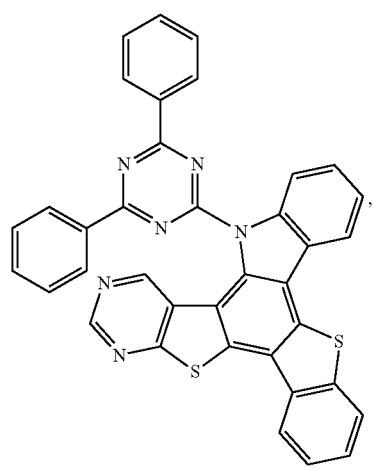
Compound 426
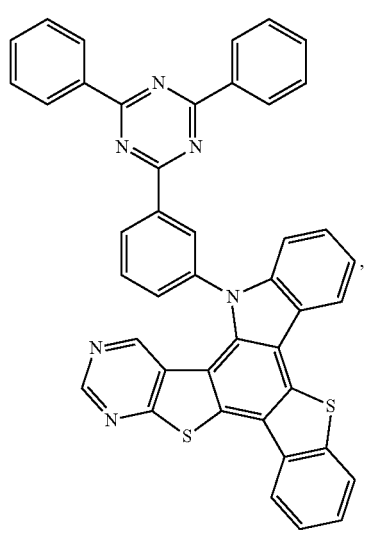
Compound 427
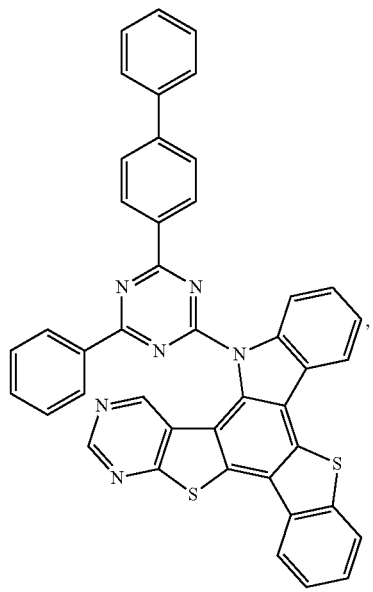
Compound 428

Compound 429
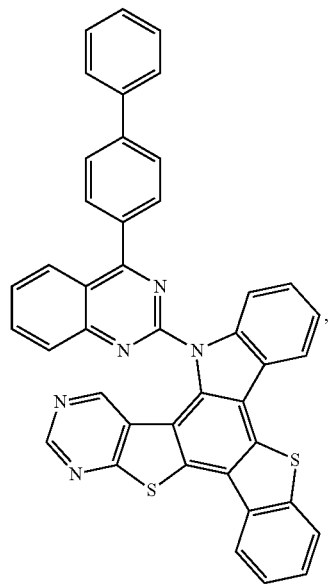
Compound 432
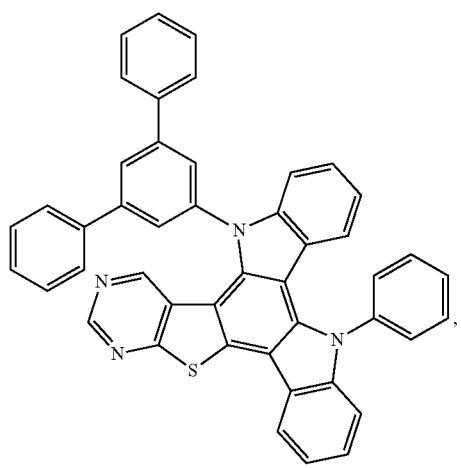
Compound 430
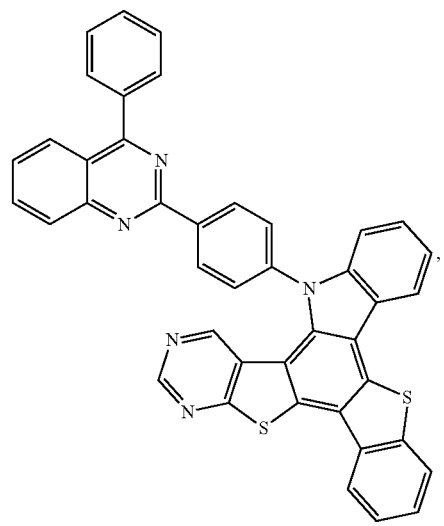
Compound 433
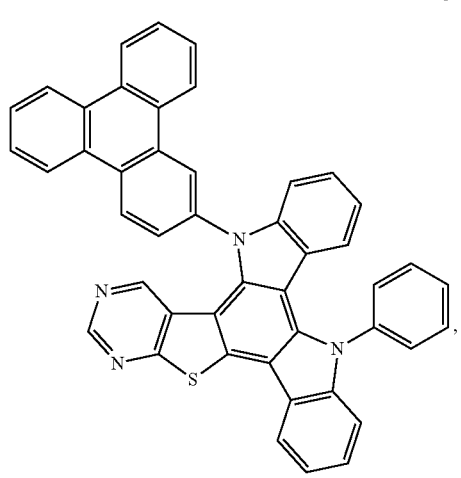
Compound 431
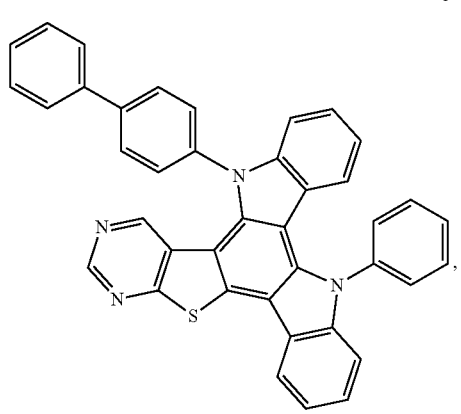
Compound 434
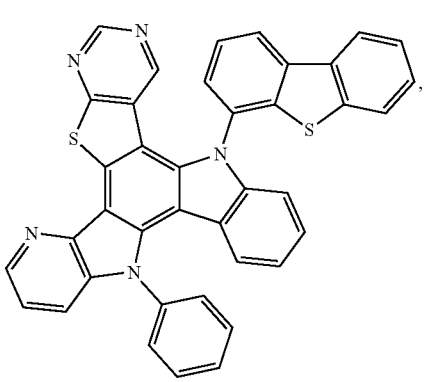

Compound 435
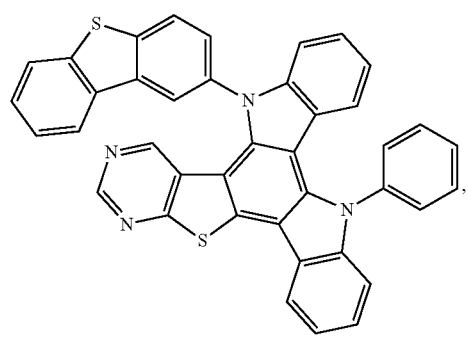
Compound 436
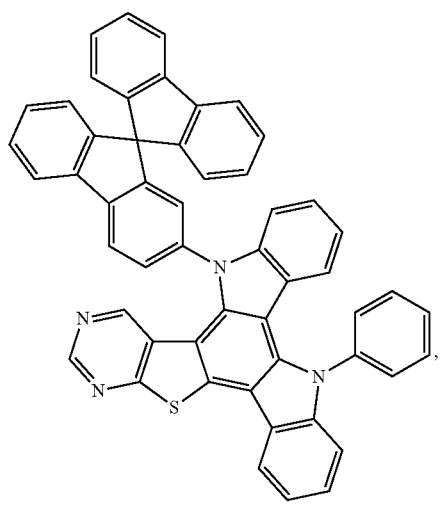
Compound 437
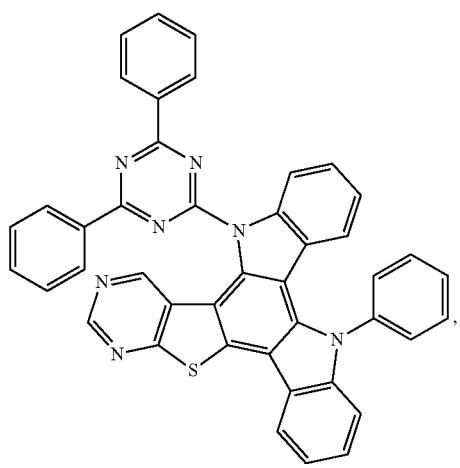
Compound 438
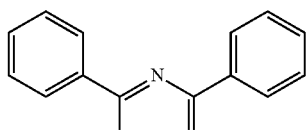
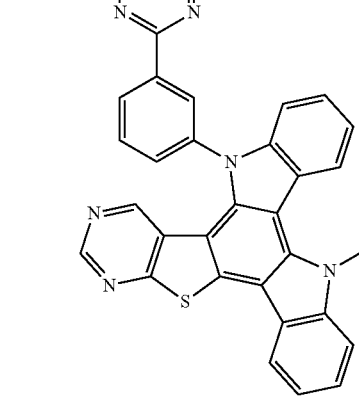
Compound 439
Compound 440
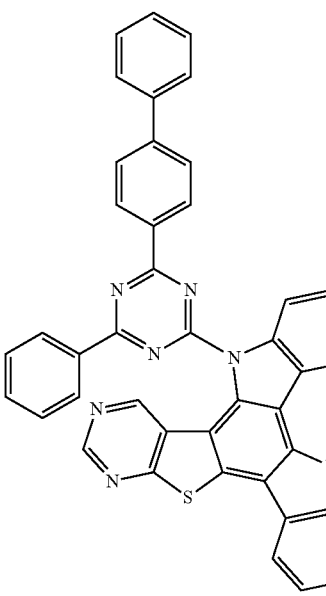

Compound 441
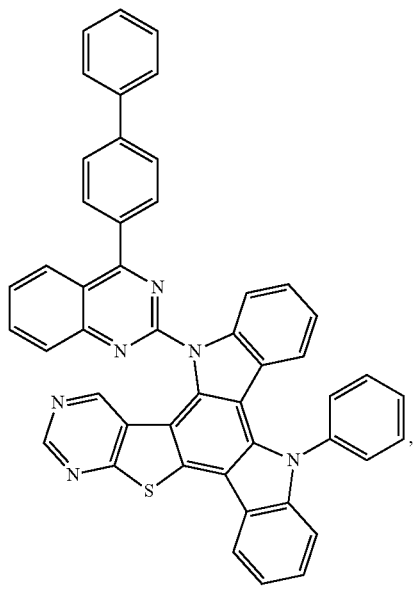
Compound 442
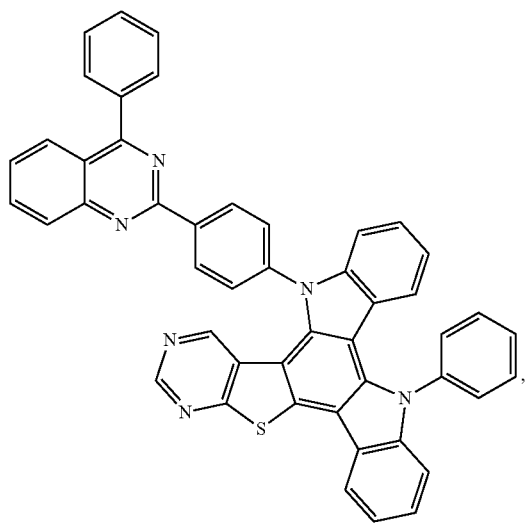
Compound 443
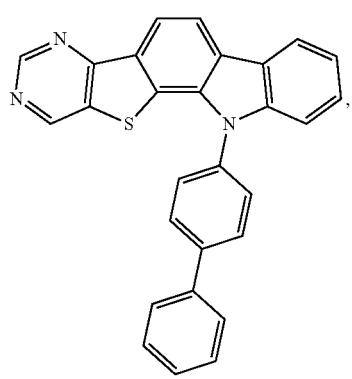
Compound 444
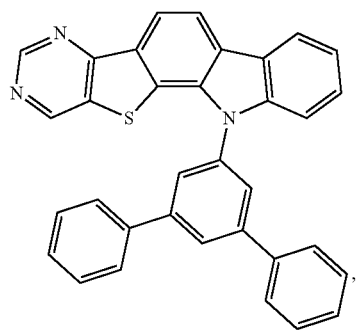
Compound 445
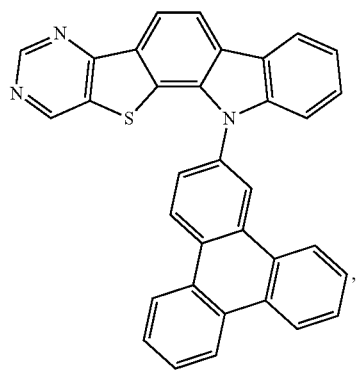
Compound 446
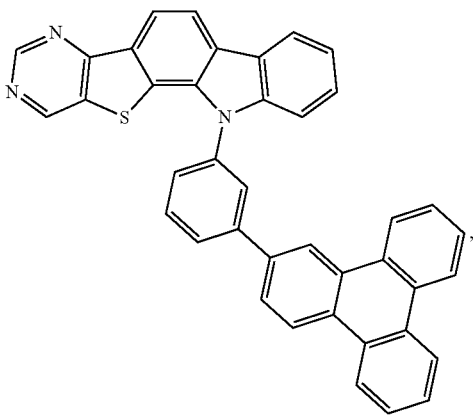
Compound 447
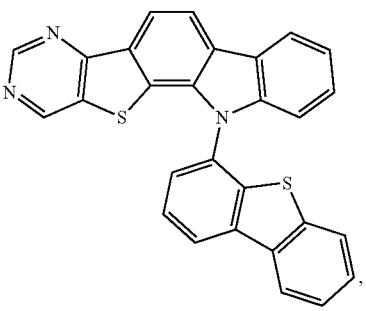

Compound 448
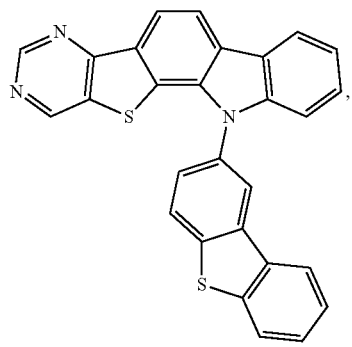
Compound 449
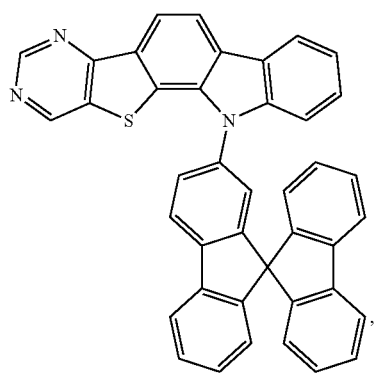
Compound 450
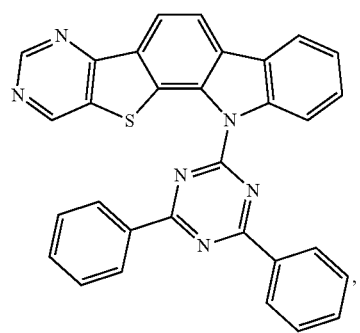
Compound 451
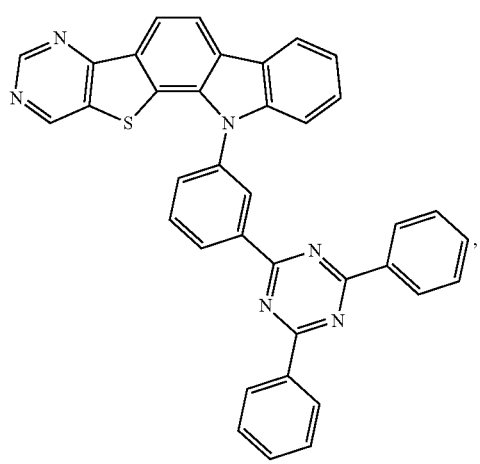
Compound 452
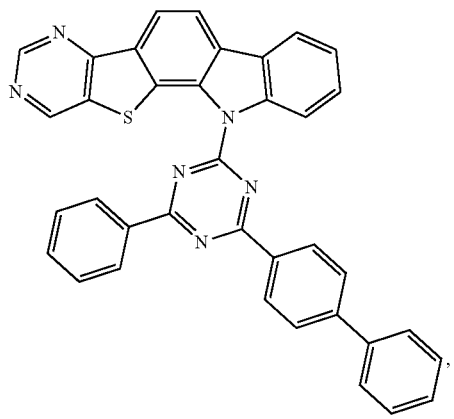
Compound 453
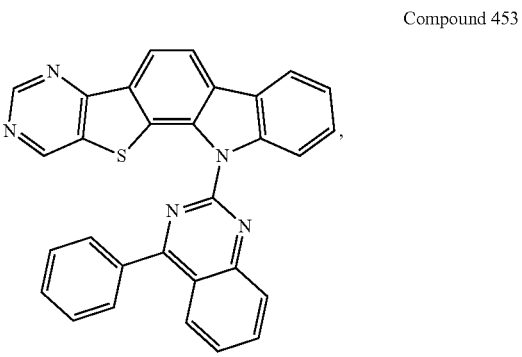
Compound 454
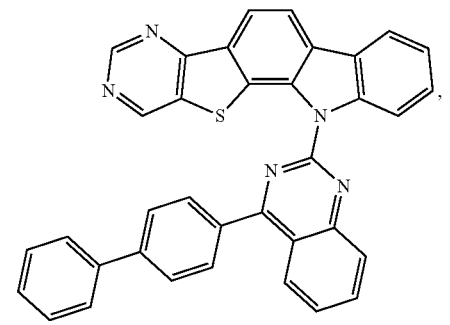
Compound 455
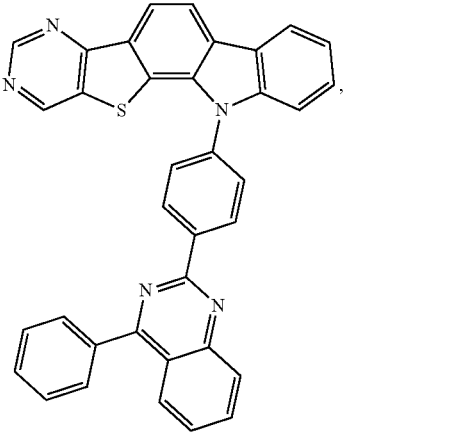

Compound 456
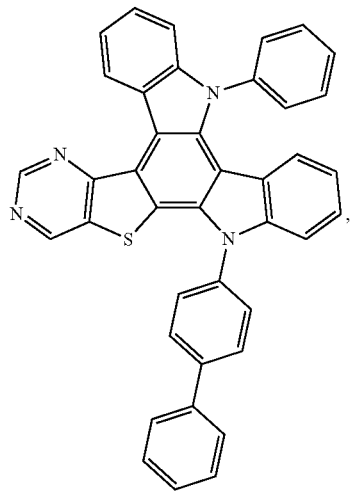
Compound 457
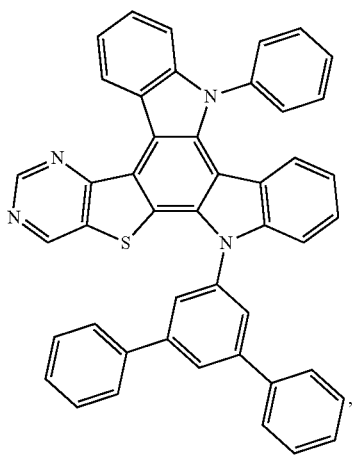
Compound 458
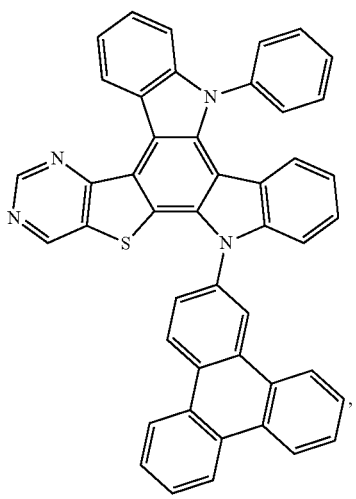
Compound 459
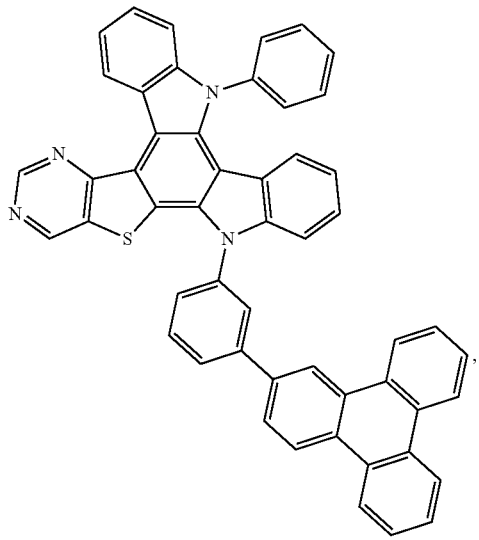
Compound 460
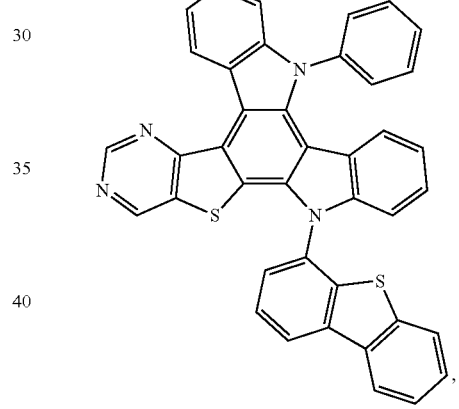
Compound 461
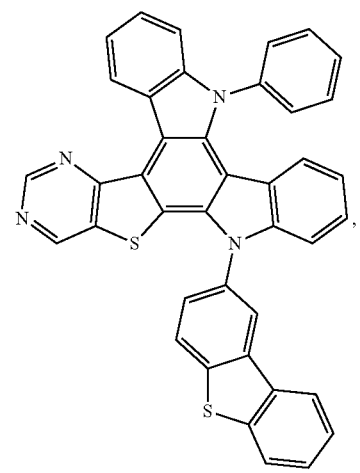

-continued
Compound 462
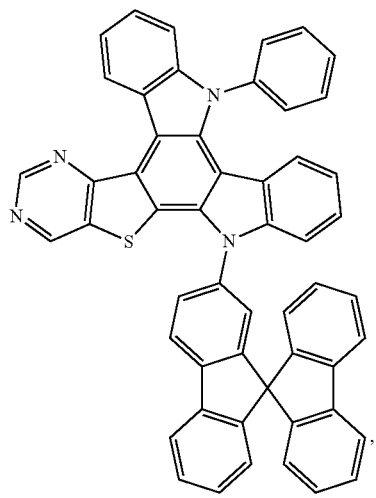
Compound 463
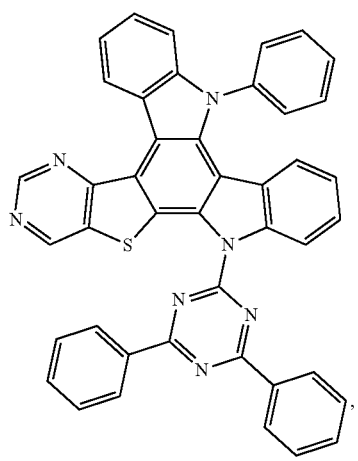
Compound 464
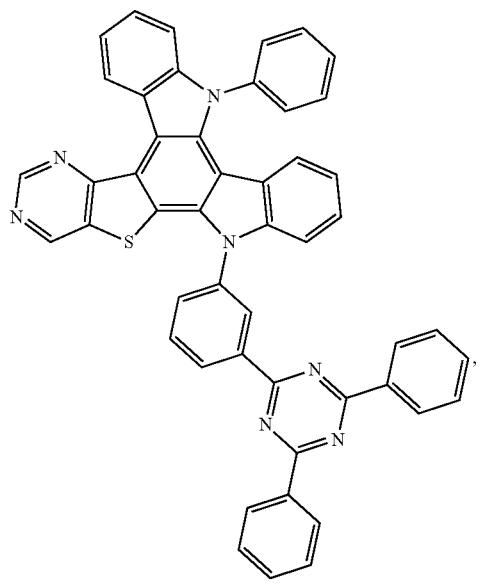
-continued
Compound 465
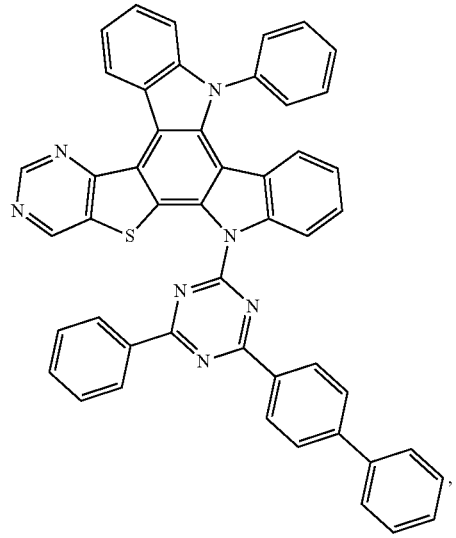
Compound 466
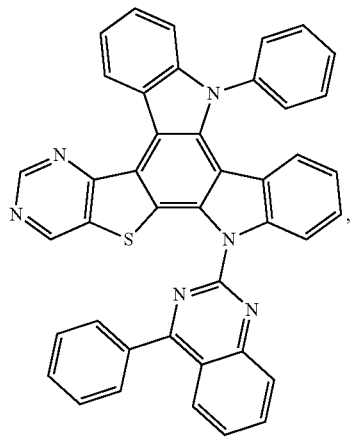
Compound 467

Compound 468
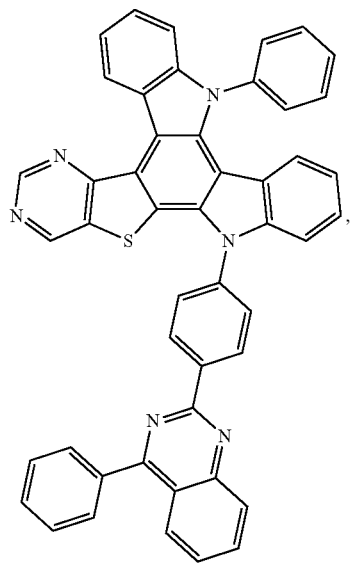
Compound 469
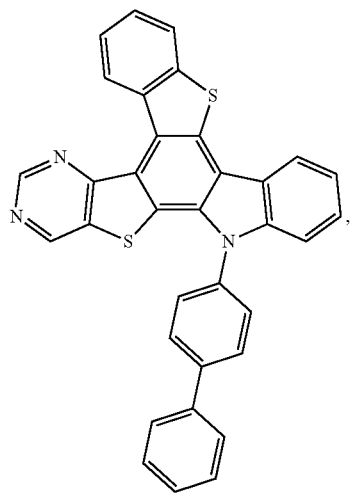
Compound 470
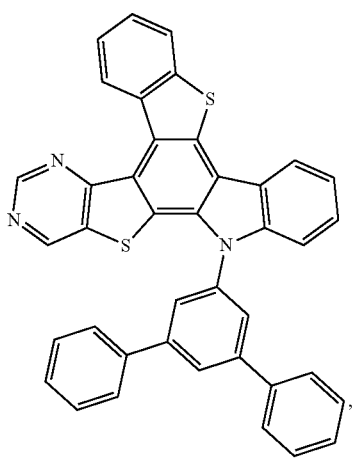
Compound 471
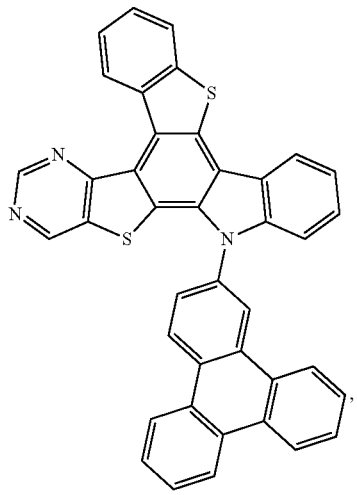
Compound 472
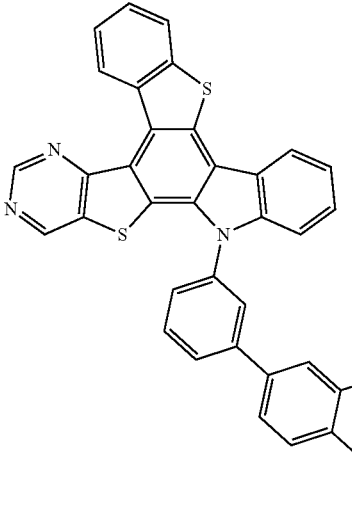
Compound 473

Compound 474
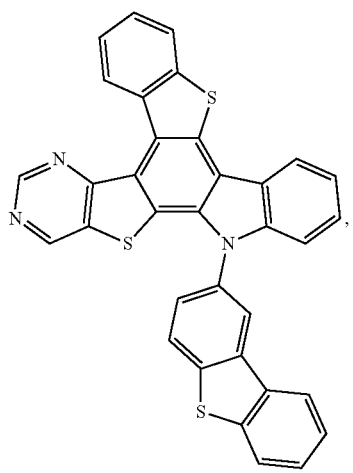
Compound 475
Compound 476
Compound 477
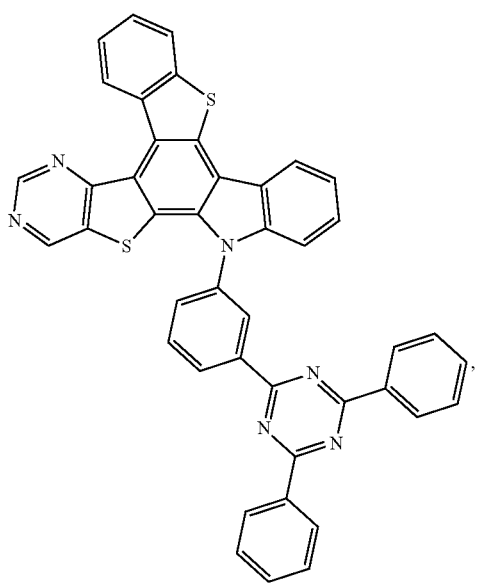
Compound 478
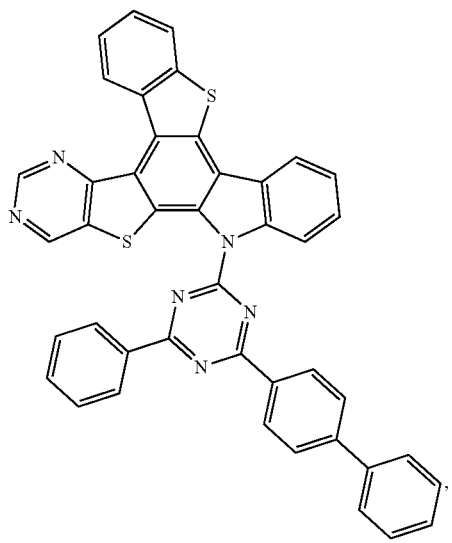
Compound 479
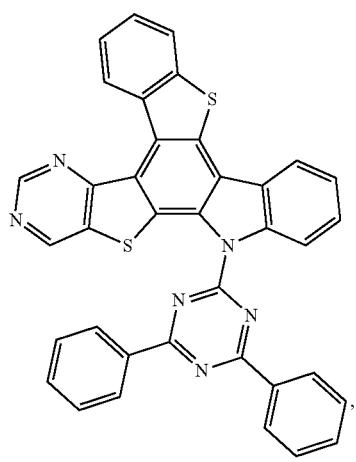
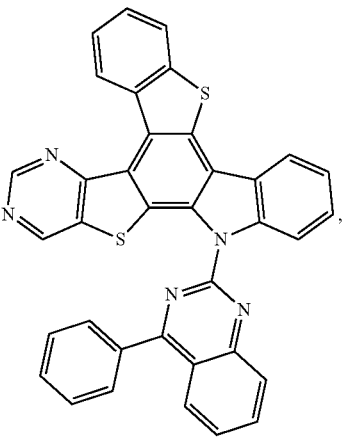

Compound 480
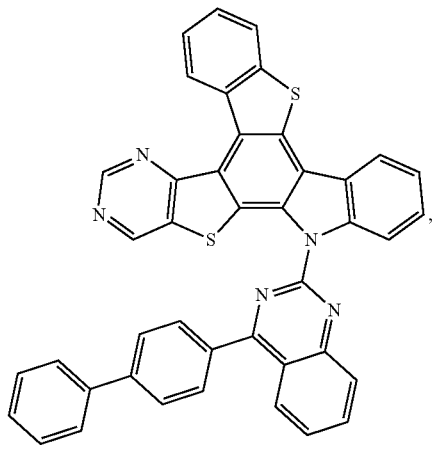
Compound 481
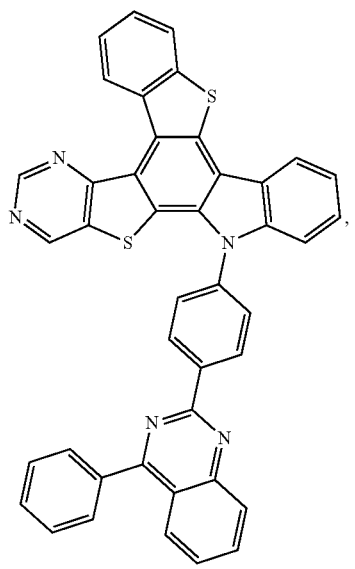
Compound 482
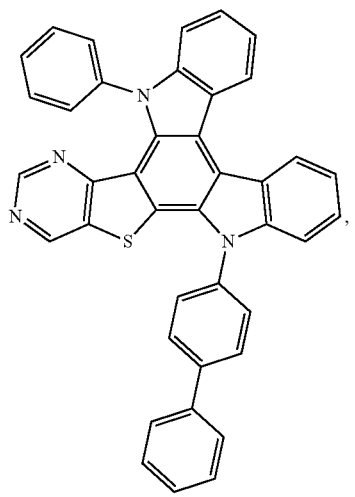
Compound 483
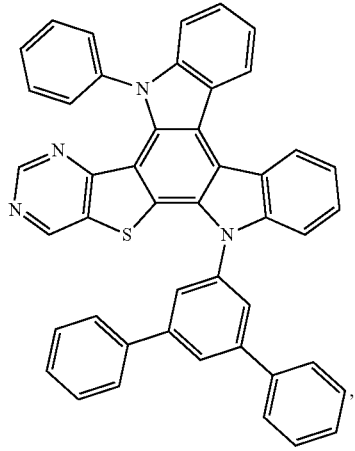
Compound 484
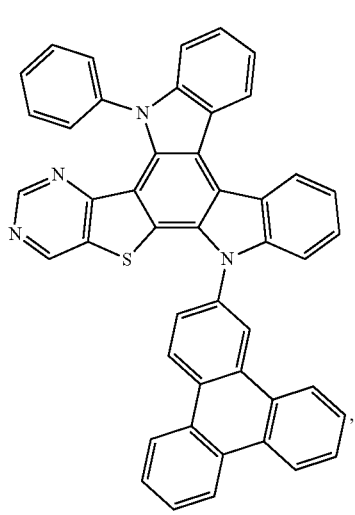
Compound 485
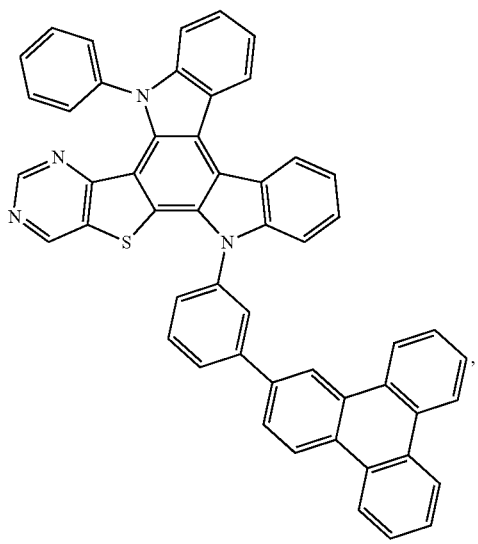

Compound 486
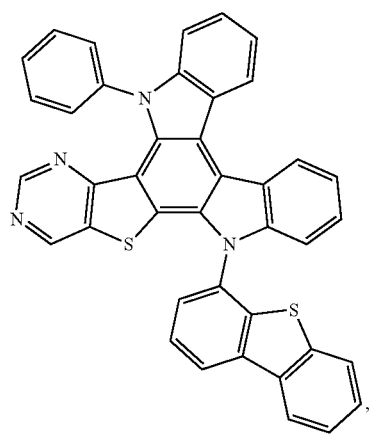
Compound 487
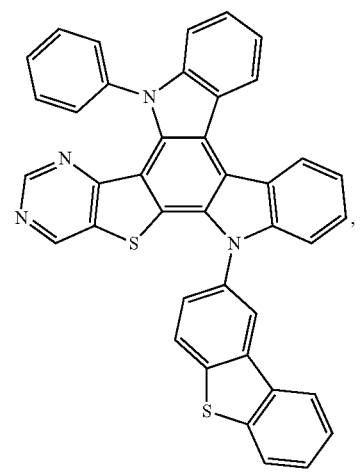
Compound 488
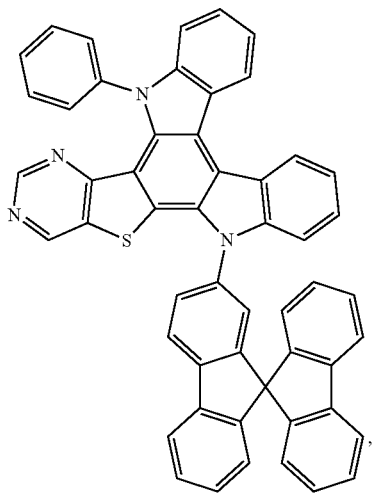
Compound 489
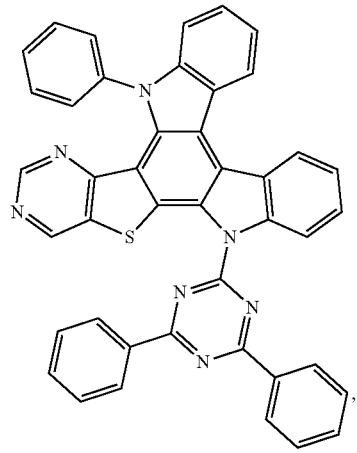
Compound 490
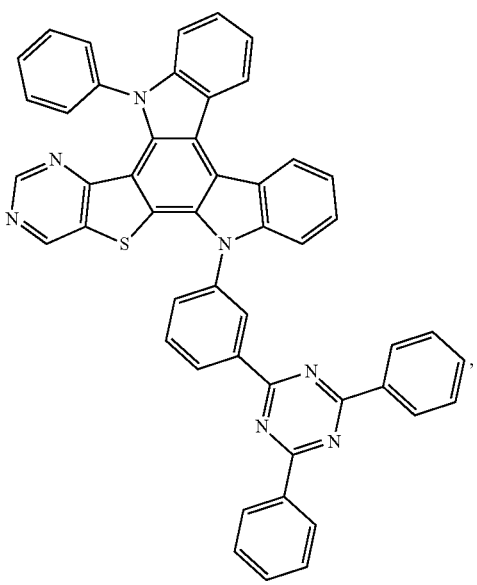
Compound 491
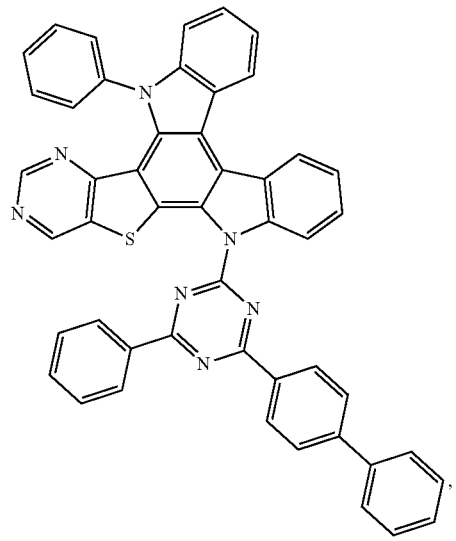

Compound 492
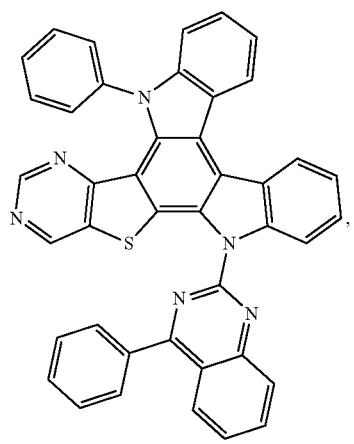
Compound 493
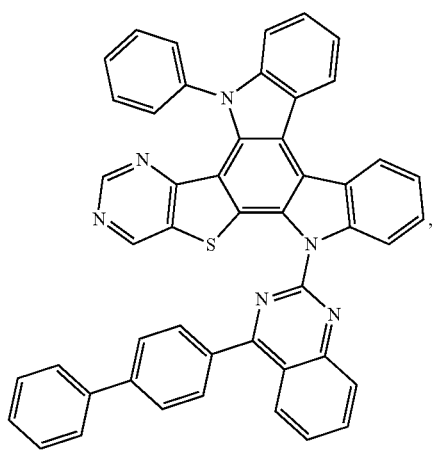
Compound 494
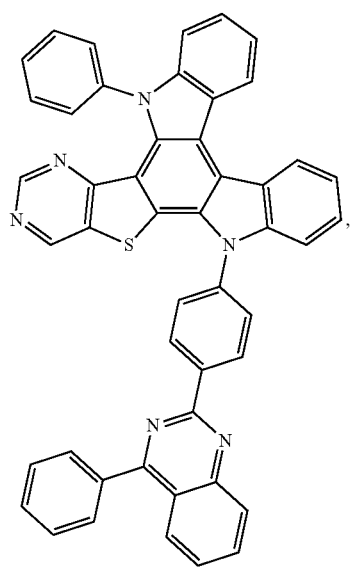
Compound 495
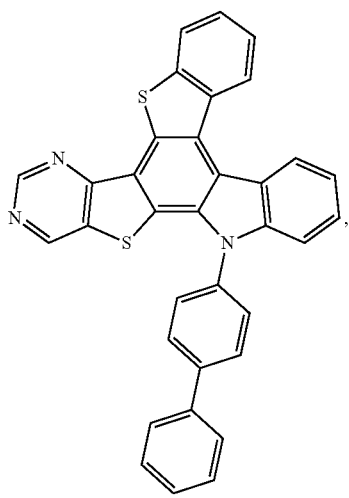
Compound 496
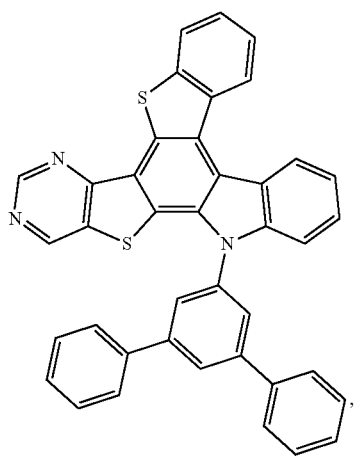
Compound 497
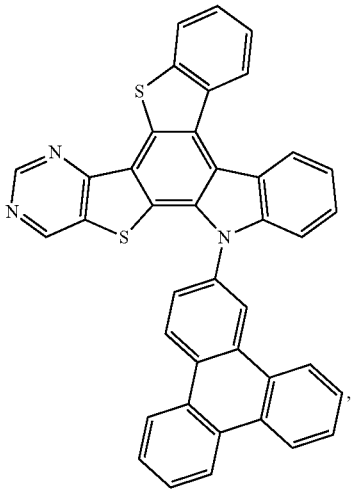

Compound 498
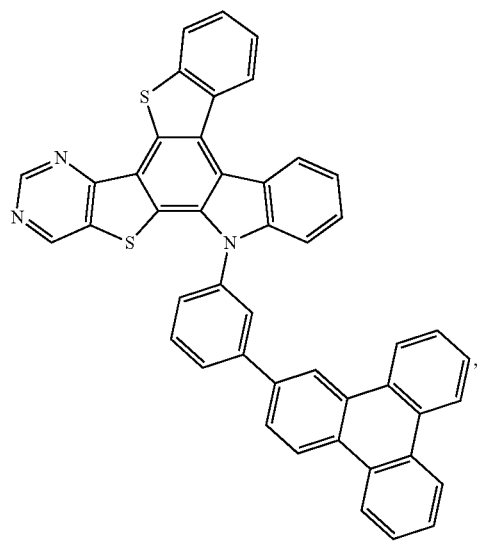
Compound 499
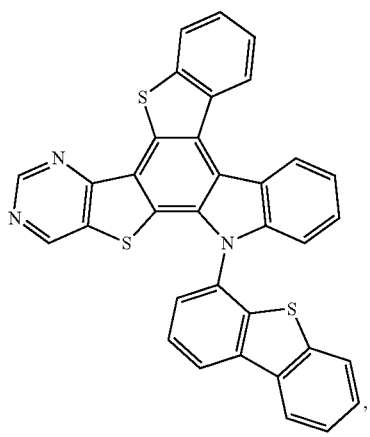
Compound 500
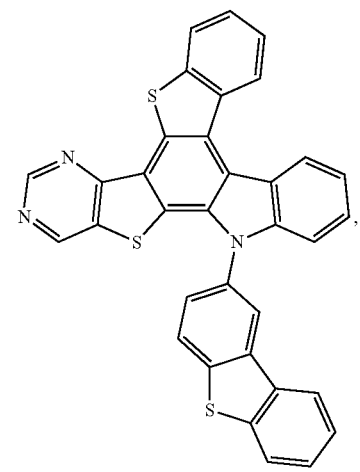
Compound 501
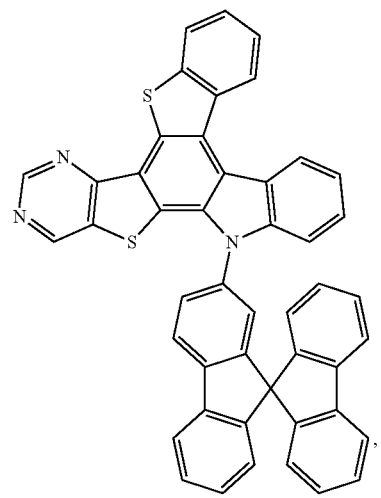
Compound 502
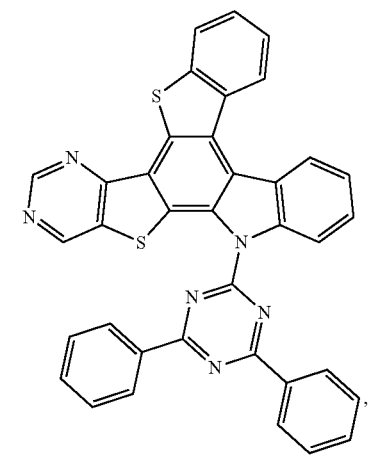
Compound 503
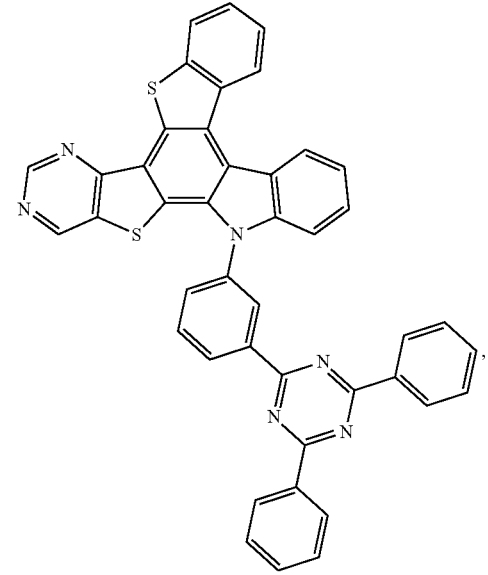

Compound 504
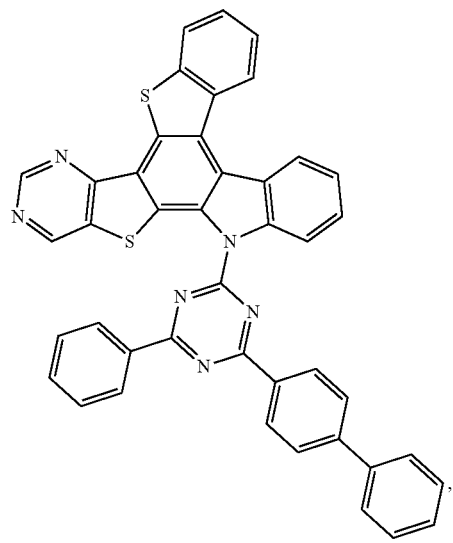
Compound 505
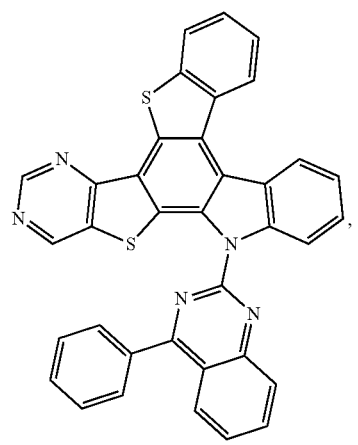
Compound 506
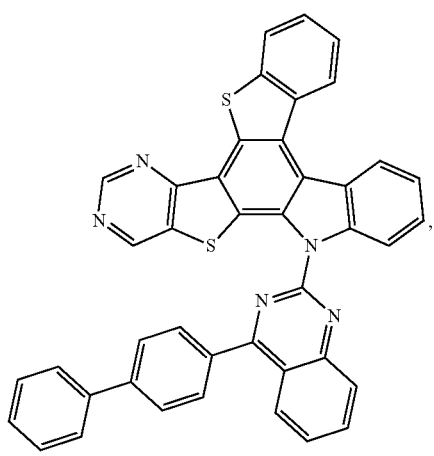
Compound 507
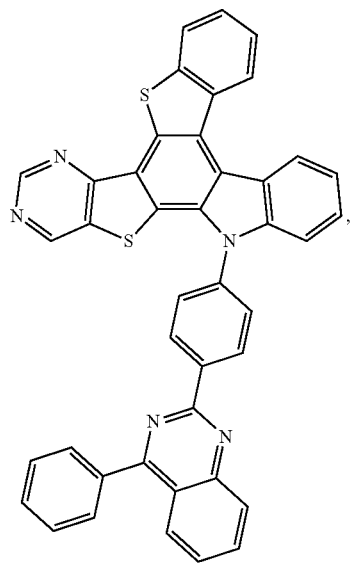
Compound 508
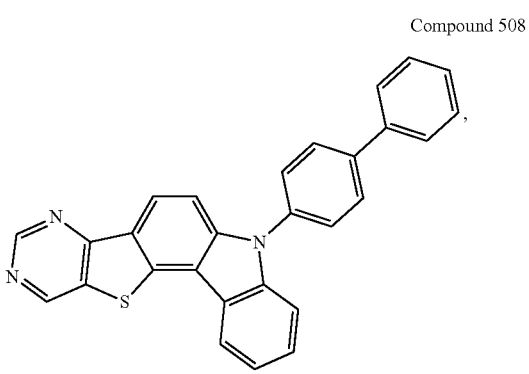
Compound 509
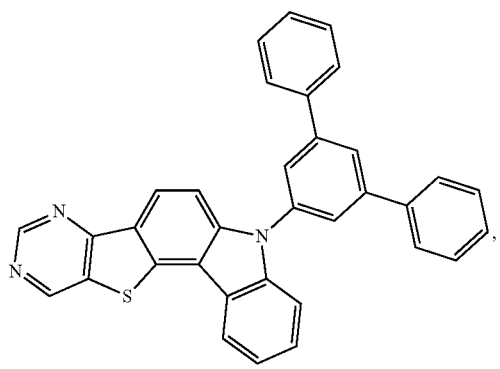

Compound 510
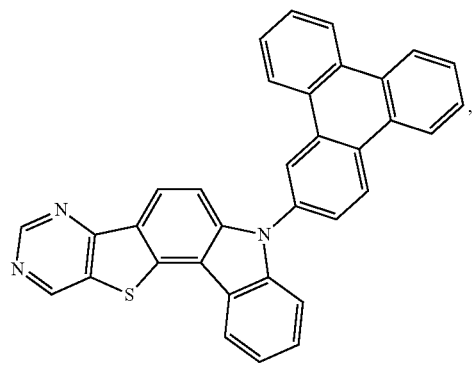
Compound 511
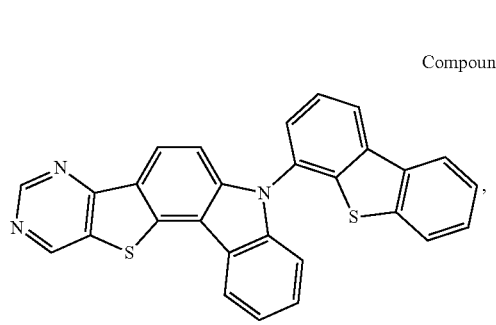
Compound 512
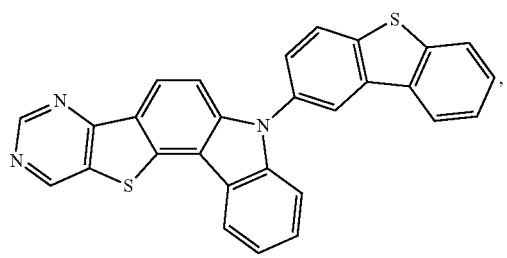
Compound 513
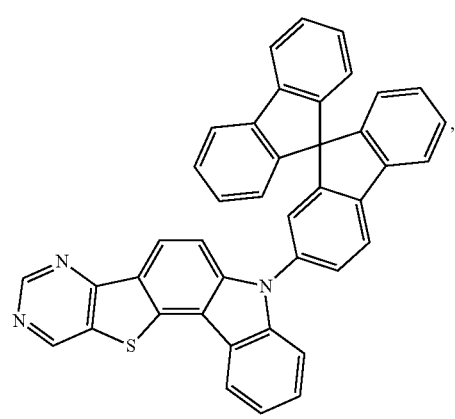
Compound 514
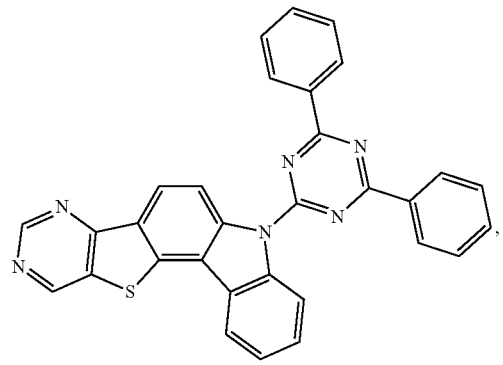
Compound 515
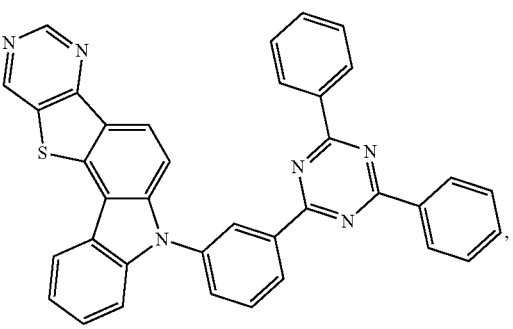
Compound 516
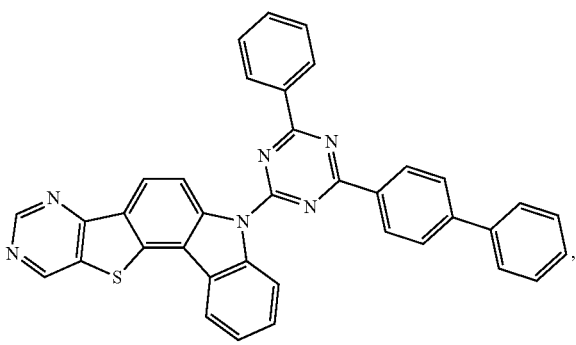
Compound 517
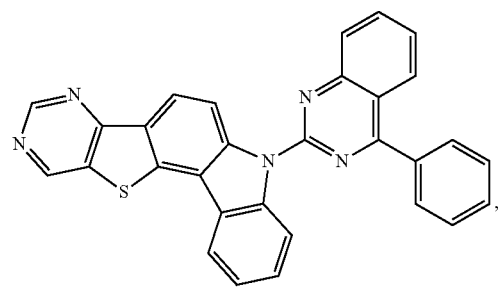

-continued
Compound 518
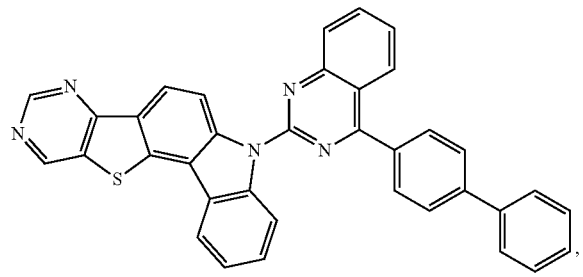
Compound 519
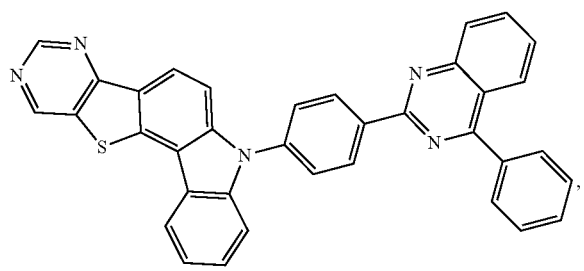
Compound 520
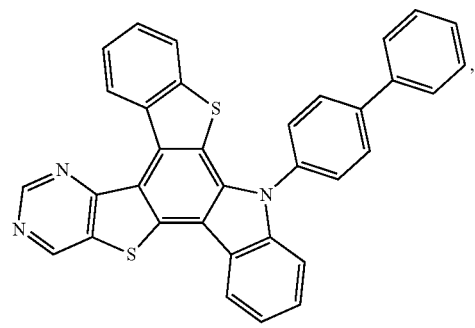
Compound 521
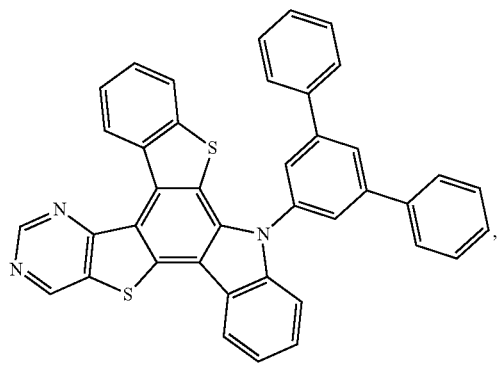
-continued
Compound 522
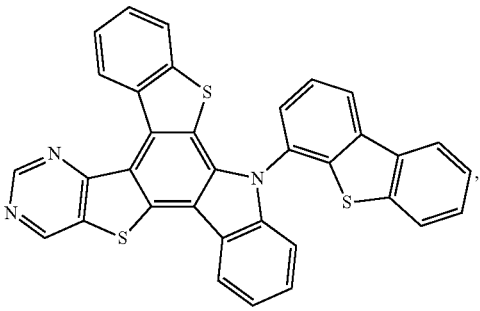
Compound 523
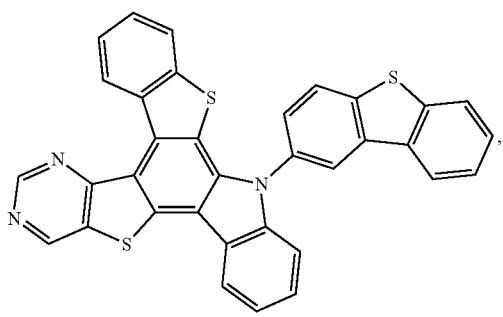
Compound 524
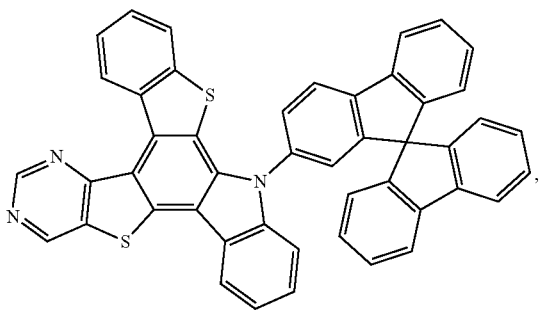
Compound 525

Compound 526
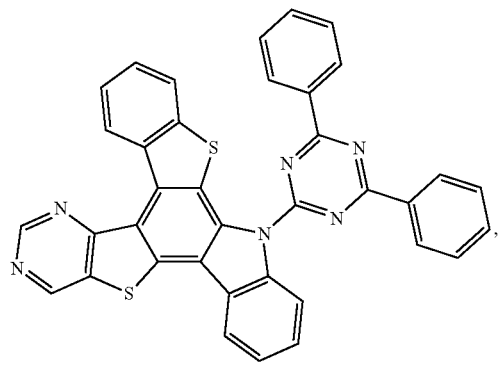
Compound 527
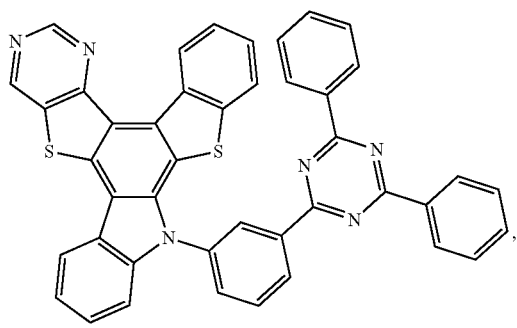
Compound 528
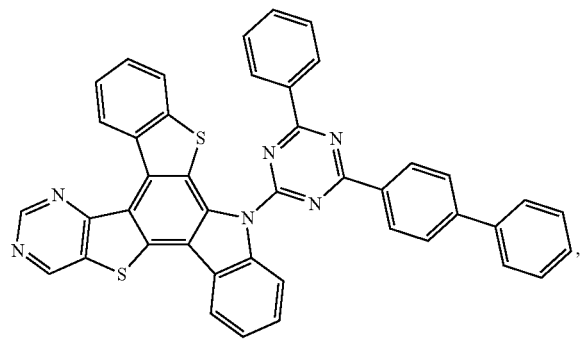
Compound 529
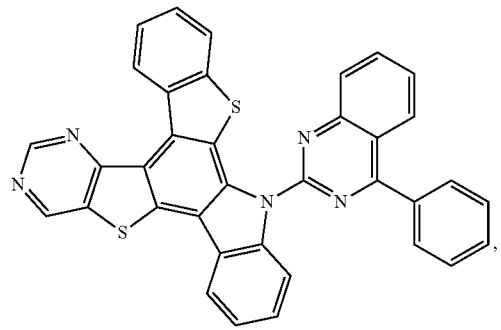
Compound 530
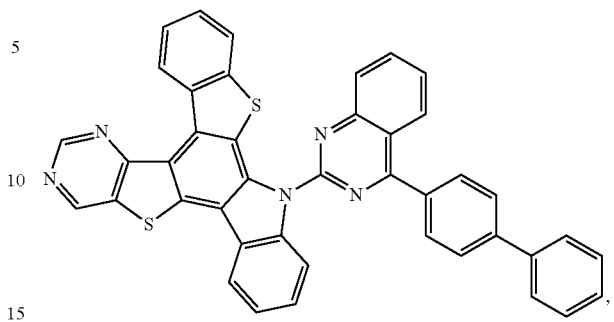
Compound 531
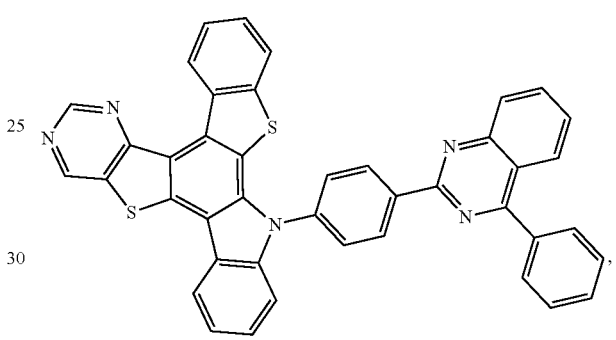
Compound 532
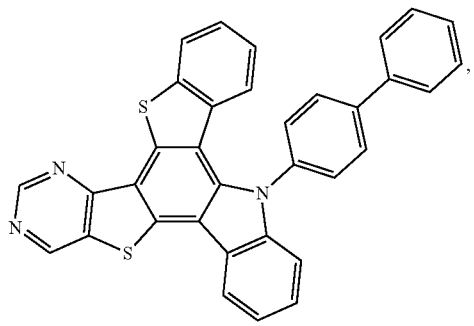
Compound 533
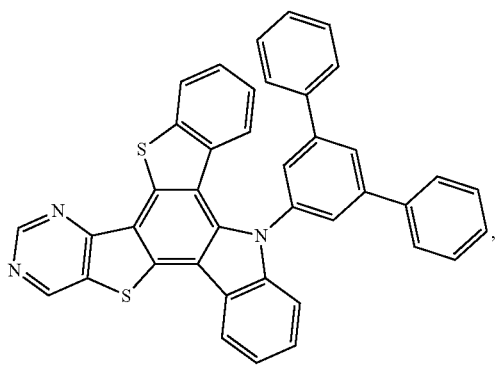

Compound 534
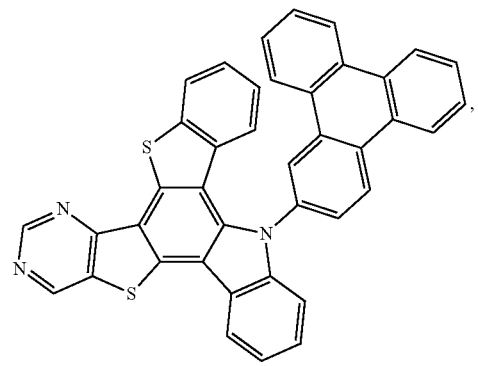
Compound 538
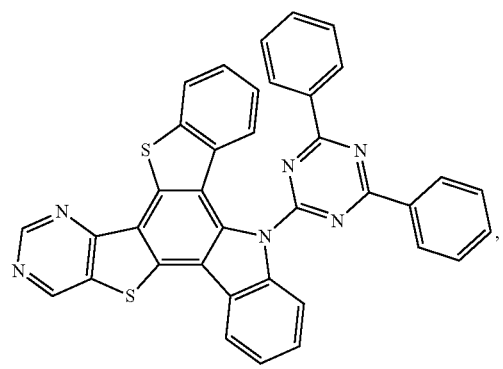
Compound 535
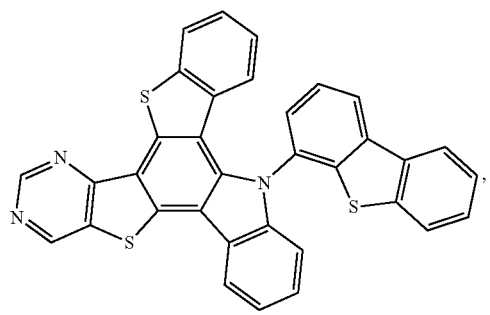
Compound 539
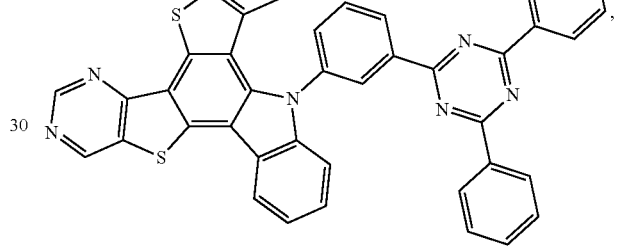
Compound 536
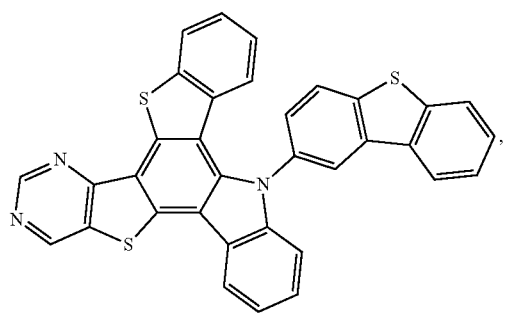
Compound 540
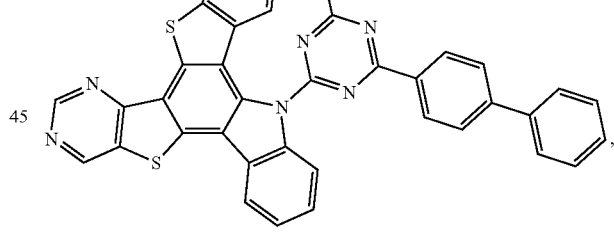
Compound 537
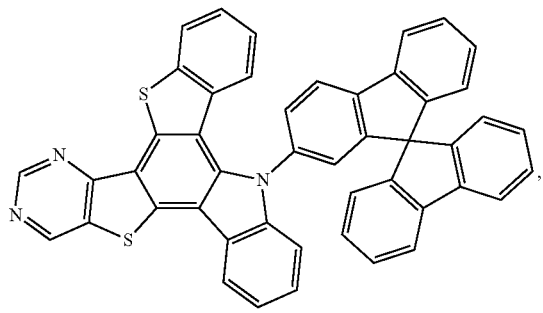
Compound 541
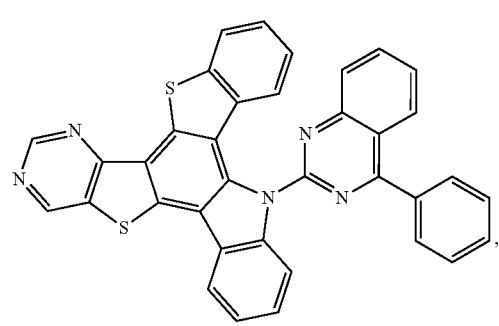

Compound 542
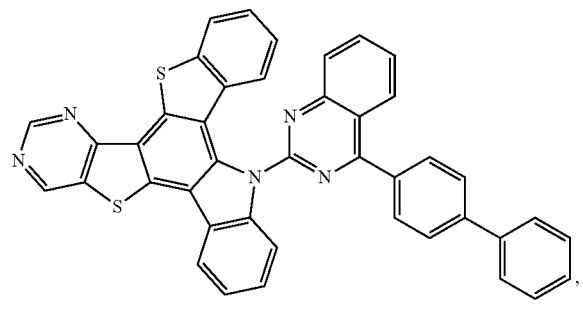
Compound 543
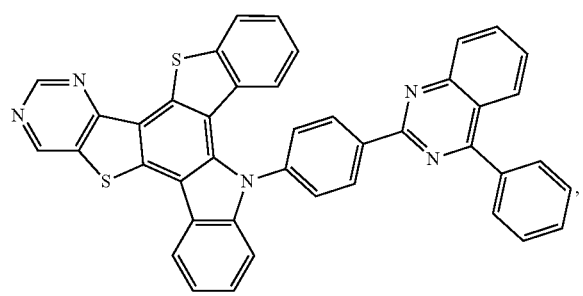
Compound 544
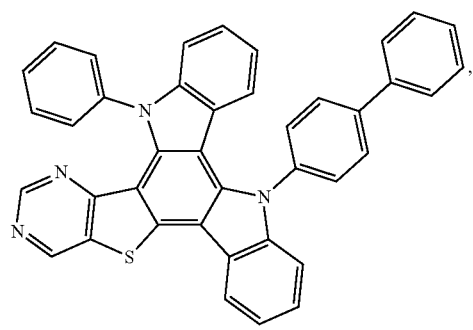
Compound 545
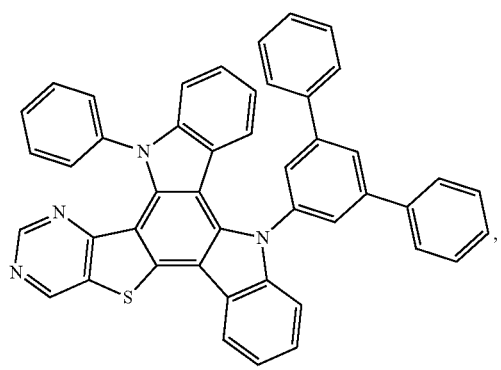
Compound 546
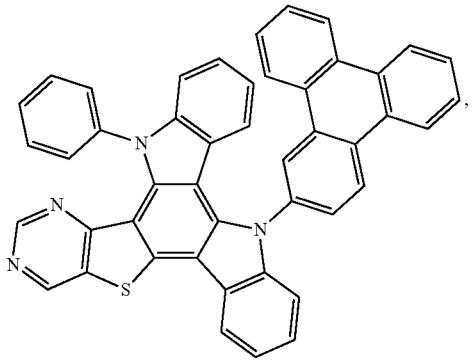
Compound 547
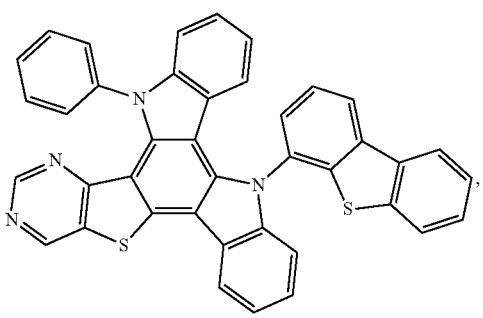
Compound 548
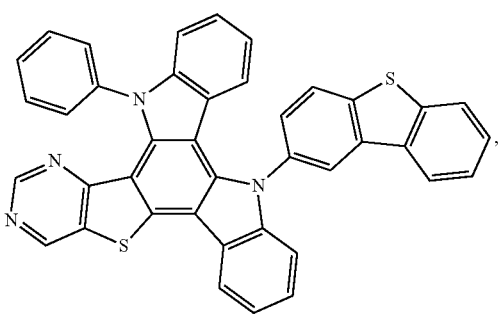
Compound 549
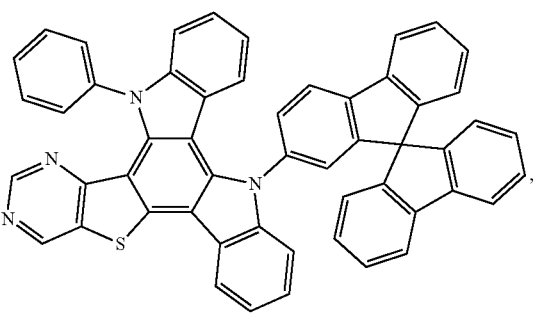

Compound 550
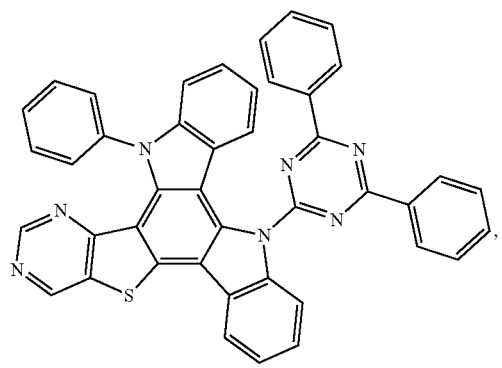
Compound 554
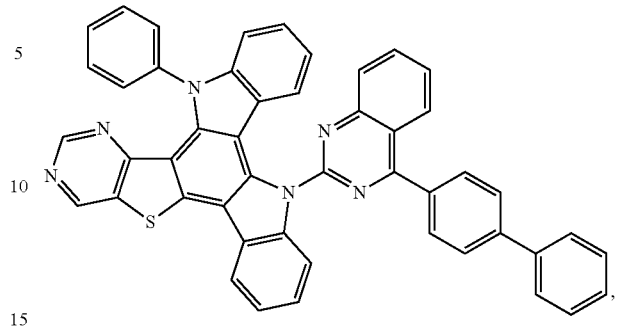
Compound 551
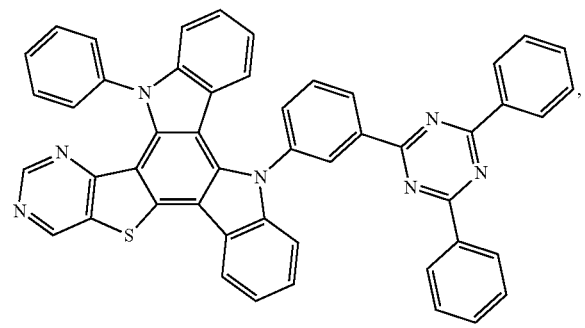
Compound 555
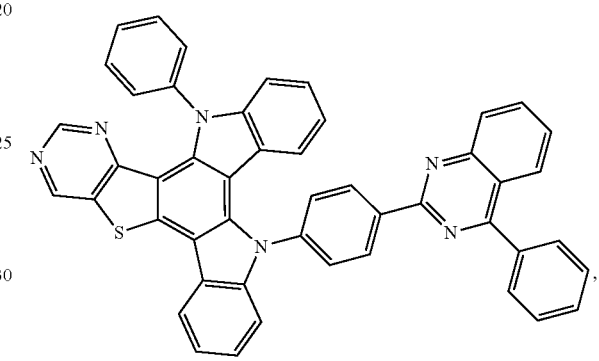
Compound 552
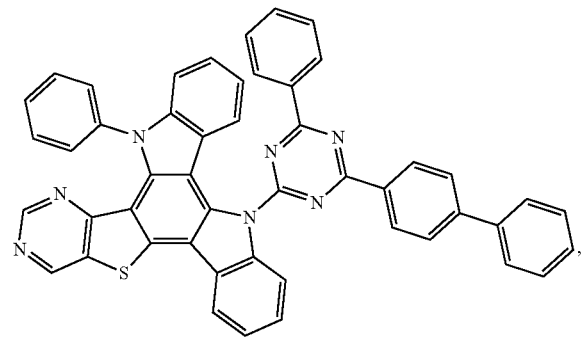
Compound 556
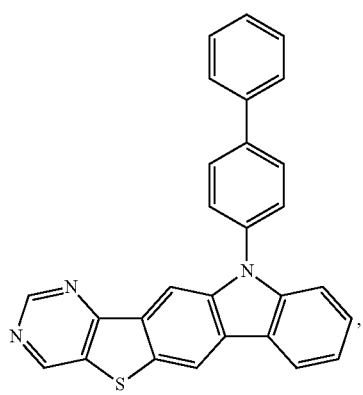
Compound 553
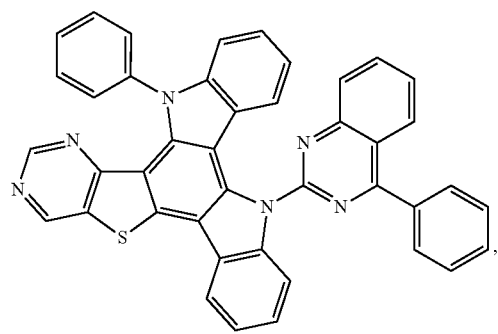
Compound 557
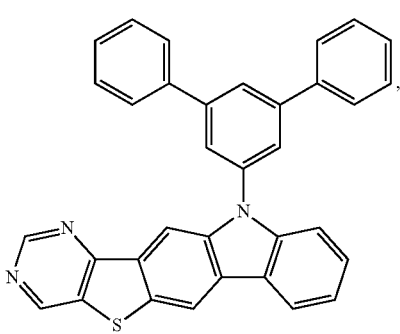

Compound 558
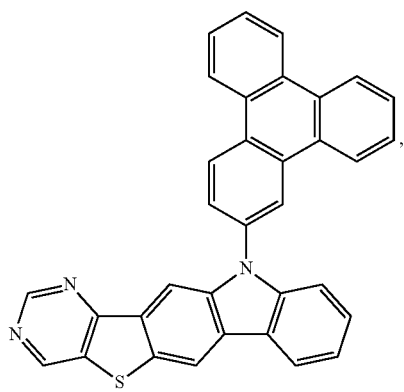
Compound 559
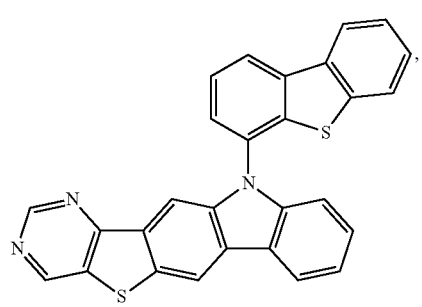
Compound 560
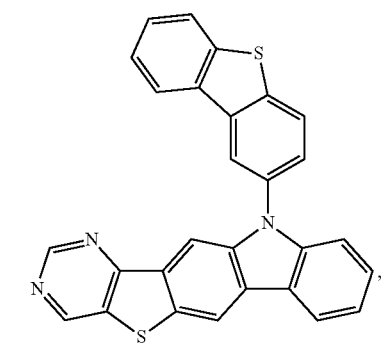
Compound 561
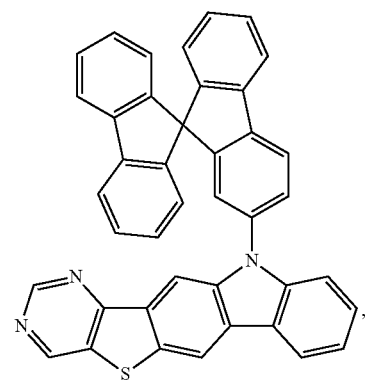
Compound 562
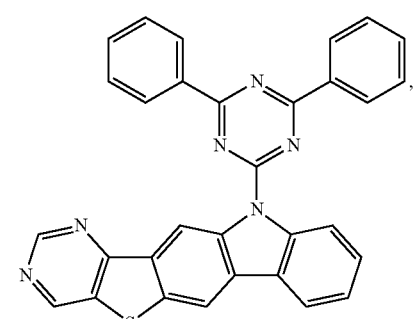
Compound 563
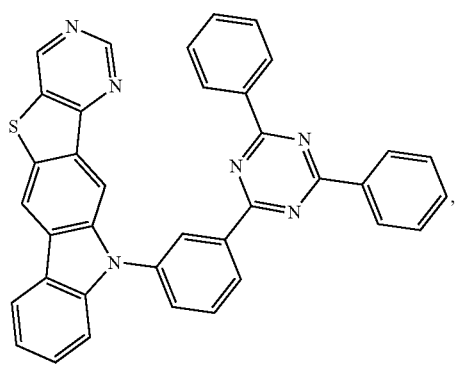
Compound 564
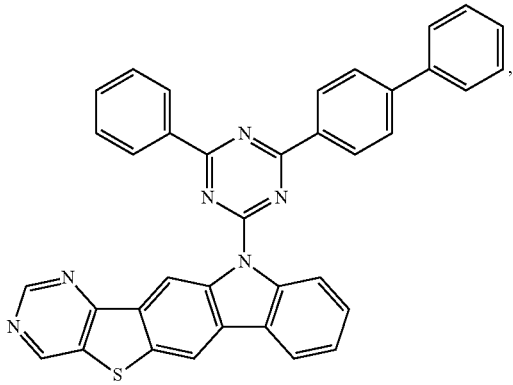
Compound 565
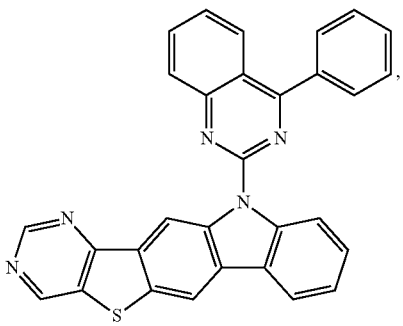

Compound 566
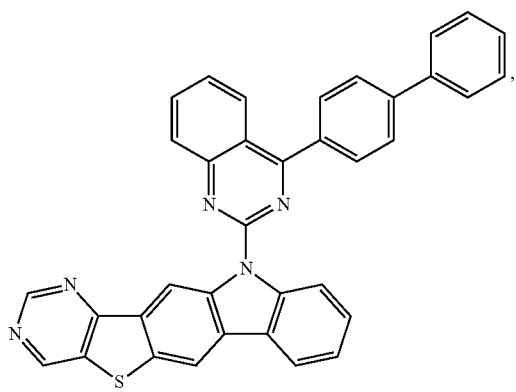
Compound 567
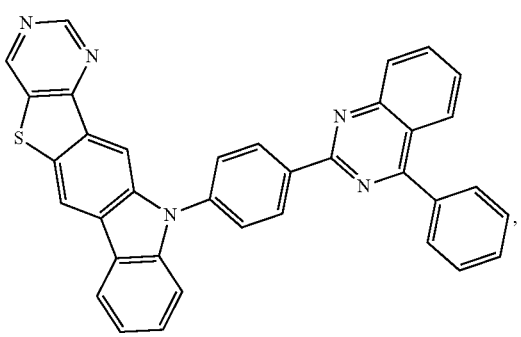
Compound 568
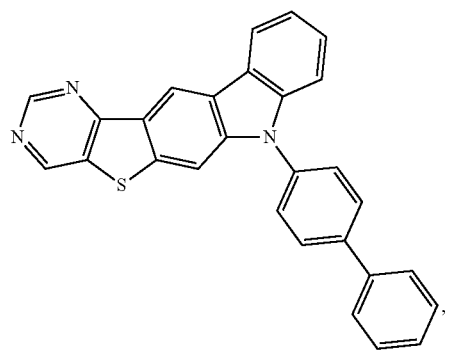
Compound 569
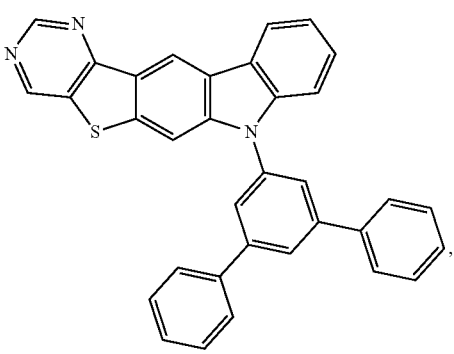
Compound 570
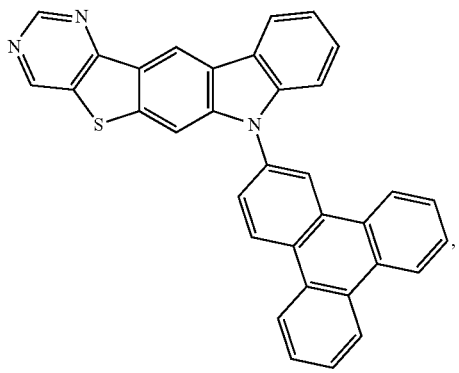
Compound 571
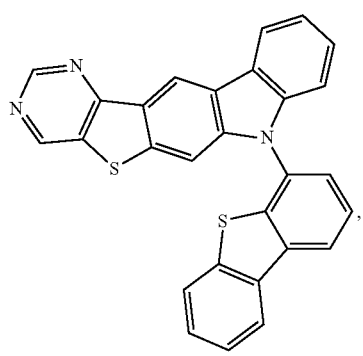
Compound 572
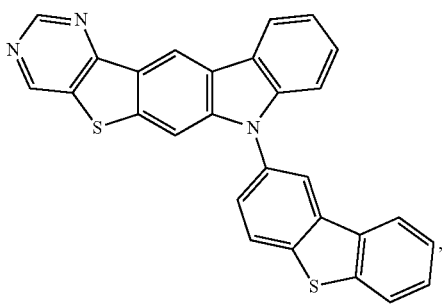
Compound 573
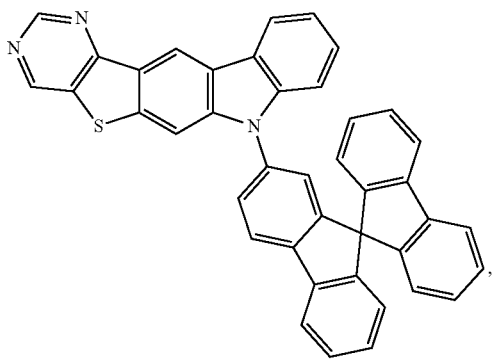

Compound 574
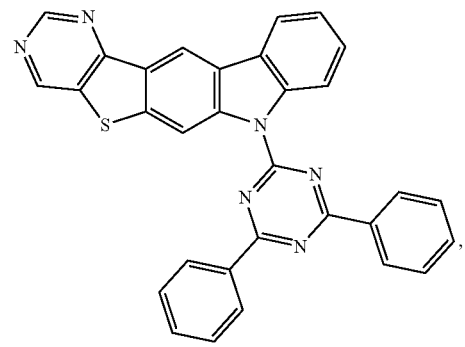
Compound 575
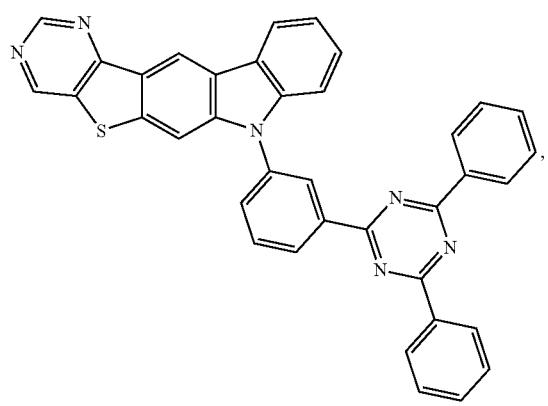
Compound 576
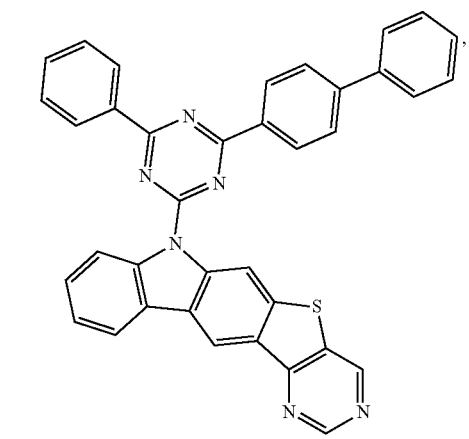
Compound 577
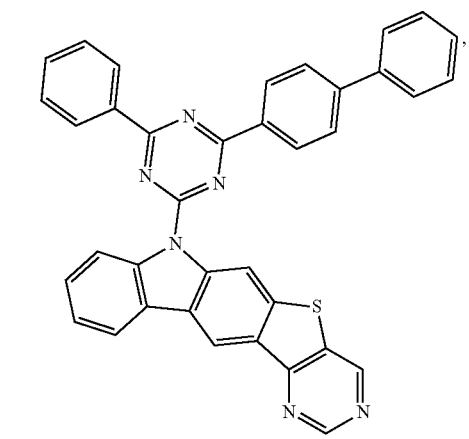
Compound 578
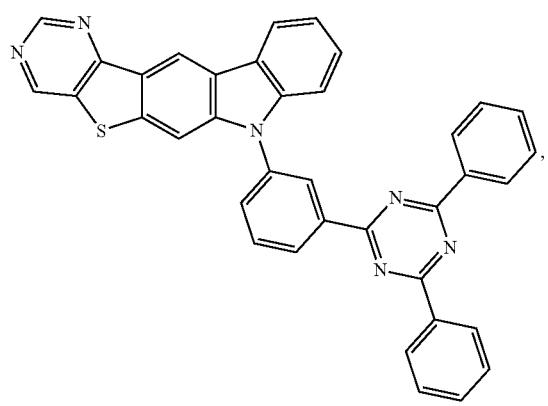
Compound 579
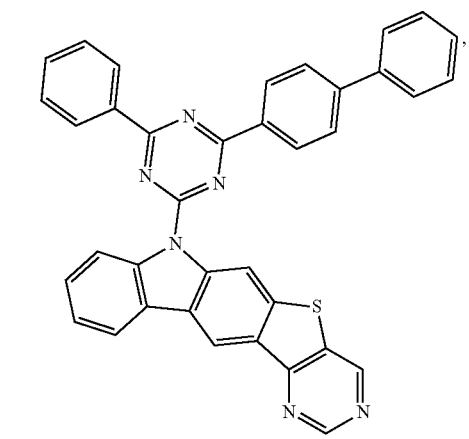
Compound 580
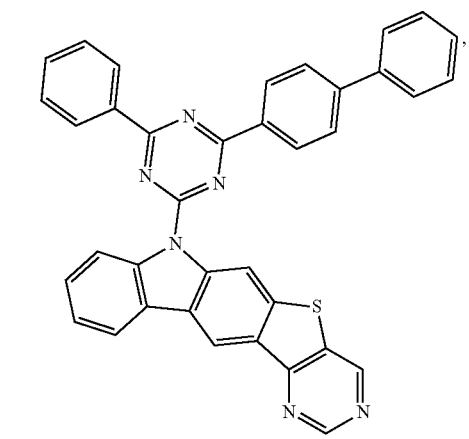
Compound 581
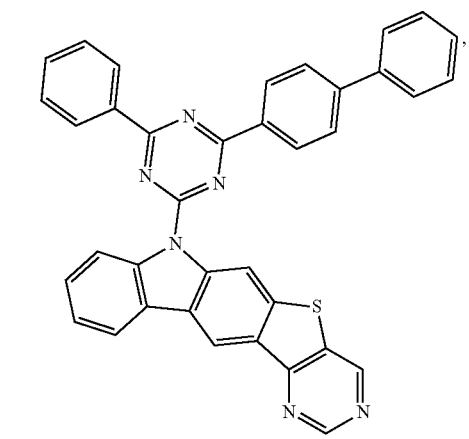

Compound 582
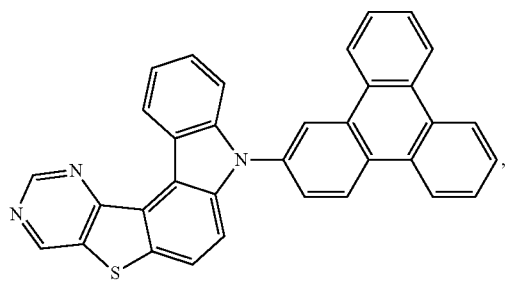
Compound 583
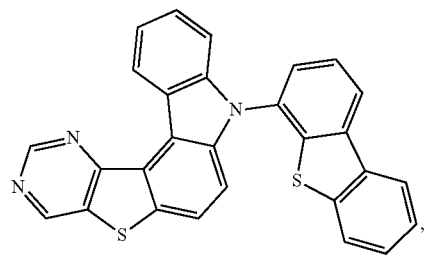
Compound 584
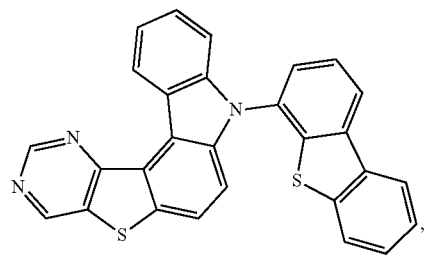
Compound 585
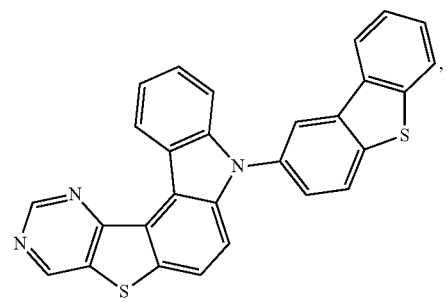
Compound 586
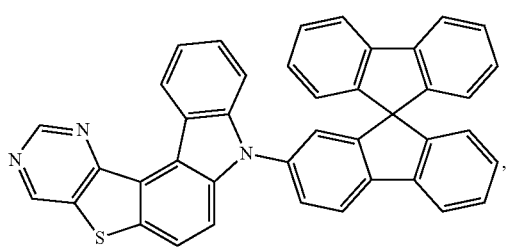
Compound 587
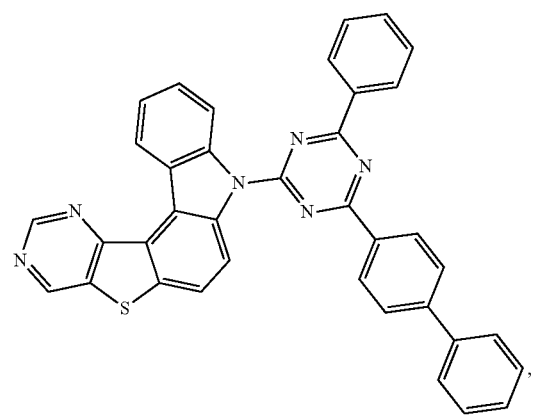
Compound 588
Compound 589
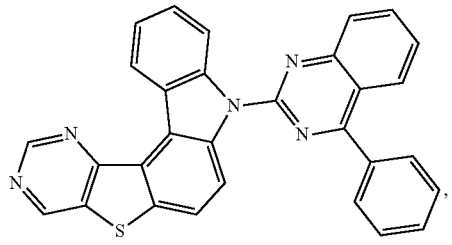
Compound 590
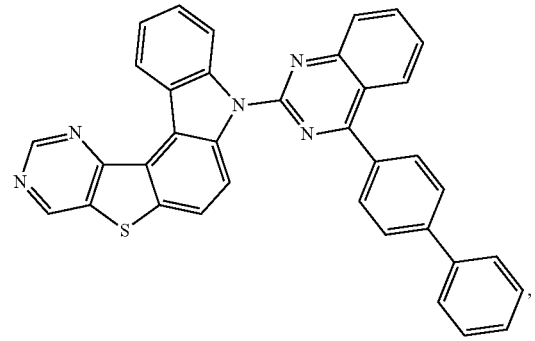

Compound 591
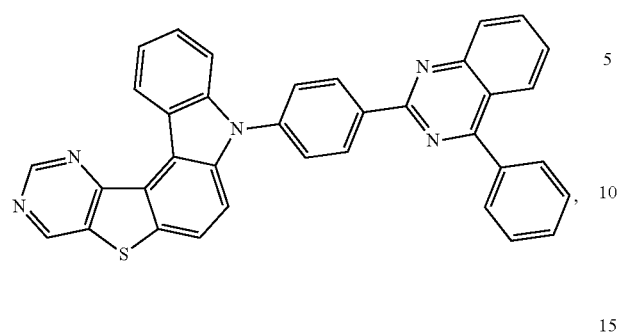
Compound 592
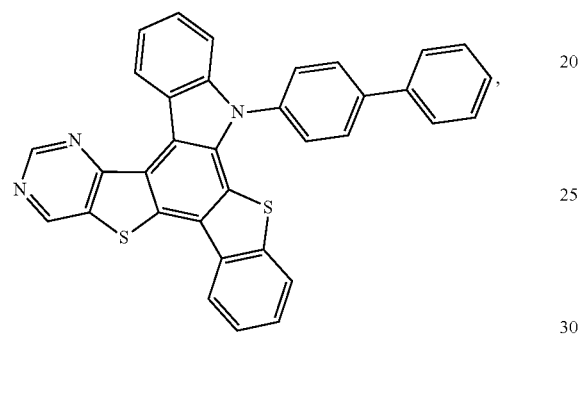
Compound 593
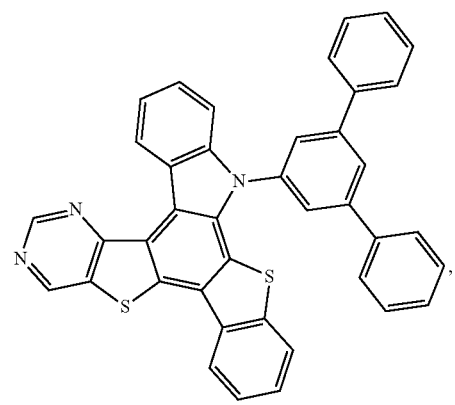
Compound 594
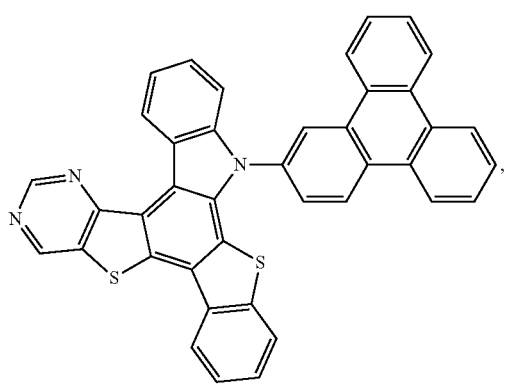
Compound 595
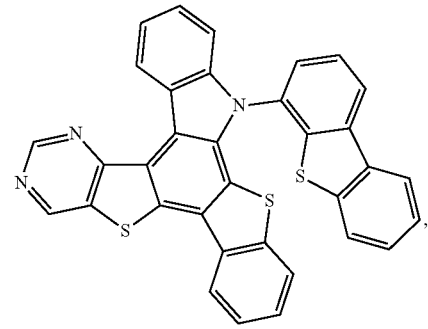
Compound 596
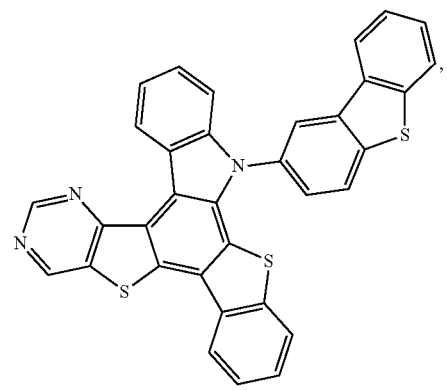
Compound 597
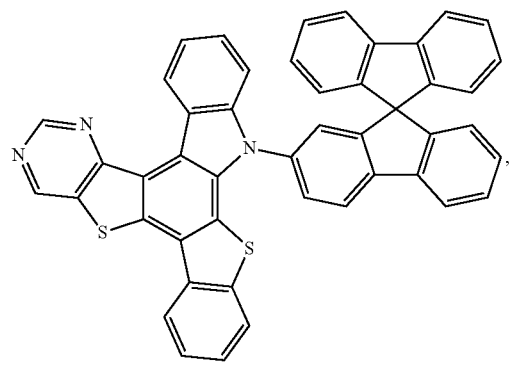
Compound 598
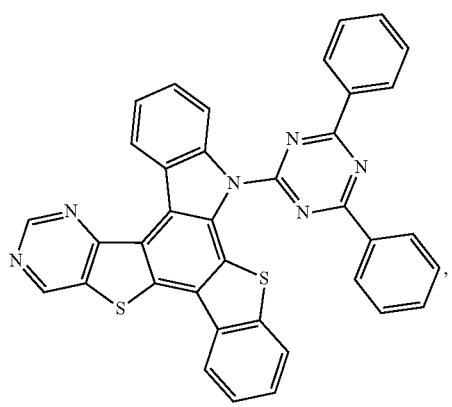

Compound 599
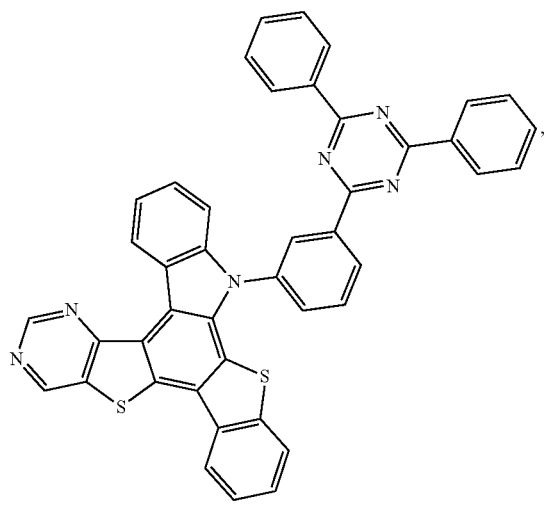
Compound 600
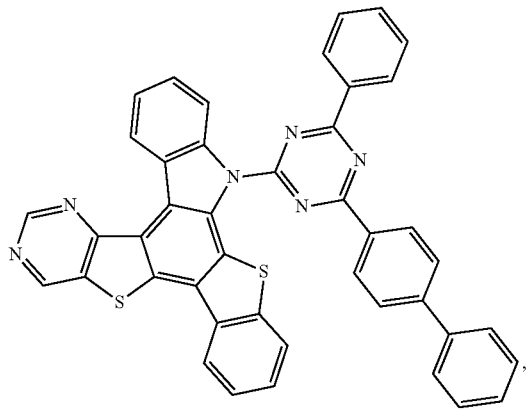
Compound 601
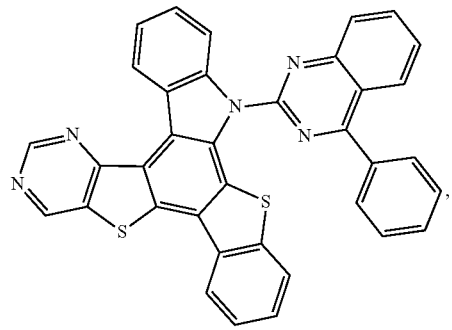
Compound 602
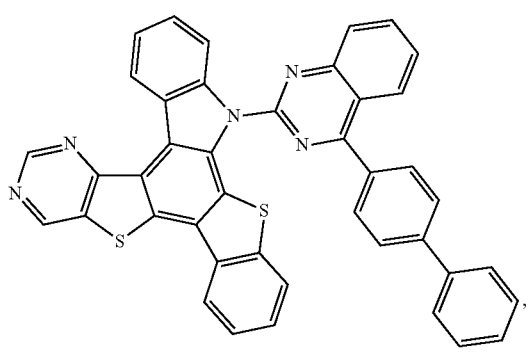
Compound 603
Compound 604
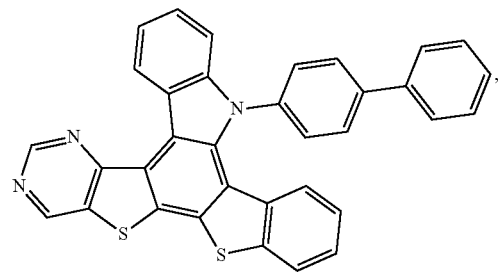
Compound 605
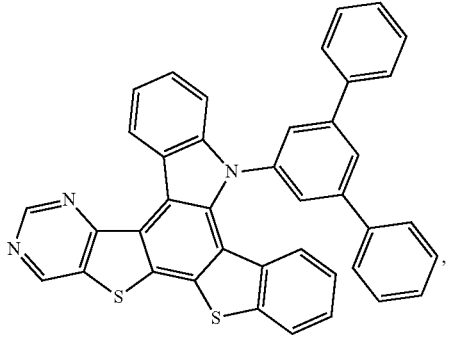

-continued
Compound 606
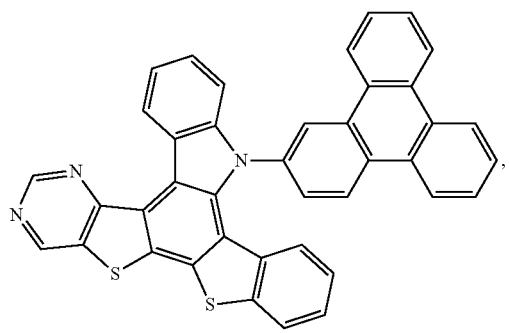
Compound 607
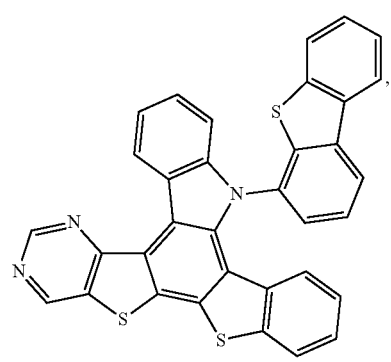
Compound 608
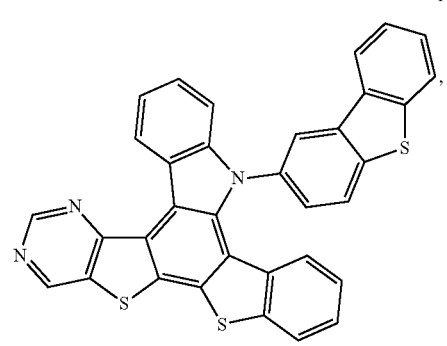
Compound 609
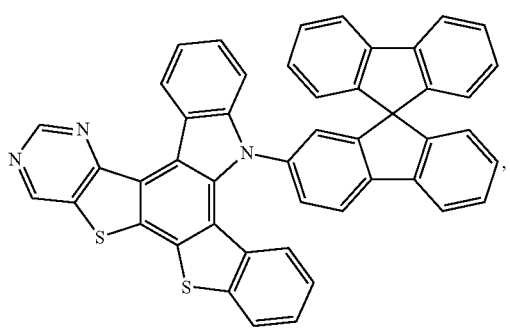
-continued
Compound 610
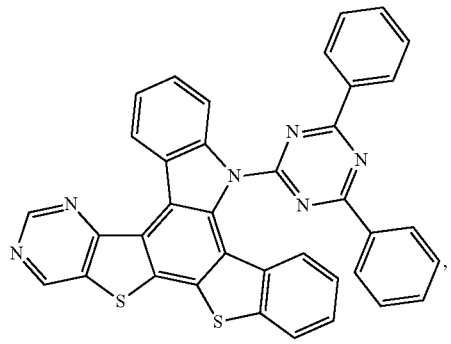
Compound 611
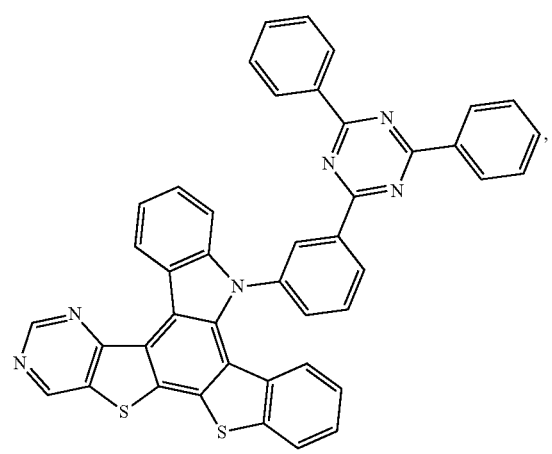
Compound 612
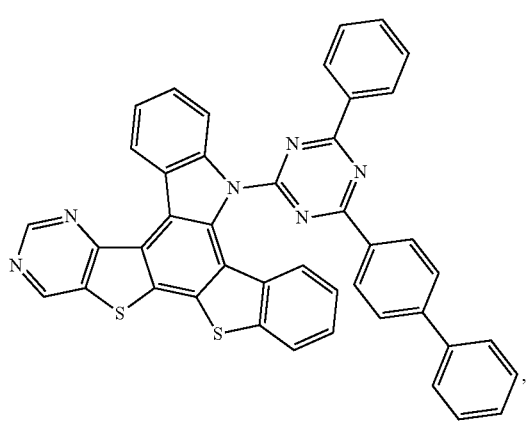
Compound 613
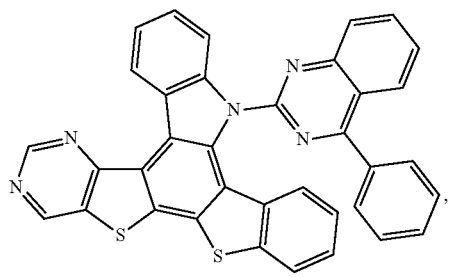

Compound 614
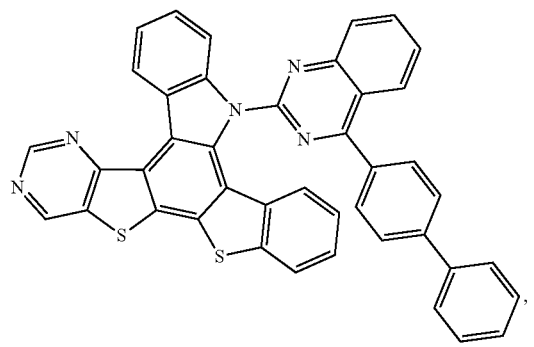
Compound 615
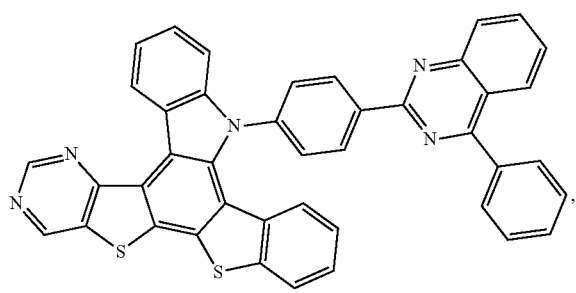
Compound 616
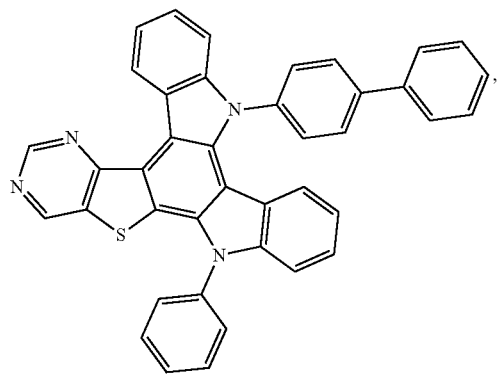
Compound 617
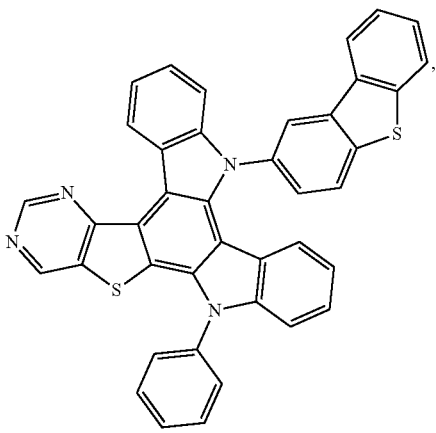
Compound 618
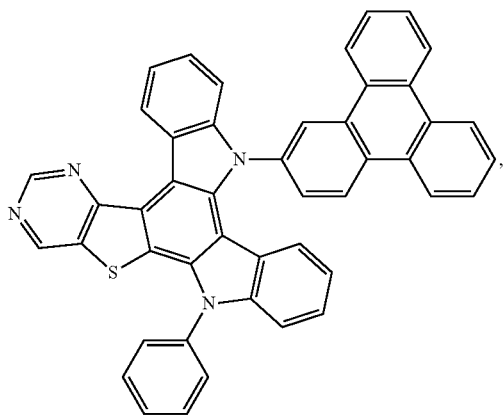
Compound 619
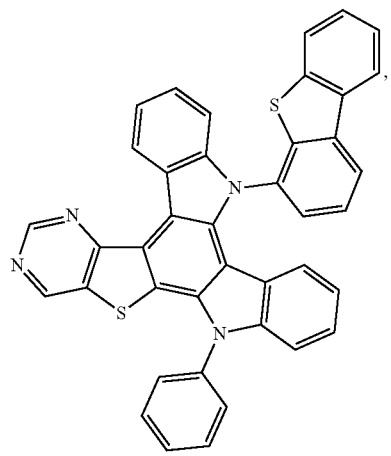
Compound 620
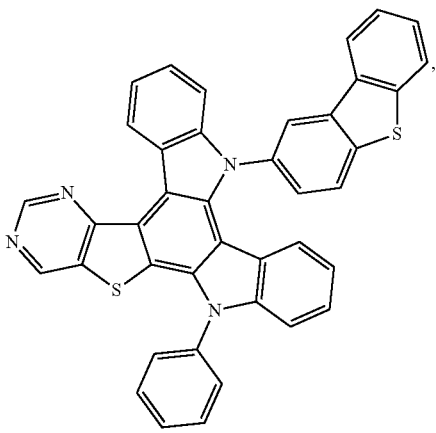

-continued
Compound 621
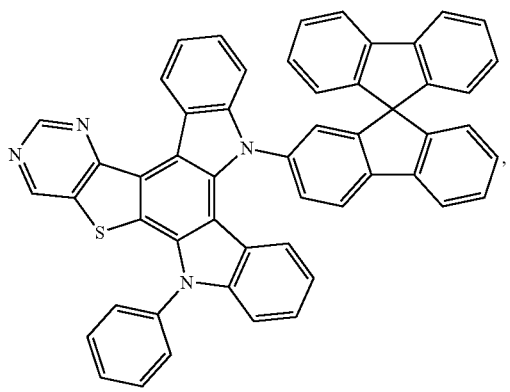
Compound 622
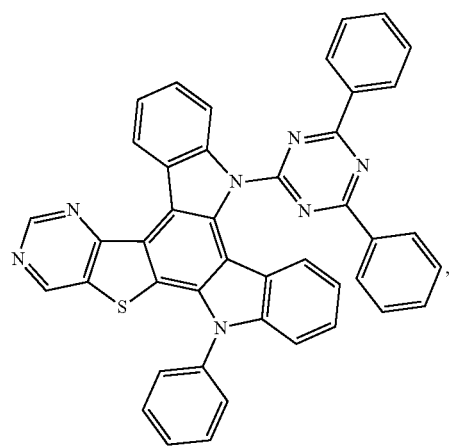
Compound 623
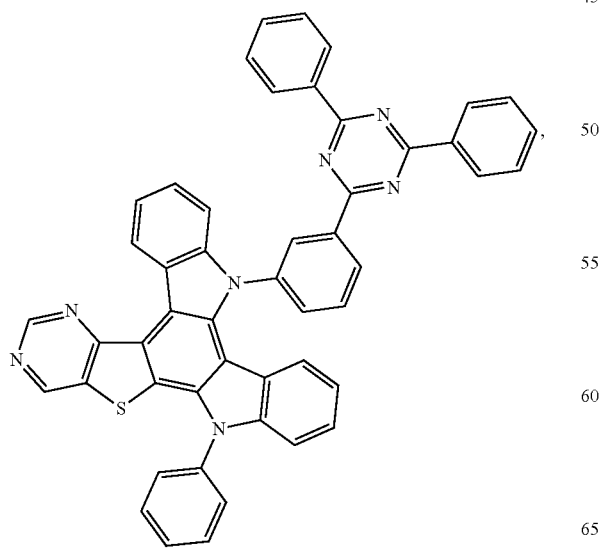
-continued
Compound 624
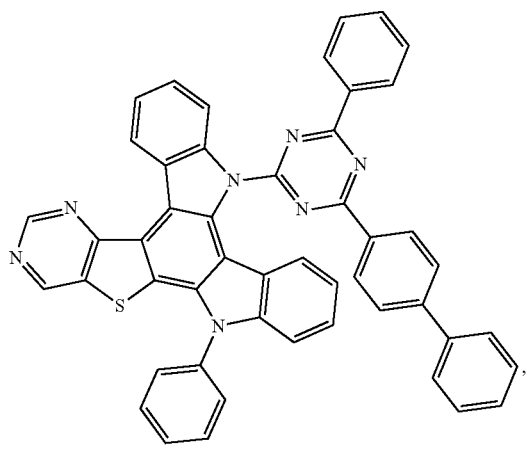
Compound 625
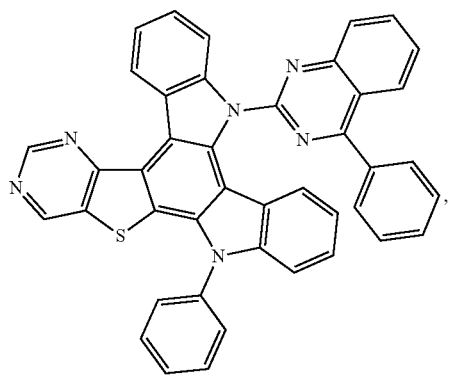
Compound 626
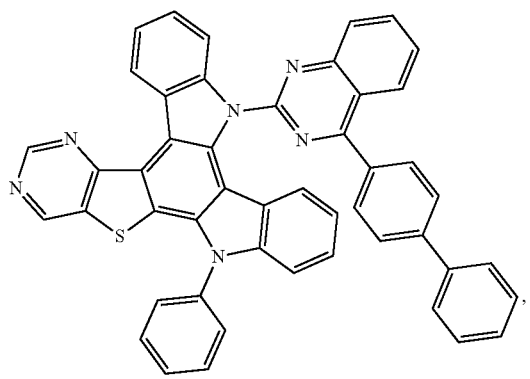

Compound 627
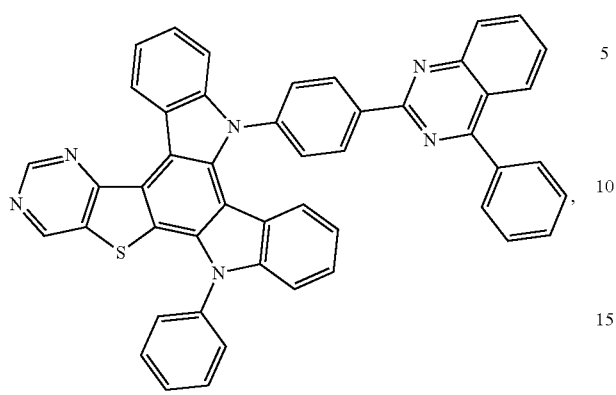
Compound 628
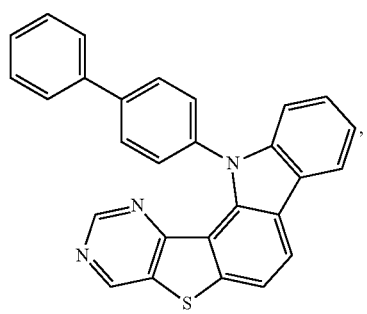
Compound 629
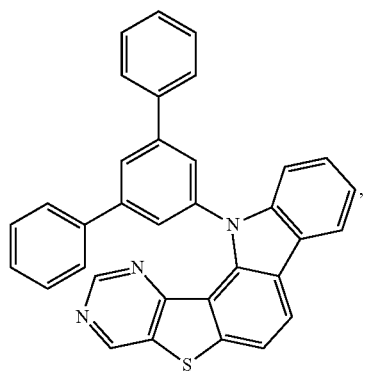
Compound 630
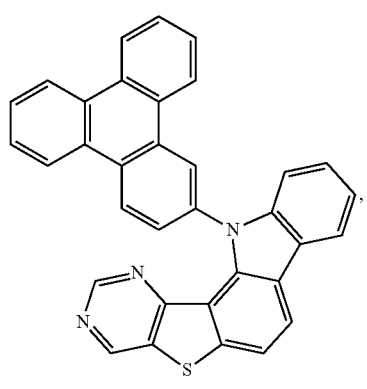
Compound 631
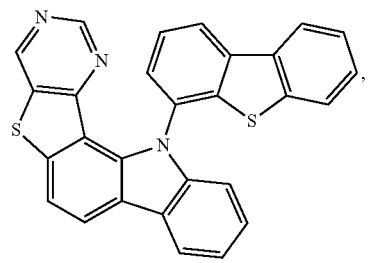
Compound 632
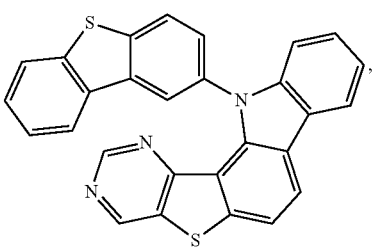
Compound 633
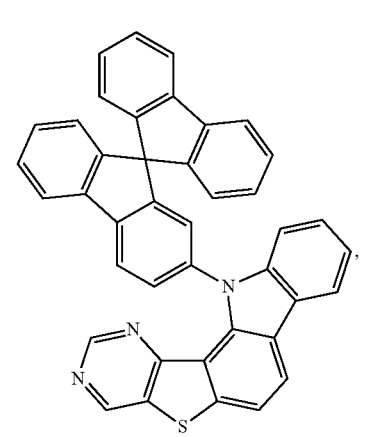
Compound 634
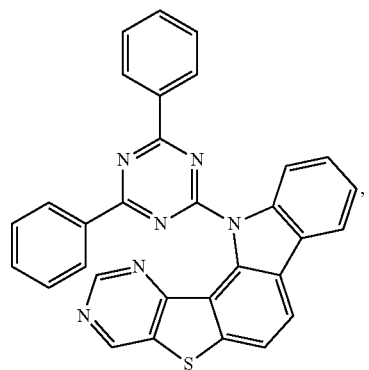

-continued
Compound 635
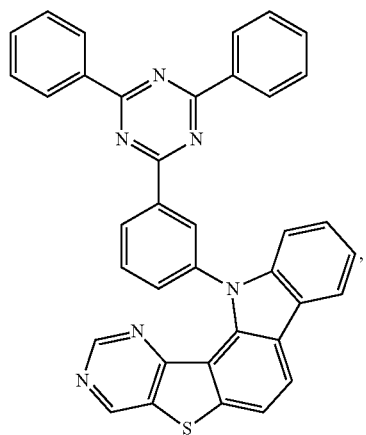
Compound 636
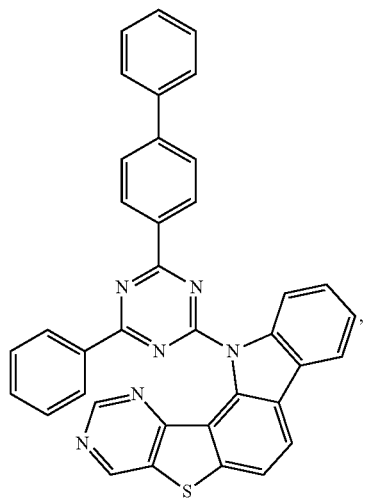
Compound 637
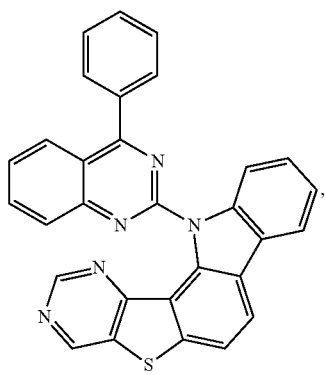
-continued
Compound 638
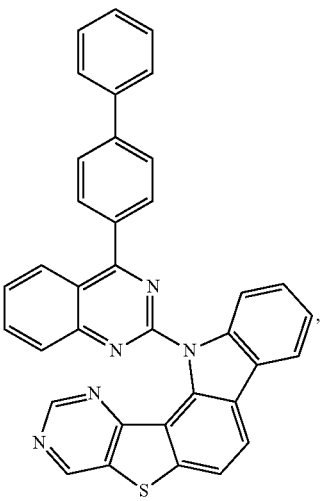
Compound 639
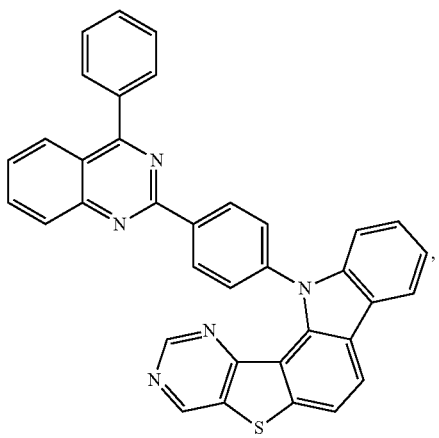
Compound 640
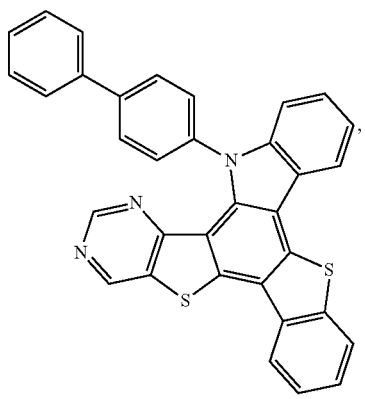

Compound 641
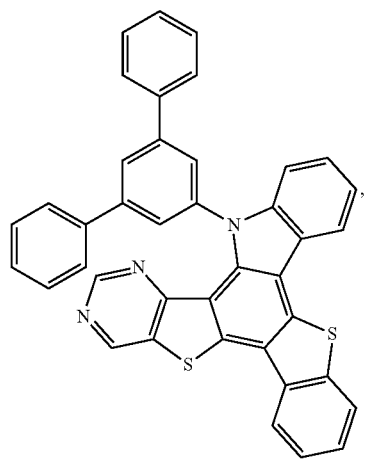
Compound 642
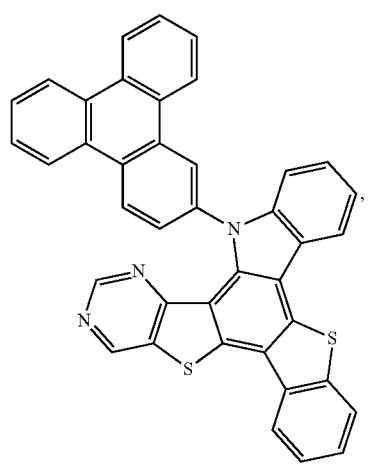
Compound 643
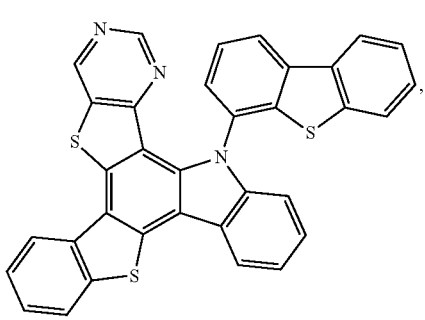
Compound 644
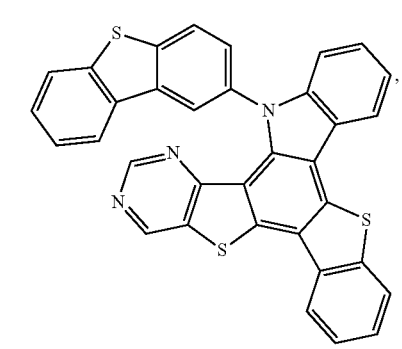
Compound 645
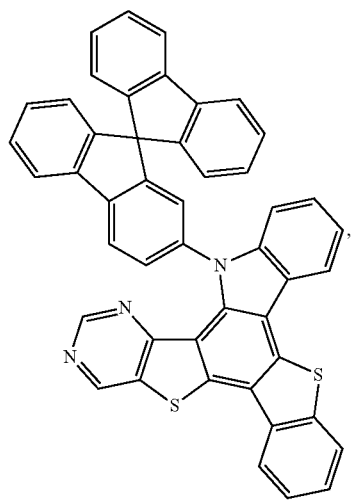
Compound 646
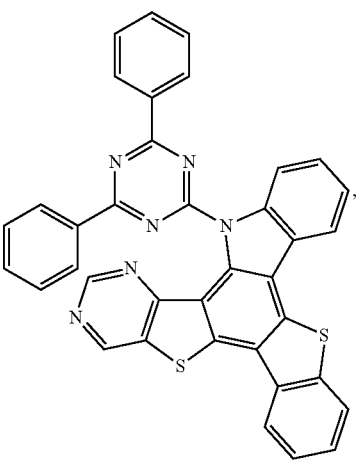
Compound 647
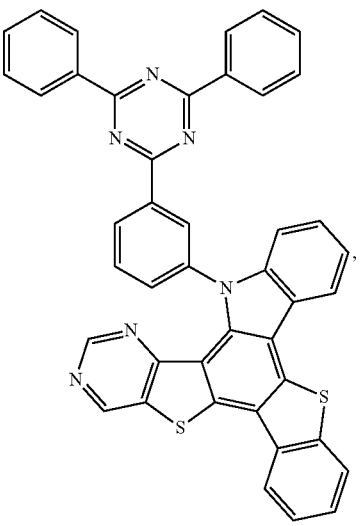

Compound 648
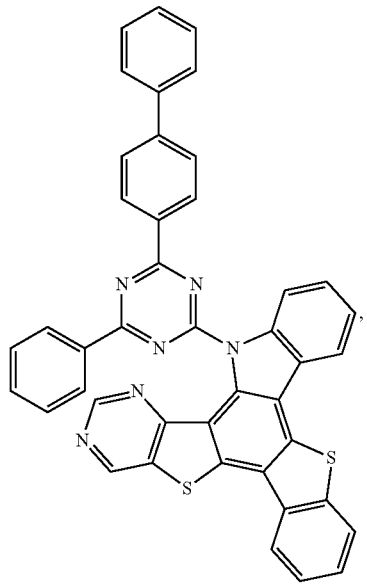
Compound 649
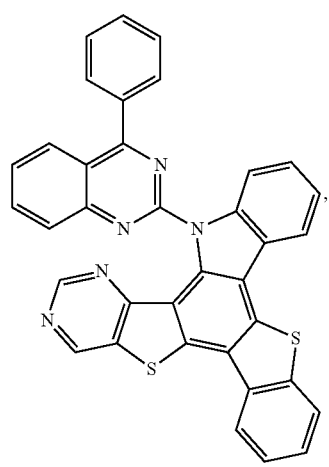
Compound 650
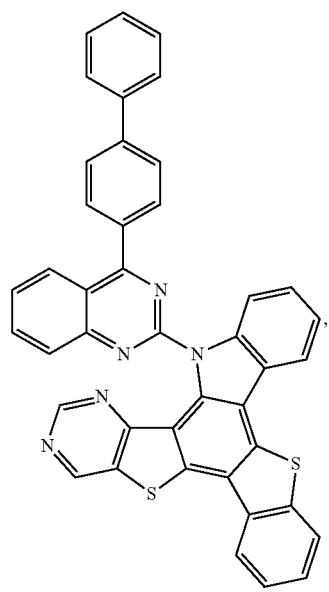
Compound 651
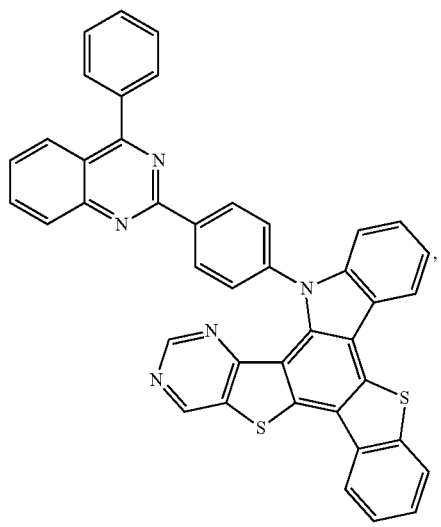
Compound 652
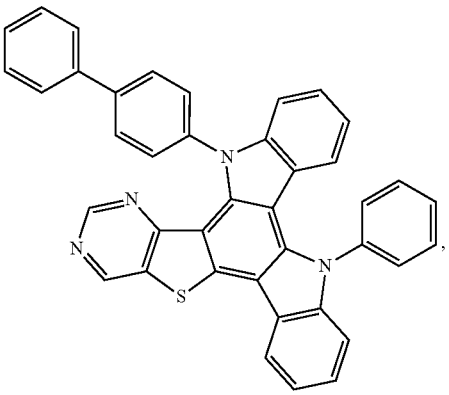
Compound 653
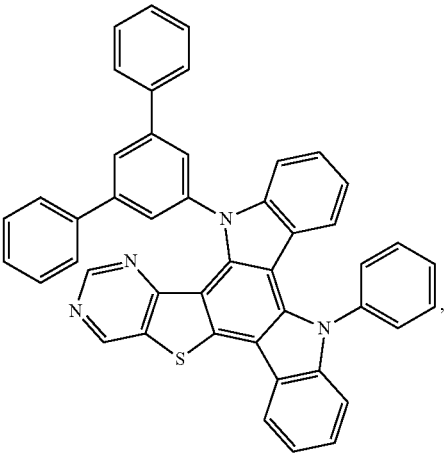

Compound 654
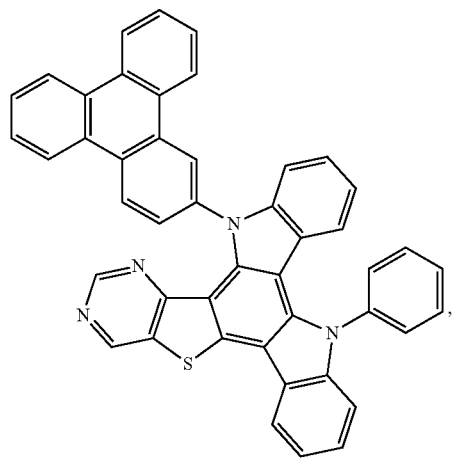
Compound 655
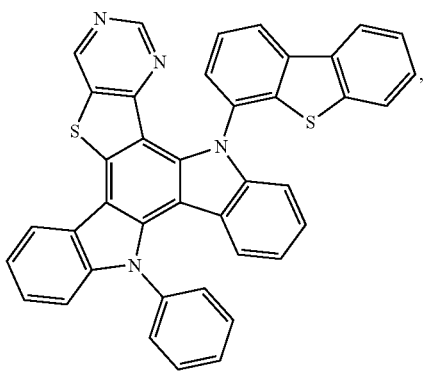
Compound 656
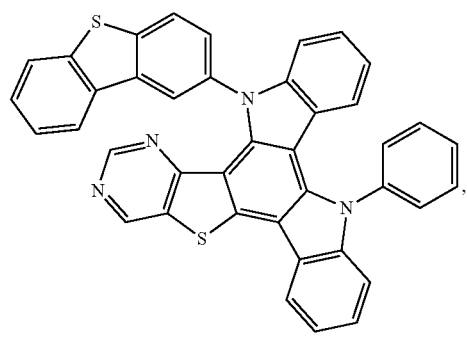
Compound 657
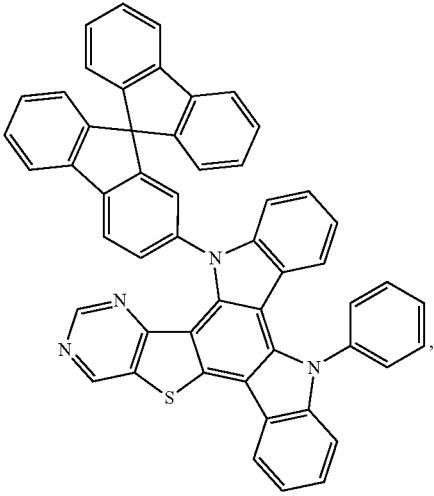
Compound 658
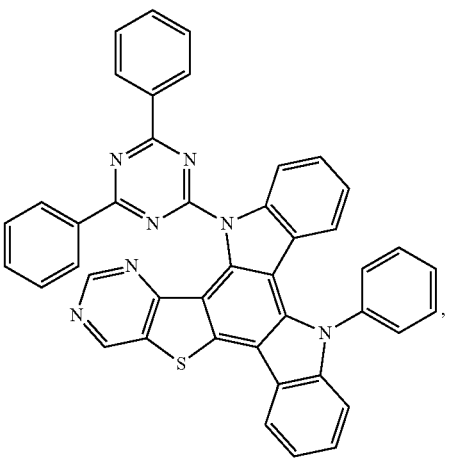
Compound 659
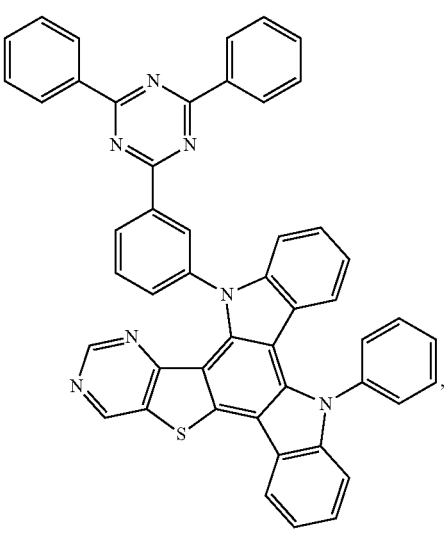

Compound 660
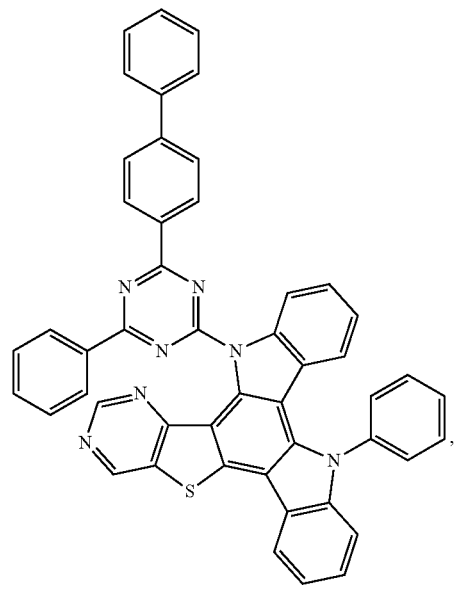
Compound 661
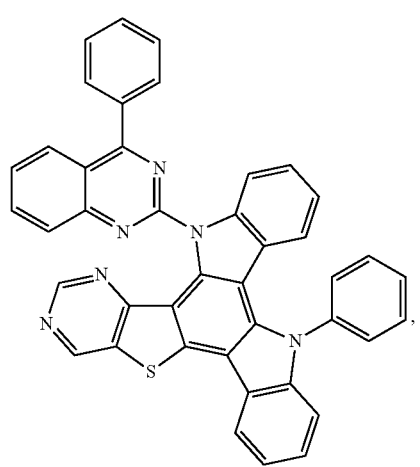
Compound 662
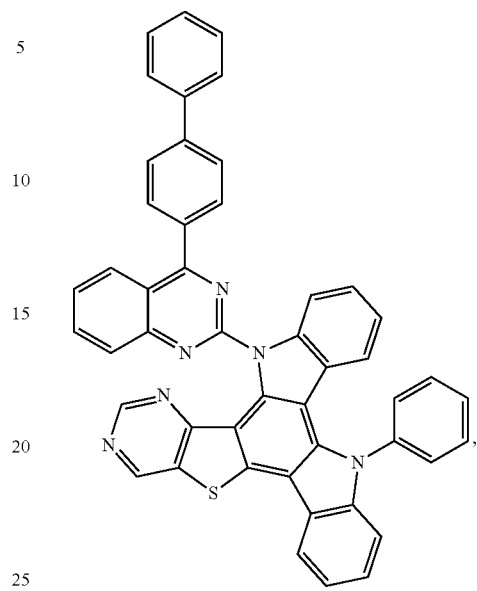
Compound 663
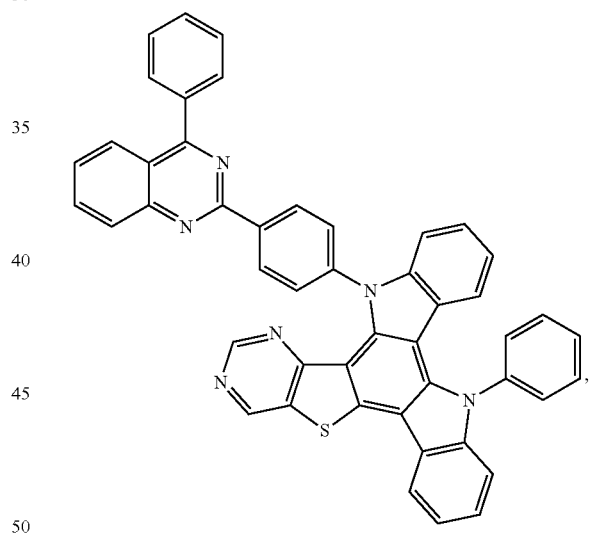
Compound 664
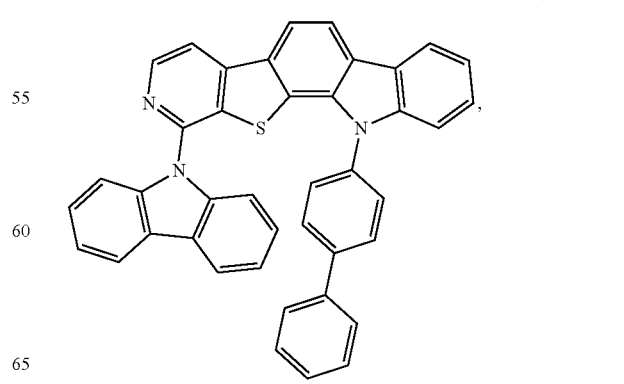

Compound 665
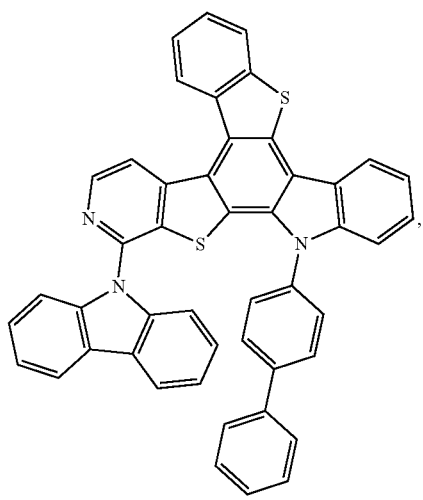
Compound 666
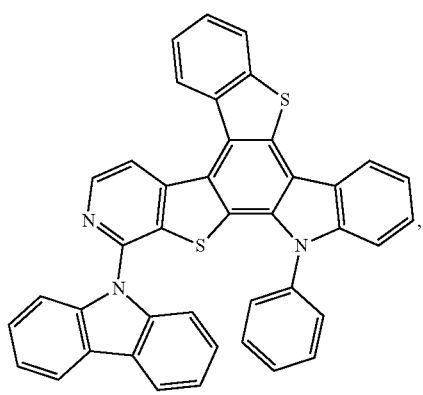
Compound 667
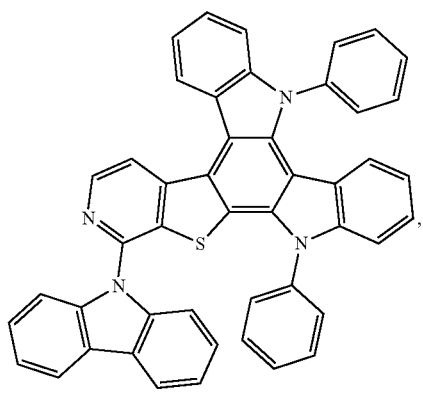
Compound 668
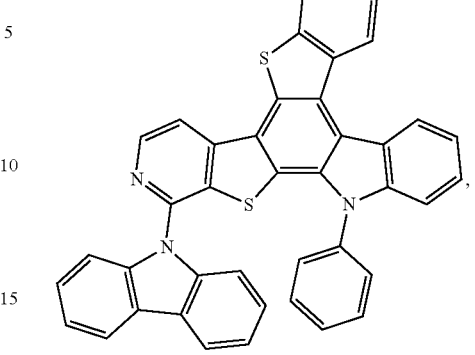
Compound 669
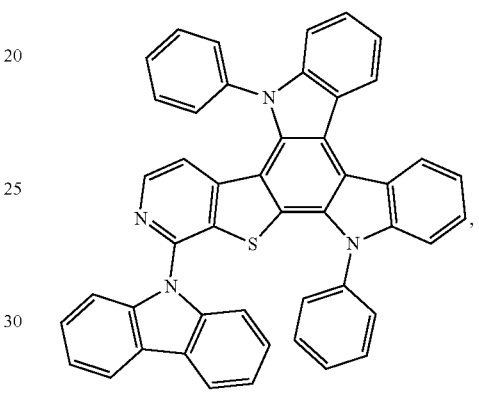
Compound 670
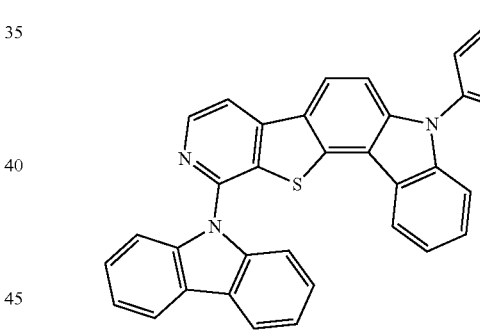
Compound 671
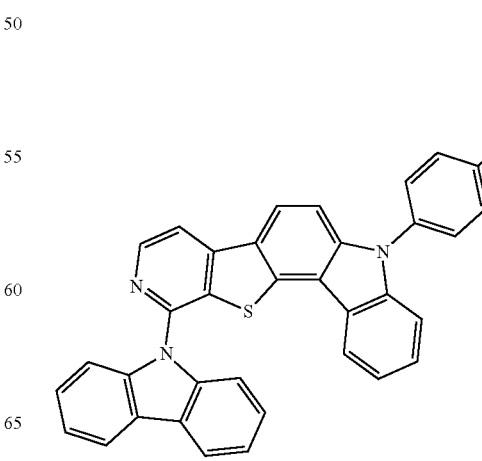

Compound 672
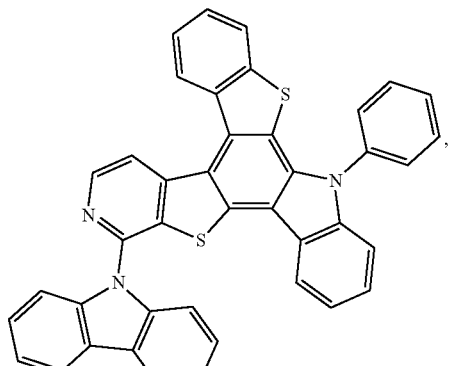
Compound 673
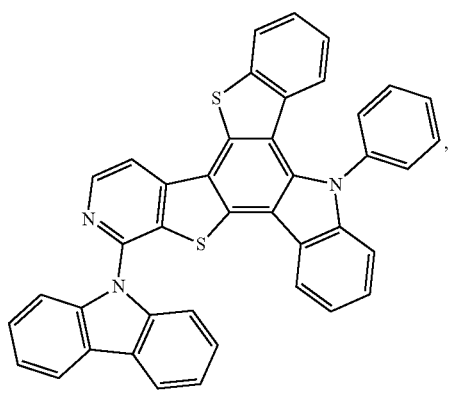
Compound 674
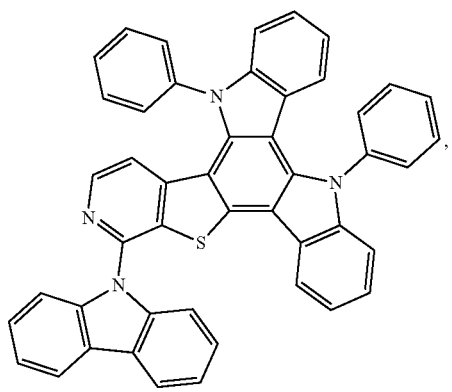
Compound 675
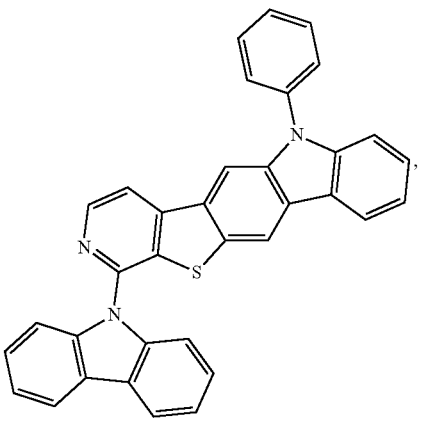
Compound 676
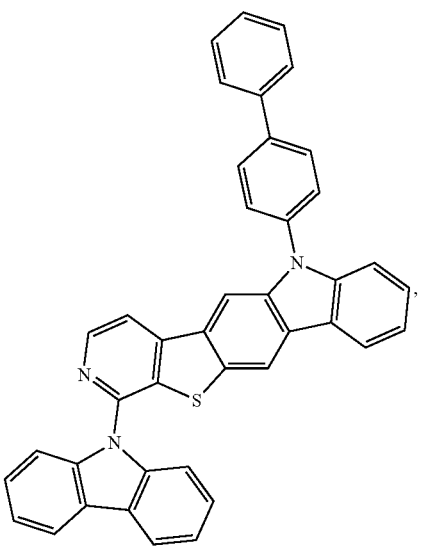
Compound 677
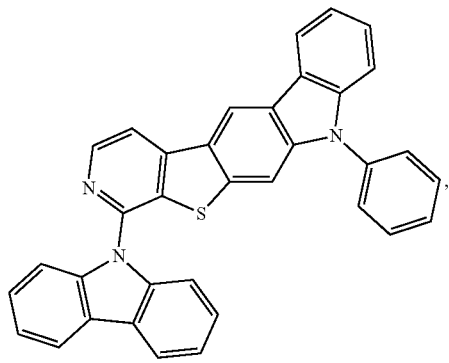

-continued
Compound 678
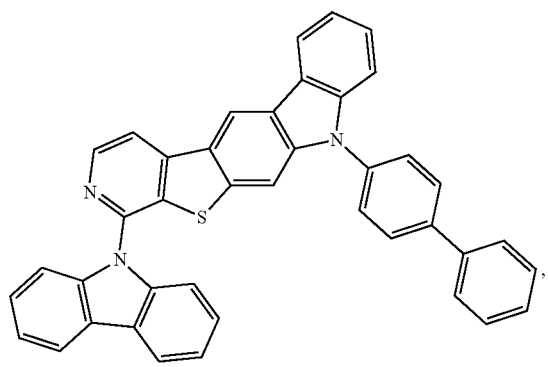
Compound 679
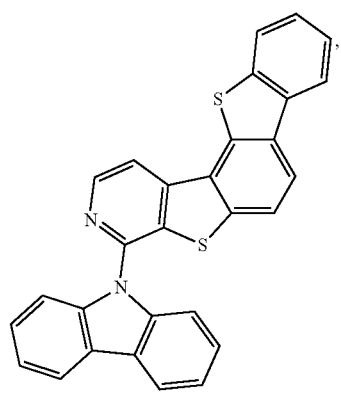
Compound 680
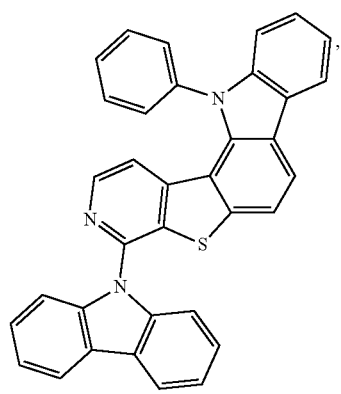
Compound 681
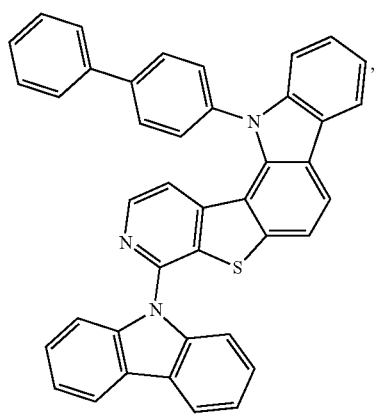
-continued
Compound 682
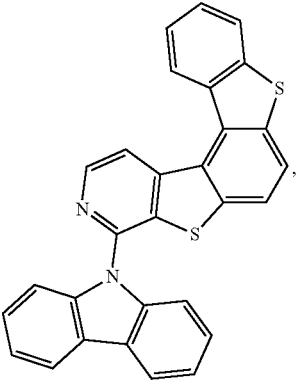
Compound 683
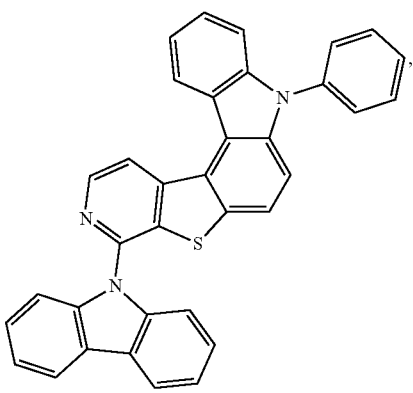
Compound 684
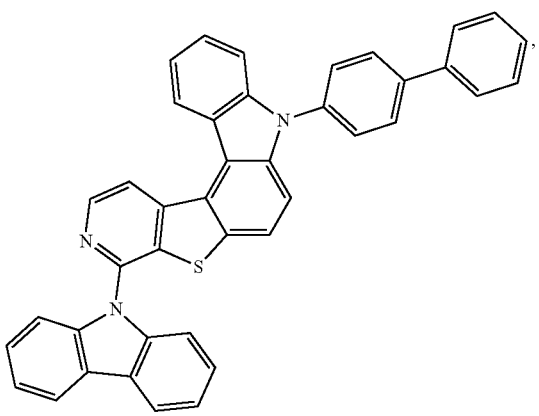
Compound 685
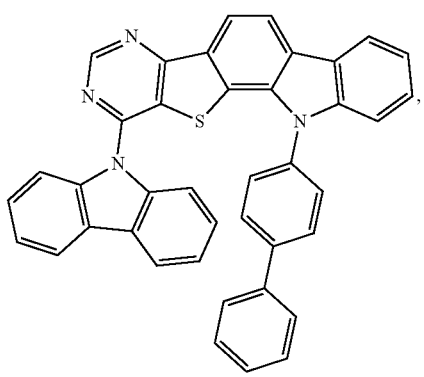

Compound 686
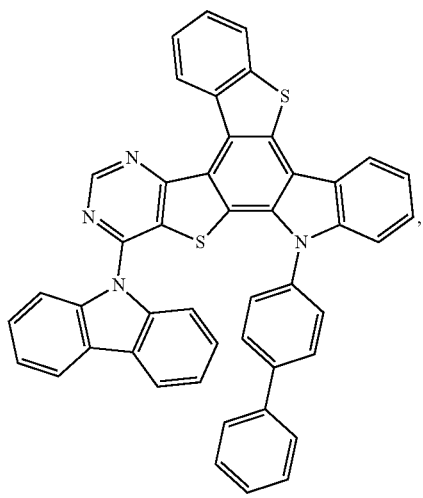
Compound 687
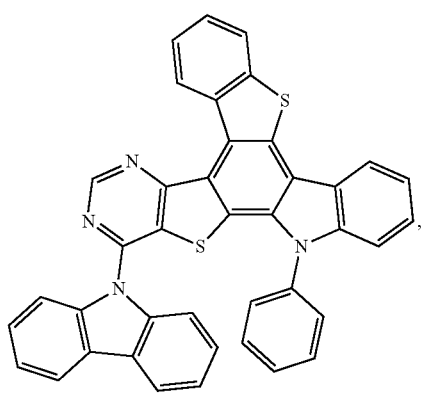
Compound 688
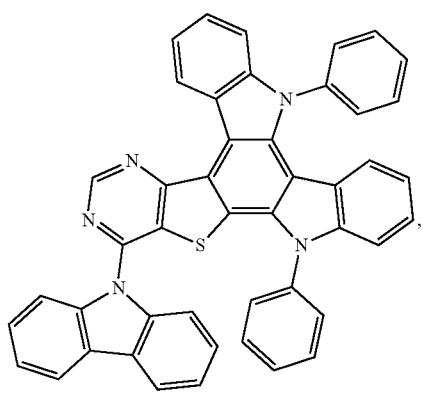
Compound 689
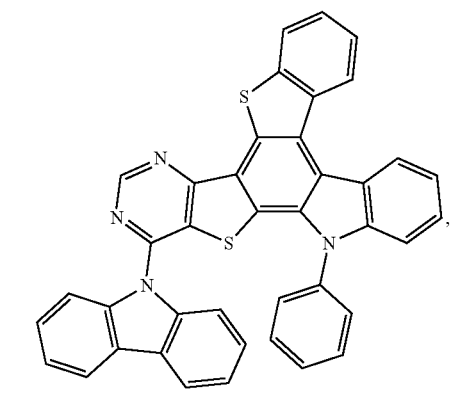
Compound 690
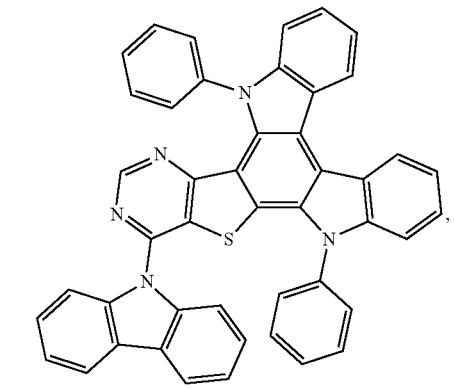
Compound 691
Compound 692
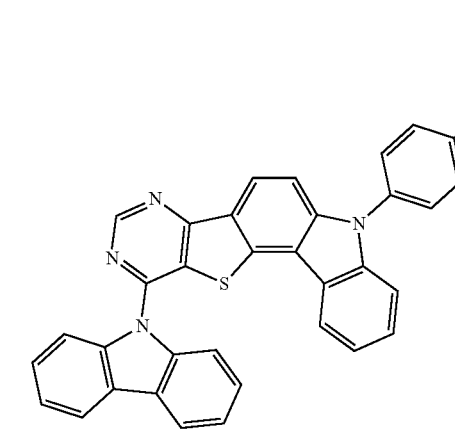

Compound 693
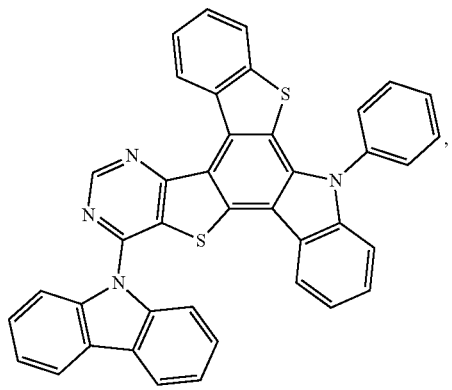
Compound 694
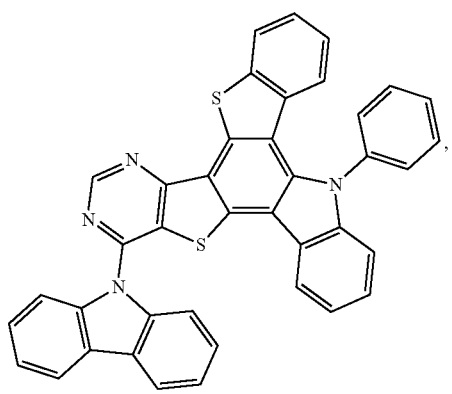
Compound 695
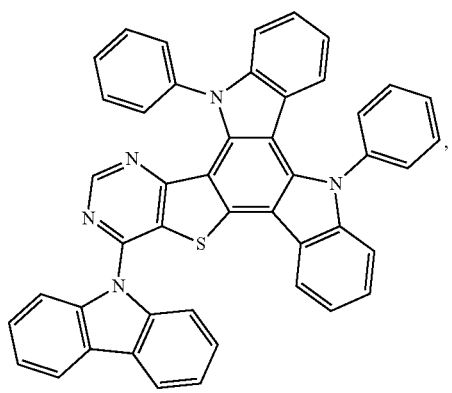
Compound 696
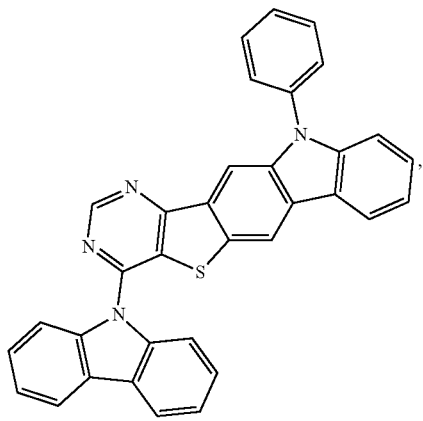
Compound 697
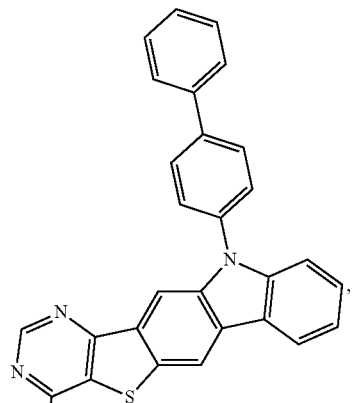
Compound 698
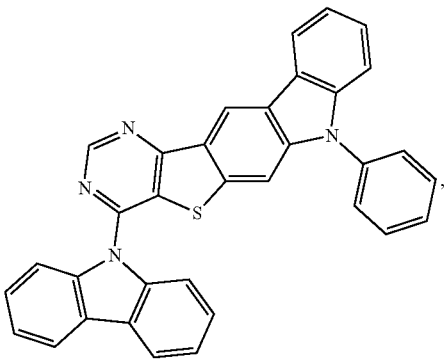
Compound 699
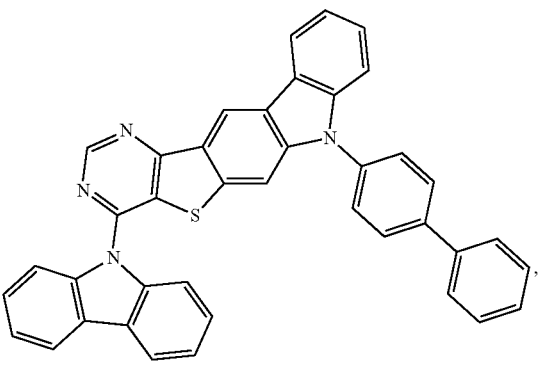

Compound 700
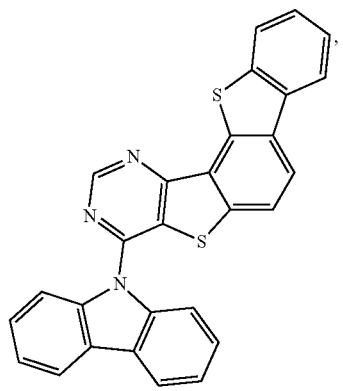
Compound 701
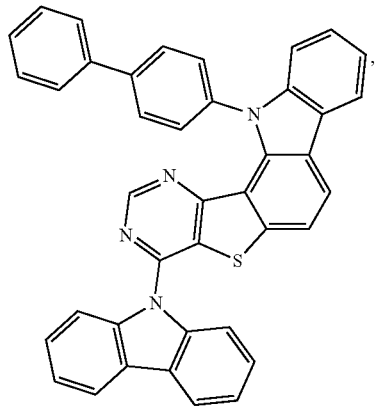
Compound 702
Compound 703
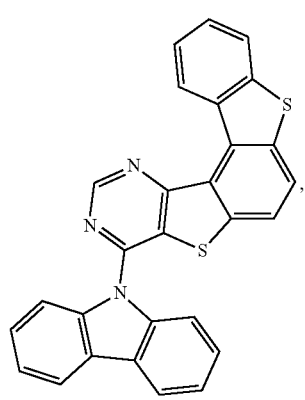
Compound 704
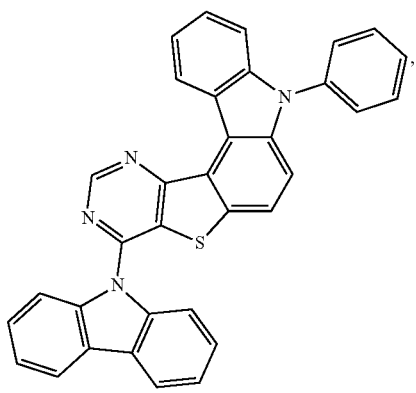
Compound 705
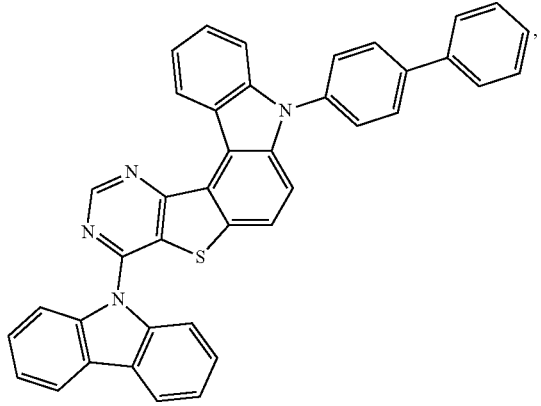
Compound 706
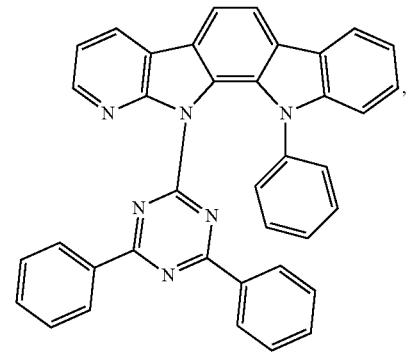
Compound 707
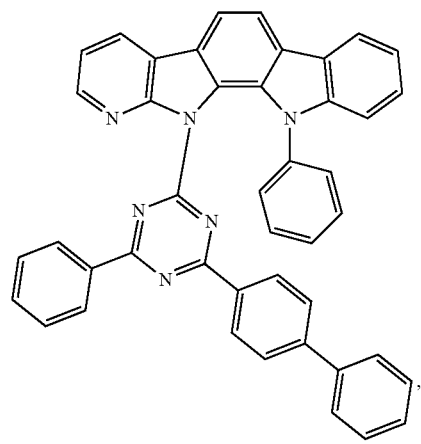

-continued
Compound 708
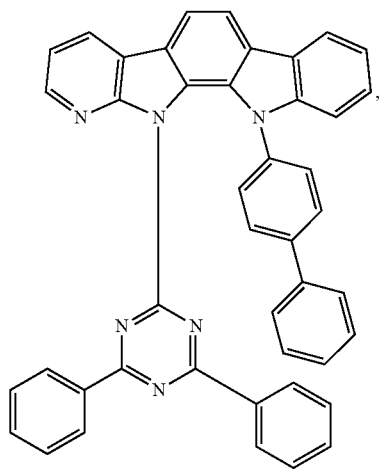
Compound 709
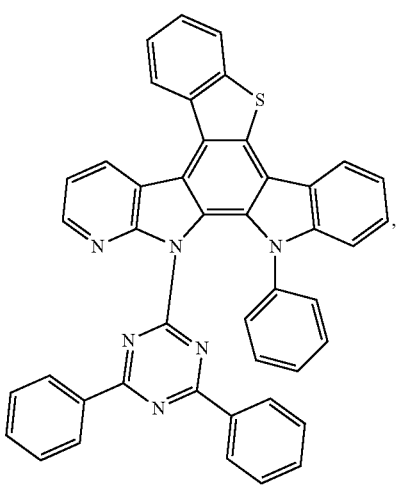
Compound 710
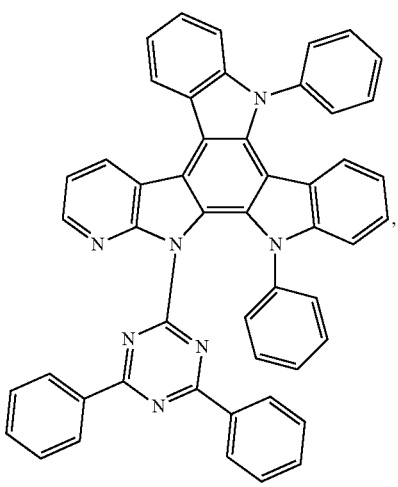
-continued
Compound 711
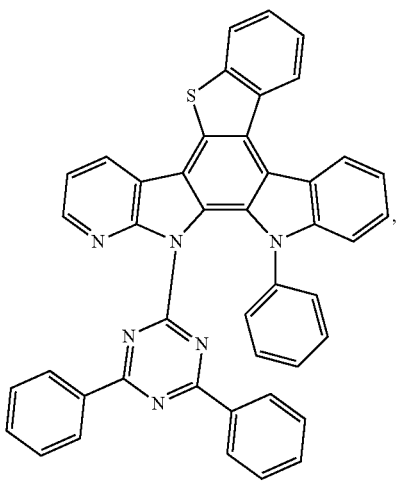
Compound 712
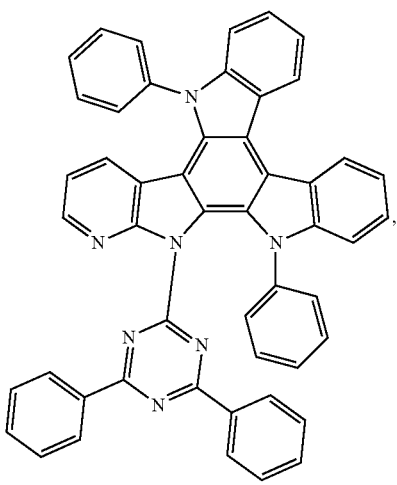
Compound 713
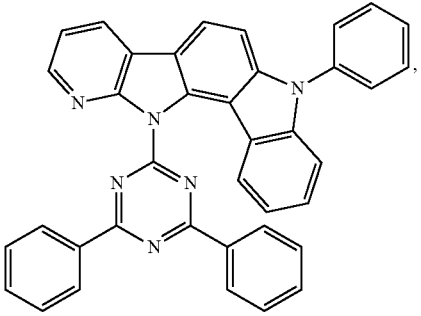

-continued
Compound 714
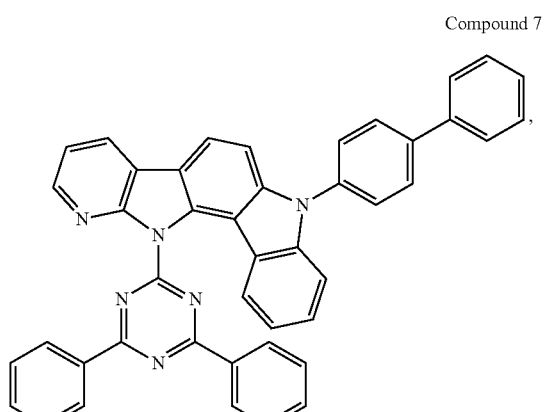
Compound 715
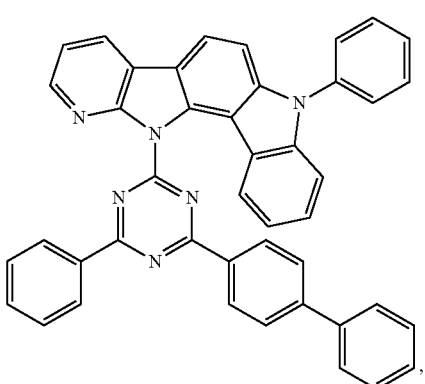
Compound 716
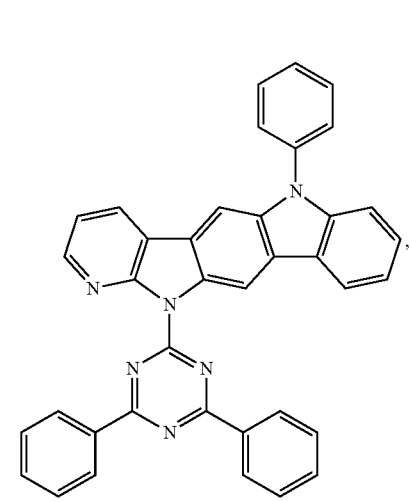
-continued
Compound 717
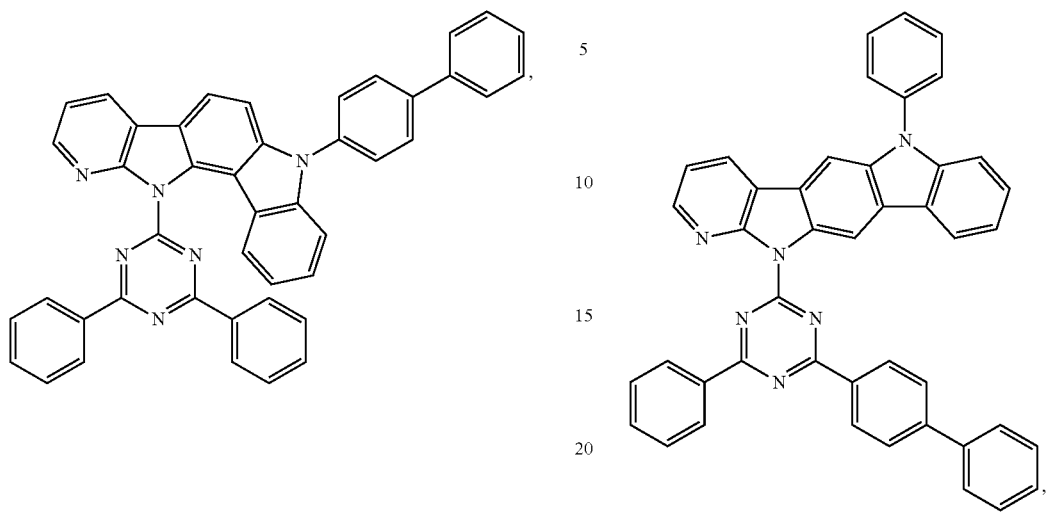
Compound 718
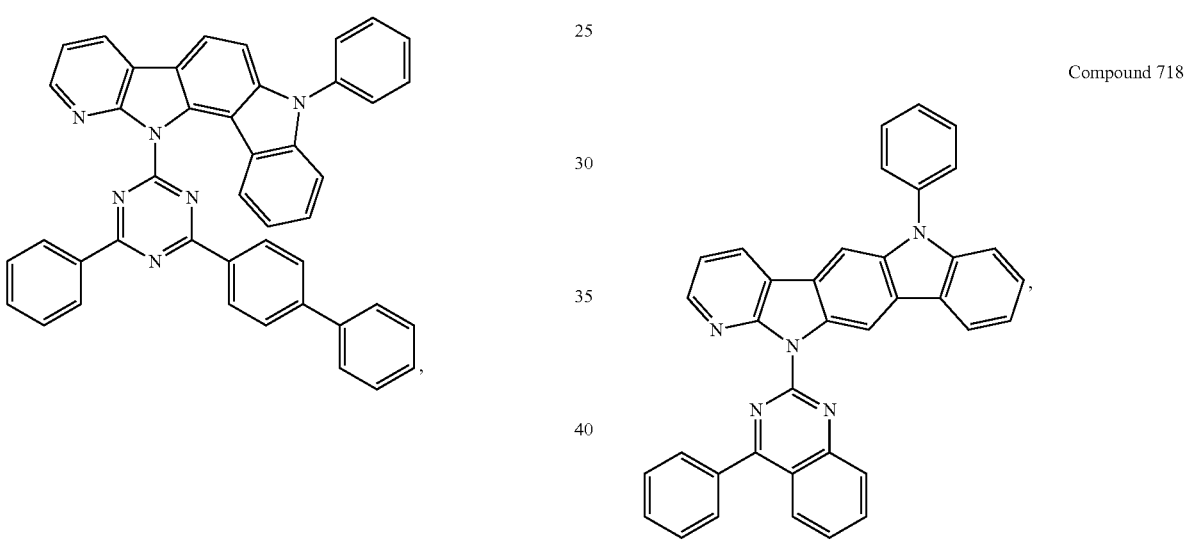
Compound 719
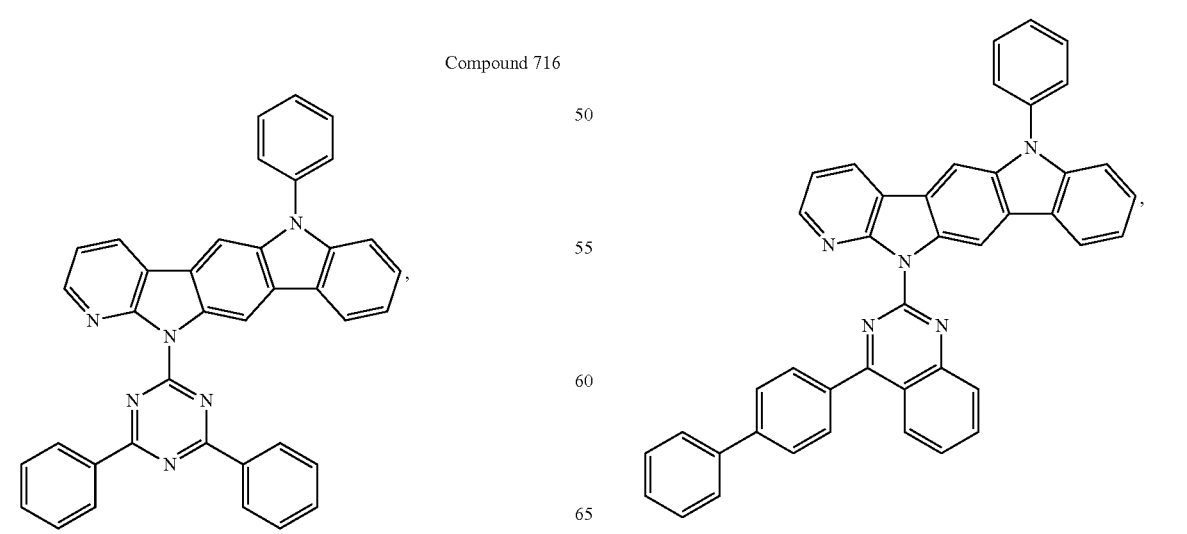

Compound 720
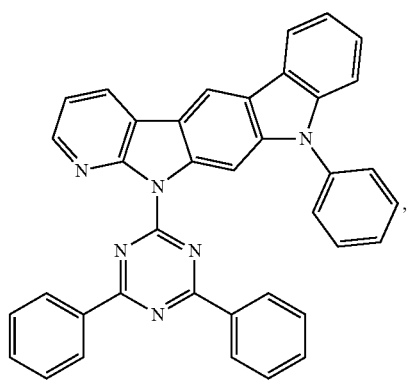
Compound 721
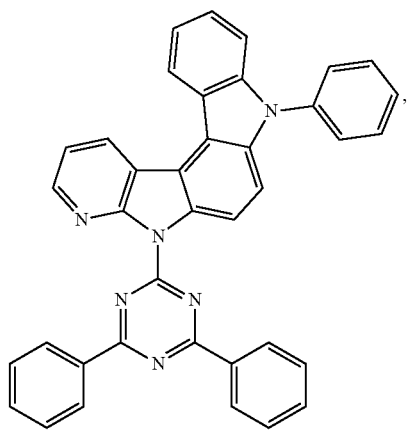
Compound 722
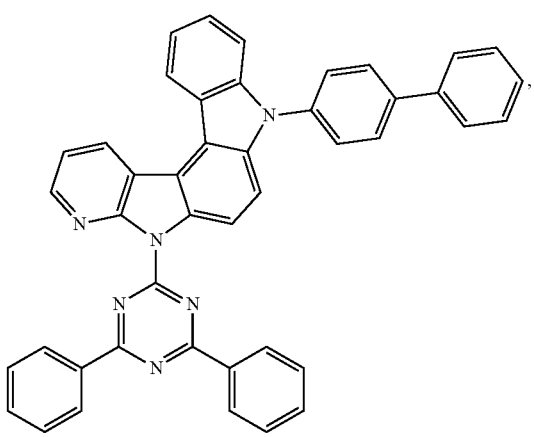
Compound 723
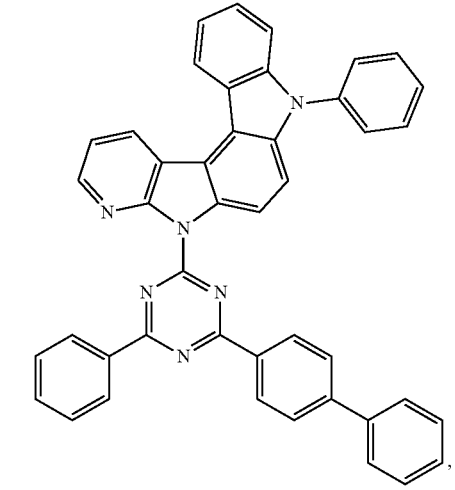
Compound 724
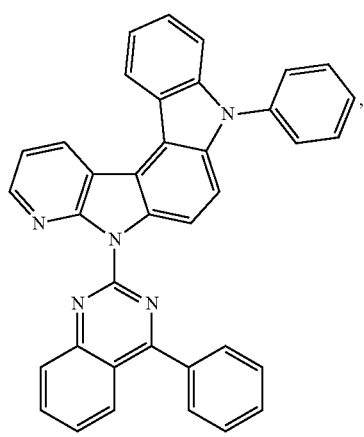
Compound 725
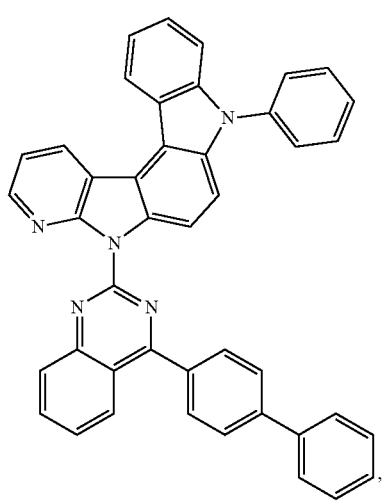

Compound 726
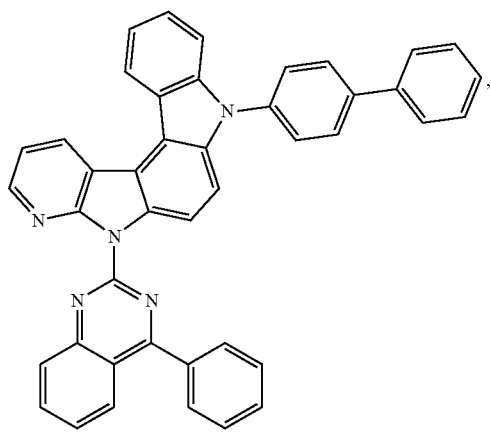
Compound 727
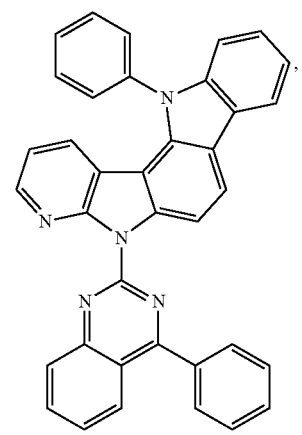
Compound 728
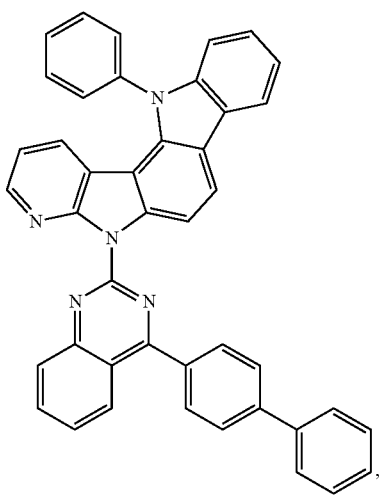
Compound 729
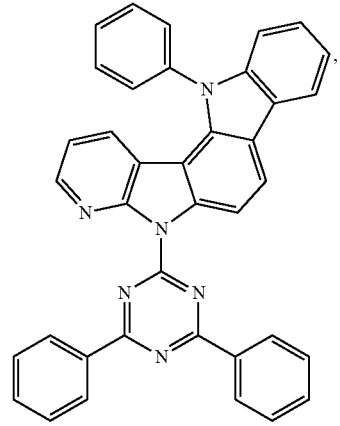
Compound 730
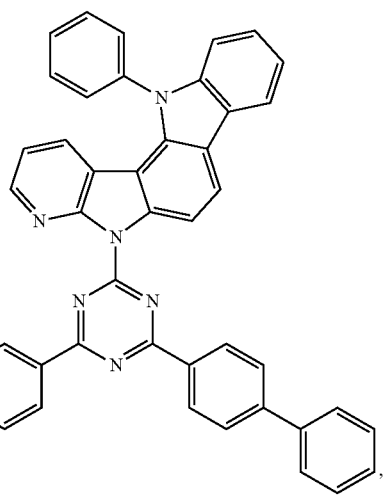
Compound 731
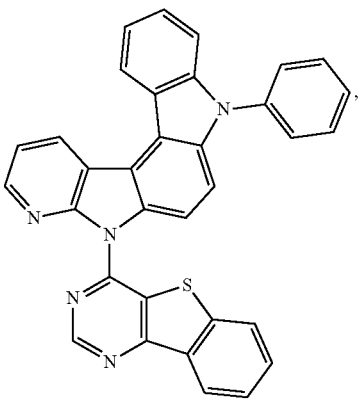

Compound 732

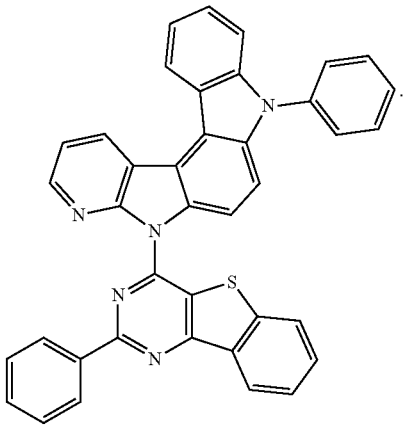

According to another embodiment, an electroluminescent device is disclosed. The electroluminescent device comprises:
an anode,
a cathode,
and an organic layer, disposed between the anode and the cathode, comprising a compound of formula 1:

Formula 1

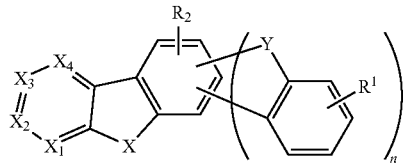

Wherein
$X_1$ to $X_4$ are each independently selected from the group consisting of CR, and N;
At least one of $X_1$ to $X_4$ is N;
X and Y are each independently selected from the group consisting of O, S, Se, NR', or CR"R'";
R1 represents mono, di, tri, or tetra substitution or no substitution;
R2 represents mono or di substitution or no substitution;
R, R', R", R''', $R_1$, and $R_2$ are each independently selected from the group consisting of hydrogen, deuterium, halogen, a substituted or unsubstituted alkyl group having 1 to 20 carbon atoms, a substituted or unsubstituted cycloalkyl group having 3 to 20 ring carbon atoms, a substituted or unsubstituted heteroalkyl group having 1 to 20 carbon atoms, a substituted or unsubstituted arylalkyl group having 7 to 30 carbon atoms, a substituted or unsubstituted alkoxy group having 1 to 20 carbon atoms, a substituted or unsubstituted aryloxy group having 6 to 30 carbon atoms, a substituted or unsubstituted alkenyl group having 2 to 20 carbon atoms, a substituted or unsubstituted aryl group having 6 to 30 carbon atoms, a substituted or unsubstituted heteroaryl group having 3 to 30 carbon atoms, a substituted or unsubstituted alkylsilyl group having 3 to 20 carbon atoms, a substituted or unsubstituted arylsilyl group having 6 to 20 carbon atoms, a substituted or unsubstituted amino group having 0 to 20 carbon atoms, an acyl group, a carbonyl group, a carboxylic acid group, an ester group, a nitrile group, an isonitrile group, a sulfanyl group, a sulfinyl group, a sulfonyl group, a phosphino group, and combinations thereof;
Any adjacent substitution can be optionally joined to form a ring or fused structure;
n is 1 or 2;
when n is 2, each Y and/or each $R_1$ can be the same or different.

In one embodiment, wherein the organic layer is a charge transporting layer.

In one embodiment, wherein the organic layer is a charge blocking layer.

In one embodiment, wherein the organic layer is an emissive layer and the compound is a host.

In one embodiment, wherein the organic layer further comprises a phosphorescent emitter.

In one embodiment, wherein the organic layer further comprises a phosphorescent emitter and the phosphorescent emitter is a metal complex having at least one ligand comprising the following structures:

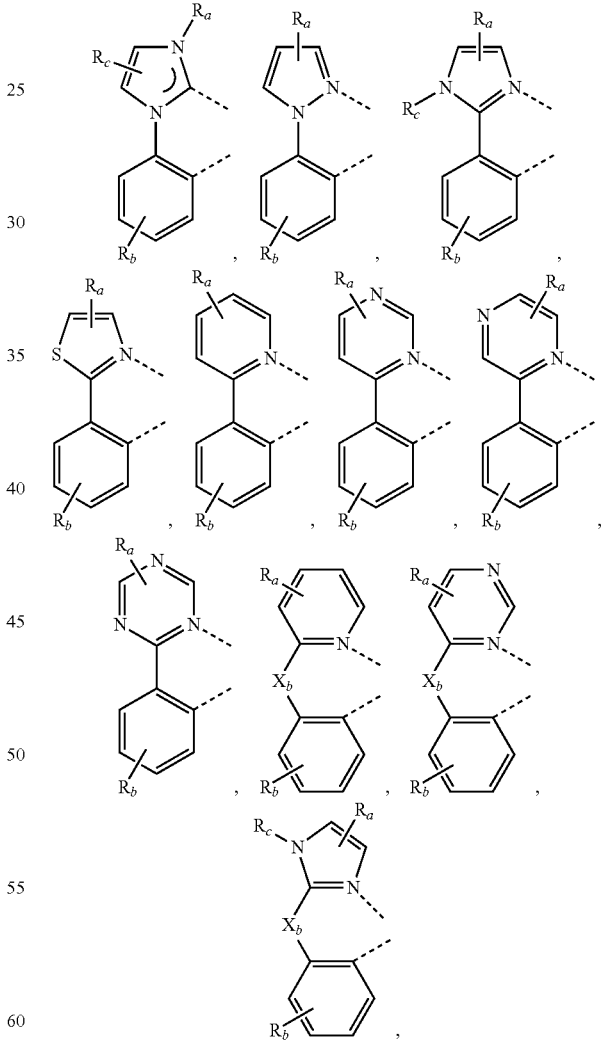

Wherein
$R_a$, $R_b$, and $R_c$ can represent mono, di, tri, or tetra substitution or no substitution;
$R_a$, $R_b$, and $R_c$ are each independently selected from the group consisting of hydrogen, deuterium, halogen, a substituted or unsubstituted alkyl group having 1 to 20 carbon atoms, a substituted or unsubstituted cycloalkyl group having 3 to 20 ring carbon atoms, a substituted or unsubstituted heteroalkyl group having 1 to 20 carbon atoms, a substituted or unsubstituted arylalkyl group having 7 to 30 carbon atoms, a substituted or unsubstituted alkoxy group having 1 to 20 carbon atoms, a substituted or unsubstituted aryloxy group having 6 to 30 carbon atoms, a substituted or unsubstituted alkenyl group having 2 to 20 carbon atoms, a substituted or unsubstituted aryl group having 6 to 30 carbon atoms, a substituted or unsubstituted heteroaryl group having 3 to 30 carbon atoms, a substituted or unsubstituted alkylsilyl group having 3 to 20 carbon atoms, a substituted or unsubstituted arylsilyl group having 6 to 20 carbon atoms, a substituted or unsubstituted amino group having 0 to 20 carbon atoms, an acyl group, a carbonyl group, a carboxylic acid group, an ester group, a nitrile group, an isonitrile group, a sulfanyl group, a sulfinyl group, a sulfonyl group, a phosphino group, and combinations thereof;

$X_b$ is selected from the group consisting of O, S, Se, $NR_{N1}$, and $CR_{C1}R_{C2}$;

$R_{N1}$, $R_{C1}$ and $R_{C2}$ are each independently selected from the group consisting of hydrogen, deuterium, halogen, a substituted or unsubstituted alkyl group having 1 to 20 carbon atoms, a substituted or unsubstituted cycloalkyl group having 3 to 20 ring carbon atoms, a substituted or unsubstituted heteroalkyl group having 1 to 20 carbon atoms, a substituted or unsubstituted arylalkyl group having 7 to 30 carbon atoms, a substituted or unsubstituted alkoxy group having 1 to 20 carbon atoms, a substituted or unsubstituted aryloxy group having 6 to 30 carbon atoms, a substituted or unsubstituted alkenyl group having 2 to 20 carbon atoms, a substituted or unsubstituted aryl group having 6 to 30 carbon atoms, a substituted or unsubstituted heteroaryl group having 3 to 30 carbon atoms, a substituted or unsubstituted alkylsilyl group having 3 to 20 carbon atoms, a substituted or unsubstituted arylsilyl group having 6 to 20 carbon atoms, a substituted or unsubstituted amino group having 0 to 20 carbon atoms, an acyl group, a carbonyl group, a carboxylic acid group, an ester group, a nitrile group, an isonitrile group, a sulfanyl group, a sulfinyl group, a sulfonyl group, a phosphino group, and combinations thereof;

two adjacent substituents are optionally joined to form a ring.

In one embodiment, wherein the organic layer is the emissive layer and the compound of formula 1 is the thermally delayed fluorescent dopant.

According to yet another embodiment, a formulation comprising the compound having formula 1 is also disclosed. The specific structure of the compound is described in any of the above embodiments.

Combination with Other Materials

The materials described herein as useful for a particular layer in an organic light emitting device may be used in combination with a wide variety of other materials present in the device. The combinations of these materials are described in more detail in U.S. Pat. App. No. 20160359122 at paragraphs 0132-0161, which are incorporated by reference in its entirety. The materials described or referred to the disclosure are non-limiting examples of materials that may be useful in combination with the compounds disclosed herein, and one of skill in the art can readily consult the literature to identify other materials that may be useful in combination.

The materials described herein as useful for a particular layer in an organic light emitting device may be used in combination with a variety of other materials present in the device. For example, emissive dopants disclosed herein may be used in combination with a wide variety of hosts, transport layers, blocking layers, injection layers, electrodes and other layers that may be present. The combination of these materials is described in detail in paragraphs 0080-0101 of U.S. Pat. App. No. 20150349273, which are incorporated by reference in its entirety. The materials described or referred to the disclosure are non-limiting examples of materials that may be useful in combination with the compounds disclosed herein, and one of skill in the art can readily consult the literature to identify other materials that may be useful in combination.

It is understood that the various embodiments described herein are by way of example only, and are not intended to limit the scope of the invention. The present invention as claimed may therefore include variations from the particular examples and preferred embodiments described herein, as will be apparent to one of skill in the art. Many of the materials and structures described herein may be substituted with other materials and structures without deviating from the spirit of the invention. It is understood that various theories as to why the invention works are not intended to be limiting.

What is claimed is:

1. A compound having the following formula

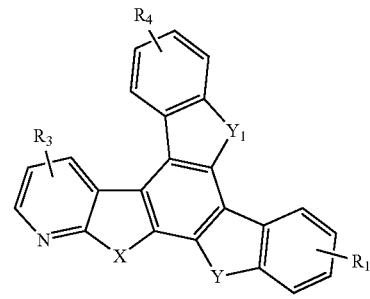

wherein

X is S, Y is NR' and $Y_1$ is selected from the group consisting of S and NR';

$R_1$ represents mono, di, tri, tetra, or no substitution;

R', $R_1$, $R_3$, and $R_4$ are each independently selected from the group consisting of hydrogen, deuterium, halogen, a substituted or unsubstituted alkyl group having 1 to 20 carbon atoms, a substituted or unsubstituted cycloalkyl group having 3 to 20 ring carbon atoms, a substituted or unsubstituted heteroalkyl group having 1 to 20 carbon atoms, a substituted or unsubstituted arylalkyl group having 7 to 30 carbon atoms, a substituted or unsubstituted alkoxy group having 1 to 20 carbon atoms, a substituted or unsubstituted aryloxy group having 6 to 30 carbon atoms, a substituted or unsubstituted alkenyl group having 2 to 20 carbon atoms, a substituted or unsubstituted aryl group having 6 to 30 carbon atoms, a substituted or unsubstituted heteroaryl group having 3 to 30 carbon atoms, a substituted or unsubstituted alkylsilyl group having 3 to 20 carbon atoms, a substituted or unsubstituted arylsilyl group having 6 to 20 carbon atoms, a substituted or unsubstituted amino group having 0 to 20 carbon atoms, an acyl group, a carbonyl group, a carboxylic acid group, an ester group, a nitrile group, an isonitrile group, a sulfanyl group, a sulfinyl group, a sulfonyl group, a phosphino group, and combinations thereof.
2. The compound of claim 1, wherein $Y_1$ is NR'.
3. The compound of claim 1, wherein $Y_1$ is S.
4. The compound of claim 1, wherein R' is selected from the group consisting of:
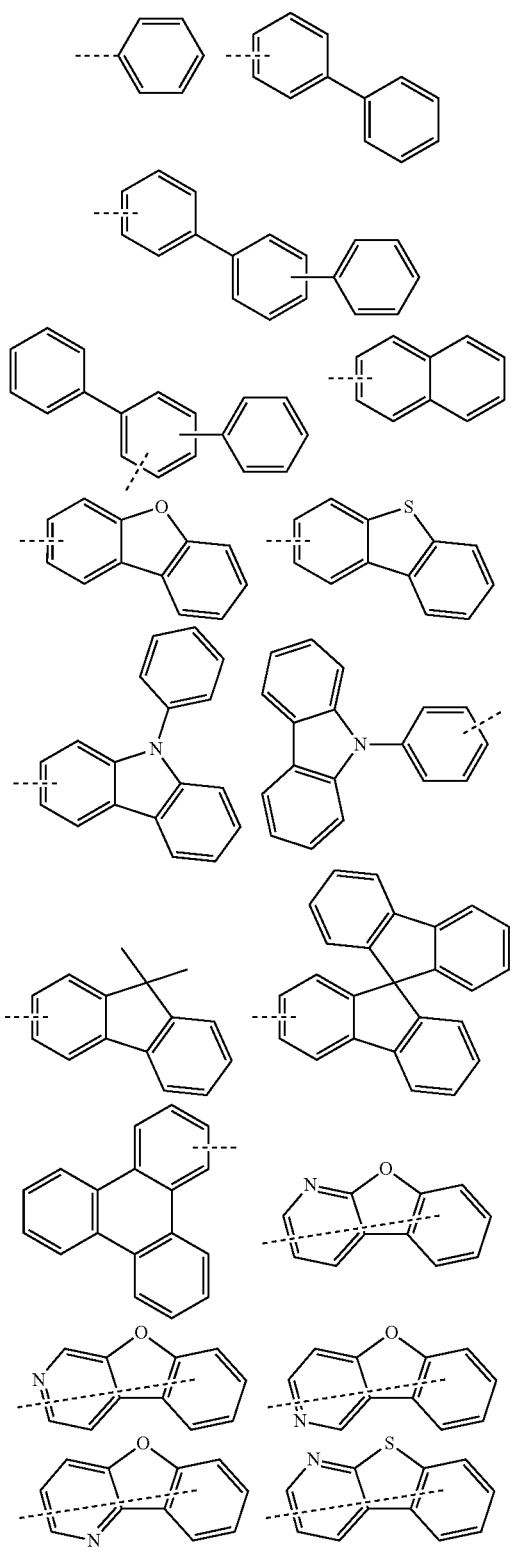
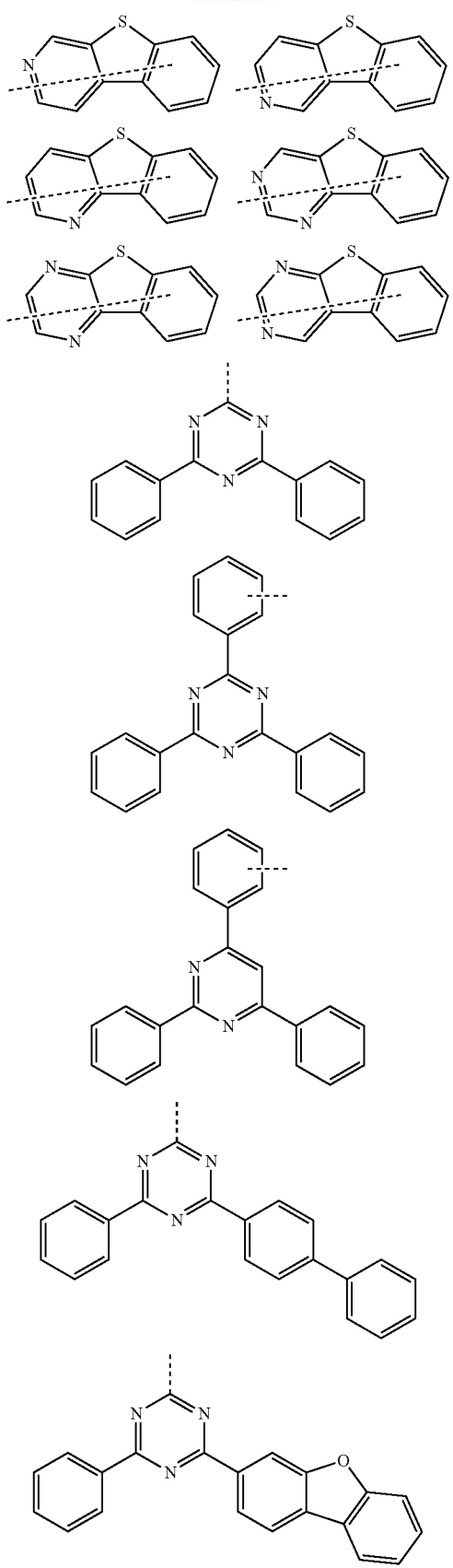

-continued
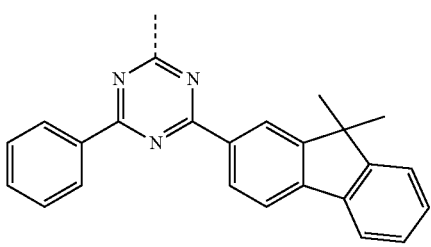
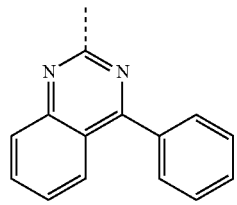
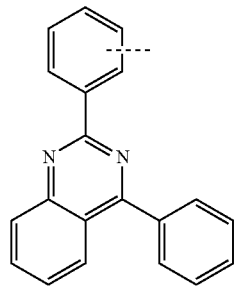
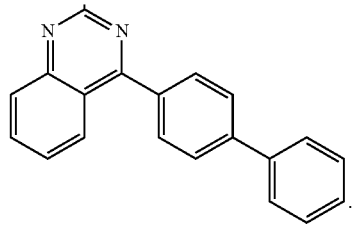
5. The compound of claim 1, wherein the compound is selected from the group consisting of:
Compound 14
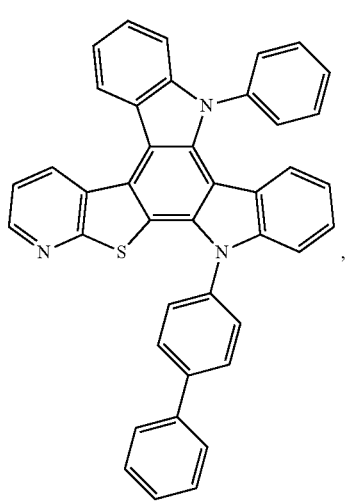
-continued
Compound 15
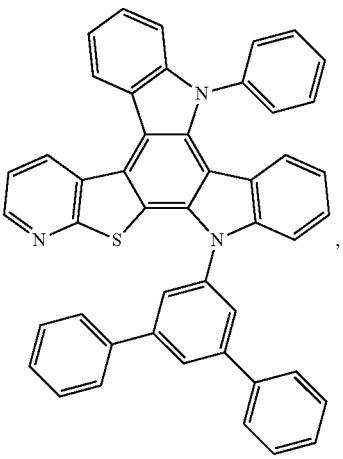
Compound 16
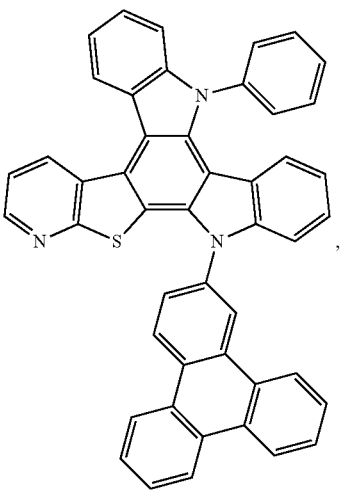
Compound 17
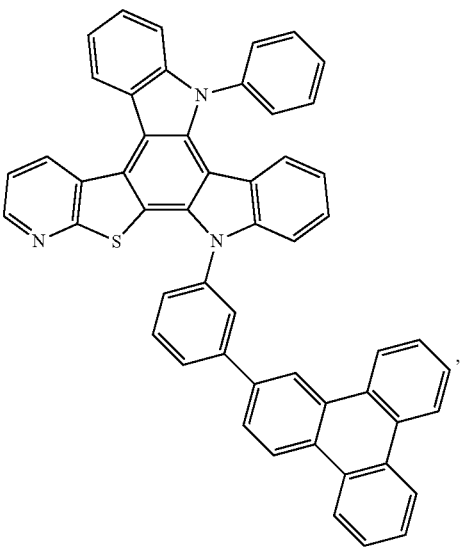

Compound 18
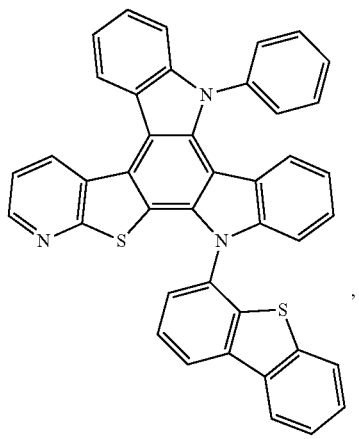
Compound 19
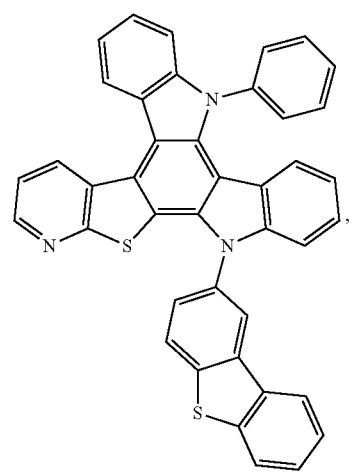
Compound 20
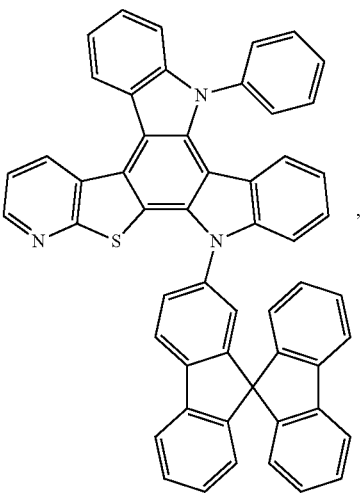
Compound 21
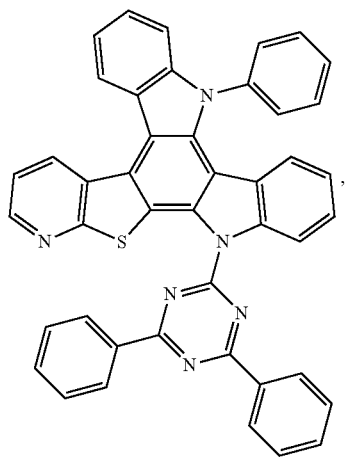
Compound 22
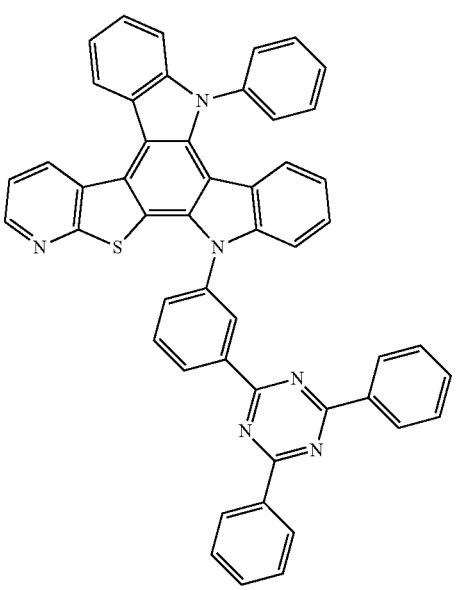
Compound 23
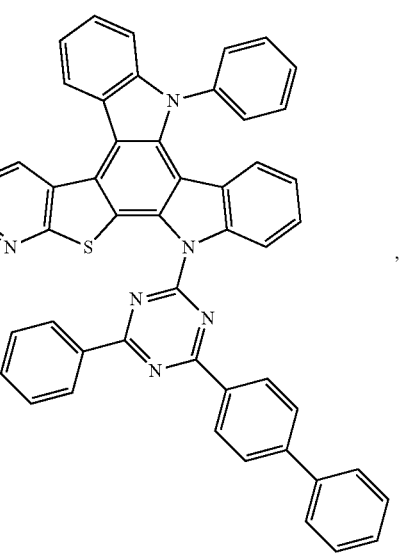

Compound 24
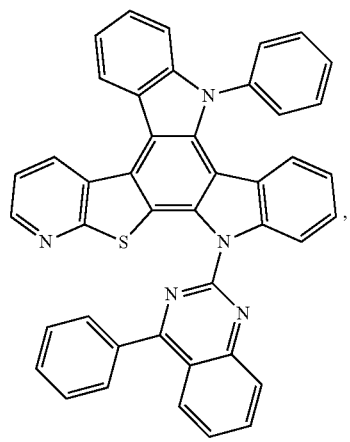
Compound 25
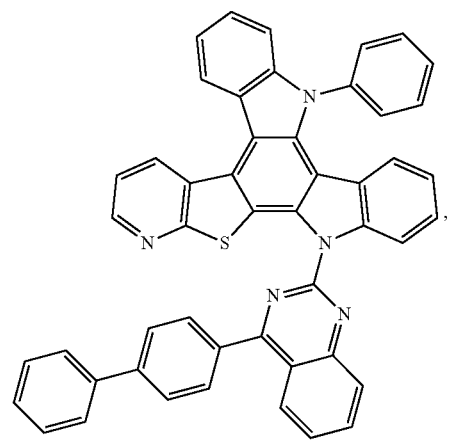
Compound 26
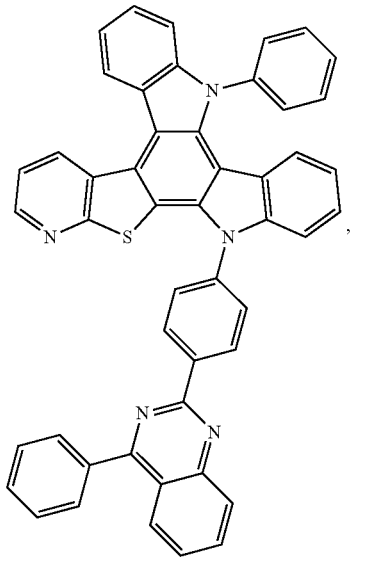
Compound 27
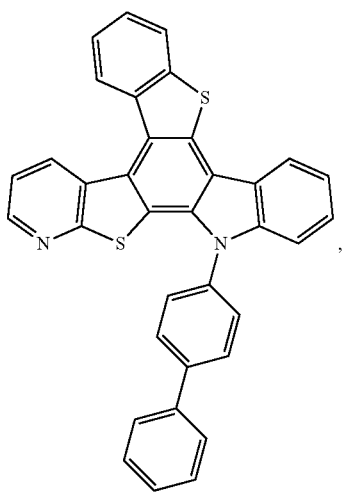
Compound 28
Compound 29

Compound 30
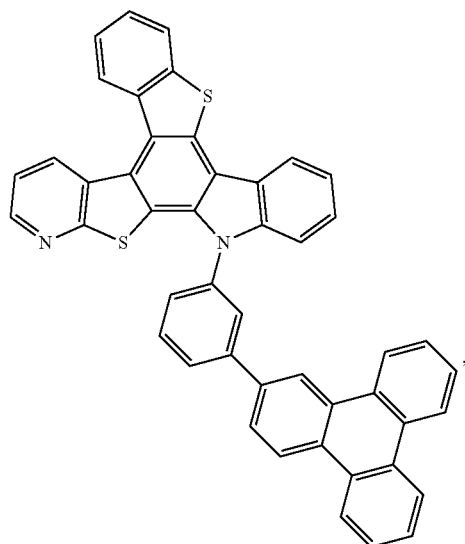
Compound 31
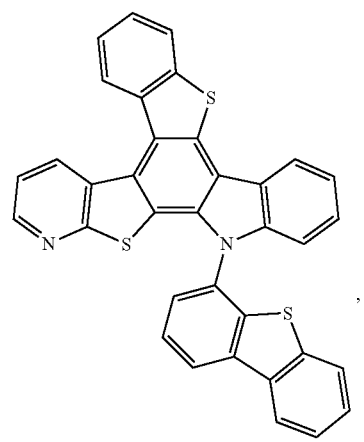
Compound 32
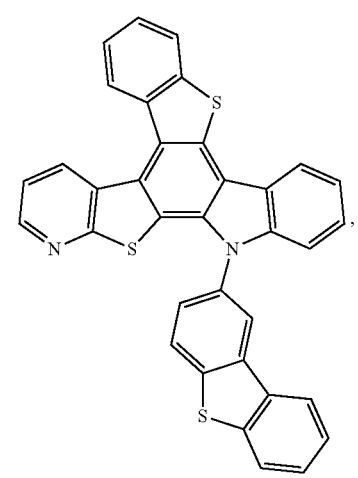
Compound 33
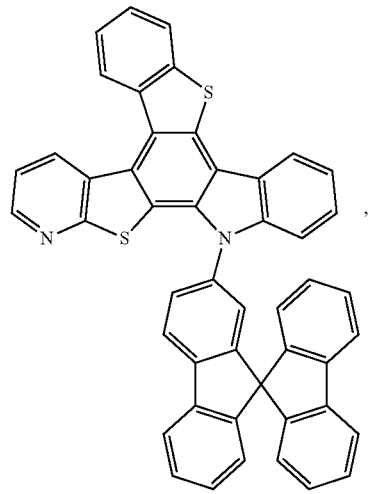
Compound 34
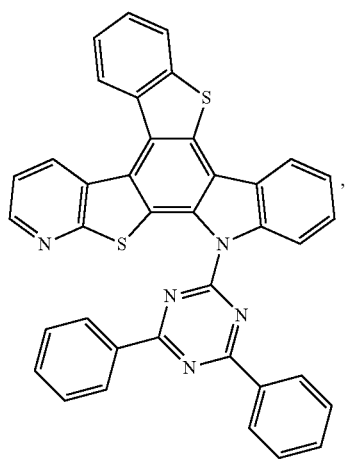
Compound 35
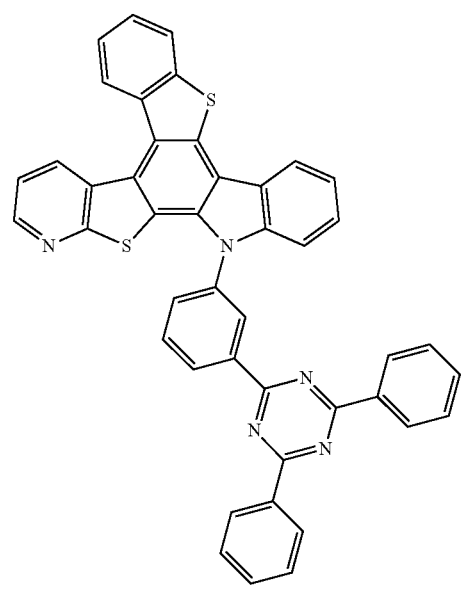

Compound 36
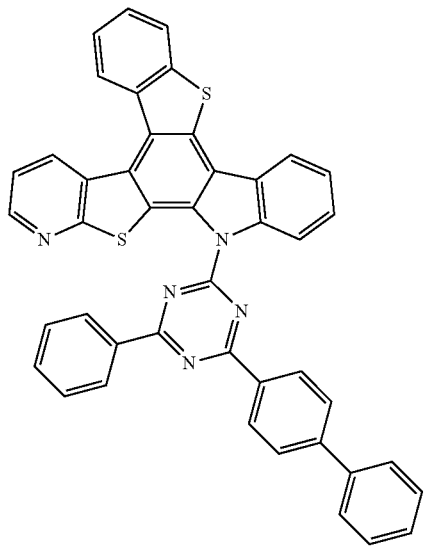
Compound 37
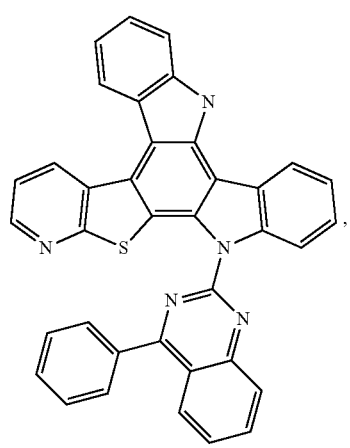
Compound 38
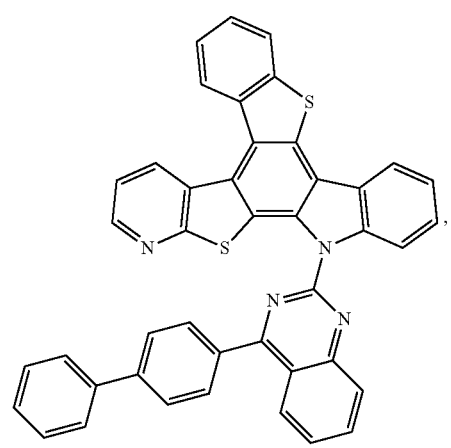
Compound 39
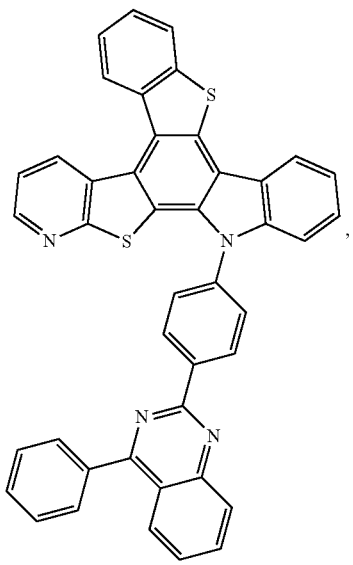
Compound 174
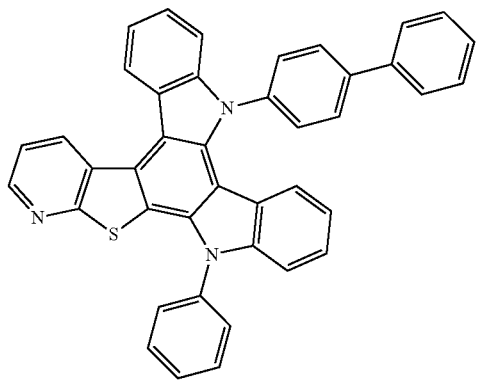
Compound 175
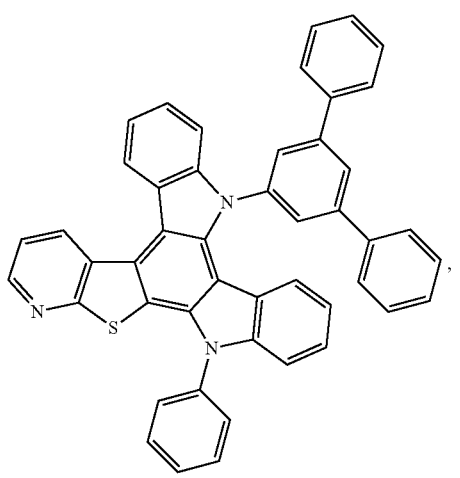

Compound 176
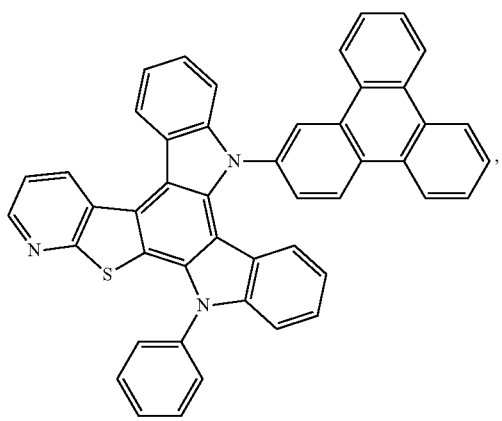
Compound 177
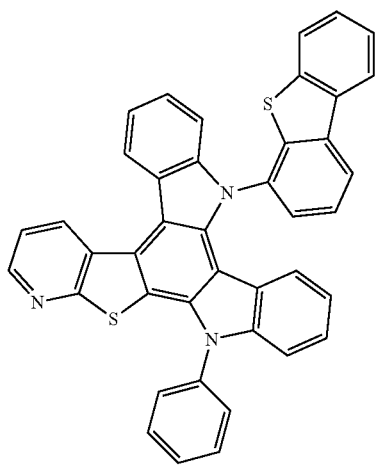
Compound 178
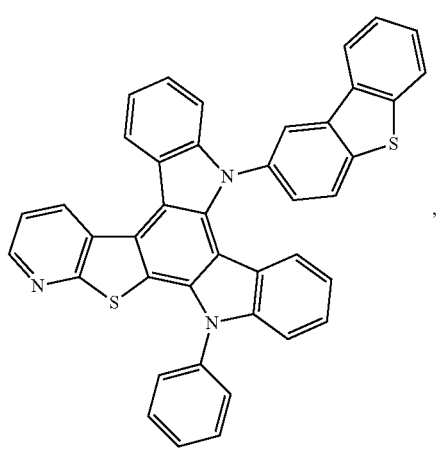
Compound 179
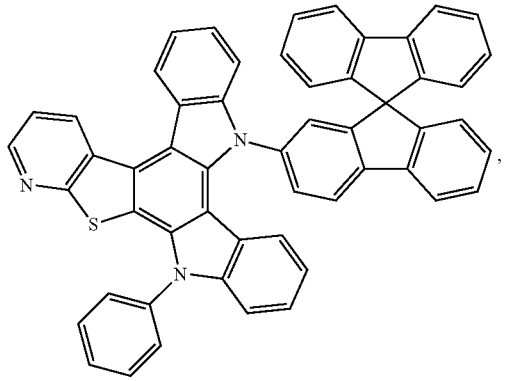
Compound 180
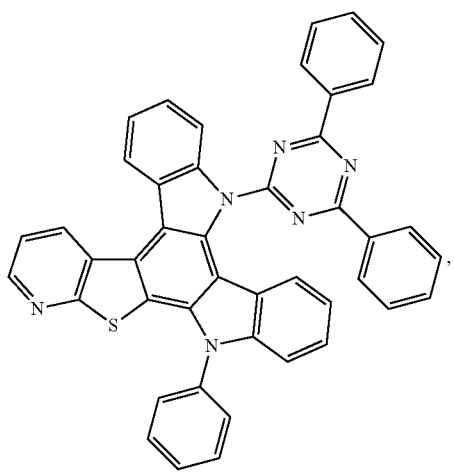
Compound 181
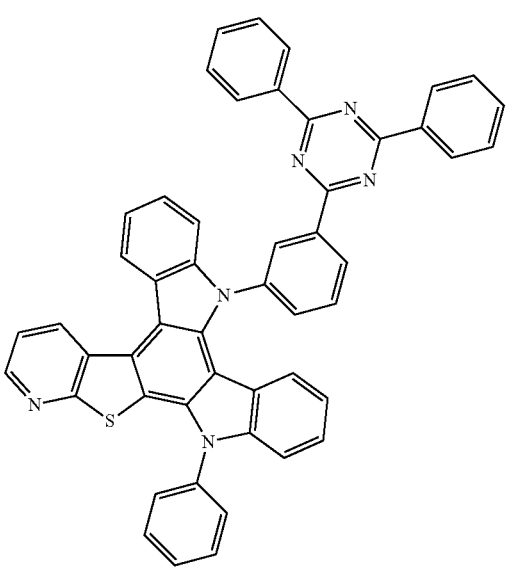

Compound 182

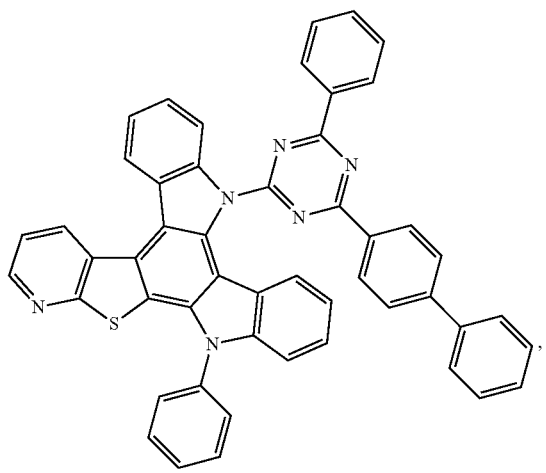

Compound 183

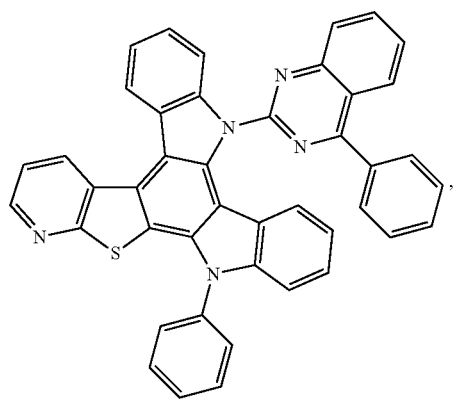

Compound 184

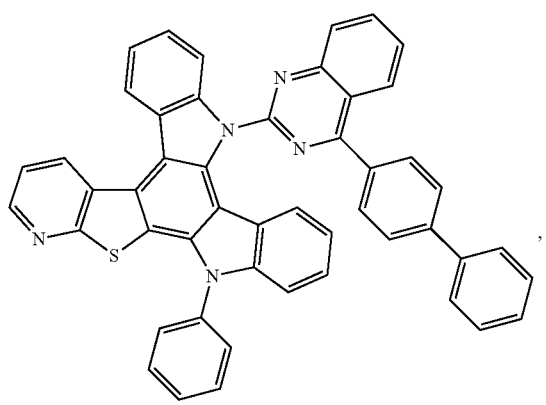

Compound 185

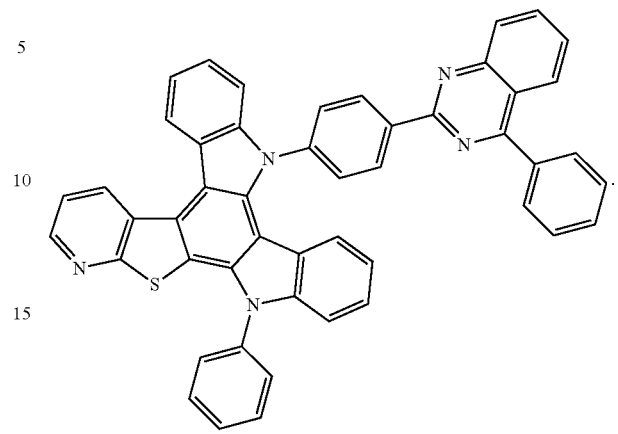

6. An electroluminescent device comprises an anode, a cathode, and an organic layer, disposed between the anode and the cathode, comprising the compound of claim 1.

7. The device of claim 6, wherein the organic layer is a charge transporting layer.

8. The device of claim 6, wherein the organic layer is a charge blocking layer.

9. The device of claim 6, wherein the organic layer is an emissive layer and the compound is a host.

10. The device of claim 6, wherein the organic layer further comprises a phosphorescent emitter.

11. The device of claim 6, wherein the organic layer further comprises a phosphorescent emitter and the phosphorescent emitter is a metal complex having at least one ligand comprising anyone of the following structures:

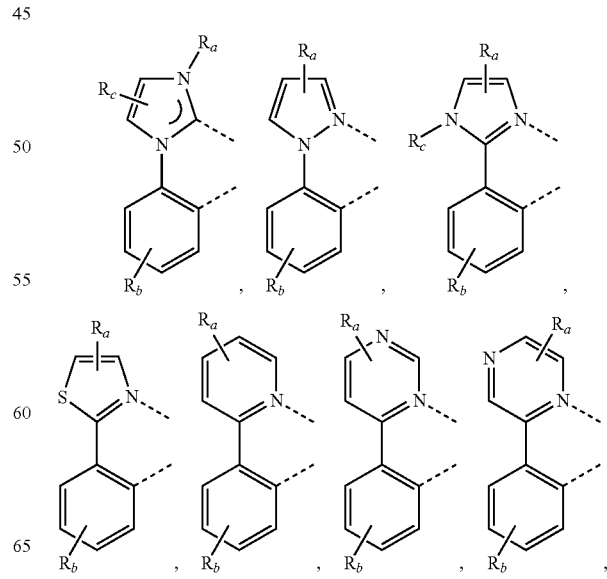

-continued

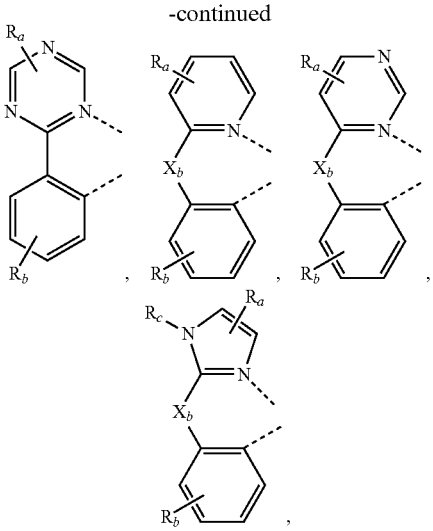

Wherein $R_a$, $R_b$, and $R_c$ can represent mono, di, tri, or tetra substitution or no substitution;

$X_b$ is selected from the group consisting of O, S, Se, $NR_{N1}$, and $CR_{C1}R_{C2}$;

$R_a$, $R_b$, $R_c$, $R_{N1}$, $R_{C1}$, and $R_{C2}$ are each independently selected from the group consisting of hydrogen, deuterium, halogen, a substituted or unsubstituted alkyl group having 1 to 20 carbon atoms, a substituted or unsubstituted cycloalkyl group having 3 to 20 ring carbon atoms, a substituted or unsubstituted heteroalkyl group having 1 to 20 carbon atoms, a substituted or unsubstituted arylalkyl group having 7 to 30 carbon atoms, a substituted or unsubstituted alkoxy group having 1 to 20 carbon atoms, a substituted or unsubstituted aryloxy group having 6 to 30 carbon atoms, a substituted or unsubstituted alkenyl group having 2 to 20 carbon atoms, a substituted or unsubstituted aryl group having 6 to 30 carbon atoms, a substituted or unsubstituted heteroaryl group having 3 to 30 carbon atoms, a substituted or unsubstituted alkylsilyl group having 3 to 20 carbon atoms, a substituted or unsubstituted arylsilyl group having 6 to 20 carbon atoms, a substituted or unsubstituted amino group having 0 to 20 carbon atoms, an acyl group, a carbonyl group, a carboxylic acid group, an ester group, a nitrile group, an isonitrile group, a sulfanyl group, a sulfinyl group, a sulfonyl group, a phosphino group, and combinations thereof;

two adjacent substituents are optionally joined to form a ring.

12. The device of claim 6, wherein the organic layer is the emissive layer and the compound of formula 1 is the thermally delayed fluorescent dopant.

13. A formulation comprises the compound of claim 1.

* * * * *